US011236349B2

(12) United States Patent
Kudithipudi et al.

(10) Patent No.: US 11,236,349 B2
(45) Date of Patent: Feb. 1, 2022

(54) GENETIC CONTROL OF AXILLARY BUD GROWTH IN TOBACCO PLANTS

(71) Applicant: ALTRIA CLIENT SERVICES LLC, Richmond, VA (US)

(72) Inventors: Chengalrayan Kudithipudi, Midlothian, VA (US); Yanxin Shen, Glen Allen, VA (US); Dongmei Xu, Glen Allen, VA (US); Jesse Frederick, Richmond, VA (US); Jaemo Yang, Richmond, VA (US)

(73) Assignee: Altria Client Services LLC, Richmond, VA (US)

( * ) Notice: Subject to any disclaimer, the term of this patent is extended or adjusted under 35 U.S.C. 154(b) by 0 days.

(21) Appl. No.: 16/589,783

(22) Filed: Oct. 1, 2019

(65) Prior Publication Data

US 2020/0032283 A1 Jan. 30, 2020

Related U.S. Application Data

(63) Continuation of application No. 14/875,928, filed on Oct. 6, 2015, now Pat. No. 10,435,700.

(60) Provisional application No. 62/060,473, filed on Oct. 6, 2014.

(51) Int. Cl.
*C12N 15/82* (2006.01)
*C07K 14/415* (2006.01)

(52) U.S. Cl.
CPC ........ *C12N 15/8218* (2013.01); *C07K 14/415* (2013.01); *C12N 15/8229* (2013.01); *C12N 15/8261* (2013.01); *C12N 15/8295* (2013.01); *Y02A 40/146* (2018.01)

(58) Field of Classification Search
None
See application file for complete search history.

(56) References Cited

U.S. PATENT DOCUMENTS

| | | | |
|---|---|---|---|
| 4,091,823 A | 5/1978 | Kallianos et al. |
| 4,516,590 A | 5/1985 | Teng |
| 4,528,993 A | 7/1985 | Sensabaugh, Jr. et al. |
| 4,638,816 A | 1/1987 | Cox et al. |
| 4,660,577 A | 4/1987 | Sensabaugh, Jr. et al. |
| 4,683,195 A | 7/1987 | Teng |
| 4,683,202 A | 7/1987 | Mullis |
| 4,732,856 A | 3/1988 | Fedoroff |
| 4,761,373 A | 8/1988 | Anderson et al. |
| 4,762,785 A | 8/1988 | Comai |
| 4,769,061 A | 9/1988 | Comai |
| 4,778,987 A | 10/1988 | Saaski et al. |
| 4,800,159 A | 1/1989 | Mullis et al. |
| 4,810,648 A | 3/1989 | Stalker |
| 4,848,373 A | 7/1989 | Lenkey |
| 4,940,835 A | 7/1990 | Shah et al. |
| 4,945,050 A | 7/1990 | Sanford et al. |
| 4,965,188 A | 10/1990 | Mullis et al. |
| 4,975,374 A | 12/1990 | Goodman et al. |
| 4,987,907 A | 1/1991 | Townsend |
| 5,004,863 A | 4/1991 | Umbeck |
| 5,013,658 A | 5/1991 | Dooner et al. |
| 5,013,659 A | 5/1991 | Bedbrook et al. |
| 5,085,325 A | 2/1992 | Jones et al. |
| 5,104,310 A | 4/1992 | Saltin |
| 5,141,131 A | 8/1992 | Miller, Jr. et al. |
| 5,149,645 A | 9/1992 | Hoekema et al. |
| 5,159,135 A | 10/1992 | Umbeck |
| 5,162,602 A | 11/1992 | Somers et al. |
| 5,164,180 A | 11/1992 | Payne et al. |
| 5,177,010 A | 1/1993 | Goldman et al. |
| 5,231,019 A | 7/1993 | Paszkowski et al. |
| 5,276,268 A | 1/1994 | Strauch et al. |
| 5,316,931 A | 5/1994 | Donson et al. |
| 5,372,149 A | 12/1994 | Roth et al. |
| 5,463,174 A | 10/1995 | Maloney et al. |
| 5,464,763 A | 11/1995 | Schilperoort et al. |
| 5,469,976 A | 11/1995 | Burchell |
| 5,491,081 A | 2/1996 | Webb |
| 5,545,565 A | 8/1996 | De Greve et al. |
| 5,561,236 A | 10/1996 | Leemans et al. |
| 5,563,055 A | 10/1996 | Townsend et al. |
| 5,565,350 A | 10/1996 | Kmiec |
| 5,589,367 A | 12/1996 | Donson et al. |
| 5,659,026 A | 8/1997 | Baszczynski et al. |
| 5,689,035 A | 11/1997 | Webb |
| 5,731,181 A | 3/1998 | Kmiec |
| 5,756,325 A | 5/1998 | Kmiec |

(Continued)

FOREIGN PATENT DOCUMENTS

CN 1824774 8/2006
CN 1824774 A 8/2006
(Continued)

OTHER PUBLICATIONS

Search Report dated Mar. 11, 2020, in Chinese Patent Application No. 2015800653477.
"2015-2016 Burley and Dark Tobacco Production Guide," Bob Pearce, editor (2014).
Akaba et al., "Production of Homo- and Hetero-Dimeric Isozymes from Two Aldehyde Oxidase Genes of Arabidopsis thaliana," *The Journal of Biochemistry*, 126:395-401 (1999).
Allen et al., "Evolution of MicroRNA Genes by Inverted Duplication of Target Gene Sequences in Arabidopsis thaliana," *Nature Genetics*, 36:1282-1290 (2004).

(Continued)

*Primary Examiner* — Charles Logsdon
(74) *Attorney, Agent, or Firm* — Arnold & Porter Kaye Scholer LLP

(57) ABSTRACT

This disclosure provides a number of sequences involved in axillary bud growth in tobacco, methods of using such sequences, tobacco plants carrying modifications to such sequences or transgenes of such sequences, and tobacco products made from tobacco leaf harvested from such plants.

20 Claims, 27 Drawing Sheets
Specification includes a Sequence Listing.

(56) References Cited

U.S. PATENT DOCUMENTS

| | | | |
|---|---|---|---|
| 5,760,012 | A | 6/1998 | Kmiec et al. |
| 5,767,366 | A | 6/1998 | Sathasivan et al. |
| 5,789,156 | A | 8/1998 | Bujard et al. |
| 5,795,972 | A | 8/1998 | Kmiec |
| 5,814,618 | A | 9/1998 | Bujard et al. |
| 5,866,785 | A | 2/1999 | Donson et al. |
| 5,871,984 | A | 2/1999 | Kmiec |
| 5,879,903 | A | 3/1999 | Strauch et al. |
| 5,879,918 | A | 3/1999 | Tomes et al. |
| 5,886,244 | A | 3/1999 | Tomes et al. |
| 5,889,190 | A | 3/1999 | Donson et al. |
| 5,889,191 | A | 3/1999 | Turpen |
| 5,928,937 | A | 7/1999 | Kakefuda et al. |
| 5,932,782 | A | 8/1999 | Bidney |
| 5,981,840 | A | 11/1999 | Zhao et al. |
| 6,072,050 | A | 6/2000 | Bowen et al. |
| 6,084,155 | A | 7/2000 | Volrath et al. |
| 6,166,302 | A | 12/2000 | Merlo et al. |
| 6,451,732 | B1 | 9/2002 | Beckett et al. |
| 6,451,735 | B1 | 9/2002 | Ottway et al. |
| 8,093,459 | B2 | 1/2012 | Thomas |
| 8,124,851 | B2 | 2/2012 | Dewey et al. |
| 8,319,011 | B2 | 11/2012 | Xu et al. |
| 9,187,759 | B2 | 11/2015 | Dewey et al. |
| 9,228,194 | B2 | 1/2016 | Dewey et al. |
| 9,228,195 | B2 | 1/2016 | Dewey et al. |
| 9,247,706 | B2 | 2/2016 | Dewey et al. |
| 2001/0016956 | A1 | 8/2001 | Ward et al. |
| 2002/0008055 | A1 | 1/2002 | Campbell et al. |
| 2004/0118422 | A1 | 6/2004 | Lundin et al. |
| 2005/0057263 | A1 | 3/2005 | Moshe et al. |
| 2005/0178398 | A1 | 8/2005 | Breslin et al. |
| 2005/0244521 | A1 | 11/2005 | Strickland et al. |
| 2006/0191548 | A1 | 8/2006 | Strickland et al. |
| 2006/0200878 | A1 | 9/2006 | Lutfiyya et al. |
| 2007/0083948 | A1 | 4/2007 | McAvoy et al. |
| 2010/0218270 | A1* | 8/2010 | Xu .................. A01H 5/12 800/270 |
| 2012/0024301 | A1 | 2/2012 | Carroll et al. |
| 2012/0031414 | A1 | 2/2012 | Atchley et al. |
| 2012/0031416 | A1 | 2/2012 | Atchley et al. |
| 2016/0281100 | A1 | 9/2016 | Kudithipudi et al. |

FOREIGN PATENT DOCUMENTS

| | | |
|---|---|---|
| CN | 101048508 A | 10/2007 |
| EP | 0 242 246 | 10/1987 |
| EP | 0821866 | 2/1998 |
| EP | 2 383 344 | 11/2011 |
| EP | 2 383 344 A1 | 11/2011 |
| WO | WO 98/49350 | 11/1998 |
| WO | WO 99/07865 | 2/1999 |
| WO | WO 0058035 | 10/2000 |
| WO | WO 2003/050287 | 6/2003 |
| WO | WO 2004/041006 | 5/2004 |
| WO | WO 2006/035221 | 4/2006 |
| WO | WO 2006/035221 A2 | 4/2006 |
| WO | WO 2008/133643 | 11/2008 |
| WO | WO 2011/027315 | 3/2011 |

OTHER PUBLICATIONS

Allen et al., "MicroRNA-Directed Phasing during Trans-Acting siRNA Biogenesis in Plants," *Cell*, 121:207-221 (2005).
Altschul et al., "Basic Local Alignment Search Tool," *Journal of Molecular Biology*, 215:403-410 (1990).
Altschul et al., "Gapped Blast and PSI-Blast: A New Generation of Protein Database Search Programs," *Nucleic Acids Research*, 25:3389-3402 (1997).
Amaya et al., "Expression of Centroradialis (CEN) and CEN-Like Genes in Tobacco Reveals a Conserved Mechanism Controlling Phase Change in Diverse Species," *Plant Cell*, 11(8): 1405-1418 (1999).
Avci et al., "Cysteine Proteases XCP1 and XCP2 Aid Micro-Autolysis within the Intact Central Vacuole during Xylogenesis in *Arabidopsis* Roots," *Plant Journal*, 56:303-315 (2008).
Axtell et al., "A Two-Hit Trigger for siRNA Biogenesis in Plants,"*Cell*, 127:565-577 (2006).
Bartel, "MicroRNAs: Genomics, Biogenesis, Mechanism, and Function," *Cell*, 116:281-297 (2004).
Beetham et al., "A Tool for Functional Plant Genomics: Chimeric RNA/DNA Oligonucleotides Cause in vivo Gene-Specific Mutations," *Proceedings of the National Academy of Sciences USA*, 96:8774-8778 (1999).
Bender et al., "Pseudomonas Syringae Phytotoxins: Mode of Action, Regulation, and Biosynthesis by Peptide and Polyketide Synthetases," *Microbiology and Molecular Biology Reviews*, 63:266-292 (1999).
Boutros et al., "Genome-Wide RNAi Analysis of Growth and Viability in Drosophila Cells," *Science*, 303:832-835 (2004).
Bowman et al., "Revised North Carolina Grade Index for Flue-Cured Tobacco," *Tobacco Science*, 32:39-40 (1988).
Canevascini et al., "Tissue-Specific Expression and Promoter Analysis of the Tobacco LTP1 Gene," *Plant Physiology*, 112:513-524 (1996).
Cermak et al., "Efficient Design and Assembly of Custom TALEN and Other TAL Effector-Based Constructs for DNA Targeting," *Nucleic Acids Research*, 39:e82 (2011).
Cheng et al., "Auxin Synthesized by the YUCCA Flavin Monooxygenases is Essential for Embryogenesis and Leaf Formation in *Arabidopsis*," *Plant Cell*, 19:2430-3439 (2007).
Christensen et al., "Maize Polyubiquitin Genes: Structure, Thermal Perturbation of Expression and Transcript Splicing, and Promoter Activity Following Transfer to Protoplasts by Electroporation," *Plant Molecular Biology*18:675-689 (1992).
Christensen et al., "Sequence Analysis and Transcriptional Regulation by Heat Shock of Polyubiquitin Transcripts from Maize," *Plant Molecular Biology*, 12:619-632 (1989).
Christou et al., "Stable Transformations of Soybean Callus by DNA-Coated Gold Particles," *Plant Physiology*, 87:671-674 (1988).
Crone et al., "The Differential Expression of a Heat Shock Promoter in Floral and Reproductive Tissues," *lant Cell Environ.*, 24:869-874 (2001).
Crossway et al., "Micromanipulation Techniques in Plant Manipulation," *Biotechniques*, 4:320-334 (1986).
Daub et al., "Field and Greenhouse Analysis of Variation for Disease Resistance in Tobacco Somaclones," *Phytopathology*, 79(5):600-605 (1989).
De Jong et al., "Chemical-Induced Apoptotic Cell Death in Tomato Cells: Involvement of Caspase-Like Proteases," *Planta*, 211:656-662 (2000).
De Wet et al., "Exogenous Gene Transfer in Maize (*Zea mays*) Using DNA-Treated Pollen," *The Experimental Manipulation of Ovule Tissues*, Chapman et al. (eds.), Longman, London, pp. 197-209 (1985).
Devarenne et al., "Adi3 is a Pdk1-Interacting AGC Kinase that Negatively Regulates Plant Cell Death," *EMBO Journal*, 25:255-265 (2006).
D'Halluin et al., "Transgenic Maize Plants by Tissue Electroporation," *The Plant Cell*, 4:1495-1505 (1992).
Dietzl et al., "A Genome-Wide Transgenic RNAi Library for Conditional Gene Inactivation in Drosophila," *Nature*, 448:151-156 (2007).
Doyle et al., "TAL Effector-Nucleotide Targeter (TALE-NT) 2.0: Tools for TAL Effector Design and Target Prediction Effector," *Nucleic Acids Research*, 40:W117-122 (2012).
Dugas et al., "MicroRNA Regulation of Gene Expression in Plants," *Current Opinion in Plant Biology*, 7:512-520 (2004).
Escamez et al., "Programmes of Cell Death and Autolysis in Tracheary Elements: When a Suicidal Cell Arranges its Own Corpse Removal," *Journal of Experimental Botany*, 65:1313-1321 (2014).
Estruch et al., "Transgenic Plants: An Emerging Approach to Pest Control," *Nature Biotechnology*, 15:137 (1997).
Fedoroff et al., "Cloning of the Bronze Locus in Maize by a Simple and Generalizable Procedure Using the Transposable Controlling Element Activator (Ac)," *Proceeding of the National Academy of Sciences USA*, 81:3825-3829 (1984).

(56) References Cited

OTHER PUBLICATIONS

Finer et al., "Transformation of Soybean via Particle Bombardment of Embryogenic Suspension Culture Tissue," *Vitro Cellular Developmental Biology*, 27P:175-182 (1991).
Fisher et al., "2015 Flue Cured Production Guide," North Carolina State University, pp. 1-199 (2014).
Fisher et al., "Topping, Managing Suckers, and Using Ethepon," *Flue-Cured Tobacco Information*, North Carolina State University, pp. 96-117 (2016).
Franco-Zorilla et al., "Target Mimicry Provides a New Mechanism for Regulation of MicroRNA Activity," *Nature Genetics*, 39:1033-1037 (2007).
Galweiler et al., "Regulation of Polar Auxin Transport by AtPIN1 in *Arabidopsis* Vascular Tissue," *Science*, 282:2226-2230 (1998).
Gatz et al., "Regulation of a Modified CaMV 35S Promoter by the Tn10-Encoded Tet Repressor in Transgenic Tobacco," *Molecular and General Genetics*, 227:229-237 (1991).
GenBank Accession M14442 dated Feb. 1, 1996.
Goldman et al., "Female Sterile Tobacco Plants Are Produced by Stigma," *EMBO Journal*, 13:2976-2984 (1994).
Gonzalez-Grandio et al., "BRANCHED1 Promotes Axillary Bud Dormancy in Response to Shade in *Arabidopsis*," *The Plant Cell*, 25(3):834-850 (2013).
Greb et al., "Molecular Analysis of the Lateral Suppressor Gene in *Arabidopsis* Reveals a Conserved Ccontrol Mechanism for Axillary Meristem Formation," *Genes & Development*, 17:1175-1187 (2003).
Griffiths-Jones et al., "Rfam: An RNA Family Database," *Nucleic Acids Research*, 31:439-441 (2003).
Guevara-Garcia et al., "Tissue-Specific and Wound-Inducible Pattern of Expression of the Mannopine Synthase Promoter is Determined by the Interaction between Positive and Negative cis-Regulatory Elements," *Plant Journal*, 4:495-505 (1993).
Guo et al., "Protein Tolerance to Random Amino Acid Change," *Proc. Natl. Acad. Sci. USA*, 101:9205-9210 (2004).
Hansen et al., "Wound-Inducible and Organ-Specific Expression of ORF13 from Agrobacterium rhiZogenes 8196 T-DNA in Transgenic Tobacco Plants," *Molecular and General Genetics*, 254:337-343 (1997).
Hartley, "Barnase and Barstar. Expression of Its Cloned Inhibitor Permits Expression of a Cloned Ribonuclease," *J. Mol. Biol.*, 202:913-915 (1988).
Hartley, "Barnase and Barstar: Two Small Proteins to Fold and Fit Together," *Trends in Biochemical Sciences*, 14:450-454 (1989).
Hildering et al., "The Use of Induced Mutations in Plant Breeding," supplement to *Radiation Botany*, 5:317-320 (1965).
Hoekema et al., "A Binary Plant Vector Strategy based on Separation of vir- and T-Region of the Agrobacterium tumefaciens Ti-Plasmid," *Nature*, 303:179-180(1983).
Horsch et al., "A Simple and General Method for Transferring Genes into Plants," *Science*, 227:1229-1231 (1985).
International Preliminary Report on Patentability in International Application No. PCT/US2015/054247, dated Apr. 11, 2017, 11 pages.
International Search Report and Written Opinion in International Application No. PCT/US2015/054247, dated Apr. 15, 2016, 20 pages.
Invitation to Pay Additional Fees in International Application PCT/US2015/054247, dated Feb. 10, 2016, 11 pages.
Jones-Rhoades et al., "Computational Identification of Plant MicroRNAs and Their Targets, Including a Stress-Induced miRNA," *Molecular Cell*, 14:787-799 (2004).
Kaeppler et al., "Silicon Carbide Fiber-Mediated DNA Delivery into Plant Cells," *Plant Cell Reports*, 9:415-418 (1990).
Kaeppler et al., "Silicon Carbide Fiber-Mediated Stable Transformation of Plant Cells," *Theoretical and Applied Genetics*, 84:560-566 (1992).
Katoh et al., "Specific Residues at Every Third Position of siRNA Shape its Efficient RNAi Activity," *Nucleic Acids Research*, 35:e27 (2007).

Kawamata et al., "Temporal and Spatial Pattern of Expression of the Pea Phenylalanine Ammonia-Lyase Gene1 Promoter in Transgenic Tobacco," *Plant and Cell Physiology*, 38:792-803 (1997).
Keller et al., "*Arabidopsis* Regulator of Axillary MERISTEMS1 Controls a Leaf Axil Stem Cell Niche and Modulates Vegetative Development," *Plant Cell*, 18:598-611 (2006).
Khvorova et al., "Functional siRNAs and miRNAs Exhibit Strand Bias," *Cell*, 115:209-216(2003).
Kim, "MicroRNA Biogenesis: Coordinated Cropping and Dicing," *Nature Reviews Molecular Cell Biology*, 6:376-385 (2005).
Lam, "Analysis of Tissue-Specific Elements in the CaMV 35S Promoter," *Results and Problems in Cell Differentiation*, 20:181-196 (1994).
Lannenpaa et al., "Prevention of Flower Development in Birch and Other Plants Using a BpFULL1::BARNASE Construct," *Plant Cell Rep*, 24:69-78 (2005).
Last et al., "pEMU: An Improved Promoter for Gene Expression in Cereal Cells," *Theoretical and Applied Genetics*, 81:581-588 (1991).
Lee et al., "A Systematic RNAi Screen Identifies a Critical Role for Mitochondria in *C. elegans* Longevity," *Nature Genetics*, 33:40-48 (2003).
Lemmetyinen et al., "Prevention of Flower Formation in Dicotyledons," *Molecular Breeding*, 7:341-350 (2001).
Liang et al., "Mediation of Flowering by a Ccalmodulin-Dependent Protein Kinase," *Science in China* (Series C), 44(5):506-512 (2001).
Liu et al., "Overexpression of Millet ZIP-Like Gene (Sipf40) Affects Lateral Bud Outgrowth in Tobacco and Millet," *Plant Physiology and Biochemistry*, 47(11-12):1051-1060 (2009).
Long et al., "A Member of the Knotted Class of Homeodomain Proteins Encoded by the STM Gene of *Arabidopsis*," *Nature*, 379:66-69 (1996).
Long et al., "Initiation of Axillary and Floral Meristems in *Arabidopsis*," *Developmental Biology*, 218:341-353 (2000).
Matsuoka et al., "Tissue-Specific Light-Regulated Expression Directed by the Promoter of a C4 Gene, Maize Pyruvate, Orthophosphate Dikinase, in a C3 Plant, Rice," *Proceedings of the National Academy of Sciences USA*, 90:9586-9590 (1993).
Mayo et al., "Genetic Transformation of Tobacco NT1 Cells with Agrobacterium tumefaciens," *Nature Protocols*, 1(3):1105-11 (2006).
McCabe et al., "Stable Transformation of Soybean (Glycine max) by Particle Acceleration," *Biotechnology*, 6:923-926 (1988).
McCallum et al., "Targeted Screening for Induced Mutations," *Nature Biotechnology*, 18:455-457 (2000).
McNellis et al., "Glucocorticoid-Inducible Expression of a Bacterial Avirulence Gene in Transgenic *Arabidopsis* Induces Hypersensitive Cell Death," *Plant Journal*, 14:247-257 (1998).
Miller et al., "A Grade Index for Type 22 and 23 Fire-Cured Tobacco," *Tobacco International*, 192:55-57 (1990).
Miller, "Memorandum on the Proposed Burley Tobacco Grade Index," Legacy Tobacco Document Library, Bates Nos. 523267826-523267833 (1988).
Muller et al., "Auxin, Cytokinin and the Control of Shoot Branching," *Annals of Botany*, 2011, 107(7):1203-1212.
Murchison et al., "miRNAs on the Move: miRNA Biogenesis and the RNAi Machinery," *Current Opinion in Cell Biology*, 16:223-229 (2004).
Neu et al., "Arabidopsis Amidase 1, a Member of the Amidase Signature Family," *FEBS Journal*, 274:3440-3451 (2007).
Odell et al., "Identification of DNA Sequences Required for Activity of the Cauliflower Mosaic Virus 35S Promoter," *Nature*, 313:810-812 (1985).
Orozco et al., "Localization of Light-Inducible and Tissue-Specific Regions of the Spinach Ribulose Bisphosphate Carboxylase/Oxygenase (Rubisco) Activase Promoter in Transgenic Tobacco Plants," *Plant Molecular Biology*, 23:1129-1138 (1993).
Ortiz-Morea et al., "Global Analysis of the Sugarcane Microtranscriptome Reveals a Unique Composition of Small RNAs Associated with Axillary Bud Outgrowth," *Journal of Experimental Botany*, 64:2307-2320 (2013).
Parizotto et al., "In vivo Investigation of the Transcription, Processing, Endonucleolytic Activity, and Functional Relevance of the Spatial Distribution of a Plant miRNA," *Genes & Development*, 18:2237-2242 (2004).

(56) References Cited

OTHER PUBLICATIONS

Paszkiwski et al., "Direct Gene Transfer to Plants," *EMBO Journal*, 3:2717-2722(1984).
Porta et al., "Use of Viral Replicons for the Expression of Genes in Plants," *Molecular Biotechnology*, 5:209-221 (1996).
Rajani et al., "The Arabidopsis myc/bHLH Gene Alcatraz Enables Cell Separation in Fruit Dehiscence," *Current Biology*, 11:1941-1922 (2001).
Reynolds et al., "Rational siRNA Design for RNA Interference," *Nature Biotechnology*, 22:326-330 (2004).
Rhoades et al., "Prediction of Plant MicroRNA Targets," *Cell*, 110:513-520 (2002).
Riggs et al., "Stable Transformation of Tobacco by Electroporation: Evidence for Plasmid Concatenation," *Proceedings of the National Academy of Sciences USA*, 83:5602-5606 (1986).
Rinehart et al., "Tissue-Specific and Developmental Regulation of Cotton Gene FbL2A," *Plant Physiology*, 112:1331-1341 (1996).
Russell et al., "Tissue-Specific Expression in Transgenic Maize of Four Endosperm Promoters From Maize and Rice," *Transgenic Research*, 6:157-168 (1997).
Schena et al., "A Steroid-Inducible Gene Expression System for Plant Cells," *Proceedings of the National Academy of Sciences USA*, 88:10421-10425 (1991).
Serrano et al., "The Folding of an Enzyme. II. Substructure of Barnase and the Contribution of Different Interactions to Protein Stability," *Journal of Molecular Biology*, 224:783-804 (1992).
Shillito et al., "Direct Gene Transfer to Protoplasts of Dicotyledonous and Monocotyledonous Plants by a Number of Methods, Including Electroporation," *Methods in Enzymology*, 153:313-336 (1987).
Singh et al., "Cytological Characterization of Transgenic Soybean," *Theoretical and Applied Genetics*, 96:319-324 (1998).
Stepanova et al., "TAA1-Mediated Auxin Biosynthesis is Essential for Hormone Crosstalk and Plant Development," *Cell*, 133:177-191 (2008).
Stirnberg et al., "MAX1 and MAX2 Control Shoot Lateral Branching in *Arabidopsis*," *Development*, 129:1131-1141 (2002).
Sun et al., "Inhibition of Tobacco Axillary Bud Differentiation by Silencing Cup-Shaped Cotyledon 3," *African Journal of Biotechnology*, 2012, 11(16):3919-3927.
Sunkar et al., "Novel and Stress-Regulated MicroRNAs and Other Small RNAs from *Arabidopsis*," *Plant Cell*, 16:2001-2019 (2004).
Suzuki Laboratory, "siExplorer," Retrieved from http://ma.chem.t.u-tokyo.ac.jp/cgi/siexplorer.htm, Lab of RNA Biochemistry, The University of Tokyo (printed Aug. 8, 2017).
Tadege et al., "Stenofolia Regulates Blade Outgrowth and Leaf Vascular Patterning in Medicago truncatula and Nicotiana sylvestris," *The Plant Cell*, 23(6):2125-2142, 33 pages (2011).
Tanaka, "Studies on Biological Effects of Ion Beams on Lethality, Molecular Nature of Mutation, Mutation Rate, and Spectrum of Mutation Phenotype for Mutation Breeding in Higher Plants," *Journal of Radiation Research*, 51:223-233 (2010).
Tanaka-Ueguchi et al., "Over-Expression of a Tobacco Homeobox Gene NTH15, Decreases the Expression of a Gibberellin Biosynthetic Gene Encoding GA 20-Oxidase," *Plant Journal*, 15:391-400 (1998).

The Bogdanove Laboratory, "TAL Effector Nucleotide Targeter 2.0," Retrieved from https://tale-nt.cac.cornell.edu/about, Cornell University (printed Aug. 4, 2017).
Tokuriki, et al., "The Stability Effects of Protein Mutations Appear to be Universally Distributed," *Journal of Molecular Biology*, 369(5): 1318-1332 (2007).
Tomes et al., "Direct DNA Transfer into Intact Plant Cells via Microprojectile Bombardment," *Plant Cell, Tissue, and Organ Culture*: Fundamental Methods, Gamborg et al., (eds.), Springer Verlag, Berlin Heidelberg, 1 pg. (1995).
Trobacher et al., "Induction of a Ricinosomal-Protease and Programmed Cell Death in Tomato Endosperm by Gibberellic Acid," *Planta*, 237:664-679 (2013).
Van Camp et al., "Tissue-Specific Activity of Two Manganese Superoxide Dismutase Promoters in Transgenic Tobacco," *Plant Physiology*, 112:525-535 (1996).
Velten et al., "Isolation of a Dual Plant Promotor Fragment from the Ti Plasmid of Agrobacterium tumefaciens," *EMBO Journal*, 3:2723-2730 (1984).
Verkerk, "Chimerism of the Tomato Plant after Seed Irradiation with Fast Neutrons," *Netherlands Journal of Agricultural Science*, 19:197-203 (1971).
Wang et al., "MicroRNA171c-Targeted SCL6-II, SCL6-III, and SCL6-IV Genes Regulate Shoot Branching in *Arabidopsis*," *Molecular Plant*, 3:794-806 (2010).
Watanabe et al., "Arabidopsis metacaspase 2d is a Positive Mediator of Cell Death Induced during Biotic and Abiotic Stresses," *Plant Journal*, 66:969-982 (2011).
Weising et al., "Foreign Genes in Plants: Transfer, Structure, Expression, and Applications," *Annual Review of Genetics*, 22:421-477 (1988).
Wernsman et al., "Tobacco," Chapter 17, *Principles of Cultivar Development*, Fehr (ed.), Macmillan Publishing Co., New York, London, pp. 669-698 (1987).
Yadav et al., "Wuschel Protein Movement Mediates Stem Cell Homeostasis in the *Arabidopsis* Shoot Apex," *Genes & Development*, 25:2025-2030 (2011).
Yamada et al., "The Transport Inhibitor Response2 Gene is Required for Auxin Synthesis and Diverse Aspects of Plant Development," *Plant Physiology*, 151:168-179 (2009).
Yamamoto et al., "Light-Responsive Elements of the Tobacco PSI-D Gene are Located both Upstream and Within the Transcribed Region," *Plant Journal*, 12:255-265 (1997).
Yamamoto et al., "The Promoter of a Pine Photosynthetic Gene Allows Expression of a jS-Glucuronidase Reporter Gene in Transgenic Rice Plants in a Light-Independent but Tissue-Specific Manner," *Plant & Cell Physiology*, 35:773-778 (1994).
Zeng et al., "Both Natural and Designed Micro RNAs can Inhibit the Expression of Cognate mRNAs when Expressed in Human Cells," *Molecular Cell*, 9:1327-1333 (2002).
Zhang et al., "Transcription Activator-Like Effector Nucleases Enable Efficient Plant Genome Engineering," *Plant Physiology*, 161:20-27 (2013).

* cited by examiner

Figure 3B

SEQUENCE LISTING

```
<160> NUMBER OF SEQ ID NOS: 196

<210> SEQ ID NO 1
<211> LENGTH: 987
<212> TYPE: DNA
<213> ORGANISM: Nicotiana tabacum
```

<400> SEQUENCE: 1

```
atgtatccgc caagcaacag ctgcaactac agccccattt caacatccc ttctccttgt    60
atgcaatatg gagacgaact attcttccaa tattatcctg accatttcct caacagcaa   120
caagtgcctt tgatagaaga tcagagtgtt gacatcttag ctgattgcac tgagaatgtt   180
actaacgaag aaactgtcat caatactgat actgtaaaag ttctttatga cacaggagct   240
gttacaaaca gtcagtgttg gggaggaaat gaagaagtag aagaaggccg cgaaaacaaa   300
agaaatgaca tgagaagcac cattagtatt attcatgtac ggaaaaacaa gaaatgttcc   360
aataaagatc gacatagcaa gattaacact gctcgtggcc tcagagaccg aaggatgaga   420
ctttcccttg atgcagctcg caagtttttc agtttacaag acatgttggg gttcgataag   480
gcaagtaaaa ctgtagaatg gttgcttatc aaatcggagt ctgaaatcga agagctagcc   540
aaaggcaata aggaggagg cattcctaaa caaagctgca gtactactaa tggaattggt   600
gcaattagta ctgcaatatc ctctatttct gagtgtgagg ttatatcagg aactgatgaa   660
tctttctcta ttacttataa aaagaagctg aaaactgcta aggagcctc gaaaagacg   720
gctaaaactg ctcgtagagc tgcatttgat cgtcttatta caagggaaac gaggaatcaa   780
gcaagggcta gggctagaga gagaacaaaa ataagaaaaa gcctcggtaa atccaaagag   840
aacagtgctg attactgtaa tttggtggat aattatggag attggagtca atttagtatc   900
ttcaactatc agaaaaatgc agttggaatt tcccatgatc aggtgggttc aataattaaa   960
caacatgatt ttttaggatt tcaatag                                       987
```

<210> SEQ ID NO 2
<211> LENGTH: 328
<212> TYPE: PRT
<213> ORGANISM: Nicotiana tabacum

<400> SEQUENCE: 2

```
Met Tyr Pro Pro Ser Asn Ser Cys Asn Tyr Ser Pro Ile Phe Asn Ile
1               5                   10                  15

Pro Ser Pro Cys Met Gln Tyr Gly Asp Glu Leu Phe Phe Gln Tyr Tyr
            20                  25                  30

Pro Asp His Phe Leu Gln Gln Gln Val Pro Leu Ile Glu Asp Gln
        35                  40                  45

Ser Val Asp Ile Leu Ala Asp Cys Thr Glu Asn Val Thr Asn Glu Glu
    50                  55                  60

Thr Val Ile Asn Thr Asp Thr Val Lys Val Leu Tyr Asp Thr Gly Ala
65                  70                  75                  80

Val Thr Asn Ser Gln Cys Trp Gly Gly Asn Glu Glu Val Glu Gly
                85                  90                  95

Arg Glu Asn Lys Arg Asn Asp Met Arg Ser Thr Ile Ser Ile Ile His
            100                 105                 110

Val Arg Lys Asn Lys Lys Cys Ser Asn Lys Asp Arg His Ser Lys Ile
        115                 120                 125

Asn Thr Ala Arg Gly Leu Arg Asp Arg Arg Met Arg Leu Ser Leu Asp
    130                 135                 140

Ala Ala Arg Lys Phe Phe Ser Leu Gln Asp Met Leu Gly Phe Asp Lys
145                 150                 155                 160

Ala Ser Lys Thr Val Glu Trp Leu Leu Ile Lys Ser Glu Ser Glu Ile
                165                 170                 175

Glu Glu Leu Ala Lys Gly Asn Lys Gly Gly Gly Ile Pro Lys Gln Ser
```

```
                180             185             190
Cys Ser Thr Thr Asn Gly Ile Gly Ala Ile Ser Thr Ala Ile Ser Ser
            195             200             205
Ile Ser Glu Cys Glu Val Ile Ser Gly Thr Asp Ser Phe Ser Ile
            210             215             220
Thr Tyr Lys Lys Lys Leu Lys Thr Ala Lys Gly Ala Ser Lys Lys Thr
225             230             235             240
Ala Lys Thr Ala Arg Arg Ala Ala Phe Asp Arg Leu Ile Thr Arg Glu
            245             250             255
Thr Arg Asn Gln Ala Arg Ala Arg Ala Arg Glu Arg Thr Lys Ile Lys
            260             265             270
Lys Ser Leu Gly Lys Ser Lys Glu Asn Ser Ala Asp Tyr Cys Asn Leu
            275             280             285
Val Asp Asn Tyr Gly Asp Trp Ser Gln Phe Ser Ile Phe Asn Tyr Gln
            290             295             300
Lys Asn Ala Val Gly Ile Ser His Asp Gln Val Gly Ser Ile Ile Lys
305             310             315             320
Gln His Asp Phe Leu Gly Phe Gln
            325

<210> SEQ ID NO 3
<211> LENGTH: 318
<212> TYPE: DNA
<213> ORGANISM: Nicotiana tabacum

<400> SEQUENCE: 3
atggctcgct ccttgtgttt catggcattt gcagtcttgg caatgatgct ctttgttgcc      60
tatgaggttc aagctagaga atgcaaaaca gaaagcaata cattccctgg attatgcatt     120
accaaaccac catgcagaaa agcttgtatc agtgagggat ttactgatgg tcattgtagc     180
aaaatcctca gaaggtgcct atgcactaag ccatgtgtgt tcgatgagaa gatgatcaaa     240
acaggagctg aaacttttgc tgaggaagca aaaacttttgg ctgcagcttt gcttgaagaa     300
gagataatgg ataactaa                                                   318

<210> SEQ ID NO 4
<211> LENGTH: 105
<212> TYPE: PRT
<213> ORGANISM: Nicotiana tabacum

<400> SEQUENCE: 4

Met Ala Arg Ser Leu Cys Phe Met Ala Phe Ala Val Leu Ala Met Met
1               5                   10                  15
Leu Phe Val Ala Tyr Glu Val Gln Ala Arg Glu Cys Lys Thr Glu Ser
            20                  25                  30
Asn Thr Phe Pro Gly Leu Cys Ile Thr Lys Pro Cys Arg Lys Ala
            35                  40                  45
Cys Ile Ser Glu Gly Phe Thr Asp Gly His Cys Ser Lys Ile Leu Arg
    50                  55                  60
Arg Cys Leu Cys Thr Lys Pro Cys Val Phe Asp Glu Lys Met Ile Lys
65                  70                  75                  80
Thr Gly Ala Glu Thr Phe Ala Glu Glu Ala Lys Thr Leu Ala Ala Ala
            85                  90                  95
Leu Leu Glu Glu Glu Ile Met Asp Asn
            100             105
```

<210> SEQ ID NO 5
<211> LENGTH: 1797
<212> TYPE: DNA
<213> ORGANISM: Nicotiana tabacum

<400> SEQUENCE: 5

```
atggcttctc ttcccttct caccaccaat gccatctctt catcagcttc ttctttaacc     60
accacacctc tttccaattt gcattcttct cctttcttta caaagacatc aaaagtttcc    120
actatagata agtgcagtaa ctatcgtttc caagtttcat gcaagggtac agaagatgac    180
caaaccatca acacttccaa atcttctgat tcttcaaaca ataagatcat tgatagaaga    240
aacatgctac ttggattagg aggcatttat ggtgctgcta ctcttgttgg tggtcatccc    300
tttgccttcg cggctcctgt gcccggacct gacgtttcca atgtggtcc tgcagatttg     360
ccaccaggtg cagcaccagt caactgttgt cctccgacaa cggcgaacat catcgacttc    420
caacttccac caccgtcaac caccctccgt acacggccag cagctcattc cgccgatagt    480
gcctatatag agaaattcaa cagagctatt cagctcatga acaacttcc agataacgat     540
ccacgtagct tcaagcaaca agcaaatgtt cattgtgctt actgtgatgg agcttatgga    600
caactaggtt tcccaagttc tgaactccaa gttcattcct cttggctttt cttcccttc     660
catcgttgtt atctctactt cttcgaaaaa atcttgggaa gtttaataaa tgaccctact    720
ttcgctatcc cattttggaa ctgggatcat cctgatggca tgagacttcc ggccatgtat    780
gcgaaccgta gttcttctct cttcgatcct ctccgtgatc agaagcatca gcctccggtc    840
attgttgatc tcgacttcaa tggagcggat cctaacataa gtaacgctca acaaacttcc    900
cagaatctga caatcatgta taggcaaatg gtctctctag aagtactccc ggcagctttc    960
ctcggagacc cttaccgtgc cggtggcgaa ccgggtggtg ctgggtccct cgagaacatt   1020
ccacatggaa cggtccatgt ttggaccggt gatagaaccc aacctaattt tgaaaatatg   1080
ggagtttttt atgcagctgg tagagaccct attttctatg ctcatcattc taatattgat   1140
agattgtgga gtgtttggaa aaccctaggt ggaagacgtc aagattttac tgaccctgat   1200
ttttaaatt cttcgttttt gttttacgat gagaaagcac aaatggtacg tattagggta   1260
cgtgactgtt tggatacaac aagacttgga tacgtttatc aaggtgtagt taatccgtgg   1320
ataaattctc gtccaagggc tagggtttca agtgctttga gtagcgtaag gaggcttgct   1380
gaagcaaaag attatttccc aacaaaactt ggccatgtga taagagtaat ggtgaaaagg   1440
ccaaataata aaagagaaa caaggaggag aaagatgcaa agaggagtt tttagtggtt    1500
gaagggatag agctggaaac tgatgttttt gtcaagtttg atgtgttgat taatgatgaa   1560
gatgagactg taatttcgcc gaataatgct gagtttgcag gtagttttgt gaacgtgcca   1620
catcttagtc atggtaagag tgacgagaaa cgtaagacta gttgaagtt ggctataact     1680
gagctgctgg aagatttaga tgctgaggat gatgatcatg tggtggtgac ttttgttcca   1740
aagaatggtt ctggtgctgt gaaaattgga ggtgtcaaga ttgtgcttga ggattga      1797
```

<210> SEQ ID NO 6
<211> LENGTH: 598
<212> TYPE: PRT
<213> ORGANISM: Nicotiana tabacum

<400> SEQUENCE: 6

```
Met Ala Ser Leu Pro Leu Leu Thr Thr Asn Ala Ile Ser Ser Ser Ala
1               5                   10                  15

Ser Ser Leu Thr Thr Thr Pro Leu Ser Asn Leu His Ser Ser Pro Phe
```

-continued

```
            20                  25                  30
Phe Thr Lys Thr Ser Lys Val Ser Thr Ile Asp Lys Cys Ser Asn Tyr
        35                  40                  45
Arg Phe Gln Val Ser Cys Lys Gly Thr Glu Asp Gln Thr Ile Asn
    50                  55                  60
Thr Ser Lys Ser Ser Asp Ser Ser Asn Asn Lys Ile Ile Asp Arg Arg
 65                  70                  75                  80
Asn Met Leu Leu Gly Leu Gly Gly Ile Tyr Gly Ala Ala Thr Leu Val
                85                  90                  95
Gly Gly His Pro Phe Ala Phe Ala Ala Pro Val Pro Gly Pro Asp Val
               100                 105                 110
Ser Lys Cys Gly Pro Ala Asp Leu Pro Pro Gly Ala Ala Pro Val Asn
               115                 120                 125
Cys Cys Pro Pro Thr Thr Ala Asn Ile Ile Asp Phe Gln Leu Pro Pro
               130                 135                 140
Pro Ser Thr Thr Leu Arg Thr Arg Pro Ala Ala His Ser Ala Asp Ser
145                 150                 155                 160
Ala Tyr Ile Glu Lys Phe Asn Arg Ala Ile Gln Leu Met Lys Gln Leu
                165                 170                 175
Pro Asp Asn Asp Pro Arg Ser Phe Lys Gln Gln Ala Asn Val His Cys
               180                 185                 190
Ala Tyr Cys Asp Gly Ala Tyr Gly Gln Leu Gly Phe Pro Ser Ser Glu
               195                 200                 205
Leu Gln Val His Ser Ser Trp Leu Phe Phe Pro Phe His Arg Cys Tyr
               210                 215                 220
Leu Tyr Phe Phe Glu Lys Ile Leu Gly Ser Leu Ile Asn Asp Pro Thr
225                 230                 235                 240
Phe Ala Ile Pro Phe Trp Asn Trp Asp His Pro Asp Gly Met Arg Leu
                245                 250                 255
Pro Ala Met Tyr Ala Asn Arg Ser Ser Ser Leu Phe Asp Pro Leu Arg
               260                 265                 270
Asp Gln Lys His Gln Pro Pro Val Ile Val Asp Leu Asp Phe Asn Gly
               275                 280                 285
Ala Asp Pro Asn Ile Ser Asn Ala Gln Gln Thr Ser Gln Asn Leu Thr
               290                 295                 300
Ile Met Tyr Arg Gln Met Val Ser Leu Gly Ser Thr Pro Ala Ala Phe
305                 310                 315                 320
Leu Gly Asp Pro Tyr Arg Ala Gly Gly Glu Pro Gly Gly Ala Gly Ser
               325                 330                 335
Leu Glu Asn Ile Pro His Gly Thr Val His Val Trp Thr Gly Asp Arg
               340                 345                 350
Thr Gln Pro Asn Phe Glu Asn Met Gly Val Phe Tyr Ala Ala Gly Arg
               355                 360                 365
Asp Pro Ile Phe Tyr Ala His His Ser Asn Ile Asp Arg Leu Trp Ser
               370                 375                 380
Val Trp Lys Thr Leu Gly Gly Arg Arg Gln Asp Phe Thr Asp Pro Asp
385                 390                 395                 400
Phe Leu Asn Ser Ser Phe Leu Phe Tyr Asp Glu Lys Ala Gln Met Val
               405                 410                 415
Arg Ile Arg Val Arg Asp Cys Leu Asp Thr Thr Arg Leu Gly Tyr Val
               420                 425                 430
Tyr Gln Gly Val Val Asn Pro Trp Ile Asn Ser Arg Pro Arg Ala Arg
               435                 440                 445
```

Val Ser Ser Ala Leu Ser Ser Val Arg Arg Leu Ala Glu Ala Lys Asp
        450                 455                 460

Tyr Phe Pro Thr Lys Leu Gly His Val Ile Arg Val Met Val Lys Arg
465                 470                 475                 480

Pro Asn Asn Lys Lys Arg Asn Lys Glu Glu Lys Asp Ala Lys Glu Glu
                485                 490                 495

Phe Leu Val Val Glu Gly Ile Glu Leu Glu Thr Asp Val Phe Val Lys
            500                 505                 510

Phe Asp Val Leu Ile Asn Asp Glu Asp Glu Thr Val Ile Ser Pro Asn
        515                 520                 525

Asn Ala Glu Phe Ala Gly Ser Phe Val Asn Val Pro His Leu Ser His
    530                 535                 540

Gly Lys Ser Asp Glu Lys Arg Lys Thr Lys Leu Lys Leu Ala Ile Thr
545                 550                 555                 560

Glu Leu Leu Glu Asp Leu Asp Ala Glu Asp Asp His Val Val Val
                565                 570                 575

Thr Phe Val Pro Lys Asn Gly Ser Gly Ala Val Lys Ile Gly Gly Val
            580                 585                 590

Lys Ile Val Leu Glu Asp
        595

<210> SEQ ID NO 7
<211> LENGTH: 1392
<212> TYPE: DNA
<213> ORGANISM: Nicotiana tabacum

<400> SEQUENCE: 7
atggtaggca aagaaatga gcctcatgtc atatttgtac cttacccaag ccaaggtcac    60
attaaccctc ttctccaatt tgcaaaacgc ttatactcca aaggtgtaaa agcaacttta   120
gccactacta aatacacagt caagtctatt aattcaccca catttcagt tgaagcaatt    180 tctgatggat ttgacgaaag tggttttttcc caagcccaaa aagcagatat atatctcaaa   240
tcattcaaag aaaatggttc aacaactcta tcagaaataa taaaaaatta cgagaattcg   300
acacatccga taagttgcat tgtttatgat tcgttttta catgggctct tgatgtggct    360
aaaaaacatg ggatttatgg agctgcgttt tttacaaatt cagccactgt ttgtgtagtt    420
tttgctcaca ttcattataa acatttttca ttgccggcga agattgaaga aaatgagcca    480
ttgttattgc ctggattgcc tagtttgtac ccaattgatg ttcctggatt tattagggag    540
cctgaaagtt accctgctta cttagccatg aaaatgagtc aattctctaa tttgaaaaat    600
gctgattggg tttttgataa ctcctttcaa gaactagaag gagagatagc aagtggagtt    660
tcaaatattt ggccagcaag gttaattgga ccaatggtgc catcatccta tttagatgac    720
ataatagaag gtgacaaagg gtacggagca agtctatgga aaccacttag tgaagaatgt    780
ctcaaatggc taaaaacaaa gccaaatcaa tcagtaatct acatttcttt tggcagcatg    840
gtatcactca caccacaaca aatggaagaa atggcaaatg ctttaataga cagcaacatg    900
aatttccttt gggttgtaag agaaaccgaa aaaggcaaat tgccaaaaaa attcatagaa    960
tccacaattg gaaagggtt aattgtgtca tggtgcaatc aattagaaat gctagcaaat   1020
caagccattg gttgttttgt gactcattgt ggatggaatt cgactcttga aggattgagc   1080
cttggcgtgc caatggtggc aatgccacaa tggtctgatc aaatgacgga tgctaaattt   1140
ataggtgaga tttgggaaat tggtgtgagg cctaagttgg ataagtttgg gattgttaga   1200

-continued

```
agagaagagc tattgttttg tttaaaggaa gtaatgggag ggaagaggag ttatgagatt   1260
aggagaaatg ctggaaaatg gaagaacttg gctaagaaag caattagtga aggaggtagc   1320
tcggacaagt ctattaatgt atttgtgaac agtcttagtc tagcatgcca gatgaagaag   1380
tacaagaaat aa                                                      1392
```

<210> SEQ ID NO 8
<211> LENGTH: 463
<212> TYPE: PRT
<213> ORGANISM: Nicotiana tabacum

<400> SEQUENCE: 8

```
Met Val Gly Lys Arg Asn Glu Pro His Val Ile Phe Val Pro Tyr Pro
1               5                   10                  15

Ser Gln Gly His Ile Asn Pro Leu Leu Gln Phe Ala Lys Arg Leu Tyr
            20                  25                  30

Ser Lys Gly Val Lys Ala Thr Leu Ala Thr Thr Lys Tyr Thr Val Lys
        35                  40                  45

Ser Ile Asn Ser Pro Asn Ile Ser Val Glu Ala Ile Ser Asp Gly Phe
    50                  55                  60

Asp Glu Ser Gly Phe Ser Gln Ala Gln Lys Ala Asp Ile Tyr Leu Lys
65                  70                  75                  80

Ser Phe Lys Glu Asn Gly Ser Thr Thr Leu Ser Glu Ile Ile Lys Asn
                85                  90                  95

Tyr Glu Asn Ser Thr His Pro Ile Ser Cys Ile Val Tyr Asp Ser Phe
            100                 105                 110

Leu Pro Trp Ala Leu Asp Val Ala Lys Lys His Gly Ile Tyr Gly Ala
        115                 120                 125

Ala Phe Phe Thr Asn Ser Ala Thr Val Cys Val Val Phe Ala His Ile
    130                 135                 140

His Tyr Lys Thr Phe Ser Leu Pro Ala Lys Ile Glu Glu Asn Glu Pro
145                 150                 155                 160

Leu Leu Leu Pro Gly Leu Pro Ser Leu Tyr Pro Ile Asp Val Pro Gly
                165                 170                 175

Phe Ile Arg Glu Pro Glu Ser Tyr Pro Ala Tyr Leu Ala Met Lys Met
            180                 185                 190

Ser Gln Phe Ser Asn Leu Glu Asn Ala Asp Trp Val Phe Asp Asn Ser
        195                 200                 205

Phe Gln Glu Leu Glu Gly Glu Ile Ala Ser Gly Val Ser Asn Ile Trp
    210                 215                 220

Pro Ala Arg Leu Ile Gly Pro Met Val Pro Ser Ser Tyr Leu Asp Asp
225                 230                 235                 240

Ile Ile Glu Gly Asp Lys Gly Tyr Gly Ala Ser Leu Trp Lys Pro Leu
                245                 250                 255

Ser Glu Glu Cys Leu Lys Trp Leu Lys Thr Lys Pro Asn Gln Ser Val
            260                 265                 270

Ile Tyr Ile Ser Phe Gly Ser Met Val Ser Leu Thr Pro Gln Gln Met
        275                 280                 285

Glu Glu Met Ala Asn Ala Leu Ile Asp Ser Asn Met Asn Phe Leu Trp
    290                 295                 300

Val Val Arg Glu Thr Glu Lys Gly Lys Leu Pro Lys Lys Phe Ile Glu
305                 310                 315                 320

Ser Thr Ile Gly Lys Gly Leu Ile Val Ser Trp Cys Asn Gln Leu Glu
                325                 330                 335
```

```
Met Leu Ala Asn Gln Ala Ile Gly Cys Phe Val Thr His Cys Gly Trp
            340                 345                 350

Asn Ser Thr Leu Glu Gly Leu Ser Leu Gly Val Pro Met Val Ala Met
        355                 360                 365

Pro Gln Trp Ser Asp Gln Met Thr Asp Ala Lys Phe Ile Gly Glu Ile
    370                 375                 380

Trp Glu Ile Gly Val Arg Pro Lys Leu Asp Lys Phe Gly Ile Val Arg
385                 390                 395                 400

Arg Glu Glu Leu Leu Phe Cys Leu Lys Glu Val Met Gly Gly Lys Arg
                405                 410                 415

Ser Tyr Glu Ile Arg Arg Asn Ala Gly Lys Trp Lys Asn Leu Ala Lys
            420                 425                 430

Lys Ala Ile Ser Glu Gly Gly Ser Ser Asp Lys Ser Ile Asn Val Phe
        435                 440                 445

Val Asn Ser Leu Ser Leu Ala Cys Gln Met Lys Lys Tyr Lys Lys
    450                 455                 460
```

<210> SEQ ID NO 9
<211> LENGTH: 405
<212> TYPE: DNA
<213> ORGANISM: Nicotiana tabacum

<400> SEQUENCE: 9

```
atggcaggga aggttgagaa agtgcttgca gtagtgatgc ttgcaatgct tctgttttcg    60
gagcatttaa tggctgctaa tcatgaaatt aaaacaactg aagataactc tactattagc   120
cctttctgct agtaaaatg tttatttgga gtgaggggt tgccacctgt acaagcatcc    180
atttgtgctg ctcaatgtta tttaaagtgc cgtgaccaag atgcggccaa tattgctgaa   240
actaagggca taattggtga gactgcatac aaccagtatg atgttggatg tgcccttggc   300
tactgctctg agttcctgtt gaattatgat gagaagaggt tcaagtgctg catggaatac   360
tgccgcgagg acaaaatgat ttgtcctgtt gaggctgcag cttga                   405
```

<210> SEQ ID NO 10
<211> LENGTH: 134
<212> TYPE: PRT
<213> ORGANISM: Nicotiana tabacum

<400> SEQUENCE: 10

```
Met Ala Gly Lys Val Glu Lys Val Leu Ala Val Val Met Leu Ala Met
1               5                   10                  15

Leu Leu Phe Ser Glu His Leu Met Ala Ala Asn His Glu Ile Lys Thr
            20                  25                  30

Thr Glu Asp Asn Ser Thr Ile Ser Pro Phe Cys Leu Val Lys Cys Leu
        35                  40                  45

Phe Gly Cys Arg Gly Leu Pro Pro Val Gln Ala Ser Ile Cys Ala Ala
    50                  55                  60

Gln Cys Tyr Leu Lys Cys Arg Asp Gln Asp Ala Ala Asn Ile Ala Glu
65                  70                  75                  80

Thr Lys Gly Ile Ile Gly Glu Thr Ala Tyr Asn Gln Tyr Asp Val Gly
                85                  90                  95

Cys Ala Leu Gly Tyr Cys Ser Glu Phe Leu Leu Asn Tyr Asp Glu Lys
            100                 105                 110

Arg Phe Lys Cys Cys Met Glu Tyr Cys Arg Glu Asp Lys Met Ile Cys
        115                 120                 125

Pro Val Glu Ala Ala Ala
```

<210> SEQ ID NO 11
<211> LENGTH: 630
<212> TYPE: DNA
<213> ORGANISM: Nicotiana tabacum

<400> SEQUENCE: 11

| | | |
|---|---|---|
| atgaattcaa agaaaaacaa ctcaccaaga aaaaggttga gaaaatatca tacaagaaaa | 60 |
| gctcctatta ttagctctta tatggacatg gctgaagcta gaagagaaat tgttcatgct | 120 |
| ttacaacttc atcgatcttc atcttcatct ccaactccgt ctattaatag cccaaagaag | 180 |
| tacacattat tgggtcaagg agttgtaagc tctcaacaat attactatta ctcaatagtg | 240 |
| gaatctatgc ctattcctga accaacatgg tctacaacgg ctccggcaat acttaatgca | 300 |
| ctgccaccgc tgccgctgcc gctgccgcca cctccgccgc tgtcttcttc ttccggtgaa | 360 |
| gttccagagt ttgaatggtg gatagggttt ttgaagtcgt tggacggcaa gaagagtgct | 420 |
| aacaatggtg aagtagtcat agaaaaatat tttcctctag aagaaaatgt tttgatggaa | 480 |
| aattcaaaga caggttttgg tcaattagaa catggattaa acagtgagtc tcctaattgt | 540 |
| atagataaga atgatgatcc taattaccaa tttccagatg agtggttgat tatccctaca | 600 |
| gctgatgatg attatgtact tgagctttaa | 630 |

<210> SEQ ID NO 12
<211> LENGTH: 209
<212> TYPE: PRT
<213> ORGANISM: Nicotiana tabacum

<400> SEQUENCE: 12

Met Asn Ser Lys Lys Asn Asn Ser Pro Arg Lys Arg Leu Arg Lys Tyr
1               5                   10                  15

His Thr Arg Lys Ala Pro Ile Ile Ser Ser Tyr Met Asp Met Ala Glu
            20                  25                  30

Ala Arg Arg Glu Ile Val His Ala Leu Gln Leu His Arg Ser Ser Ser
        35                  40                  45

Ser Ser Pro Thr Pro Ser Ile Asn Ser Pro Lys Lys Tyr Thr Leu Leu
    50                  55                  60

Gly Gln Gly Val Val Ser Ser Gln Gln Tyr Tyr Tyr Ser Ile Val
65                  70                  75                  80

Glu Ser Met Pro Ile Pro Glu Pro Thr Trp Ser Thr Thr Ala Pro Ala
                85                  90                  95

Ile Leu Asn Ala Leu Pro Pro Leu Pro Leu Pro Leu Pro Pro Pro
            100                 105                 110

Pro Leu Ser Ser Ser Ser Gly Glu Val Pro Glu Phe Glu Trp Trp Ile
        115                 120                 125

Gly Phe Leu Lys Ser Leu Asp Gly Lys Lys Ser Ala Asn Asn Gly Glu
    130                 135                 140

Val Val Ile Glu Lys Tyr Phe Pro Leu Glu Glu Asn Val Leu Met Glu
145                 150                 155                 160

Asn Ser Lys Thr Gly Phe Gly Gln Leu Glu His Gly Leu Asn Ser Glu
                165                 170                 175

Ser Pro Asn Cys Ile Asp Lys Asn Asp Asp Pro Asn Tyr Gln Phe Pro
            180                 185                 190

Asp Glu Trp Leu Ile Ile Pro Thr Ala Asp Asp Tyr Val Leu Glu
        195                 200                 205

Leu

<210> SEQ ID NO 13
<211> LENGTH: 1143
<212> TYPE: DNA
<213> ORGANISM: Nicotiana tabacum

<400> SEQUENCE: 13

```
atgtatccgt caagcaacag ctgtaattac agcctcaata tttcctcctc aaataactta      60
tttcacattc catctccgaa ttctatgcaa tatgaacacg aacttttcca atattttcat     120
gaccatcatc tccttcaacc ccaacaacaa caacaacaac aacaactctt gactacacct     180
gatcattata tggcagcaga ttccaacaaa gacaccgtaa tcagtagtac taatcaagat     240
cctgaagaag ttgaattaca aggccgctgc aagaacaaaa aaggtgacaa taagagacgt     300
gttgcttaca agaaagatag acacagcaag attaacactg ctcacggccc tagagaccga     360
agaatgagac tttctctcga tgtagctcgc aaattttttca atttgcaaga cttgcttgga     420
ttcgataagg ctagcaaaac tgtggagtgg ttgctaacaa agtccaaatg tgctgtcaat     480
gagctcgtcc aaggcataaa taagaaaat tgcgctactg ctaatattgg tgcaattagt     540
acatgctcta ctacatctga gtgtgaagtt gtatcaggaa ttgatgaatc tacaaccact     600
aatgatattc agaagcagtc aaatagaggt aaagtagggg agaagaagaa ggctaataaa     660
ctagttcgta gagctgcatt taatcctgtg gcaaaggaat caagaaagca agctagagcg     720
agggcaaggg agagaacaaa aataaagaaa agctttttaa atattggtga tcagtctatg     780
gcggctgatg atttaaaacg attaggatgt tggagtcttt ttgaaacagg tgaagaatca     840
ggtattcaag gtactaatca tcaaattgaa gaacacacca cgcaccacga ggagcctctt     900
ttggggacta atgagaatgt tgatgattgt aatttggttg ttaccggcaa ctggaaccca     960
tataccatct tcaattatca ccacagtact gaaatttctc acgaggtagg ttttacactt    1020
catttaaatc aagagtaat tcttttagag ttcaagattc tgatattttt tttggtggcg    1080
agacccttc ttatatcaaa gcaaccttca aggtacatac aagattggat aaaccaattc    1140
tga                                                                 1143
```

<210> SEQ ID NO 14
<211> LENGTH: 380
<212> TYPE: PRT
<213> ORGANISM: Nicotiana tabacum

<400> SEQUENCE: 14

```
Met Tyr Pro Ser Ser Asn Ser Cys Asn Tyr Ser Leu Asn Ile Ser Ser
1               5                   10                  15

Ser Asn Asn Leu Phe His Ile Pro Ser Pro Asn Ser Met Gln Tyr Glu
            20                  25                  30

His Glu Leu Phe Gln Tyr Phe His Asp His His Leu Leu Gln Pro Gln
        35                  40                  45

Gln Gln Gln Gln Gln Gln Leu Leu Thr Thr Pro Asp His Tyr Met
    50                  55                  60

Ala Ala Asp Ser Asn Lys Asp Thr Val Ile Ser Ser Thr Asn Gln Asp
65                  70                  75                  80

Pro Glu Glu Val Glu Leu Gln Gly Arg Cys Lys Asn Lys Lys Gly Asp
                85                  90                  95

Asn Lys Arg Arg Val Ala Tyr Lys Lys Asp Arg His Ser Lys Ile Asn
            100                 105                 110
```

```
Thr Ala His Gly Pro Arg Asp Arg Arg Met Arg Leu Ser Leu Asp Val
            115                 120                 125
Ala Arg Lys Phe Phe Asn Leu Gln Asp Leu Leu Gly Phe Asp Lys Ala
        130                 135                 140
Ser Lys Thr Val Glu Trp Leu Leu Thr Lys Ser Lys Cys Ala Val Asn
145                 150                 155                 160
Glu Leu Val Gln Gly Ile Asn Lys Glu Asn Cys Ala Thr Ala Asn Ile
                165                 170                 175
Gly Ala Ile Ser Thr Cys Ser Thr Ser Glu Cys Glu Val Val Ser
            180                 185                 190
Gly Ile Asp Glu Ser Thr Thr Thr Asn Asp Ile Gln Lys Gln Ser Asn
            195                 200                 205
Arg Gly Lys Val Gly Glu Lys Lys Ala Asn Lys Leu Val Arg Arg
        210                 215                 220
Ala Ala Phe Asn Pro Val Ala Lys Glu Ser Arg Lys Gln Ala Arg Ala
225                 230                 235                 240
Arg Ala Arg Glu Arg Thr Lys Ile Lys Lys Ser Phe Leu Asn Ile Gly
                245                 250                 255
Asp Gln Ser Met Ala Ala Asp Asp Leu Lys Arg Leu Gly Cys Trp Ser
            260                 265                 270
Leu Phe Glu Thr Gly Glu Glu Ser Gly Ile Gln Gly Thr Asn His Gln
        275                 280                 285
Ile Glu Glu His Thr Thr His His Glu Glu Pro Leu Leu Gly Thr Asn
        290                 295                 300
Glu Asn Val Asp Asp Cys Asn Leu Val Val Thr Gly Asn Trp Asn Pro
305                 310                 315                 320
Tyr Thr Ile Phe Asn Tyr His His Ser Thr Glu Ile Ser His Glu Val
                325                 330                 335
Gly Phe Thr Leu His Leu Asn Pro Arg Val Ile Leu Leu Glu Phe Lys
            340                 345                 350
Ile Leu Ile Phe Phe Leu Val Ala Arg Pro Phe Leu Ile Ser Lys Gln
            355                 360                 365
Pro Ser Arg Tyr Ile Gln Asp Trp Ile Asn Gln Phe
        370                 375                 380

<210> SEQ ID NO 15
<211> LENGTH: 915
<212> TYPE: DNA
<213> ORGANISM: Nicotiana tabacum

<400> SEQUENCE: 15
atggaaaagg ttcatgagaa accgctatct ctttataatg gatcattatc tgttttaga      60
ttaggagatt tggctgtgaa ataacaaag gtgaaaaagg gatcattaaa taatgataat     120
ctttcacccc caacttcatt gttagttgtt tcaccaatca taccaggaac ttatccagtt     180
ttactctttt ttcatggctt cgttctcaag cctatatggt acaagtctct ccttcaacat     240
atttcttccc acggctatat agttgttgct ccacaggttt ctcaaagcga agaagtgaaa     300
aaagcagcca aagttacaga atggttaagt aaagccctcg aatccgtact gccggagaaa     360
gtacagccgg atctactcca gctcgccgtc tccggccaca gcagaggtgg taaaatagca     420
tttgcactag ctttaggata tggcatcaaa tttcaagcac ttctaggaat tgatccagtt     480
gcaggttttt ctccgtccaa ccgatctgct ccaaaaattc ttaaatatat tcctcgtatt     540
ttcgatcaga cggtccctgt ggcggtgatc ggcgctggct tgtcaaacca aagtgcgaat     600
```

```
tgtatctttc caccctccgc accaaacggt gtcaaccatt cggagttttt taacgagtcc    660
aaaccacctt gctgttattt tctggctaaa aattatggac atactgatat gttagatgac    720
agaattgctg caattgcgag ttggatttca aagagtggga agggacccaa ggaccttatg    780
agaaaggctg ttggagggat tgttgtggct tttcttgagg ctaaattggg agagaaagtg    840
gataatctaa atgccattgt tcaagaacct tctcttgctc ccatcatcct tgacccagtc    900
atatctgtca aataa                                                    915
```

<210> SEQ ID NO 16
<211> LENGTH: 304
<212> TYPE: PRT
<213> ORGANISM: Nicotiana tabacum

<400> SEQUENCE: 16

```
Met Glu Lys Val His Glu Lys Pro Leu Ser Leu Tyr Asn Gly Ser Leu
1               5                   10                  15

Ser Val Phe Arg Leu Gly Asp Leu Ala Val Lys Ile Thr Lys Val Lys
            20                  25                  30

Lys Gly Ser Leu Asn Asn Asp Asn Leu Ser Pro Pro Thr Ser Leu Leu
        35                  40                  45

Val Val Ser Pro Ile Ile Pro Gly Thr Tyr Pro Val Leu Leu Phe Phe
    50                  55                  60

His Gly Phe Val Leu Lys Pro Ile Trp Tyr Lys Ser Leu Leu Gln His
65                  70                  75                  80

Ile Ser Ser His Gly Tyr Ile Val Val Ala Pro Gln Val Ser Gln Ser
                85                  90                  95

Glu Glu Val Lys Lys Ala Ala Lys Val Thr Glu Trp Leu Ser Lys Ala
            100                 105                 110

Leu Glu Ser Val Leu Pro Glu Lys Val Gln Pro Asp Leu Leu Gln Leu
        115                 120                 125

Ala Val Ser Gly His Ser Arg Gly Gly Lys Ile Ala Phe Ala Leu Ala
    130                 135                 140

Leu Gly Tyr Gly Ile Lys Phe Gln Ala Leu Leu Gly Ile Asp Pro Val
145                 150                 155                 160

Ala Gly Phe Ser Pro Ser Asn Arg Ser Ala Pro Lys Ile Leu Lys Tyr
                165                 170                 175

Ile Pro Arg Ile Phe Asp Gln Thr Val Pro Val Ala Val Ile Gly Ala
            180                 185                 190

Gly Leu Ser Asn Gln Ser Ala Asn Cys Ile Phe Pro Pro Phe Ala Pro
        195                 200                 205

Asn Gly Val Asn His Ser Glu Phe Phe Asn Glu Ser Lys Pro Pro Cys
    210                 215                 220

Cys Tyr Phe Leu Ala Lys Asn Tyr Gly His Thr Asp Met Leu Asp Asp
225                 230                 235                 240

Arg Ile Ala Ala Ile Ala Ser Trp Ile Ser Lys Ser Gly Lys Gly Pro
                245                 250                 255

Lys Asp Leu Met Arg Lys Ala Val Gly Gly Ile Val Val Ala Phe Leu
            260                 265                 270

Glu Ala Lys Leu Gly Lys Val Asp Asn Leu Asn Ala Ile Val Gln
        275                 280                 285

Glu Pro Ser Leu Ala Pro Ile Ile Leu Asp Pro Val Ile Ser Val Lys
    290                 295                 300
```

<210> SEQ ID NO 17

```
<211> LENGTH: 1353
<212> TYPE: DNA
<213> ORGANISM: Nicotiana tabacum

<400> SEQUENCE: 17
atgtgtttgt taataaaggt ggcgaatcca ggagaatccg gcgagcatga cagaattcca      60
tcaacgggag gtgattcaga aagtacaact actaccacag aaggaggaat ccgcagcta     120 tatgaacaat acaatcaca atcacaatca tttgaagaaa tgttgcggca acaaatacaa     180
caagaaacag agtatttgat gtcttcatct gcaactccta tgttttcacg gtatagtcag     240
acaagggaga gtgtcggcaat ggtaacggcg ttaacgcatg tggtatcagg acggagagag     300
ggagagtgga cttacaggcc ggatattagt gccggcgctg ttacgacgtc gtttgctggt     360
ggttcgagta tttattcggc gagttcgccg tcgtcttcaa gttcagggtc atgggctgga     420
cagaagagaa gacgtgatca agaagaaagt gttgctgcag agcaagttca aagggtttat     480
ggagcttttg gtgaatttag aggtggagaa tcatcttcct ctgttaaaac tgaagaagct     540
tcaagcatgg tagcaccacc aaccaccacc agcactacca ccacaaccac cacggcggcg     600
caaacaccac cagaaccagc ggaaggagga ggagctgaag aaacagggga aggaggagg      660 agatacagag gagtaagaca aaggccatgg ggaaaatggg cagcagaaat aagagatcca     720
cacaaagcag ctagagtttg gttaggcaca tttgatacag ctgaagctgc tgctagagct     780
tatgatgaag ctgcccttag attcagagga acagagctaa aactcaattt ccccgaaaat     840
gtccgcatat taccacaaca acaacagcaa caacctcaag ccacaacaag atcagccatt     900
tccagctcct ccgcagcttc acaattccca ttaatggctg cagcaacaac tccatcacca     960 ttttttccaaa cttatcaacc tcagcagcag cagctgcctt ttcagagttc agaaatggtt    1020
agagattatt gggaatactc acagttactt caaaatccag agagtttca tttacaacaa    1080 cagccttcag ccttgttaga gcaaatgttg tttgcttctt catcaatggg tcttttgcaa    1140
tcacacacat tccttctta ttcttcatct tcctcattag ctacttcctc tgcagcttct    1200
tcccctgcat atcccctgtt ttactctgct caacaatcac gtttctttca gccccacaa    1260 agtactcatc aaaatcaaac tagtagcagc agctccagtt ttcctgcacc attttggact    1320
agttcaaccc actacccacc ttcttctagt taa                                 1353

<210> SEQ ID NO 18
<211> LENGTH: 450
<212> TYPE: PRT
<213> ORGANISM: Nicotiana tabacum

<400> SEQUENCE: 18

Met Cys Leu Leu Ile Lys Val Ala Asn Pro Gly Glu Ser Gly Glu His
1               5                   10                  15

Asp Arg Ile Pro Ser Thr Gly Gly Asp Ser Glu Ser Thr Thr Thr Thr
            20                  25                  30

Thr Glu Gly Gly Ile Pro Gln Leu Tyr Glu Gln Leu Gln Ser Gln Ser
        35                  40                  45

Gln Ser Phe Glu Glu Met Leu Arg Gln Gln Ile Gln Gln Gln Thr Glu
    50                  55                  60

Tyr Leu Met Ser Ser Ser Ala Thr Pro Met Phe Ser Arg Tyr Ser Gln
65                  70                  75                  80

Thr Arg Glu Met Ser Ala Met Val Thr Ala Leu Thr His Val Val Ser
                85                  90                  95

Gly Arg Arg Glu Gly Glu Trp Thr Tyr Arg Pro Asp Ile Ser Ala Gly
```

|  |  |  |  | 100 |  |  |  | 105 |  |  |  | 110 |  |  |
|---|---|---|---|---|---|---|---|---|---|---|---|---|---|---|
| Ala | Val | Thr | Thr | Ser | Phe | Ala | Gly | Gly | Ser | Ser | Ile | Tyr | Ser | Ala | Ser |
|  |  |  | 115 |  |  |  |  | 120 |  |  |  | 125 |  |  |  |

Ser Pro Ser Ser Ser Ser Gly Ser Trp Ala Gly Gln Lys Arg Arg
    130                     135             140

Arg Asp Gln Glu Glu Ser Val Ala Ala Glu Gln Val Gln Arg Val Tyr
145                 150                 155                 160

Gly Ala Phe Gly Glu Phe Arg Gly Gly Glu Ser Ser Ser Val Lys
                165                 170                 175

Thr Glu Glu Ala Ser Ser Met Val Ala Pro Thr Thr Ser Thr
                180                 185                 190

Thr Thr Thr Thr Thr Thr Ala Ala Gln Thr Pro Pro Glu Pro Ala Glu
            195                 200                 205

Gly Gly Gly Ala Glu Glu Thr Gly Glu Arg Arg Arg Tyr Arg Gly
            210                 215                 220

Val Arg Gln Arg Pro Trp Gly Lys Trp Ala Ala Glu Ile Arg Asp Pro
225                 230                 235                 240

His Lys Ala Ala Arg Val Trp Leu Gly Thr Phe Asp Thr Ala Glu Ala
                245                 250                 255

Ala Ala Arg Ala Tyr Asp Glu Ala Ala Leu Arg Phe Arg Gly Asn Arg
            260                 265                 270

Ala Lys Leu Asn Phe Pro Glu Asn Val Arg Ile Leu Pro Gln Gln Gln
        275                 280                 285

Gln Gln Gln Pro Gln Ala Thr Thr Arg Ser Ala Ile Ser Ser Ser Ser
    290                 295                 300

Ala Ala Ser Gln Phe Pro Leu Met Ala Ala Thr Thr Pro Ser Pro
305                 310                 315                 320

Phe Phe Gln Thr Tyr Gln Pro Gln Gln Gln Leu Pro Phe Gln Ser
                325                 330                 335

Ser Glu Met Val Arg Asp Tyr Trp Glu Tyr Ser Gln Leu Leu Gln Asn
            340                 345                 350

Pro Gly Glu Phe His Leu Gln Gln Gln Pro Ser Ala Leu Leu Glu Gln
        355                 360                 365

Met Leu Phe Ala Ser Ser Ser Met Gly Leu Leu Gln Ser His Thr Phe
    370                 375                 380

Pro Ser Tyr Ser Ser Ser Ser Leu Ala Thr Ser Ser Ala Ala Ser
385                 390                 395                 400

Ser Pro Ala Tyr Pro Leu Phe Tyr Ser Ala Gln Gln Ser Arg Phe Phe
                405                 410                 415

Gln Pro Pro Gln Ser Thr His Gln Asn Gln Thr Ser Ser Ser Ser
            420                 425                 430

Ser Phe Pro Ala Pro Phe Trp Thr Ser Ser Thr His Tyr Pro Pro Ser
        435                 440                 445

Ser Ser
   450

<210> SEQ ID NO 19
<211> LENGTH: 732
<212> TYPE: DNA
<213> ORGANISM: Nicotiana tabacum

<400> SEQUENCE: 19
atggcacatt tcttctctat aaattcaacg ttagcaggaa cgaataaagc atccaaaaca      60
aatttcacat attcaactca agaaacagaa aaaccaaaaa taaagatcat cttactcttg     120

-continued

```
tttctcttg cattagttcc cttgtcagcg atggcaactt gcaccactga tactccaaac    180
caagcactat tgagggatgt acacgatata gatggtaacc cccttcaagt aaaagccagg    240
tacttcatat ttccagttat tggcggtggt ggtgtacggc ttgctaatct tggagatcaa    300
gacgaaaacg cttgtgccac agcggtggtg ctatcacgca gtgaagttga caaaggtaaa    360
gcagtcaact tcatacctaa agaccccaaa catgagaaga ttgtggaggc ctcttcagta    420
aacatccagt tttatcttga ttattataag tgtgctaacc taactgtgtg aaagtagac     480 aactaccctaa cacttccaag tcgctacacc ataagcacag gtgcaacgcc gggaaatccc   540
ctagagttga atagctggtt tcaaattatg tctcttggtg gctcgacgta taagatagtc    600
ttctgtccct ttggagaatg ccaaaatgtt ggcattgccg aggaaaatgg atataatcgt    660
ttggttctcg cagagaatgc aaaggccttt gttttcataa agcaaggcgg atatggaaag    720
gccgaagcat ga                                                         732
```

<210> SEQ ID NO 20
<211> LENGTH: 243
<212> TYPE: PRT
<213> ORGANISM: Nicotiana tabacum

<400> SEQUENCE: 20

```
Met Ala His Phe Phe Ser Ile Asn Ser Thr Leu Ala Gly Thr Asn Lys
1               5                   10                  15

Ala Ser Lys Thr Asn Phe Thr Tyr Ser Thr Gln Glu Thr Glu Lys Pro
            20                  25                  30

Lys Ile Lys Ile Ile Leu Leu Leu Phe Ser Leu Ala Leu Val Pro Leu
        35                  40                  45

Ser Ala Met Ala Thr Cys Thr Thr Asp Thr Pro Asn Gln Ala Leu Leu
    50                  55                  60

Arg Asp Val His Asp Ile Asp Gly Asn Pro Leu Gln Val Lys Ala Arg
65                  70                  75                  80

Tyr Phe Ile Phe Pro Val Ile Gly Gly Gly Val Arg Leu Ala Asn
                85                  90                  95

Leu Gly Asp Gln Asp Glu Asn Ala Cys Ala Thr Ala Val Val Leu Ser
            100                 105                 110

Arg Ser Glu Val Asp Lys Gly Lys Ala Val Asn Phe Ile Pro Lys Asp
        115                 120                 125

Pro Lys His Glu Lys Ile Val Glu Ala Ser Ser Val Asn Ile Gln Phe
    130                 135                 140

Tyr Leu Asp Tyr Tyr Lys Cys Ala Asn Leu Thr Val Trp Lys Val Asp
145                 150                 155                 160

Asn Tyr Pro Thr Leu Pro Ser Arg Tyr Thr Ile Ser Thr Gly Ala Thr
                165                 170                 175

Pro Gly Asn Pro Leu Glu Leu Asn Ser Trp Phe Gln Ile Met Ser Leu
            180                 185                 190

Gly Gly Ser Thr Tyr Lys Ile Val Phe Cys Pro Phe Gly Glu Cys Gln
        195                 200                 205

Asn Val Gly Ile Ala Glu Glu Asn Gly Tyr Asn Arg Leu Val Leu Ala
    210                 215                 220

Glu Asn Ala Lys Ala Phe Val Phe Ile Lys Gln Gly Gly Tyr Gly Lys
225                 230                 235                 240

Ala Glu Ala
```

<210> SEQ ID NO 21
<211> LENGTH: 471
<212> TYPE: DNA
<213> ORGANISM: Nicotiana tabacum

<400> SEQUENCE: 21

```
atggctgagc aacaccagcg ccaccagcaa cagcagcagc agcagcagat gcaagtgggc    60
cacccgacgg aggcaatcaa gagccttctt cctcaaaggg gtccctctaa atcccaagtc   120
cttgctgtcg tcactctctt ccctgttggt ggggccctcc tctgccttgc tggactgacg   180
ctcgccggaa ctctgatcgg gcttgcagtc gctacgccgg ttttcttact gttcagcccg   240
gttttggtcc ccgctgccct gacaatcgcg ttggccgtca ctggattctt gacttccggc   300
gcctttggaa taacggcgct gtcgtcgctc tcgtggatca ttaactatat gaggagaatc   360
acaggtccag cagcagagca gatggagcat gcaaagcgga gggtgcagga cactgctggt   420
catatgggac agagaggtgg acagaagatt caagaaactg ctagaacttg a            471
```

<210> SEQ ID NO 22
<211> LENGTH: 156
<212> TYPE: PRT
<213> ORGANISM: Nicotiana tabacum

<400> SEQUENCE: 22

```
Met Ala Glu Gln His Gln Arg His Gln Gln Gln Gln Gln Gln Gln
1               5                   10                  15

Met Gln Val Gly His Pro Thr Glu Ala Ile Lys Ser Leu Leu Pro Gln
                20                  25                  30

Arg Gly Pro Ser Lys Ser Gln Val Leu Ala Val Val Thr Leu Phe Pro
            35                  40                  45

Val Gly Gly Ala Leu Leu Cys Leu Ala Gly Leu Thr Leu Ala Gly Thr
        50                  55                  60

Leu Ile Gly Leu Ala Val Ala Thr Pro Val Phe Leu Leu Phe Ser Pro
65                  70                  75                  80

Val Leu Val Pro Ala Ala Leu Thr Ile Ala Leu Ala Val Thr Gly Phe
                85                  90                  95

Leu Thr Ser Gly Ala Phe Gly Ile Thr Ala Leu Ser Ser Leu Ser Trp
            100                 105                 110

Ile Ile Asn Tyr Met Arg Arg Ile Thr Gly Pro Ala Ala Glu Gln Met
        115                 120                 125

Glu His Ala Lys Arg Arg Val Gln Asp Thr Ala Gly His Met Gly Gln
    130                 135                 140

Arg Gly Gly Gln Lys Ile Gln Glu Thr Ala Arg Thr
145                 150                 155
```

<210> SEQ ID NO 23
<211> LENGTH: 1437
<212> TYPE: DNA
<213> ORGANISM: Nicotiana tabacum

<400> SEQUENCE: 23

```
atggatagtg ataggaggga ttgccacttg aacatgttgt ccaaaatggc tatgtgcaaa    60
tcacacgggc aagactcttc ctatttcata ggatggcaag aatatgagaa gaacccttat   120
catcccattc aaaatccttc tggtattatt cagatgggtc ttgctgagaa tcagctctca   180
ttcgatcttc ttgaatcatg gctcacaaga accaagatg taatccagtt tagagaaaat   240
ggaggatcta tgttcagaga cttggctctt ttccaagatt atcatggatt gcaggctttc   300
```

```
aagaacgtac tagtgtcatt catgggtgag atcagaagaa ggaaagtaaa atttgatcca    360
gagaagctag tactcacagc tggttcaact tcagcaaacg aaaccctcat attttgctta    420
gctgaacctg agaagctct ccttcttcca actccttatt atccagggtt tgatagagat     480
ctaaaatgga gaacagggc tgaaattgta cccatacact gctacagttc aaataacttc     540
agaataactg agtctgccct gaagatgca tatgaagaag cccaacgact taatttaaga    600
gtcaagggtg tatttatcac aaatccttca aatccactag gacaaccat gtcacgagac    660
gaattaaaca atcttatcac ctttgccatg ccaaaaata ttcatatagt tagcgacgaa    720
atatacgctg aacagttttt cgattcgcca aaattcataa gcataatgga agctttaatt   780
gacagaaaac atgaaaaatc caaatgtgg agtcaagttc acattgtgtc aagtctatca    840
aaagatctag gtctaccagg tttcagaatt gggatgattt attcaaacaa tgaaactctt   900
atagctgctg ctacaaaaat gtcaagttt ggactcattt catctcaaac tcagtatcta    960
ctatctaaaa ttcttggaga taaaaattt ataaaacgtt acattaaaga aaacaagaaa    1020
ggattgaaaa agaggaggga aatgcttgtt tccgggttag agaatagtgg gattgagtgt   1080
ttgaaaagta atgctggatt attttgtttt gtggacatga ggcatttgct aaattcaaac   1140
acatttgaag cagaaatgga actgtggaga aaaatactac taagtgatgt tggtttaaat   1200
gtgtctcctg gatcttcttg tcactgtagt gaacctggtt ggtttaaaat ttgttttgca   1260
aatattgccg aagaaactct tgatctcgcg atgcagagga ttaatgattt tgtcagttct   1320
atgaatcttc aacggcgaca gctgatcgcg gcggcgtcgg cgtctagctc aaggaggagg   1380
acacttgcga actgggttgt taagttatct tcaggtgaag gaaaaacata tcgttaa     1437
```

<210> SEQ ID NO 24
<211> LENGTH: 478
<212> TYPE: PRT
<213> ORGANISM: Nicotiana tabacum

<400> SEQUENCE: 24

```
Met Asp Ser Asp Arg Arg Asp Cys His Leu Asn Met Leu Ser Lys Met
1               5                   10                  15

Ala Met Cys Lys Ser His Gly Gln Asp Ser Ser Tyr Phe Ile Gly Trp
            20                  25                  30

Gln Glu Tyr Glu Lys Asn Pro Tyr His Pro Ile Gln Asn Pro Ser Gly
        35                  40                  45

Ile Ile Gln Met Gly Leu Ala Glu Asn Gln Leu Ser Phe Asp Leu Leu
    50                  55                  60

Glu Ser Trp Leu Thr Arg Asn Gln Asp Val Ile Gln Phe Arg Glu Asn
65                  70                  75                  80

Gly Gly Ser Met Phe Arg Asp Leu Ala Leu Phe Gln Asp Tyr His Gly
                85                  90                  95

Leu Gln Ala Phe Lys Asn Val Leu Val Ser Phe Met Gly Glu Ile Arg
            100                 105                 110

Arg Arg Lys Val Lys Phe Asp Pro Glu Lys Leu Val Leu Thr Ala Gly
        115                 120                 125

Ser Thr Ser Ala Asn Glu Thr Leu Ile Phe Cys Leu Ala Glu Pro Gly
    130                 135                 140

Glu Ala Leu Leu Leu Pro Thr Pro Tyr Tyr Pro Gly Phe Asp Arg Asp
145                 150                 155                 160

Leu Lys Trp Arg Thr Gly Ala Glu Ile Val Pro Ile His Cys Tyr Ser
                165                 170                 175
```

Ser Asn Asn Phe Arg Ile Thr Glu Ser Ala Leu Glu Asp Ala Tyr Glu
              180                 185                 190

Glu Ala Gln Arg Leu Asn Leu Arg Val Lys Gly Val Phe Ile Thr Asn
            195                 200                 205

Pro Ser Asn Pro Leu Gly Thr Thr Met Ser Arg Asp Glu Leu Asn Asn
        210                 215                 220

Leu Ile Thr Phe Ala Met Ala Lys Asn Ile His Ile Val Ser Asp Glu
225                 230                 235                 240

Ile Tyr Ala Gly Thr Val Phe Asp Ser Pro Lys Phe Ile Ser Ile Met
                245                 250                 255

Glu Ala Leu Ile Asp Arg Lys His Glu Lys Ser Lys Met Trp Ser Gln
            260                 265                 270

Val His Ile Val Ser Ser Leu Ser Lys Asp Leu Gly Leu Pro Gly Phe
        275                 280                 285

Arg Ile Gly Met Ile Tyr Ser Asn Asn Glu Thr Leu Ile Ala Ala Ala
        290                 295                 300

Thr Lys Met Ser Ser Phe Gly Leu Ile Ser Ser Gln Thr Gln Tyr Leu
305                 310                 315                 320

Leu Ser Lys Ile Leu Gly Asp Lys Lys Phe Ile Lys Arg Tyr Ile Lys
                325                 330                 335

Glu Asn Lys Lys Gly Leu Lys Lys Arg Arg Glu Met Leu Val Ser Gly
            340                 345                 350

Leu Glu Asn Ser Gly Ile Glu Cys Leu Lys Ser Asn Ala Gly Leu Phe
        355                 360                 365

Cys Phe Val Asp Met Arg His Leu Leu Asn Ser Asn Thr Phe Glu Ala
    370                 375                 380

Glu Met Glu Leu Trp Arg Lys Ile Leu Leu Ser Asp Val Gly Leu Asn
385                 390                 395                 400

Val Ser Pro Gly Ser Ser Cys His Cys Ser Glu Pro Gly Trp Phe Lys
                405                 410                 415

Ile Cys Phe Ala Asn Ile Ala Glu Glu Thr Leu Asp Leu Ala Met Gln
            420                 425                 430

Arg Ile Asn Asp Phe Val Ser Ser Met Asn Leu Gln Arg Arg Gln Leu
        435                 440                 445

Ile Ala Ala Ser Ala Ser Ser Ser Arg Arg Arg Thr Leu Ala Asn
450                 455                 460

Trp Val Val Lys Leu Ser Ser Gly Glu Gly Lys Thr Tyr Arg
465                 470                 475

<210> SEQ ID NO 25
<211> LENGTH: 645
<212> TYPE: DNA
<213> ORGANISM: Nicotiana tabacum

<400> SEQUENCE: 25
atgaacggtg gttcatgtgg tggtgctgat cgtgagtata ataacaataa caacaataat      60
gttgtaggtg gaggaggtgg cgggccttgt ggtgcatgca gtttcttag aagaaaatgt     120 gtgaggggat gcatatttgc accttatttt gattctgatc aaggcactgc tcatttcgct     180
gctgtacata aggtgtttgg tgctagcaat gcctctaaat gctgctcag aattccagcg     240 cataaacgtc tggatgctgt cgttacactt gctatgagg ctcttgctag agttagagac     300
cctatctatg ttgtgttgc tcacatcttt actcttcagc aacaggttgt aactttgcaa     360
gctgagttag catatgttca agcccgcctt tctaccctac cacacctacc tatgcgacaa     420

```
agtccaatta caccaacagg gctgcaatca tcttcagata tcttctgcac tacttcaagc    480
atatcatctt caagtaataa tatggaatat cctcaatttg acataactgc gggtttaagt    540
gattcgttcg atgaaaaaga actggagaac tttgagctcc atacattagc acgagagttg    600
gtttctagac acttacctgg agttagattt agaccttcac cataa                    645
```

<210> SEQ ID NO 26
<211> LENGTH: 214
<212> TYPE: PRT
<213> ORGANISM: Nicotiana tabacum

<400> SEQUENCE: 26

```
Met Asn Gly Gly Ser Cys Gly Gly Ala Asp Arg Glu Tyr Asn Asn
1               5                   10                  15

Asn Asn Asn Val Val Gly Gly Gly Gly Gly Pro Cys Gly Ala
            20                  25                  30

Cys Lys Phe Leu Arg Arg Lys Cys Val Arg Gly Cys Ile Phe Ala Pro
            35                  40                  45

Tyr Phe Asp Ser Asp Gln Gly Thr Ala His Phe Ala Ala Val His Lys
50                  55                  60

Val Phe Gly Ala Ser Asn Ala Ser Lys Leu Leu Leu Arg Ile Pro Ala
65                  70                  75                  80

His Lys Arg Leu Asp Ala Val Val Thr Leu Cys Tyr Glu Ala Leu Ala
                85                  90                  95

Arg Val Arg Asp Pro Ile Tyr Gly Cys Val Ala His Ile Phe Thr Leu
            100                 105                 110

Gln Gln Gln Val Val Thr Leu Gln Ala Glu Leu Ala Tyr Val Gln Ala
            115                 120                 125

Arg Leu Ser Thr Leu Pro His Leu Pro Met Arg Gln Ser Pro Ile Thr
130                 135                 140

Pro Thr Gly Leu Gln Ser Ser Ser Asp Ile Phe Cys Thr Thr Ser Ser
145                 150                 155                 160

Ile Ser Ser Ser Ser Asn Asn Met Glu Tyr Pro Gln Phe Asp Ile Thr
                165                 170                 175

Ala Gly Leu Ser Asp Ser Phe Asp Glu Lys Glu Leu Glu Asn Phe Glu
            180                 185                 190

Leu His Thr Leu Ala Arg Glu Leu Val Ser Arg His Leu Pro Gly Val
            195                 200                 205

Arg Phe Arg Pro Ser Pro
        210
```

<210> SEQ ID NO 27
<211> LENGTH: 2205
<212> TYPE: DNA
<213> ORGANISM: Nicotiana tabacum

<400> SEQUENCE: 27

```
atgtcggata aaaaatctgt ctcgacgcca tttgaatgtt gcagaatctt gtttaagttt     60
ctgctgttta tggttattat cagtaatgtg gcgatccatg taacagcttt gagtgggcga    120
gaaggaataa ccccaagtac ggaatggggt ttggggcctc tggtgaagag aggagaaaga    180
aaactagtag tttcaactga aatggggag gtctcttcag tcagagtagc tgatggaatc    240
accggttcct atcatcttca gttcatcaca ttggagccca ttccctctt ccttcctgtt    300 gttctacatg cagatatggt cttctatgtc cacactgggt cgggaaggct gacttggatg    360
gatgaaactg aacaaaagtc agtggattta agaattggag atgttttcag gttgcccttt    420
```

-continued

```
ggaactattt tcttcataga gagcaactta gagcctgcgc gacagaaact tagagtttat    480 tccatctttaa ccaattcagg ggatgatttg agagagccgt tgtccggacc acactctagc   540
atccgtgata tggttcttgg attcgatagg aaagttctcc aggcggcatt tcatgtacca    600
gaggatgtga tagatgaagt gttgaatggg acagaagtac cagccatcat acatggtgtg    660
cccaagacaa caaaaaagac cctgtgggaa atggaggctc aattcatgaa aagtcttcta    720 ggaagggggtg gtcacggttt ctttgactcc caaagcaata aaagaagac tgaattgttc    780 aatattttca aagagaaacc agattttgag aattgcaatg gctggagcac tgtaattaca    840
cggaaaaaat tacccgcatt aaagggttcc cacattggta tttatgtagt gaacttaacc    900
aagggatcaa tgatggcgcc acactggaat ccaacggcaa ctgaaatagg aatagcattg    960
caaggagaag gaatggtaag ggtagtttgc tcaagcacgg gaacaaagca aggatgccaa   1020
aacatgaggt ttaaggtgga agaaggagat gtatttgcag tgccaaggtt tcgtcctatg   1080
gctcaaatgg ctttcaacaa caactcattt gtctttgttg gttttagtac aactacaaag   1140
agacatcatc ctcagtacct aacagggaag gcttcagtcc tccgaacact ggataggcaa   1200
atcttggcag cttcctttaa tgtgactaac acaacaatgg atcggattct ggaggcacag   1260
ggtgagtcag tcatactgga gtgtacttct tgtgctgaag aagaagtgag attaatggag   1320
gaagaaagga ggagggcaga ggaggaagaa aggagaaggg aagaagagga ggcaaggcag   1380
agggaggaag aaaggaggag ggaagaagag gaagctagaa ggaaggaaga ggaagaagca   1440
aggaaggctg aagaagaaag aagaaagaga gaggcagaag aagcaagaag acgagaagag   1500
gaggcaacaa gggagaaaga ggaacaaagg aggagacaag aagaagaagc caggagaagg   1560
gaagaggagg aagccagaag gcaagaagaa gaaatcagaa ggagacaaga agaaggggaa   1620
gctaggaaga gagaagagga agaagcagct agaaggcaac aggaggaaga agctgagaga   1680
gaggcagaag aagcgaggac aagagaagag gaagaggcag ctagaaggca gcaggggaa    1740 gaagcacaaa gggaggcaga ggaagcaaga aggagagagg aagaagcagc aaggaggagg   1800
gaggaacaag cgcagagaga ggcggaggaa gcaagtagga gagaggagga agcagcagct   1860
agaaggagac aggaacgaga ggaagcagaa agggaaagca agcagagga agccaggagg    1920 gagggagagg aaacaaggag acatgaagaa gaagaagaag aagaaggaga ggaggaggaa   1980
acaaggagag agagaggggg agaggaggag gaggaaggag gaagaaaaga gaggaggcg    2040 gcaagagagg ccgagaaaag aaggcaagaa gaagcccaga gacaacaaga agcagctagg   2100
agacaggaag aagaaatgga aagaaggcat caagaagaag aaaccgagga agaggagcag   2160
ggtccttacg cacggaggaa aagaacattc cttaaaacag catga                   2205
```

<210> SEQ ID NO 28
<211> LENGTH: 734
<212> TYPE: PRT
<213> ORGANISM: Nicotiana tabacum

<400> SEQUENCE: 28

```
Met Ser Asp Lys Lys Ser Val Ser Thr Pro Phe Glu Cys Cys Arg Ile
1               5                   10                  15

Leu Phe Lys Phe Leu Leu Phe Met Val Ile Ile Ser Asn Val Ala Ile
                20                  25                  30

His Val Thr Ala Leu Ser Gly Arg Glu Gly Ile Thr Pro Ser Thr Glu
            35                  40                  45

Trp Gly Leu Gly Pro Leu Val Lys Arg Gly Glu Arg Lys Leu Val Val
```

-continued

```
                50                  55                  60
Ser Thr Glu Asn Gly Glu Val Ser Val Arg Val Ala Asp Gly Ile
 65                  70                  75                  80

Thr Gly Ser Tyr His Leu Gln Phe Ile Thr Leu Glu Pro Asn Ser Leu
                 85                  90                  95

Phe Leu Pro Val Val Leu His Ala Asp Met Val Phe Tyr Val His Thr
                100                 105                 110

Gly Ser Gly Arg Leu Thr Trp Met Asp Glu Thr Glu Gln Lys Ser Val
                115                 120                 125

Asp Leu Arg Ile Gly Asp Val Phe Arg Leu Pro Phe Gly Thr Ile Phe
130                 135                 140

Phe Ile Glu Ser Asn Leu Glu Pro Ala Arg Gln Lys Leu Arg Val Tyr
145                 150                 155                 160

Ser Ile Phe Thr Asn Ser Gly Asp Asp Leu Arg Glu Pro Leu Ser Gly
                165                 170                 175

Pro His Ser Ser Ile Arg Asp Met Val Leu Gly Phe Asp Arg Lys Val
                180                 185                 190

Leu Gln Ala Ala Phe His Val Pro Glu Asp Val Ile Asp Glu Val Leu
                195                 200                 205

Asn Gly Thr Glu Val Pro Ala Ile Ile His Gly Val Pro Lys Thr Thr
210                 215                 220

Lys Lys Thr Leu Trp Glu Met Glu Ala Gln Phe Met Lys Ser Leu Leu
225                 230                 235                 240

Gly Arg Gly Gly His Gly Phe Phe Asp Ser Gln Ser Asn Lys Lys Lys
                245                 250                 255

Thr Glu Leu Phe Asn Ile Phe Lys Glu Lys Pro Asp Phe Glu Asn Cys
                260                 265                 270

Asn Gly Trp Ser Thr Val Ile Thr Arg Lys Leu Pro Ala Leu Lys
                275                 280                 285

Gly Ser His Ile Gly Ile Tyr Val Val Asn Leu Thr Lys Gly Ser Met
                290                 295                 300

Met Ala Pro His Trp Asn Pro Thr Ala Thr Glu Ile Gly Ile Ala Leu
305                 310                 315                 320

Gln Gly Glu Gly Met Val Arg Val Val Cys Ser Ser Thr Gly Thr Lys
                325                 330                 335

Gln Gly Cys Gln Asn Met Arg Phe Lys Val Glu Glu Gly Asp Val Phe
                340                 345                 350

Ala Val Pro Arg Phe Arg Pro Met Ala Gln Met Ala Phe Asn Asn Asn
                355                 360                 365

Ser Phe Val Phe Val Gly Phe Ser Thr Thr Thr Lys Arg His His Pro
370                 375                 380

Gln Tyr Leu Thr Gly Lys Ala Ser Val Leu Arg Thr Leu Asp Arg Gln
385                 390                 395                 400

Ile Leu Ala Ala Ser Phe Asn Val Thr Asn Thr Thr Met Asp Arg Ile
                405                 410                 415

Leu Glu Ala Gln Gly Glu Ser Val Ile Leu Glu Cys Thr Ser Cys Ala
                420                 425                 430

Glu Glu Glu Val Arg Leu Met Glu Glu Arg Arg Ala Glu Glu
                435                 440                 445

Glu Glu Arg Arg Arg Glu Glu Glu Ala Gln Arg Glu Glu
                450                 455                 460

Arg Arg Arg Glu Glu Glu Ala Arg Arg Lys Glu Glu Glu Glu Ala
465                 470                 475                 480
```

```
Arg Lys Ala Glu Glu Arg Lys Arg Glu Ala Glu Glu Ala Arg
                485                 490                 495
Arg Arg Glu Glu Glu Ala Thr Arg Glu Lys Glu Gln Arg Arg
            500                 505                 510
Gln Glu Glu Glu Ala Arg Arg Arg Glu Glu Glu Ala Arg Arg Gln
            515                 520                 525
Glu Glu Glu Ile Arg Arg Arg Gln Glu Glu Gly Glu Ala Arg Lys Arg
            530                 535                 540
Glu Glu Glu Glu Ala Ala Arg Arg Gln Gln Glu Glu Ala Glu Arg
545                 550                 555                 560
Glu Ala Glu Glu Ala Arg Thr Arg Glu Glu Glu Ala Ala Arg Arg
                565                 570                 575
Gln Gln Gly Glu Glu Ala Gln Arg Glu Ala Glu Glu Ala Arg Arg Arg
            580                 585                 590
Glu Glu Glu Ala Ala Arg Arg Arg Glu Glu Gln Ala Gln Arg Glu Ala
                595                 600                 605
Glu Glu Ala Ser Arg Arg Glu Glu Glu Ala Ala Arg Arg Arg Gln
            610                 615                 620
Glu Arg Glu Glu Ala Glu Arg Glu Arg Gln Ala Glu Glu Ala Arg Arg
625                 630                 635                 640
Glu Gly Glu Glu Thr Arg Arg His Glu Glu Glu Glu Glu Glu Glu
                645                 650                 655
Glu Glu Glu Glu Thr Arg Arg Gly Glu Arg Gly Glu Glu Glu Glu
                660                 665                 670
Gly Gly Arg Lys Glu Glu Glu Ala Arg Glu Ala Glu Lys Arg Arg
            675                 680                 685
Gln Glu Glu Ala Gln Arg Gln Gln Glu Ala Ala Arg Arg Gln Glu Glu
            690                 695                 700
Glu Met Glu Arg Arg His Gln Glu Glu Glu Thr Glu Glu Glu Glu Gln
705                 710                 715                 720
Gly Pro Tyr Ala Arg Arg Lys Arg Thr Phe Leu Lys Thr Ala
                725                 730

<210> SEQ ID NO 29
<211> LENGTH: 1302
<212> TYPE: DNA
<213> ORGANISM: Nicotiana tabacum

<400> SEQUENCE: 29
atgggcgtac cagaatcgga ggtggtgtca caaggtgagg ttgaatcacc attgcaacca      60
gatcaaaacc agcacaagaa ccatcagttc ccgtccctcg gtagacaagc atcgatctac     120
tccctcactc tcgacgaatt ccaacacacc ctatgtgaaa gtggcaagaa tttcgggtcg     180
atgaatatgg atgaattcct taacagcatt tggactgctg aagaaaacca gcccacgca     240 cacgcccatg cccatgccgc gcacgggcat gcgcacgcgc attctcatgc tcatagccaa     300
gcaccaagta caggggaagc cactagcaca ccacattttg cgataggaca gagcaatgtt     360
tcaatggaga aagctattgc caagcagcca agcttgccaa gacagggttc tcttacgctt     420
ccggaacctt tgtgtcggaa aactgtggat gaagtttggt cagaaattca aagagccaa      480 aaagagcaac atcagaataa tgggggcagt gtcccggaca cgggtaattc cgctcaacgg     540
caggttacat ttggcgaaat gacacttgag gatttcttgg tcaaagcagg ggtagtacgc     600
gaacaggaga atgcccctgc acctcctcaa cagcaatcat atatgatgta tcaaaacagc     660
```

```
aacaatcccg ctatggccaa tatggctcga cctgttattg gcttaggtgg agtcacgggc    720
agcgttggag ttggcattcc tagctatcca ccacttcctc agaccggggt ggttgaggcc    780
ccaatatacc cggtaagtat gaaaaggggt gccggattcc cacaacagcc aacggctgtt    840

tacggcggga gaatggggaa tggtggcggg gtcgggtatg ggcaagtaca aggagtggcc    900
gggatggggt cgccactaag tccagtgtcg tcggatggat tatgcgttaa tcaagtcgat    960
agcgggggtc aatacgggtt ggaaatggga atgagaggag gaagaaaacg cataatagat   1020
ggtccggtag agaaagtggt ggaaaggagg caaaggagaa tgatcaagaa tagagaatca   1080
gcagcaagat caagagcaag aaagcaggct tacacagtag aacttgaggc agaactgaac   1140
cagctaaaag aagagaatgc acatctgaaa caggccctgg cggagctcga gaggaaaagg   1200
aaacaacagt actttgacga agggaaaatg aaagtgcaaa cgaaagcgca aaaggcgact   1260
aacaaattga gaggtatgag gaggagtttg agttgccctt ga                      1302

<210> SEQ ID NO 30
<211> LENGTH: 433
<212> TYPE: PRT
<213> ORGANISM: Nicotiana tabacum

<400> SEQUENCE: 30

Met Gly Val Pro Glu Ser Glu Val Val Ser Gln Gly Glu Val Glu Ser
1               5                   10                  15

Pro Leu Gln Pro Asp Gln Asn Gln His Lys Asn His Gln Phe Pro Ser
            20                  25                  30

Leu Gly Arg Gln Ala Ser Ile Tyr Ser Leu Thr Leu Asp Glu Phe Gln
        35                  40                  45

His Thr Leu Cys Glu Ser Gly Lys Asn Phe Gly Ser Met Asn Met Asp
    50                  55                  60

Glu Phe Leu Asn Ser Ile Trp Thr Ala Glu Glu Asn Gln Ala His Ala
65                  70                  75                  80

His Ala His Ala His Ala Ala His Gly His Ala His Ala His Ser His
                85                  90                  95

Ala His Ser Gln Ala Pro Ser Thr Gly Glu Ala Thr Ser Thr Pro His
            100                 105                 110

Phe Ala Ile Gly Gln Ser Asn Val Ser Met Glu Lys Ala Ile Ala Lys
        115                 120                 125

Gln Pro Ser Leu Pro Arg Gln Gly Ser Leu Thr Leu Pro Glu Pro Leu
    130                 135                 140

Cys Arg Lys Thr Val Asp Glu Val Trp Ser Glu Ile His Lys Ser Gln
145                 150                 155                 160

Lys Glu Gln His Gln Asn Asn Gly Gly Ser Val Pro Asp Thr Gly Asn
                165                 170                 175

Ser Ala Gln Arg Gln Val Thr Phe Gly Glu Met Thr Leu Glu Asp Phe
            180                 185                 190

Leu Val Lys Ala Gly Val Val Arg Glu Gln Glu Asn Ala Pro Ala Pro
        195                 200                 205

Pro Gln Gln Gln Ser Tyr Met Met Tyr Gln Asn Ser Asn Asn Pro Ala
    210                 215                 220

Met Ala Asn Met Ala Arg Pro Val Ile Gly Leu Gly Gly Val Thr Gly
225                 230                 235                 240

Ser Val Gly Val Gly Ile Pro Ser Tyr Pro Pro Leu Pro Gln Thr Gly
                245                 250                 255

Val Val Glu Ala Pro Ile Tyr Pro Val Ser Met Lys Arg Gly Ala Gly
```

```
                260              265              270
Phe Pro Gln Gln Pro Thr Ala Val Tyr Gly Gly Arg Met Gly Asn Gly
            275              280              285
Gly Gly Val Gly Tyr Gly Gln Val Gln Gly Val Ala Gly Met Gly Ser
        290              295              300
Pro Leu Ser Pro Val Ser Ser Asp Gly Leu Cys Val Asn Gln Val Asp
305              310              315              320
Ser Gly Gly Gln Tyr Gly Leu Glu Met Gly Met Arg Gly Gly Arg Lys
            325              330              335
Arg Ile Ile Asp Gly Pro Val Glu Lys Val Val Glu Arg Gln Arg
            340              345              350
Arg Met Ile Lys Asn Arg Glu Ser Ala Ala Arg Ser Arg Ala Arg Lys
            355              360              365
Gln Ala Tyr Thr Val Glu Leu Glu Ala Glu Leu Asn Gln Leu Lys Glu
        370              375              380
Glu Asn Ala His Leu Lys Gln Ala Leu Ala Glu Leu Glu Arg Lys Arg
385              390              395              400
Lys Gln Gln Tyr Phe Asp Glu Gly Lys Met Lys Val Gln Thr Lys Ala
            405              410              415
Gln Lys Ala Thr Asn Lys Leu Arg Gly Met Arg Arg Ser Leu Ser Cys
            420              425              430
Pro
```

<210> SEQ ID NO 31
<211> LENGTH: 1266
<212> TYPE: DNA
<213> ORGANISM: Nicotiana tabacum

<400> SEQUENCE: 31

```
atggaggaaa aagatgaact tgaggaagaa gaagaatatg ttgatgatga aatcaagaac    60
aatttaccag tccaaaactc atcttcaata agttggttca caaaaatgat atctttacaa   120
gtagagatct tcaccactat cttagtttcc cccatttcct atatcctctc ttttgtatct   180
gacttcaact tcctccgccc tgaagaaacc gaaaagaacg tagctgtagc tgtaaatgct   240
gctgctacag taccttcaaa agtagtacat ggaagtactt tactgctcaa gaaatttggt   300
gttggaattc ttggagctgc ttatgttgga atggttttga caacgttgtt gattttgtcg   360
ggggttctgg gatttgggtt agtgagaatg tgggcggaag agcctgtggt attgagagag   420
aagctgtatt tgattatgc agatgtttat cctaaggctg ttttttcttt tgctgaatat   480
ggtctggaga attataacca taattttatg atgttgaagc agaagaagaa ttttggtgtg   540
ccagttgggc atacaatgta tgtttctttg tttctactga tgcctgaatc tgatttcaac   600
agagatattg gtgttttcca gttggttgca gaagcgttat cagccgaggg gatcataatg   660
gcaagatcaa gtcatccacg tatgttgcga ttcagaagcc tgccaatccg tctcatgcga   720
gaatttatta tgagtgtgcc cctagtactt ggacttacag ctgaaacaca aggatgatc   780
attccaatgt taaagcataa ggaaggtatt ccaagaacag aggcaatcaa ataactatg   840
atacctcgag ctggaacgct agccctgccg cagctttatc aatcggagat catattgaag   900
tctcatcctc cttggtataa agacttggca tacaagtgga atggacatt ctccgtctgg   960
acctctatgt atatgtatgt tacactgctc ataattctac tcaactggtg cagaccgctc  1020
gtatttccag tgatcgcaac aagctttagg acacgcgttg atgagagttt aacagtggaa  1080
gcatcagaag aaccacaaga gaaagctcga gaagaaagtg atgtgtcgga gtcggtaaga  1140
```

```
agatggcggc agagcagaag aaagaggaag gcaatgcttc aacagagtgt ctcgccagag   1200
ttcgcggatg attctgcatc aagcatttct gtgactaggg aggatacagc tgagtcaagc   1260
gagtaa                                                              1266
```

<210> SEQ ID NO 32
<211> LENGTH: 421
<212> TYPE: PRT
<213> ORGANISM: Nicotiana tabacum

<400> SEQUENCE: 32

| Met | Glu | Glu | Lys | Asp | Glu | Leu | Glu | Glu | Glu | Glu | Tyr | Val | Asp | Asp |
|---|---|---|---|---|---|---|---|---|---|---|---|---|---|---|
| 1 | | | | 5 | | | | | 10 | | | | | 15 |

Glu Ile Lys Asn Asn Leu Pro Val Gln Asn Ser Ser Ile Ser Trp
              20                  25                  30

Phe Thr Lys Met Ile Ser Leu Gln Val Glu Ile Phe Thr Thr Ile Leu
              35                  40                  45

Val Ser Pro Ile Phe Tyr Ile Leu Ser Phe Val Ser Asp Phe Asn Phe
 50                          55                  60

Leu Arg Pro Glu Glu Thr Glu Lys Asn Val Ala Val Ala Val Asn Ala
 65                  70                  75                  80

Ala Ala Thr Val Pro Ser Lys Val Val His Gly Ser Thr Leu Leu Leu
                  85                  90                  95

Lys Lys Phe Gly Val Gly Ile Leu Ala Ala Tyr Val Gly Met Val
                100                 105                 110

Leu Thr Thr Leu Leu Ile Leu Ser Gly Val Leu Gly Phe Gly Leu Val
              115                 120                 125

Arg Met Trp Ala Glu Pro Val Val Leu Arg Glu Lys Leu Tyr Phe
 130                 135                 140

Asp Tyr Ala Asp Val Tyr Pro Lys Ala Val Phe Ser Phe Ala Glu Tyr
145                 150                 155                 160

Gly Leu Glu Asn Tyr Asn His Asn Phe Met Met Leu Lys Gln Lys Lys
                165                 170                 175

Asn Phe Gly Val Pro Val Gly His Thr Met Tyr Val Ser Leu Phe Leu
              180                 185                 190

Leu Met Pro Glu Ser Asp Phe Asn Arg Asp Ile Gly Val Phe Gln Leu
              195                 200                 205

Val Ala Glu Ala Leu Ser Ala Glu Gly Ile Ile Met Ala Arg Ser Ser
 210                 215                 220

His Pro Arg Met Leu Arg Phe Arg Ser Leu Pro Ile Arg Leu Met Arg
225                 230                 235                 240

Glu Phe Ile Met Ser Val Pro Leu Val Leu Gly Leu Thr Ala Glu Thr
                245                 250                 255

Gln Arg Met Ile Ile Pro Met Leu Lys His Lys Glu Gly Ile Pro Arg
              260                 265                 270

Thr Glu Ala Ile Lys Ile Thr Met Ile Pro Arg Ala Gly Thr Leu Ala
              275                 280                 285

Leu Pro Gln Leu Tyr Gln Ser Glu Ile Ile Leu Lys Ser His Pro Pro
 290                 295                 300

Trp Tyr Lys Asp Leu Ala Tyr Lys Trp Lys Trp Thr Phe Ser Val Trp
305                 310                 315                 320

Thr Ser Met Tyr Met Tyr Val Thr Leu Leu Ile Ile Leu Leu Asn Trp
                325                 330                 335

Cys Arg Pro Leu Val Phe Pro Val Ile Ala Thr Ser Phe Arg Thr Arg

```
              340                 345                 350
Val Asp Glu Ser Leu Thr Val Glu Ala Ser Glu Glu Pro Gln Glu Lys
                355                 360                 365

Ala Arg Glu Glu Ser Asp Val Ser Glu Ser Val Arg Arg Trp Arg Gln
            370                 375                 380

Ser Arg Arg Lys Arg Lys Ala Met Leu Gln Gln Ser Val Ser Pro Glu
385                 390                 395                 400

Phe Ala Asp Asp Ser Ala Ser Ser Ile Ser Val Thr Arg Glu Asp Thr
                405                 410                 415

Ala Glu Ser Ser Glu
            420

<210> SEQ ID NO 33
<211> LENGTH: 597
<212> TYPE: DNA
<213> ORGANISM: Nicotiana tabacum

<400> SEQUENCE: 33
atgtataact caagcaacta cagctgtaat tacaacccca ttttctcatc taatttattc      60
aacatccctt ctccttgtat gcaatatgaa cacgaacttt tcttccaata ttaccatgat    120
caacttcaac agaatcttga cgataccta gctgagatca gtactgagac tgccattatt     180
aacacggcag attccagcaa agacgaggct ataatcagta gaaatgaact tgaacaagat    240
caggaagcgc gtaagaataa aaagggtaaa gtaagcagca caagagagt gtctaagaaa     300 gatagacaca gcaagattaa cactgctaaa ggcccgagag accgaagaat aagactttca    360
attgatattg ctcgcaattt tttcaattta caagacatgt tgaggttcga aaggccagc    420 aaaactctgg agtggttgct tataaagtca aatctgata tcaaggagct ctccaaaagt     480
cgaataagca aattaagatg tagtactgtt atgggtgcaa atagtgaaac ctccacttct    540
gaatgtgaag ttgtatcagg aattgatgaa tctccatcca atcaaggcaa atgctaa      597

<210> SEQ ID NO 34
<211> LENGTH: 198
<212> TYPE: PRT
<213> ORGANISM: Nicotiana tabacum

<400> SEQUENCE: 34

Met Tyr Asn Ser Ser Asn Tyr Ser Cys Asn Tyr Asn Pro Ile Phe Ser
1               5                   10                  15

Ser Asn Leu Phe Asn Ile Pro Ser Pro Cys Met Gln Tyr Glu His Glu
            20                  25                  30

Leu Phe Phe Gln Tyr Tyr His Asp Gln Leu Gln Gln Asn Leu Asp Asp
        35                  40                  45

Thr Leu Ala Glu Ile Ser Thr Glu Thr Ala Ile Ile Asn Thr Ala Asp
    50                  55                  60

Ser Ser Lys Asp Glu Ala Ile Ile Ser Arg Asn Glu Leu Glu Gln Asp
65                  70                  75                  80

Gln Glu Ala Arg Lys Asn Lys Lys Gly Lys Val Ser Ser Asn Lys Arg
                85                  90                  95

Val Ser Lys Lys Asp Arg His Ser Lys Ile Asn Thr Ala Lys Gly Pro
            100                 105                 110

Arg Asp Arg Arg Ile Arg Leu Ser Ile Asp Ile Ala Arg Asn Phe Phe
        115                 120                 125

Asn Leu Gln Asp Met Leu Arg Phe Glu Lys Ala Ser Lys Thr Leu Glu
    130                 135                 140
```

Trp Leu Leu Ile Lys Ser Lys Ser Asp Ile Lys Glu Leu Ser Lys Ser
145                 150                 155                 160

Arg Ile Ser Lys Leu Arg Cys Ser Thr Val Met Gly Ala Asn Ser Glu
            165                 170                 175

Thr Ser Thr Ser Glu Cys Glu Val Val Ser Gly Ile Asp Glu Ser Pro
        180                 185                 190

Ser Asn Gln Gly Lys Cys
        195

<210> SEQ ID NO 35
<211> LENGTH: 1038
<212> TYPE: DNA
<213> ORGANISM: Nicotiana tabacum

<400> SEQUENCE: 35
atgtatccgt caagcaacat ctgtaattac aaccccaata tttcctcctc aaataactta      60
tttcacattc catctcctaa ttctatgcaa tatgaacacg aacttttcca atatttccac     120
gaccatcatc tccttcaacc ccaacaacaa caactactct tgactacacc tgatcattac     180
atggcagcag attccaacaa agataccgta atcagtagta ctattaatca actggaaggt     240 cctaagaag ttgaattaca aggcagctgc aagaacaaaa atggtgaaaa taagagagct      300
gttgcttaca agaagatag acacagcaag attaatacag ctcacggccc tagagatcga      360
agaatgagac tttctctcga tgttgctcgc aaattttca atttgcaaga cttgcttgga      420
ttcgataagg ccagcaaaac tgtggagtgg ttgcttacca agtccaaatc tgctatcaat     480
gagctcgtcc aaagtactgc tactggtgca attagtacat cctctacgac atccgagtgt     540
gaagtgatat caggaattga tgaatctaca accactaatg atattcagaa gcagccaaat     600
agaagtaaag taggggagaa gaaaaaggct aataaactag ctcgtagagc tgcatttaat     660
cctgtggcaa aggaatcaag gaaacaagct agagcgaggg caagggagag aacaaaaata     720
aagaaaagcc ttttaaatat tggtgatcag tctatggcgg ctgatgattt aaaacgatta     780
ggatgttgga gtccttttga acaggtgaa gaatcaggta ttcaaggcta tagtactaat      840
catcaagtag aagaccaaca cactacgaac cacgaggagc atcttttggg gactaaagag     900
aatgttgatg ctgtaatttt ggttgttact ggcaactgga acccatttac tatcttcaac     960
tatcaccaca atactgaaat ttctcacgag caacaattta caaacttcca gttttctggg    1020
aagttttggg aagtttag                                                   1038

<210> SEQ ID NO 36
<211> LENGTH: 345
<212> TYPE: PRT
<213> ORGANISM: Nicotiana tabacum

<400> SEQUENCE: 36

Met Tyr Pro Ser Ser Asn Ile Cys Asn Tyr Asn Pro Asn Ile Ser Ser
1               5                   10                  15

Ser Asn Asn Leu Phe His Ile Pro Ser Pro Asn Ser Met Gln Tyr Glu
            20                  25                  30

His Glu Leu Phe Gln Tyr Phe His Asp His His Leu Leu Gln Pro Gln
        35                  40                  45

Gln Gln Gln Leu Leu Leu Thr Thr Pro Asp His Tyr Met Ala Ala Asp
    50                  55                  60

Ser Asn Lys Asp Thr Val Ile Ser Ser Thr Ile Asn Gln Leu Glu Gly
65                  70                  75                  80

Pro Lys Glu Val Glu Leu Gln Gly Ser Cys Lys Asn Lys Asn Gly Glu
                85                  90                  95

Asn Lys Arg Ala Val Ala Tyr Lys Lys Asp Arg His Ser Lys Ile Asn
            100                 105                 110

Thr Ala His Gly Pro Arg Asp Arg Arg Met Arg Leu Ser Leu Asp Val
        115                 120                 125

Ala Arg Lys Phe Phe Asn Leu Gln Asp Leu Leu Gly Phe Asp Lys Ala
    130                 135                 140

Ser Lys Thr Val Glu Trp Leu Leu Thr Lys Ser Lys Ser Ala Ile Asn
145                 150                 155                 160

Glu Leu Val Gln Ser Thr Ala Thr Gly Ala Ile Ser Thr Ser Ser Thr
                165                 170                 175

Thr Ser Glu Cys Glu Val Ile Ser Gly Ile Asp Glu Ser Thr Thr Thr
            180                 185                 190

Asn Asp Ile Gln Lys Gln Pro Asn Arg Ser Lys Val Gly Glu Lys Lys
        195                 200                 205

Lys Ala Asn Lys Leu Ala Arg Arg Ala Ala Phe Asn Pro Val Ala Lys
    210                 215                 220

Glu Ser Arg Lys Gln Ala Arg Ala Arg Ala Arg Glu Arg Thr Lys Ile
225                 230                 235                 240

Lys Lys Ser Leu Leu Asn Ile Gly Asp Gln Ser Met Ala Ala Asp Asp
                245                 250                 255

Leu Lys Arg Leu Gly Cys Trp Ser Pro Phe Glu Thr Gly Glu Glu Ser
            260                 265                 270

Gly Ile Gln Gly Tyr Ser Thr Asn His Gln Val Glu Asp Gln His Thr
        275                 280                 285

Thr Asn His Glu Glu His Leu Leu Gly Thr Lys Glu Asn Val Asp Gly
    290                 295                 300

Cys Asn Leu Val Val Thr Gly Asn Trp Asn Pro Phe Thr Ile Phe Asn
305                 310                 315                 320

Tyr His His Asn Thr Glu Ile Ser His Glu Gln Gln Phe Thr Asn Phe
                325                 330                 335

Gln Phe Ser Gly Lys Phe Trp Glu Val
            340                 345

<210> SEQ ID NO 37
<211> LENGTH: 1014
<212> TYPE: DNA
<213> ORGANISM: Nicotiana tabacum

<400> SEQUENCE: 37
atgtatccgc caagcaatag ctgcaactac agccccattt tcaacatccc ttctccttgt      60
atgcaatatg gagacgaact attcttccaa tattatcatg acgattaccT tcaagagcaa     120
caagtaccgt tgatagaaga tcagagtctt gacatcttag ctgagagcac tgagactgtt     180
actaataaca agaaaccgt catcaattct gatcatagtg taaaagttta acatagaa       240 actgttacaa acagtcaggg tttgggagga atgaagaaa aaagagtaga aggccgcgaa      300
aacaaaagag atgatatgag cggcaccatt agtatcattc atggacggaa aaacaagaaa     360
tgttcccata agatcgaca tagcaagatt agcactgctc gtggccttag agatcgaagg     420
atgagacttt cccttgatgc agctcgcaag ttttttcagtt tacaagacat gttggggttc     480
gataaggcaa gtaaaactgt agaatggttg cttaccaaat cggagtctga aatcgaagag     540
ctagctaaag gcaataaaga aggagaatcc cttcctaaac aaagctgcag tactaccaat     600

```
ggaattggtg caattagtac tgcaatatcc tctatttctg agtgtgaggt tatatcagga    660
actgatgaat cttcttctat tactgataaa agaagctgg aaactgctaa aggaccgttg     720
aaaaagaagg gtaaaactgc tcgtagagct acatttgatc ctcttattac aagggaatcg   780
aggaatcaag caagggttag ggctagagag cgaacaaaac taagaaaaag ccttagtaaa   840
tccaaagcca tgactcatga gaacagtgct gatgactgta atttggtggt taattttgga   900
gattggagtc aatttagcat cttcaactat cagcaaaatg cagttggaat tcccatgat    960 cagcagcaat ttacagactt ccaattttgt ggtaataagc tgtgggaagt ctag         1014
```

<210> SEQ ID NO 38
<211> LENGTH: 337
<212> TYPE: PRT
<213> ORGANISM: Nicotiana tabacum

<400> SEQUENCE: 38

```
Met Tyr Pro Pro Ser Asn Ser Cys Asn Tyr Ser Pro Ile Phe Asn Ile
1               5                   10                  15

Pro Ser Pro Cys Met Gln Tyr Gly Asp Glu Leu Phe Phe Gln Tyr Tyr
                20                  25                  30

His Asp Asp Tyr Leu Gln Glu Gln Gln Val Pro Leu Ile Glu Asp Gln
            35                  40                  45

Ser Leu Asp Ile Leu Ala Glu Ser Thr Glu Thr Val Thr Asn Asn Lys
50                  55                  60

Glu Thr Val Ile Asn Ser Asp His Ser Val Lys Val Tyr Asn Ile Glu
65                  70                  75                  80

Thr Val Thr Asn Ser Gln Gly Leu Gly Gly Asn Glu Glu Lys Arg Val
                85                  90                  95

Glu Gly Arg Glu Asn Lys Arg Asp Asp Met Ser Gly Thr Ile Ser Ile
            100                 105                 110

Ile His Gly Arg Lys Asn Lys Lys Cys Ser His Lys Asp Arg His Ser
        115                 120                 125

Lys Ile Ser Thr Ala Arg Gly Leu Arg Asp Arg Arg Met Arg Leu Ser
130                 135                 140

Leu Asp Ala Ala Arg Lys Phe Phe Ser Leu Gln Asp Met Leu Gly Phe
145                 150                 155                 160

Asp Lys Ala Ser Lys Thr Val Glu Trp Leu Leu Thr Lys Ser Glu Ser
                165                 170                 175

Glu Ile Glu Glu Leu Ala Lys Gly Asn Lys Glu Gly Glu Ser Leu Pro
            180                 185                 190

Lys Gln Ser Cys Ser Thr Thr Asn Gly Ile Gly Ala Ile Ser Thr Ala
        195                 200                 205

Ile Ser Ser Ile Ser Glu Cys Glu Val Ile Ser Gly Thr Asp Glu Ser
    210                 215                 220

Ser Ser Ile Thr Asp Lys Lys Leu Glu Thr Ala Lys Gly Pro Leu
225                 230                 235                 240

Lys Lys Lys Gly Lys Thr Ala Arg Arg Ala Thr Phe Asp Pro Leu Ile
                245                 250                 255

Thr Arg Glu Ser Arg Asn Gln Ala Arg Val Arg Ala Arg Glu Arg Thr
            260                 265                 270

Lys Leu Lys Lys Ser Leu Ser Lys Ser Lys Ala Met Thr His Glu Asn
        275                 280                 285

Ser Ala Asp Asp Cys Asn Leu Val Val Asn Phe Gly Asp Trp Ser Gln
    290                 295                 300
```

Phe Ser Ile Phe Asn Tyr Gln Gln Asn Ala Val Gly Ile Ser His Asp
305                 310                 315                 320

Gln Gln Gln Phe Thr Asp Phe Gln Phe Cys Gly Asn Lys Leu Trp Glu
            325                 330                 335

Val

<210> SEQ ID NO 39
<211> LENGTH: 867
<212> TYPE: DNA
<213> ORGANISM: Nicotiana tabacum

<400> SEQUENCE: 39

```
atgggcctct cacaatatcc agctccagca gatgcaggag tactgtgtgt gattcttgta      60
aacacagcca tatctatttc cattgtcaag gagatagtcc gatcgatcct tcacgttatt     120
ggcatccata tcgcatcatg gaagattat tctttttgaag gatcatttga atgccgcgga     180
agcccatcag agtcatacat ggaggagttt agaagccgaa cacctgcatt cgttatgac     240
tcggtgtgta tctctaacca ccctgagcaa gaatgctctg tgtgcctgac taaattcgag     300
cctgacacag agataaaccg tctctcctgt ggccatgttt ccataagct gtgtctagag     360
aagtggctca agtattggca tgtaacttgc cctctttgca ggaaacacat gatgcctcac     420
gagcaagagg acgatacatg tccaatgtca ttttccagct atgttgcgcg aactctccaa     480
aatgctaccg catttatgtt ggatcctcca aaaatgcact acttttggag gatccgacat     540
gtgcctgatg acatttttcgg agaatctgag caacattgct ttccagtagc caactcagag     600
agtttcgagc caactgacat gctagtgcga gtcaacgcag ggttcctgtg gtatctgcac     660
ctgaaagaac ctgcatgtgt agttggtgag cacaagcagc tgtaccttac acttgatgtc     720
tttcgcaatg ctgacggtga agaaggcgtc gaggatggta atggtgccat agttggttgt     780
ggttgttcag ccatccttca gcagattctg cagaagaaat taatagatat gaacaagaaa     840
ttctggattg actatgaggt agagtag                                         867
```

<210> SEQ ID NO 40
<211> LENGTH: 288
<212> TYPE: PRT
<213> ORGANISM: Nicotiana tabacum

<400> SEQUENCE: 40

Met Gly Leu Ser Gln Tyr Pro Ala Pro Ala Asp Ala Gly Val Leu Cys
1               5                   10                  15

Val Ile Leu Val Asn Thr Ala Ile Ser Ile Ser Ile Val Lys Glu Ile
            20                  25                  30

Val Arg Ser Ile Leu His Val Ile Gly Ile His Ile Ala Ser Trp Glu
        35                  40                  45

Asp Tyr Ser Phe Glu Gly Ser Phe Glu Cys Arg Gly Ser Pro Ser Glu
    50                  55                  60

Ser Tyr Met Glu Glu Phe Arg Ser Arg Thr Pro Ala Phe Arg Tyr Asp
65                  70                  75                  80

Ser Val Cys Ile Ser Asn His Pro Glu Gln Glu Cys Ser Val Cys Leu
                85                  90                  95

Thr Lys Phe Glu Pro Asp Thr Glu Ile Asn Arg Leu Ser Cys Gly His
            100                 105                 110

Val Phe His Lys Leu Cys Leu Glu Lys Trp Leu Lys Tyr Trp His Val
        115                 120                 125

```
Thr Cys Pro Leu Cys Arg Lys His Met Met Pro His Glu Gln Glu Asp
        130                 135                 140

Asp Thr Cys Pro Met Ser Phe Ser Ser Tyr Val Ala Arg Thr Leu Gln
145                 150                 155                 160

Asn Ala Thr Ala Phe Met Leu Asp Pro Pro Lys Met His Tyr Phe Trp
                165                 170                 175

Arg Ile Arg His Val Pro Asp Asp Ile Phe Gly Glu Ser Glu Gln His
                180                 185                 190

Cys Phe Pro Val Ala Asn Ser Glu Ser Phe Glu Pro Thr Asp Met Leu
            195                 200                 205

Val Arg Val Asn Ala Gly Phe Leu Trp Tyr Leu His Leu Lys Glu Pro
210                 215                 220

Ala Cys Val Val Gly Glu His Lys Gln Leu Tyr Leu Thr Leu Asp Val
225                 230                 235                 240

Phe Arg Asn Ala Asp Gly Glu Gly Val Glu Asp Gly Asn Gly Ala
                245                 250                 255

Ile Val Gly Cys Gly Cys Ser Ala Ile Leu Gln Gln Ile Leu Gln Lys
                260                 265                 270

Lys Leu Ile Asp Met Asn Lys Lys Phe Trp Ile Asp Tyr Glu Val Glu
            275                 280                 285
```

<210> SEQ ID NO 41
<211> LENGTH: 2562
<212> TYPE: DNA
<213> ORGANISM: Nicotiana tabacum

<400> SEQUENCE: 41

```
atgaatcttc aggtggatga tcaaatgata ctcatttctc agtactatcc tggtatctac      60
actcaagagt taccgaaaca aggggaggcg aaacaaagga ggagacgaaa gaagaacaaa     120
ggagaagcaa gtgaggttat gaggaaaaga aagcttagtg aagaacaagt gaatctgctt     180
gaacagagct ttgggaaaga gcacaaactg agtccgaga ggaaagacaa gcttgcctct     240
gagctggggc ttgatcctag caagttgct gtctggtttc agaacagaag gctagatgg     300
aagaacaaga agttggagga ggaatactct aagttgaagt ctgagcatga cactaacatt     360
gttcataatt gccgtcttga aaatgaggtt ttgaagctga aggaacagtt gtctgaagca     420
gagaaagaga tacaaaggtt gctgatggag agatgtgatg gggttaattc gagcaatagc     480
ccaactactt catcactctc aatggaagca gccaatatgg aacctccttt tcttggggaa     540
tttggaatgg aaggatttga caatacattt tatgtgccag aaaacactta ctctcaggga     600
ttggaatgga atggaccatt ttttgcacct cctgatattg attatgggat cattaggttc     660
cagacattac ccgaccccac tattcctggg cagtatgcga actacacatg gggtagtgaa     720
tcttatacac aattgcttca gtccgttagg cacaagctca acccttctgt tcatttttat     780
gtcattcgag gcattgcact agctatgcaa atatggttgt atgagtgttg ctctaccgtc     840
aacactgata tagctacaag gatttctaat tcaatctctc gcatacttag ctggtcagct     900
agtaaggaca agatatggtt atctgcaatt gaagatagaa tgatcaaacc atcatggatc     960
aagttcacca acataattga agcaccagag gagctttcaa gaatgaattt gccaaataaa    1020
gttgaataca ttcttgaaga agttgaaaca aagtccgagc atccgataga tgctccatct    1080
ccatccgttg gttcagatct tggaactttc aagaaagagg ttttgaaga actagataca    1140
gggcaggtga atgatataaa aattatggag aatgttcctg taggtgttga tttatcttcc    1200
caatttgaag gggcatttga tgaagagaat gcagagaagg aaactatgca tgtagaatct    1260
```

-continued

```
ccaaaacaga aagctacaat aagcattcca ggaaaacaaa aaaatgagga gaaggagaca  1320
aaaatacaat ctcacattca agaagagaac gttatacaac aaggagatga ttgttgtgaa  1380
gatttcagtg gtgaatcagc cgactacatt aatataggtg attcagacaa tgactctaga  1440
tctgaaaaaa gagaagtaac acttgatgat tttgagctgc cagagaactt ctcccagatt  1500
attaattctg gggggagaac ttctgttgga cctccaattt tcctcatcaa gcatccattt  1560
actggggtta ttggcgaaga tgttgatcct gacttattgg aagaattcaa taagtggtta  1620
tactttggta tcgatacagt ttcaaagagg aggaaggcgc ttattctgt aaaagataac  1680 cagcttaagc cgtggtatga ttttggagtg agaaagttg ataaaaatga gaggttttat  1740
actttggtac accccgggca agtcctcaac gatacgcaca ttgatgttat tttatactat  1800
ttgagaaaga gaggaaagta tggtcgtcaa acaaaaatat ggtttacaat cattgattgt  1860
atgttcaaca ctagaattga acaaatttat cagaggtaca tcaatactcc tgccgataag  1920
aagcttgttg ttgtcaaatc ccaagacgtc gtatcagaat acatattggg gtacagatta  1980
ctcgcaaata ttgcattgga tcaagttgat tttgtgatta tgcccataaa cattgtgaaa  2040
aaattttatt ggttgttggt tgtgtttgac attaccgata gggttctata tgtttatgat  2100
tctatgttct cttcacgaaa tcacaacctt gttgaatttg ttgtcaacaa gtttgctgtt  2160
atgatccccc tctacttgtc atgcaccgac ttctatggca agcgtccaga catcaactac  2220
aagaacacaa aagcatacat tgaaaaatgt gttactgacc ctcttgacat tcagtggttg  2280
gtcggtgaga tactccatca aaatgaggga tcacttgact gtagtgtata cgtggctgca  2340
tttacagaat atgtcagcat tggagagcta gcagtttcaa aggaagacct ttctgatatt  2400
gatcaacatc gtagacgcta tggagcgcta ctttgggatt atgataggaa gaagcaagat  2460
actggtgcaa ttagtgagag cgaggtgact ggcagattag caagaagaaa aggtgcacca  2520
gctgtgaacg agagaacaca agtccggaag aagaagaatt ag                     2562
```

<210> SEQ ID NO 42
<211> LENGTH: 853
<212> TYPE: PRT
<213> ORGANISM: Nicotiana tabacum

<400> SEQUENCE: 42

```
Met Asn Leu Gln Val Asp Asp Gln Met Ile Leu Ile Ser Gln Tyr Tyr
1               5                   10                  15

Pro Gly Ile Tyr Thr Gln Glu Leu Pro Glu Gln Gly Glu Ala Lys Gln
            20                  25                  30

Arg Arg Arg Arg Lys Lys Asn Lys Gly Glu Ala Ser Glu Val Met Arg
        35                  40                  45

Lys Arg Lys Leu Ser Glu Glu Gln Val Asn Leu Glu Gln Ser Phe
    50                  55                  60

Gly Lys Glu His Lys Leu Glu Ser Glu Arg Lys Asp Lys Leu Ala Ser
65                  70                  75                  80

Glu Leu Gly Leu Asp Pro Arg Gln Val Ala Val Trp Phe Gln Asn Arg
                85                  90                  95

Arg Ala Arg Trp Lys Asn Lys Lys Leu Glu Glu Glu Tyr Ser Lys Leu
            100                 105                 110

Lys Ser Glu His Asp Thr Asn Ile Val His Asn Cys Arg Leu Glu Asn
        115                 120                 125

Glu Val Leu Lys Leu Lys Glu Gln Leu Ser Glu Ala Glu Lys Glu Ile
    130                 135                 140
```

```
Gln Arg Leu Leu Met Glu Arg Cys Asp Gly Val Asn Ser Ser Asn Ser
145                 150                 155                 160

Pro Thr Thr Ser Ser Leu Ser Met Glu Ala Ala Asn Met Glu Pro Pro
            165                 170                 175

Phe Leu Gly Glu Phe Gly Met Glu Gly Phe Asp Asn Thr Phe Tyr Val
            180                 185                 190

Pro Glu Asn Thr Tyr Ser Gln Gly Leu Glu Trp Asn Gly Pro Phe Phe
            195                 200                 205

Ala Pro Pro Asp Ile Asp Tyr Gly Ile Ile Arg Phe Gln Thr Leu Pro
            210                 215                 220

Asp Pro Thr Ile Pro Gly Gln Tyr Ala Asn Tyr Thr Trp Gly Ser Glu
225                 230                 235                 240

Ser Tyr Thr Gln Leu Leu Gln Ser Val Arg His Lys Leu Asn Pro Ser
            245                 250                 255

Val His Phe Tyr Val Ile Arg Gly Ile Ala Leu Ala Met Gln Ile Trp
            260                 265                 270

Leu Tyr Glu Cys Cys Ser Thr Val Asn Thr Asp Ile Ala Thr Arg Ile
            275                 280                 285

Ser Asn Ser Ile Ser Arg Ile Leu Ser Trp Ser Ala Ser Lys Asp Lys
290                 295                 300

Ile Trp Leu Ser Ala Ile Glu Asp Arg Met Ile Lys Pro Ser Trp Ile
305                 310                 315                 320

Lys Phe Thr Asn Ile Ile Glu Ala Pro Glu Glu Leu Ser Arg Met Asn
            325                 330                 335

Leu Pro Asn Lys Val Glu Tyr Ile Leu Glu Glu Val Glu Thr Lys Ser
            340                 345                 350

Glu His Pro Ile Asp Ala Pro Ser Pro Ser Val Gly Ser Asp Leu Gly
            355                 360                 365

Thr Phe Lys Lys Glu Val Phe Glu Glu Leu Asp Thr Gly Gln Val Asn
            370                 375                 380

Asp Ile Lys Ile Met Glu Asn Val Pro Val Gly Val Asp Leu Ser Ser
385                 390                 395                 400

Gln Phe Glu Gly Ala Phe Asp Glu Glu Asn Ala Glu Lys Glu Thr Met
            405                 410                 415

His Val Glu Ser Pro Lys Gln Lys Ala Thr Ile Ser Ile Pro Gly Lys
            420                 425                 430

Gln Lys Asn Glu Glu Lys Glu Thr Lys Ile Gln Ser His Ile Gln Glu
            435                 440                 445

Glu Asn Val Ile Gln Gln Gly Asp Asp Cys Cys Glu Asp Phe Ser Gly
            450                 455                 460

Glu Ser Ala Asp Tyr Ile Asn Ile Gly Asp Ser Asp Asn Asp Ser Arg
465                 470                 475                 480

Ser Glu Lys Arg Glu Val Thr Leu Asp Asp Phe Glu Leu Pro Glu Asn
            485                 490                 495

Phe Ser Gln Ile Ile Asn Ser Gly Gly Arg Thr Ser Val Gly Pro Pro
            500                 505                 510

Ile Phe Leu Ile Lys His Pro Phe Thr Gly Val Ile Gly Glu Asp Val
            515                 520                 525

Asp Pro Asp Leu Leu Glu Glu Phe Asn Lys Trp Leu Tyr Phe Gly Ile
            530                 535                 540

Asp Thr Val Ser Lys Arg Arg Lys Ala Pro Tyr Ser Val Lys Asp Asn
545                 550                 555                 560
```

```
Gln Leu Lys Pro Trp Tyr Asp Phe Gly Val Glu Val Asp Lys Asn
                565                 570                 575

Glu Arg Phe Tyr Thr Leu Val His Pro Gly Gln Val Leu Asn Asp Thr
            580                 585                 590

His Ile Asp Val Ile Leu Tyr Tyr Leu Arg Lys Arg Gly Lys Tyr Gly
            595                 600                 605

Arg Gln Asn Lys Ile Trp Phe Thr Ile Ile Asp Cys Met Phe Asn Thr
        610                 615                 620

Arg Ile Glu Gln Ile Tyr Gln Arg Tyr Ile Asn Thr Pro Ala Asp Lys
625                 630                 635                 640

Lys Leu Val Val Val Lys Ser Gln Asp Val Ser Glu Tyr Ile Leu
                645                 650                 655

Gly Tyr Arg Leu Leu Ala Asn Ile Ala Leu Asp Gln Val Asp Phe Val
            660                 665                 670

Ile Met Pro Ile Asn Ile Val Lys Lys Phe Tyr Trp Leu Val Val
        675                 680                 685

Phe Asp Ile Thr Asp Arg Val Leu Tyr Val Tyr Asp Ser Met Phe Ser
    690                 695                 700

Ser Arg Asn His Asn Leu Val Glu Phe Val Val Asn Lys Phe Ala Val
705                 710                 715                 720

Met Ile Pro Leu Tyr Leu Ser Cys Thr Asp Phe Tyr Gly Lys Arg Pro
                725                 730                 735

Asp Ile Asn Tyr Lys Asn Thr Lys Ala Tyr Ile Glu Lys Cys Val Thr
            740                 745                 750

Asp Pro Leu Asp Ile Gln Trp Leu Val Gly Glu Ile Leu His Gln Asn
            755                 760                 765

Glu Gly Ser Leu Asp Cys Ser Val Tyr Val Ala Ala Phe Thr Glu Tyr
        770                 775                 780

Val Ser Ile Gly Glu Leu Ala Val Ser Lys Glu Asp Leu Ser Asp Ile
785                 790                 795                 800

Asp Gln His Arg Arg Tyr Gly Ala Leu Leu Trp Asp Tyr Asp Arg
                805                 810                 815

Lys Lys Gln Asp Thr Gly Ala Ile Ser Glu Ser Glu Val Thr Gly Arg
            820                 825                 830

Leu Ala Arg Arg Lys Gly Ala Pro Ala Val Asn Glu Arg Thr Gln Val
        835                 840                 845

Arg Lys Lys Lys Asn
    850

<210> SEQ ID NO 43
<211> LENGTH: 2790
<212> TYPE: DNA
<213> ORGANISM: Nicotiana tabacum

<400> SEQUENCE: 43
atgatagtag taagatggtg gatgacaaca ttccaattga cagagctgtt tgtgagttgt      60
ttagttcatt tgacttacgg gctttacata ttcagcacag cagtggccgg tgatgtttcc     120
cagactctga gcgattggct tttcaagcca aatttggaaa ctagccttaa aacagatgat     180
tcaaaaaaga ctaacactga tttgcctcct attgtgttgg tcatggaat ctttggtttt     240 ggcaaaggga gatttggagg actttcatat ttcgctggtg cagagaaaaa ggatgaaagg     300
gttctagtac cggatttggg ttcacttact agcatttatg acagggcacg tgaattgttt     360
tattatttga aaggagggca ggttgattat ggggaggaac acagtaaggc ttgtgggcat     420
```

```
tcccaatttg acgaatttta tgaacaagga cactacccccg agtgggatga agatcatcct    480
attcattttg tgggccattc agctggagca caggttgttc gagtcttgca acagatgctg    540
gctgacaagg cattcaaagg ttacgacaac acttcagaga actgggtgtt aagcctaaca    600
tcattatctg gagcacttaa cgggacaacc cgaacttact ttgatggaat gcaacctgaa    660
gatgggaagt ccttaacgcc cgtatgtttg ctccaacttt gccgcattgg agtaataatt    720
tatgagtggc ttgacattcc cttgctgaag gactattaca actttggctt tgaccacttc    780
agtatgtcct ggaggaaaag tggtatccgg ggttttgttg attgcctttt agggaatggc    840
ggtccatttg cttcgggaga ttggatactt ccagatctta ctatccaggg gtcaatgaag    900
ttgaacagcc acttacgtac atttccgcaa acatactact tcagctatgc taccaagcgt    960
accacacaag taatgggtct tacagttcct tctggcgttc tagggataca tccgctgcta   1020
ttcatcagag tcctgcaaat gagccaatgg cggcatccac aagatgtttc tcctccgtac   1080
aagggctata gggatgaaga ttggtgggac aatgacggtg ctctcaacac catatctatg   1140
acgcacccac gcttgccggt tgaacacccg agtcaccttg tcgttaaaga ttctgattgt   1200
cagcccttgc aacctggcat ctggaatcat caagtttcct cttctgtgca gttgttatca   1260
ccaccattgg ctcgtaggct ttccgtgggg aaatgtgaaa gggaaatatc tgtcattctc   1320
agttatgtta cggaaagatc agctctcacc attagaaacc ccgatggaag ccaacaacaa   1380
accaccaaga tcctctcttca ccaccagaag tgcgcatgcc ttccgtctta ctgtgaacgc   1440
ccacgtccaa tggaatttct gggaaggatt tcaagaaatg tagaaggaaa tgatactaag   1500
gctaggattt ctgcagctat tttactagtt tgcattatcc ttccttttgct agcctcagca   1560 tttcttgatc atcttcctga atttctagaa catgattcta gaaataaaga tgtaacaatc   1620
cgtggtgata ataatattgt tcgtgccaat gacaatgact ttactcttcc tcgctcacat   1680
gagaaaaaga atgaaagatc tttaagagaa aagaagtcaa agaagaagaa gcataagaag   1740
aagaagaaca agaagggaaa gaaatcacac aaagataaaa ttttttgattt tgaccatatt   1800 tttggaggaa accaacaaga aggagatgaa ttttccccctt attttgcaacc atttgatgtg   1860 cctcaaacaa cagaagaaca agaacagacc gagaattatg atggattacg tgagggattt   1920
taccagaaaa catgtcctca agcagagaat attataagaa atggtctaat cagggccttt   1980
cagaatgact ctaccattgc tgctgcatta ccctcgcctttc tcttgcatga ttgctttgtc   2040
aatggatgtg atgggtcgat attactagat acaacaccca gtggtgcaag agtggagaag   2100
ttagcaggca caaatggtgc tacagtcaag ggatttgaac tcatagacga gatcaaagcc   2160
gagctcgaga gacaatgccc tggcattgtc tcctgctctg atattttggc atacttgtcg   2220
cgcgatgcct ttgttttatc aggcctcccc aattacaacg tgctaggtgg tcgacgcgat   2280
ggcatggaat ccaatgaagc aaacgttgtt ggaaacctac cacttcctgg cgacacagtg   2340
gatcaaatga ttgatctttt tcaaaagaaa ggcctaaatt cggaagattt ggttgtccta   2400
attggtgcac attcaattgg agtagcccat tgtttcaact tcctttacag attggacgaa   2460
ccagagaagg cacaaatgtt agatccaagg cttgctggag tcatgagatt tatttgtact   2520
aaccaaatga ataccttacc ttttgatccc acaacacagt acaagatgga ttcaattttc   2580
tacaagcaac taatgatgaa gaaagggttg attgaatcgg atcaaatact ggctcaagat   2640
attagaacga ggggcttggt gcaaaagttt ggtgatgatg aaatgggatg gtttgataag   2700
tttggtaagg ctatgaataa attgggagca attgaagtgc tcactggaaa ccaaggccag   2760
atcaggagac agtgtagagc tgttaactga                                    2790
```

<210> SEQ ID NO 44
<211> LENGTH: 929
<212> TYPE: PRT
<213> ORGANISM: Nicotiana tabacum

<400> SEQUENCE: 44

```
Met Ile Val Val Arg Trp Trp Met Thr Thr Phe Gln Leu Thr Glu Leu
1               5                   10                  15

Phe Val Ser Cys Leu Val His Leu Thr Tyr Gly Leu Tyr Ile Phe Ser
            20                  25                  30

Thr Ala Val Ala Gly Asp Val Ser Gln Thr Leu Ser Asp Trp Leu Phe
        35                  40                  45

Lys Pro Asn Leu Glu Thr Ser Leu Lys Thr Asp Asp Ser Lys Lys Thr
    50                  55                  60

Asn Thr Asp Leu Pro Pro Ile Val Leu Val His Gly Ile Phe Gly Phe
65                  70                  75                  80

Gly Lys Gly Arg Leu Gly Leu Ser Tyr Phe Ala Gly Ala Glu Lys
                85                  90                  95

Lys Asp Glu Arg Val Leu Val Pro Asp Leu Gly Ser Leu Thr Ser Ile
            100                 105                 110

Tyr Asp Arg Ala Arg Glu Leu Phe Tyr Tyr Leu Lys Gly Gly Gln Val
        115                 120                 125

Asp Tyr Gly Glu Glu His Ser Lys Ala Cys Gly His Ser Gln Phe Gly
    130                 135                 140

Arg Ile Tyr Glu Gln Gly His Tyr Pro Glu Trp Asp Glu Asp His Pro
145                 150                 155                 160

Ile His Phe Val Gly His Ser Ala Gly Ala Gln Val Val Arg Val Leu
                165                 170                 175

Gln Gln Met Leu Ala Asp Lys Ala Phe Lys Gly Tyr Asp Asn Thr Ser
            180                 185                 190

Glu Asn Trp Val Leu Ser Leu Thr Ser Leu Ser Gly Ala Leu Asn Gly
        195                 200                 205

Thr Thr Arg Thr Tyr Phe Asp Gly Met Gln Pro Glu Asp Gly Lys Ser
    210                 215                 220

Leu Thr Pro Val Cys Leu Leu Gln Leu Cys Arg Ile Gly Val Ile Ile
225                 230                 235                 240

Tyr Glu Trp Leu Asp Ile Pro Leu Leu Lys Asp Tyr Tyr Asn Phe Gly
                245                 250                 255

Phe Asp His Phe Ser Met Ser Trp Arg Lys Ser Gly Ile Arg Gly Phe
            260                 265                 270

Val Asp Cys Leu Leu Gly Asn Gly Gly Pro Phe Ala Ser Gly Asp Trp
        275                 280                 285

Ile Leu Pro Asp Leu Thr Ile Gln Gly Ser Met Lys Leu Asn Ser His
    290                 295                 300

Leu Arg Thr Phe Pro Gln Thr Tyr Tyr Phe Ser Tyr Ala Thr Lys Arg
305                 310                 315                 320

Thr Thr Gln Val Met Gly Leu Thr Val Pro Ser Gly Val Leu Gly Ile
                325                 330                 335

His Pro Leu Leu Phe Ile Arg Val Leu Gln Met Ser Gln Trp Arg His
            340                 345                 350

Pro Gln Asp Val Ser Pro Pro Tyr Lys Gly Tyr Arg Asp Glu Asp Trp
        355                 360                 365

Trp Asp Asn Asp Gly Ala Leu Asn Thr Ile Ser Met Thr His Pro Arg
```

-continued

```
              370                 375                 380
Leu Pro Val Glu His Pro Ser His Leu Val Val Lys Asp Ser Asp Cys
385                 390                 395                 400

Gln Pro Leu Gln Pro Gly Ile Trp Asn His Gln Val Ser Ser Ser Val
                    405                 410                 415

Gln Leu Leu Ser Pro Pro Leu Ala Arg Arg Leu Ser Val Gly Lys Cys
                420                 425                 430

Glu Arg Glu Ile Ser Val Ile Leu Ser Tyr Val Thr Glu Arg Ser Ala
            435                 440                 445

Leu Thr Ile Arg Asn Pro Asp Gly Ser Gln Gln Thr Thr Lys Ile
        450                 455                 460

Leu Phe His His Gln Lys Cys Ala Cys Leu Pro Ser Tyr Cys Glu Arg
465                 470                 475                 480

Pro Arg Pro Met Glu Phe Leu Gly Arg Ile Ser Arg Asn Val Glu Gly
                    485                 490                 495

Asn Asp Thr Lys Ala Arg Ile Ser Ala Ala Ile Leu Leu Val Cys Ile
                500                 505                 510

Ile Leu Pro Leu Leu Ala Ser Ala Phe Leu Asp His Leu Pro Glu Phe
            515                 520                 525

Leu Glu His Asp Ser Arg Asn Lys Asp Val Thr Ile Arg Gly Asp Asn
        530                 535                 540

Asn Ile Val Arg Ala Asn Asp Asn Asp Phe Thr Leu Pro Arg Ser His
545                 550                 555                 560

Glu Lys Lys Asn Glu Arg Ser Leu Arg Glu Lys Lys Ser Lys Lys Lys
                    565                 570                 575

Lys His Lys Lys Lys Asn Lys Lys Gly Lys Lys Ser His Lys Asp
                580                 585                 590

Lys Ile Phe Asp Phe Asp His Ile Phe Gly Gly Asn Gln Gln Glu Gly
            595                 600                 605

Asp Glu Phe Ser Pro Tyr Leu Gln Pro Phe Asp Val Pro Gln Thr Thr
        610                 615                 620

Glu Glu Gln Glu Gln Thr Glu Asn Tyr Asp Gly Leu Arg Glu Gly Phe
625                 630                 635                 640

Tyr Gln Lys Thr Cys Pro Gln Ala Glu Asn Ile Ile Arg Asn Gly Leu
                    645                 650                 655

Ile Arg Ala Phe Gln Asn Asp Ser Thr Ile Ala Ala Ala Leu Pro Arg
                660                 665                 670

Leu Leu Leu His Asp Cys Phe Val Asn Gly Cys Asp Gly Ser Ile Leu
            675                 680                 685

Leu Asp Thr Thr Pro Ser Gly Ala Arg Val Glu Lys Leu Ala Gly Thr
        690                 695                 700

Asn Gly Ala Thr Val Lys Gly Phe Glu Leu Ile Asp Glu Ile Lys Ala
705                 710                 715                 720

Glu Leu Glu Arg Gln Cys Pro Gly Ile Val Ser Cys Ser Asp Ile Leu
                    725                 730                 735

Ala Tyr Leu Ser Arg Asp Ala Phe Val Leu Ser Gly Leu Pro Asn Tyr
                740                 745                 750

Asn Val Leu Gly Gly Arg Arg Asp Gly Met Glu Ser Asn Glu Ala Asn
            755                 760                 765

Val Val Gly Asn Leu Pro Leu Pro Gly Asp Thr Val Asp Gln Met Ile
        770                 775                 780

Asp Leu Phe Gln Lys Lys Gly Leu Asn Ser Glu Asp Leu Val Val Leu
785                 790                 795                 800
```

Ile Gly Ala His Ser Ile Gly Val Ala His Cys Phe Asn Phe Leu Tyr
            805                 810                 815

Arg Leu Asp Glu Pro Glu Lys Ala Gln Met Leu Asp Pro Arg Leu Ala
        820                 825                 830

Gly Val Met Arg Phe Ile Cys Thr Asn Gln Met Asn Thr Leu Pro Phe
    835                 840                 845

Asp Pro Thr Thr Gln Tyr Lys Met Asp Ser Ile Phe Tyr Lys Gln Leu
850                 855                 860

Met Met Lys Lys Gly Leu Ile Glu Ser Asp Gln Ile Leu Ala Gln Asp
865                 870                 875                 880

Ile Arg Thr Arg Gly Leu Val Gln Lys Phe Gly Asp Asp Glu Met Gly
            885                 890                 895

Trp Phe Asp Lys Phe Gly Lys Ala Met Asn Lys Leu Gly Ala Ile Glu
        900                 905                 910

Val Leu Thr Gly Asn Gln Gly Gln Ile Arg Arg Gln Cys Arg Ala Val
    915                 920                 925

Asn

<210> SEQ ID NO 45
<211> LENGTH: 2478
<212> TYPE: DNA
<213> ORGANISM: Nicotiana tabacum

<400> SEQUENCE: 45

| | | | | | | |
|---|---|---|---|---|---|---|
| gtatgtttca | gtctcacaga | gatcgttcat | cgataccaca | gccatgtgga | agcagaaaaa | 60 |
| gagagctctg | cagaagtttt | ggacaccgag | cactctaaat | atgcaagctt | catgacagtg | 120 |
| ggacaactgt | tacaaacggt | aggaaggcaa | ctcgaggaac | ctgctgttga | tgatctcagt | 180 |
| gtaactgacc | ttgtccattt | ggaaaaccaa | ctgccaactg | ctctaatgca | agtcagatct | 240 |
| agcaagacgc | atttgatgat | tgaatctatc | aaaagtcttc | gtgagaagga | aaaactgctg | 300 |
| agtgaagaaa | acaaacatct | ggagaacaag | tacactccag | cttacaactt | caaatcagca | 360 |
| atggctctac | ctatcgacct | cgaagccggc | cttcaagatg | aaaccaacaa | cttggcgccc | 420 |
| ggggccggaa | ggctacctga | cgacggcaac | gaggctcgaa | tcgaagaacc | cgaaattcga | 480 |
| gccgaagtac | cattggatat | caattcacaa | atagctctag | aagcgaatca | gcgttctgaa | 540 |
| ccggaaagaa | gcgttcaggg | cggtgctcga | cccatagccc | gagacaccta | cagcacgggg | 600 |
| gaaatcgggg | tcagcttgcg | tatgattttc | gaaatgttac | aagcccaaca | agcagcgata | 660 |
| gctcagttgc | agagccgaac | tcatatgcaa | agcgggccga | actccaatcc | gcttcttcga | 720 |
| gaagtcaccc | ccagaacgga | gcccgccgta | gtgaaatcaa | acgagcagga | atcggggacc | 780 |
| gctcctgaaa | ttgctaaatt | gctcgaggaa | ctcacaaaac | gagtcgaagc | caacgacaaa | 840 |
| aaagtggaaa | cgtataacgc | tagggtcgat | caaatcccgg | gggctccgcc | aatgataaaa | 900 |
| gggctcgatt | cgaaaaaatt | catacaaaag | ccttttccct | cgagcgcggc | cccaaaacca | 960 |
| atccccaaaa | aattccgtat | gcccgaaatt | cccaaatata | acggtacgac | cgatcctaac | 1020 |
| gaacatgtca | cctcctacac | atgtgccatc | aaaggcaacg | atttggagga | cgatgagatc | 1080 |
| gaatccgtgt | tgttgaaaaa | gttcggagag | accctcgcaa | aggagcaat | gatctggtat | 1140 |
| cacaacttac | caccaaattc | cattgattct | tttgccatgt | tagcagattc | gttcgtaaaa | 1200 |
| gcacatgctg | gtgccataaa | ggttgcaaca | aggaaatcag | acctcttcaa | agtaaaacaa | 1260 |
| agggtaacg | aaatgctgag | ggaattcgta | tcccgatttc | aaatggaacg | tatggacttg | 1320 |

-continued

```
ccaccggtca cagacgattg ggccgtacaa gctttcaccc aaggactgaa cgggctaagt    1380
tcgacagcat cacatcggat gaacaacggt tcagcacgtg atacggttcg gaacaaccga    1440
aggactgatc gggggcaaaa ttctcgggga cttatgagca agagcggctt tgataaatat    1500
gccgatccta tagaagtccc tcgattatcg gagtataact tcaacattga tacatccgcc    1560
atcgtatcgg ccatcggacg catcaaagac accagatggc ctcgacccat gcagaccgat    1620
cctgcccaaa ggaatcccaa tcaaatgtgc gaatatcatg cacccatgg ccacagaacg     1680 gaagattgca ggcaactaag agaggaagtg gcccgcttat ttaacaaagg acaccttcgg    1740
gaatttctga gtgatagggc gaagaaccat tttaggaaca aggaattcgg caagcaaaac    1800
gagccagaag aaccgcaaca cgtcattcac atgatcatcg gcggcgtcga tgcccctcag    1860
ggaccgatgc ttaaacgcac taaaacatcg attgtgaggg aaaagcgatc tcgaactcaa    1920
gattatacac ccatagggac tttgtccttc agtgatgaag atacagaggg aatcatccaa    1980
ccccataacg atgcactggt aatatccgta ctcatgaata aaactaagat taagcgtgtg    2040
ttaattgatc caggtagctc ggccaatatc atcagatcga gggtcgtaga acagctcggc    2100
ctgcaagatc aggtcgtacc cgcaactctg gttctaaacg gattcaatat ggcatgtgaa    2160
accaccaaag gcgagattac cctaccgata acgtggccg gaaccatcca ggaaacaaag     2220
tttcacgtga tcgaaggtga tatgagatat aacgcccttt tcggaaggcc gtggatccac    2280
agcatgagag ccgtaccctc gaccctacac caggtcctca aattcccaac atcgggaggt    2340
gtcaaaatag tgtacggaga acaaccggcc gcaaaggaaa tgttctccgt cgaagaagca    2400
aaatcaatat cctcgtcttc gccgataaaa ggatcaggtt cagaaggaga cacaatcgga    2460
gagcagagcg ccaaatag                                                  2478
```

```
<210> SEQ ID NO 46
<211> LENGTH: 825
<212> TYPE: PRT
<213> ORGANISM: Nicotiana tabacum

<400> SEQUENCE: 46

Val Cys Phe Ser Leu Thr Glu Ile Val His Arg Tyr His Ser His Val
1               5                   10                  15

Glu Ala Glu Lys Glu Ser Ser Ala Glu Val Leu Asp Thr Glu His Ser
            20                  25                  30

Lys Tyr Ala Ser Phe Met Thr Val Gly Gln Leu Leu Gln Thr Val Gly
        35                  40                  45

Arg Gln Leu Glu Glu Pro Ala Val Asp Asp Leu Ser Val Thr Asp Leu
    50                  55                  60

Val His Leu Glu Asn Gln Leu Pro Thr Ala Leu Met Gln Val Arg Ser
65                  70                  75                  80

Ser Lys Thr His Leu Met Ile Glu Ser Ile Lys Ser Leu Arg Glu Lys
                85                  90                  95

Glu Lys Leu Leu Ser Glu Glu Asn Lys His Leu Glu Asn Lys Tyr Thr
            100                 105                 110

Pro Ala Tyr Asn Phe Lys Ser Ala Met Ala Leu Pro Ile Asp Leu Glu
        115                 120                 125

Ala Gly Leu Gln Asp Glu Thr Asn Asn Leu Ala Pro Gly Ala Gly Arg
    130                 135                 140

Leu Pro Asp Asp Gly Asn Glu Ala Arg Ile Glu Glu Pro Glu Ile Arg
145                 150                 155                 160

Ala Glu Val Pro Leu Asp Ile Asn Ser Gln Ile Ala Leu Glu Ala Asn
```

```
                    165                 170                 175
        Gln Arg Ser Glu Pro Glu Arg Ser Val Gln Gly Gly Ala Arg Pro Ile
                        180                 185                 190
        Ala Arg Asp Thr Tyr Ser Thr Gly Glu Ile Gly Val Ser Leu Arg Met
                        195                 200                 205
        Ile Phe Glu Met Leu Gln Ala Gln Ala Ala Ile Ala Gln Leu Gln
                        210                 215                 220
        Ser Arg Thr His Met Gln Ser Gly Pro Asn Ser Asn Pro Leu Leu Arg
        225                 230                 235                 240
        Glu Val Thr Pro Arg Thr Glu Pro Ala Val Lys Ser Asn Glu Gln
                            245                 250                 255
        Glu Ser Gly Thr Ala Pro Glu Ile Ala Lys Leu Leu Glu Glu Leu Thr
                        260                 265                 270
        Lys Arg Val Glu Ala Asn Asp Lys Lys Val Glu Thr Tyr Asn Ala Arg
                        275                 280                 285
        Val Asp Gln Ile Pro Gly Ala Pro Pro Met Ile Lys Gly Leu Asp Ser
                        290                 295                 300
        Lys Lys Phe Ile Gln Lys Pro Phe Pro Ser Ser Ala Ala Pro Lys Pro
        305                 310                 315                 320
        Ile Pro Lys Lys Phe Arg Met Pro Glu Ile Pro Lys Tyr Asn Gly Thr
                            325                 330                 335
        Thr Asp Pro Asn Glu His Val Thr Ser Tyr Thr Cys Ala Ile Lys Gly
                        340                 345                 350
        Asn Asp Leu Glu Asp Asp Glu Ile Glu Ser Val Leu Leu Lys Lys Phe
                        355                 360                 365
        Gly Glu Thr Leu Ala Lys Gly Ala Met Ile Trp Tyr His Asn Leu Pro
                        370                 375                 380
        Pro Asn Ser Ile Asp Ser Phe Ala Met Leu Ala Asp Ser Phe Val Lys
        385                 390                 395                 400
        Ala His Ala Gly Ala Ile Lys Val Ala Thr Arg Lys Ser Asp Leu Phe
                        405                 410                 415
        Lys Val Lys Gln Arg Gly Asn Glu Met Leu Arg Glu Phe Val Ser Arg
                        420                 425                 430
        Phe Gln Met Glu Arg Met Asp Leu Pro Pro Val Thr Asp Asp Trp Ala
                        435                 440                 445
        Val Gln Ala Phe Thr Gln Gly Leu Asn Gly Leu Ser Ser Thr Ala Ser
                        450                 455                 460
        His Arg Met Asn Asn Gly Ser Ala Arg Asp Thr Val Arg Asn Arg
        465                 470                 475                 480
        Arg Thr Asp Arg Gly Gln Asn Ser Arg Gly Leu Met Ser Lys Ser Gly
                            485                 490                 495
        Phe Asp Lys Tyr Ala Asp Pro Ile Glu Val Pro Arg Leu Ser Glu Tyr
                        500                 505                 510
        Asn Phe Asn Ile Asp Thr Ser Ala Ile Val Ser Ala Ile Gly Arg Ile
                        515                 520                 525
        Lys Asp Thr Arg Trp Pro Arg Pro Met Gln Thr Asp Pro Ala Gln Arg
                        530                 535                 540
        Asn Pro Asn Gln Met Cys Glu Tyr His Gly Thr His Gly His Arg Thr
        545                 550                 555                 560
        Glu Asp Cys Arg Gln Leu Arg Glu Val Ala Arg Leu Phe Asn Lys
                            565                 570                 575
        Gly His Leu Arg Glu Phe Leu Ser Asp Arg Ala Lys Asn His Phe Arg
                        580                 585                 590
```

```
Asn Lys Glu Phe Gly Lys Gln Asn Glu Pro Glu Pro Gln His Val
        595                 600                 605

Ile His Met Ile Ile Gly Gly Val Asp Ala Pro Gln Gly Pro Met Leu
    610                 615                 620

Lys Arg Thr Lys Thr Ser Ile Val Arg Glu Lys Arg Ser Arg Thr Gln
625                 630                 635                 640

Asp Tyr Thr Pro Ile Gly Thr Leu Ser Phe Ser Asp Glu Asp Thr Glu
                645                 650                 655

Gly Ile Ile Gln Pro His Asn Asp Ala Leu Val Ile Ser Val Leu Met
                660                 665                 670

Asn Lys Thr Lys Ile Lys Arg Val Leu Ile Asp Pro Gly Ser Ser Ala
                675                 680                 685

Asn Ile Ile Arg Ser Arg Val Val Glu Gln Leu Gly Leu Gln Asp Gln
            690                 695                 700

Val Val Pro Ala Thr Leu Val Leu Asn Gly Phe Asn Met Ala Cys Glu
705                 710                 715                 720

Thr Thr Lys Gly Glu Ile Thr Leu Pro Ile Asn Val Ala Gly Thr Ile
                725                 730                 735

Gln Glu Thr Lys Phe His Val Ile Glu Gly Asp Met Arg Tyr Asn Ala
                740                 745                 750

Leu Phe Gly Arg Pro Trp Ile His Ser Met Arg Ala Val Pro Ser Thr
            755                 760                 765

Leu His Gln Val Leu Lys Phe Pro Thr Ser Gly Val Lys Ile Val
        770                 775                 780

Tyr Gly Glu Gln Pro Ala Ala Lys Glu Met Phe Ser Val Glu Glu Ala
785                 790                 795                 800

Lys Ser Ile Ser Ser Ser Pro Ile Lys Gly Ser Gly Ser Glu Gly
                805                 810                 815

Asp Thr Ile Gly Glu Gln Ser Ala Lys
                820                 825

<210> SEQ ID NO 47
<211> LENGTH: 1152
<212> TYPE: DNA
<213> ORGANISM: Nicotiana tabacum

<400> SEQUENCE: 47
atgcagtctg tactctggaa cctaaggaag attgaaattc aagataaatt ctgcgatatt      60
gaaaggataa gtcctgcata cctcaacaca aatgacacgg caaagaaaat tcaagaagaa     120
atcaatggct tgcattgtaa actggaggag gctgagggat tattaagaat atttgaacca     180
gatacaaaaa aaattacatc actccatgag cttgatttgt gtgaaaaacg tcttcaggtt     240
gccttgaacc aagttaggca agaatggaa caactctcca caatcataa tacatcaagt      300 tatgaagata tatggagca ataaatgca ctccttcaat acatagacaa cacacaaact       360
gaggacacaa accctcgtt ggaggaatct ccctatgact tatggctaga gcttgaagat     420
tatagttaca caaactatat taatgacaac aacaatagtc atctctatgc tgcctcagaa    480
acatcttctc ttactcaaag ttctatgagc ctttcttctc caattattta tgatgcaata   540
tcccaaacaa gtataagtgg tgtgactaat tatcataaag aagggacttt tagttctta     600 actgatgaga attttaagca atcacaacat tcaaccagaa ccttcccaac tctcacttta    660
caaacttcat tcaaatttgc caagcctgaa atggaaactc ccacatctgc actacggccg    720
gtagcgccat atctgcatgt tgaagcaaca gcagcgtgta gccagcaacc agtttcaagt    780
```

-continued

```
gattattata aagagaacaa tgaactcgac tgcagatttc aacctaaagt tacaacgtct      840
aactatcaaa tgtcccaaaa acgtactgca aaggaagtt ttagttcctt aactgatgaa       900
agctttaagc aatcacaatg ttcaaccagg atcttcccac ctatcgctcc attacaaact     960
tcattctcat ttgccacgcc tgaaatggaa actccaacct cagcattgcg gccggtggca    1020
ccatatctgc aggctgaagc agcagcatcc tctaaccagc agctaccttc taataatatt    1080
gaagaagaga accatgaaat ctcttggttt cagcctcaaa tgaaaaagtc gaagtatcat    1140
catttagctt ga                                                        1152
```

<210> SEQ ID NO 48
<211> LENGTH: 383
<212> TYPE: PRT
<213> ORGANISM: Nicotiana tabacum

<400> SEQUENCE: 48

```
Met Gln Ser Val Leu Trp Asn Leu Arg Lys Ile Glu Ile Gln Asp Lys
1               5                   10                  15

Phe Cys Asp Ile Glu Arg Ile Ser Pro Ala Tyr Leu Asn Thr Asn Asp
                20                  25                  30

Thr Ala Lys Lys Ile Gln Glu Glu Ile Asn Gly Leu His Cys Lys Leu
            35                  40                  45

Glu Glu Ala Glu Gly Leu Leu Arg Ile Phe Glu Pro Asp Thr Lys Lys
        50                  55                  60

Ile Thr Ser Leu His Glu Leu Asp Leu Cys Glu Lys Arg Leu Gln Val
65                  70                  75                  80

Ala Leu Asn Gln Val Arg Gln Arg Met Glu Gln Leu Ser Asn Asn His
                85                  90                  95

Asn Thr Ser Ser Tyr Glu Asp Asn Met Glu Gln Ile Asn Ala Leu Leu
            100                 105                 110

Gln Tyr Ile Asp Asn Thr Gln Thr Glu Asp Thr Lys Pro Ser Leu Glu
        115                 120                 125

Glu Ser Pro Tyr Asp Leu Trp Leu Glu Leu Glu Asp Tyr Ser Tyr Thr
    130                 135                 140

Asn Tyr Ile Asn Asp Asn Asn Ser His Leu Tyr Ala Ala Ser Glu
145                 150                 155                 160

Thr Ser Ser Leu Thr Gln Ser Ser Met Ser Leu Ser Ser Pro Ile Ile
                165                 170                 175

Tyr Asp Ala Ile Ser Gln Thr Ser Ile Ser Gly Val Thr Asn Tyr His
            180                 185                 190

Lys Glu Gly Thr Phe Ser Ser Leu Thr Asp Glu Asn Phe Lys Gln Ser
        195                 200                 205

Gln His Ser Thr Arg Thr Phe Pro Thr Leu Thr Gln Thr Ser Phe
    210                 215                 220

Lys Phe Ala Lys Pro Glu Met Glu Thr Pro Thr Ser Ala Leu Arg Pro
225                 230                 235                 240

Val Ala Pro Tyr Leu His Val Glu Ala Thr Ala Ala Cys Ser Gln Gln
                245                 250                 255

Pro Val Ser Ser Asp Tyr Tyr Lys Glu Asn Asn Glu Leu Asp Cys Arg
            260                 265                 270

Phe Gln Pro Lys Val Thr Thr Ser Asn Tyr Gln Met Ser Gln Lys Arg
        275                 280                 285

Thr Ala Glu Gly Ser Phe Ser Ser Leu Thr Asp Glu Ser Phe Lys Gln
    290                 295                 300
```

```
Ser Gln Cys Ser Thr Arg Ile Phe Pro Pro Ile Ala Pro Leu Gln Thr
305                 310                 315                 320

Ser Phe Ser Phe Ala Thr Pro Glu Met Glu Thr Pro Thr Ser Ala Leu
            325                 330                 335

Arg Pro Val Ala Pro Tyr Leu Gln Ala Glu Ala Ala Ser Ser Asn
        340                 345                 350

Gln Gln Leu Pro Ser Asn Asn Ile Glu Glu Asn His Glu Ile Ser
    355                 360                 365

Trp Phe Gln Pro Gln Met Lys Lys Ser Lys Tyr His His Leu Ala
    370                 375                 380
```

<210> SEQ ID NO 49
<211> LENGTH: 813
<212> TYPE: DNA
<213> ORGANISM: Nicotiana tabacum

<400> SEQUENCE: 49

```
atgggaactg gtacttatgg agaagtggga cgtacaatac atcaaagatc aggaacacat      60
atacctcaaa ttctcgatcc gcctttgcta ggggatagtg attgcaagcg agaaggcaaa     120
catgtagaat ttatgcctcc aatcatgggt gaaaacttaa aagcagctaa tcaatttgaa     180
ctgatggccc cgtcaattgc attcaaatca tatccctatt cggaggtacc acaatattct     240
ggtggcaatg tggctgctgc atgtggtgaa tctttggtac atcaaaatat agaaagatca     300
gtgcataatg gtagaatgat tttgccaatt gaagtgaagg aggagcctat gtatgtaaat     360
gccaaacaat accatggaat tctaaggcga aggcaacttc gtgcaaaggc tgtgttggag     420
caaaaagtgg ttaaatctag aaagccttat cttcatgaat ctcggcaccg gcatgcgatg     480
agaagagcta gagatggtgg aggccgattt ctcaacacaa aaagaagat ccaacttcct      540
gctaataata atattaatac aactactcca gtagtaaag gcaaaggttg tgcagcctcg      600
gaagtcagtt ccatggactc tgatttctct caaaattact tgctcaattc tggacatatt     660
ggatcatcca atgctacttc tgttgaagga ttccagttcc aaggaataca taatacagat     720
aatcctcaat gggttgtca ttatcagtgg aatctcaatg acaaccattg ctattgcatg      780
cagtcaggag cttctaatct ccaaccattt tga                                  813
```

<210> SEQ ID NO 50
<211> LENGTH: 270
<212> TYPE: PRT
<213> ORGANISM: Nicotiana tabacum

<400> SEQUENCE: 50

```
Met Gly Thr Gly Thr Tyr Gly Glu Val Gly Arg Thr Ile His Gln Arg
1               5                   10                  15

Ser Gly Thr His Ile Pro Gln Ile Leu Asp Pro Pro Leu Leu Gly Asp
            20                  25                  30

Ser Asp Cys Lys Arg Glu Gly Lys His Val Phe Met Pro Pro Ile
        35                  40                  45

Met Gly Glu Asn Leu Lys Ala Ala Asn Gln Phe Glu Leu Met Ala Pro
    50                  55                  60

Ser Ile Ala Phe Lys Ser Tyr Pro Tyr Ser Glu Val Pro Gln Tyr Ser
65                  70                  75                  80

Gly Gly Asn Val Ala Ala Ala Cys Gly Glu Ser Leu Val His Gln Asn
            85                  90                  95

Ile Glu Arg Ser Val His Asn Gly Arg Met Ile Leu Pro Ile Glu Val
```

```
            100                 105                 110
Lys Glu Glu Pro Met Tyr Val Asn Ala Lys Gln Tyr His Gly Ile Leu
            115                 120                 125

Arg Arg Arg Gln Leu Arg Ala Lys Ala Val Leu Glu Gln Lys Val Val
        130                 135                 140

Lys Ser Arg Lys Pro Tyr Leu His Glu Ser Arg His Arg His Ala Met
145                 150                 155                 160

Arg Arg Ala Arg Asp Gly Gly Gly Arg Phe Leu Asn Thr Lys Lys Lys
                165                 170                 175

Ile Gln Leu Pro Ala Asn Asn Asn Ile Asn Thr Thr Pro Ser Ser
            180                 185                 190

Lys Gly Lys Gly Cys Ala Ala Ser Glu Val Ser Ser Met Asp Ser Asp
            195                 200                 205

Phe Ser Gln Asn Tyr Leu Leu Asn Ser Gly His Ile Gly Ser Ser Asn
            210                 215                 220

Ala Thr Ser Val Glu Gly Phe Gln Phe Gln Gly Ile His Asn Thr Asp
225                 230                 235                 240

Asn Pro Gln Leu Gly Cys His Tyr Gln Trp Asn Leu Asn Asp Asn His
                245                 250                 255

Cys Tyr Cys Met Gln Ser Gly Ala Ser Asn Leu Gln Pro Phe
                260                 265                 270

<210> SEQ ID NO 51
<211> LENGTH: 762
<212> TYPE: DNA
<213> ORGANISM: Nicotiana tabacum

<400> SEQUENCE: 51
atgggagctg gtgcttttgg agaagccgga cgtacaatat atcaaaagtc cgatagtgat      60
tgcaagcgag atggcaaacg tgtagaattt atgcctccaa tcatgggtga aaacttaaga     120
gcagctaatc aatttgaact gatgcccccc tcaattgcat tcagatcata tccctattca     180
gaagtaccac aatattctgg tggcaatgtg ctgctgcat ttggcgaatc tacggtacat      240
caaaatatag aaagatcagt gcataatggt agaatgattt tgccacttga agtgaaggag     300
gagcctatgt atgtaaatgc caaacaatac catggaattc taaggcgaag gcaactccgt     360
gcaaaggctg tgttggagca aaaggtggtc aaatctagaa agccttatct tcatgaatct     420
cggcaccggc atgcgatgag aagagctaga gatggtggcg gccgatttct caacacaaag     480
aagaagatcc aacttactac taataataat aataataatg gaatactaa tgcaactcca      540 agtagtaaag gcaaaggttc ttcagcctca gaagtcagtt ccatggactc ttattctgga     600
catattggat catccaatag tactgctcat gtccagggga ttcagttcca aggaatacat     660
aatacagaaa atcctcaact gggttgtcat tatcagtgga atctcaatga taaccattgc     720
aattgcatgc agtcaggagc ttctaatatc caaccatttt ga                        762

<210> SEQ ID NO 52
<211> LENGTH: 253
<212> TYPE: PRT
<213> ORGANISM: Nicotiana tabacum

<400> SEQUENCE: 52

Met Gly Ala Gly Ala Phe Gly Glu Ala Gly Arg Thr Ile Tyr Gln Lys
1               5                   10                  15

Ser Asp Ser Asp Cys Lys Arg Asp Gly Lys Arg Val Glu Phe Met Pro
            20                  25                  30
```

Pro Ile Met Gly Glu Asn Leu Arg Ala Ala Asn Gln Phe Glu Leu Met
            35                  40                  45

Pro Pro Ser Ile Ala Phe Arg Ser Tyr Pro Tyr Ser Glu Val Pro Gln
        50                  55                  60

Tyr Ser Gly Gly Asn Val Ala Ala Phe Gly Glu Ser Thr Val His
 65                  70                  75                  80

Gln Asn Ile Glu Arg Ser Val His Asn Gly Arg Met Ile Leu Pro Leu
                85                  90                  95

Glu Val Lys Glu Glu Pro Met Tyr Val Asn Ala Lys Gln Tyr His Gly
            100                 105                 110

Ile Leu Arg Arg Arg Gln Leu Arg Ala Lys Ala Val Leu Glu Gln Lys
            115                 120                 125

Val Val Lys Ser Arg Lys Pro Tyr Leu His Glu Ser Arg His Arg His
        130                 135                 140

Ala Met Arg Arg Ala Arg Asp Gly Gly Arg Phe Leu Asn Thr Lys
145                 150                 155                 160

Lys Lys Ile Gln Leu Thr Thr Asn Asn Asn Asn Asn Gly Asn Thr
                165                 170                 175

Asn Ala Thr Pro Ser Ser Lys Gly Lys Gly Ser Ser Ala Ser Glu Val
                180                 185                 190

Ser Ser Met Asp Ser Tyr Ser Gly His Ile Gly Ser Ser Asn Ser Thr
            195                 200                 205

Ala His Val Gln Gly Phe Gln Phe Gln Gly Ile His Asn Thr Glu Asn
210                 215                 220

Pro Gln Leu Gly Cys His Tyr Gln Trp Asn Leu Asn Asp Asn His Cys
225                 230                 235                 240

Asn Cys Met Gln Ser Gly Ala Ser Asn Ile Gln Pro Phe
                245                 250

<210> SEQ ID NO 53
<211> LENGTH: 753
<212> TYPE: DNA
<213> ORGANISM: Nicotiana tabacum

<400> SEQUENCE: 53
atgcaatatg aacacgaatt tttcttccaa tattaccatg atcaacttca acagaatctt      60
gatgatacct agctgagat cagtactgag actgccatta ttaacacggc agattccaac     120
aaagacgacg ctttaataag tagaaatgaa cttgaacaag aggaaggatg tgagaataaa     180
aagggtaaaa taagcagcaa caagagagtg tctaagaaag atagacacag tgcaaatagt     240
gaatcctcta cttctgaatg tgaagttgta tcagaaattg atgaatctcc atctaatcat     300
aaggcaaatc taaaggaaa ttcttgcaac aaggagaagg agaagaagaa gaaggagaag     360
gagaaatcag ttcgtcgagc tgcatttat catccatttg caaagaatc aaggaaacaa     420 gcaagagaga gggcaaggga gagaacaaaa ctaaagaaaa acttttgtaa atctcatcat     480
ttgaacttaa gatcttggaa tttctccgaa gggggcgaag aatcagcggg atatattagc     540
atgaatcttc cttgtcaaga aatgcaagct gaaatagttg aagaactcac ctcccacaat     600
gagaagcagc ttttattagg gattaaagaa acattgcta atgattgtaa tttggtggct     660
actggcaatt ggagcccaaa tgccattttc aactatcaac aaaatgctgg aattcctcat     720
gagcatcaaa ttacagacat tccgttttca tga                                 753

<210> SEQ ID NO 54

<211> LENGTH: 250
<212> TYPE: PRT
<213> ORGANISM: Nicotiana tabacum

<400> SEQUENCE: 54

```
Met Gln Tyr Glu His Glu Phe Phe Gln Tyr Tyr His Asp Gln Leu
1               5                   10                  15

Gln Gln Asn Leu Asp Asp Thr Leu Ala Glu Ile Ser Thr Glu Thr Ala
            20                  25                  30

Ile Ile Asn Thr Ala Asp Ser Asn Lys Asp Asp Ala Leu Ile Ser Arg
            35                  40                  45

Asn Glu Leu Glu Gln Glu Glu Gly Cys Glu Asn Lys Lys Gly Lys Ile
50                  55                  60

Ser Ser Asn Lys Arg Val Ser Lys Lys Asp Arg His Ser Ala Asn Ser
65                  70                  75                  80

Glu Ser Ser Thr Ser Glu Cys Glu Val Val Ser Glu Ile Asp Glu Ser
                85                  90                  95

Pro Ser Asn His Lys Ala Asn Ala Lys Gly Asn Ser Cys Asn Lys Glu
            100                 105                 110

Lys Glu Lys Lys Lys Lys Glu Lys Glu Lys Ser Val Arg Arg Ala Ala
            115                 120                 125

Phe Tyr His Pro Phe Ala Lys Glu Ser Arg Lys Gln Ala Arg Glu Arg
            130                 135                 140

Ala Arg Glu Arg Thr Lys Leu Lys Lys Asn Phe Cys Lys Ser His His
145                 150                 155                 160

Leu Asn Leu Arg Ser Trp Asn Phe Ser Glu Gly Gly Glu Ser Ala
                165                 170                 175

Gly Tyr Ile Ser Met Asn Leu Pro Cys Gln Glu Met Gln Ala Glu Ile
            180                 185                 190

Val Glu Glu Leu Thr Ser His Asn Glu Lys Gln Leu Leu Leu Gly Ile
            195                 200                 205

Lys Glu Asn Ile Ala Asn Asp Cys Asn Leu Val Ala Thr Gly Asn Trp
            210                 215                 220

Ser Pro Asn Ala Ile Phe Asn Tyr Gln Gln Asn Ala Gly Ile Pro His
225                 230                 235                 240

Glu His Gln Ile Thr Asp Ile Pro Phe Ser
                245                 250
```

<210> SEQ ID NO 55
<211> LENGTH: 1422
<212> TYPE: DNA
<213> ORGANISM: Arabidopsis thaliana

<400> SEQUENCE: 55

```
atgatgaagc atatagtaca tctgggctcc acctcaaatc ttacagtagc agctagaggc      60
catggtcact cgcttcaagg acaagctcta gctcatcaag gtgttgtcat caaaatggag     120
tcacttcgaa gtcctgatat caggatttat aagggaagc aaccatatgt tgatgtctca     180
ggtggtgaaa tatggataaa cattctacgc gagactctaa atacggtct tcaccaaag      240 tcctggacag actaccttca tttgaccgtt ggaggtacac tatctaatgc tggaatcagc    300
ggtcaagcat tcaagcatgg accccaaatc aacaacgtct accagctaga gattgttaca    360
gggaaaggag aagtcgtaac ctgttctgag aagcggaatt ctgaactttt cttcagtgtt    420
cttggcgggc ttggacagtt tggcataatc cccgggcac ggatctctct tgaaccagca     480
ccgcatatgg ttaaatggat caggtactc tactctgact tttctgcatt tcaagggac      540
```

-continued

```
caagaatatc tgatttcgaa ggagaaaact tttgattacg ttgaaggatt tgtgataatc    600
aatagaacag accttctcaa taattggcga tcgtcattca gtcccaacga ttccacacag    660
gcaagcagat tcaagtcaga tgggaaaact ctttattgcc tagaagtggt caaatatttc    720
aacccagaag aagctagctc tatggatcag gaaactggca agttactttc agagttaaat    780
tatattccat ccactttgtt ttcatctgaa gtgccatata tcgagtttct ggatcgcgtg    840
catatcgcag agagaaaact aagagcaaag ggtttatggg aggttccaca tccctggctg    900
aatctcctga ttcctaagag cagcatatac caatttgcta cagaagtttt caacaacatt    960
ctcacaagca acaacaacgg tcctatcctt atttatccag tcaatcaatc caagtggaag   1020
aaacatacat ctttgataac tccaaatgaa gatatattct atctcgtagc ctttctcccc   1080
tctgcagtgc caaattcctc agggaaaaac gatctagagt accttttgaa acaaaaccaa   1140
agagttatga acttctgcgc agcagcaaac ctcaacgtga agcagtattt gccccattat   1200
gaaactcaaa aagagtggaa atcacacttt ggcaaaagat gggaaacatt tgcacagagg   1260
aaacaagcct acgaccctct agcgattcta gcacctggcc aaagaatatt ccaaaagaca   1320
acaggaaaat tatctcccat ccaactcgca aagtcaaagg caacaggaag tcctcaaagg   1380
taccattacg catcaatact gccgaaacct agaactgtat aa                      1422
```

<210> SEQ ID NO 56
<211> LENGTH: 473
<212> TYPE: PRT
<213> ORGANISM: Arabidopsis thaliana

<400> SEQUENCE: 56

```
Met Met Lys His Ile Val His Leu Gly Ser Thr Ser Asn Leu Thr Val
1               5                   10                  15

Ala Ala Arg Gly His Gly His Ser Leu Gln Gly Gln Ala Leu Ala His
                20                  25                  30

Gln Gly Val Val Ile Lys Met Glu Ser Leu Arg Ser Pro Asp Ile Arg
            35                  40                  45

Ile Tyr Lys Gly Lys Gln Pro Tyr Val Asp Val Ser Gly Gly Glu Ile
        50                  55                  60

Trp Ile Asn Ile Leu Arg Glu Thr Leu Lys Tyr Gly Leu Ser Pro Lys
65                  70                  75                  80

Ser Trp Thr Asp Tyr Leu His Leu Thr Val Gly Gly Thr Leu Ser Asn
                85                  90                  95

Ala Gly Ile Ser Gly Gln Ala Phe Lys His Gly Pro Gln Ile Asn Asn
                100                 105                 110

Val Tyr Gln Leu Glu Ile Val Thr Gly Lys Gly Glu Val Val Thr Cys
            115                 120                 125

Ser Glu Lys Arg Asn Ser Glu Leu Phe Phe Ser Val Leu Gly Gly Leu
        130                 135                 140

Gly Gln Phe Gly Ile Ile Thr Arg Ala Arg Ile Ser Leu Glu Pro Ala
145                 150                 155                 160

Pro His Met Val Lys Trp Ile Arg Val Leu Tyr Ser Asp Phe Ser Ala
                165                 170                 175

Phe Ser Arg Asp Gln Glu Tyr Leu Ile Ser Lys Glu Lys Thr Phe Asp
                180                 185                 190

Tyr Val Glu Gly Phe Val Ile Ile Asn Arg Thr Asp Leu Leu Asn Asn
            195                 200                 205

Trp Arg Ser Ser Phe Ser Pro Asn Asp Ser Thr Gln Ala Ser Arg Phe
```

```
                    210                 215                 220
Lys Ser Asp Gly Lys Thr Leu Tyr Cys Leu Glu Val Lys Tyr Phe
225                 230                 235                 240

Asn Pro Glu Glu Ala Ser Ser Met Asp Gln Glu Thr Gly Lys Leu Leu
                245                 250                 255

Ser Glu Leu Asn Tyr Ile Pro Ser Thr Leu Phe Ser Ser Glu Val Pro
            260                 265                 270

Tyr Ile Glu Phe Leu Asp Arg Val His Ile Ala Glu Arg Lys Leu Arg
            275                 280                 285

Ala Lys Gly Leu Trp Glu Val Pro His Pro Trp Leu Asn Leu Leu Ile
        290                 295                 300

Pro Lys Ser Ser Ile Tyr Gln Phe Ala Thr Glu Val Phe Asn Asn Ile
305                 310                 315                 320

Leu Thr Ser Asn Asn Asn Gly Pro Ile Leu Ile Tyr Pro Val Asn Gln
                325                 330                 335

Ser Lys Trp Lys Lys His Thr Ser Leu Ile Thr Pro Asn Glu Asp Ile
            340                 345                 350

Phe Tyr Leu Val Ala Phe Leu Pro Ser Ala Val Pro Asn Ser Ser Gly
            355                 360                 365

Lys Asn Asp Leu Glu Tyr Leu Leu Lys Gln Asn Gln Arg Val Met Asn
        370                 375                 380

Phe Cys Ala Ala Ala Asn Leu Asn Val Lys Gln Tyr Leu Pro His Tyr
385                 390                 395                 400

Glu Thr Gln Lys Glu Trp Lys Ser His Phe Gly Lys Arg Trp Glu Thr
                405                 410                 415

Phe Ala Gln Arg Lys Gln Ala Tyr Asp Pro Leu Ala Ile Leu Ala Pro
            420                 425                 430

Gly Gln Arg Ile Phe Gln Lys Thr Thr Gly Lys Leu Ser Pro Ile Gln
            435                 440                 445

Leu Ala Lys Ser Lys Ala Thr Gly Ser Pro Gln Arg Tyr His Tyr Ala
        450                 455                 460

Ser Ile Leu Pro Lys Pro Arg Thr Val
465                 470
```

<210> SEQ ID NO 57
<211> LENGTH: 1659
<212> TYPE: DNA
<213> ORGANISM: Nicotiana tabacum

<400> SEQUENCE: 57

| | | | | | |
|---|---|---|---|---|---|
| atgaagtcac | caccaactca | tgtcttcttt | aaacataaaa | gtatgcttct | taggttgctt | 60 |
| atattcatac | taggcatttg | ctcaataaac | agaactaacc | tttgttgtga | ccaacctttt | 120 |
| gccaccccaa | tatcttcttc | ttcttctacc | ccttcaagtt | tttcagtgat | tcaatcatca | 180 |
| ttgaaacagt | taaatattga | agggtatttt | agtttcaaga | atttcgatca | cgcggccaaa | 240 |
| gactttggca | acagatatca | cttcttgcca | tcggcagttc | tgtatccaaa | tcagtttct | 300 |
| gatatatcat | ctaccataaa | acatgttttt | gacatgggtg | ttactacaga | cctaactgtt | 360 |
| gctgctagag | ccatggcca | ttctttagaa | ggccaagctc | aagcttacca | aggagtagtg | 420 |
| atcaatatgg | aatcgcttcg | agcgccagca | atgcgtttcc | acacagggaa | tcaagaactg | 480 |
| ccttttgttg | atgtctctgc | aggagaactt | tggataaaca | tcctgcatga | aagtcttaaa | 540 |
| cttggattaa | caccaaaatc | ttggactgat | tatcttcacc | tcaccgttgg | agggactttg | 600 |
| tcgaatgccg | gaatcagtgg | tcaagcattc | aaacatggac | cacagatcaa | taatgtttac | 660 |

```
caacttgagg ttgtcactgg taaaggagag gtgattactt gttcagagga gaagaatgct    720
gacctgttct atggtgtatt aggaggacta ggccagtttg gtatcatcac aagggctaga    780
attgctcttg aaccagcacc taaaaaggta aagtggatca gagtgctgta ttcagatttc    840
tccacatttt cctatgatca agaacacttg atatcatccg agaactcttt tgactatata    900
gaaggatttg tcattatcaa tagaacagga ttgttaaaca actggaggtc tactttcaat    960
cctaaagatc cacttctagc caaagagttc agttctgagg aaaagttct gtactgccta   1020 gaagttgcca atacttcaa tccagaagag acaaccaaaa ctgatcagaa tgttgatgtt   1080
cttttatcaa agttgaatta tatccaatcg acgctgttcc aatcagaagt atcctacgtg   1140
gatttcctcg acagagttca cgtatccgag atgaaacttc aagagaaggg gttatgggat   1200
attcctcatc catggctaaa ccttctaatt ccaaagagca agattcatga ctttgcacga   1260 gaagttttg ggaagatact taccgacact agccacggtc ctatactcat ctacccagtc   1320
aacaaatcaa agtggagaaa aggaacatca gtagttacac ctgaagaaga tgttatgtat   1380
ctaatagcat ttctatcttc tgccatgcca tcttcaacag gaaaggacgg cgtagaatat   1440
attctaaata gaataagaa gatactaaac ttttgcagaa aagcacatat tggaatgaaa   1500
cagtatttgc cacactacac aacgcaggaa gactggaaag gtcactttgg tccccagtgg   1560
gaaacattta aaggaggaa atctacatat gaccctttgg ctatcctagc tcctggccag   1620
agaattttta gaagagcatc aggcgttcaa caacaatga                          1659
```

<210> SEQ ID NO 58
<211> LENGTH: 552
<212> TYPE: PRT
<213> ORGANISM: Nicotiana tabacum

<400> SEQUENCE: 58

```
Met Lys Ser Pro Pro Thr His Val Phe Phe Lys His Lys Ser Met Leu
1               5                   10                  15

Leu Arg Leu Leu Ile Phe Ile Leu Gly Ile Cys Ser Ile Asn Arg Thr
            20                  25                  30

Asn Leu Cys Cys Asp Gln Pro Phe Ala Thr Pro Ile Ser Ser Ser Ser
        35                  40                  45

Ser Thr Pro Ser Ser Phe Ser Val Ile Gln Ser Ser Leu Lys Gln Leu
    50                  55                  60

Asn Ile Glu Gly Tyr Phe Ser Phe Lys Asn Phe Asp His Ala Ala Lys
65                  70                  75                  80

Asp Phe Gly Asn Arg Tyr His Phe Leu Pro Ser Ala Val Leu Tyr Pro
                85                  90                  95

Lys Ser Val Ser Asp Ile Ser Ser Thr Ile Lys His Val Phe Asp Met
            100                 105                 110

Gly Val Thr Thr Asp Leu Thr Val Ala Ala Arg Gly His Gly His Ser
        115                 120                 125

Leu Glu Gly Gln Ala Gln Ala Tyr Gln Gly Val Val Ile Asn Met Glu
    130                 135                 140

Ser Leu Arg Ala Pro Ala Met Arg Phe His Thr Gly Asn Gln Glu Leu
145                 150                 155                 160

Pro Phe Val Asp Val Ser Ala Gly Glu Leu Trp Ile Asn Ile Leu His
                165                 170                 175

Glu Ser Leu Lys Leu Gly Leu Thr Pro Lys Ser Trp Thr Asp Tyr Leu
            180                 185                 190
```

-continued

His Leu Thr Val Gly Gly Thr Leu Ser Asn Ala Gly Ile Ser Gly Gln
            195                 200                 205

Ala Phe Lys His Gly Pro Gln Ile Asn Asn Val Tyr Gln Leu Glu Val
    210                 215                 220

Val Thr Gly Lys Gly Glu Val Ile Thr Cys Ser Glu Glu Lys Asn Ala
225                 230                 235                 240

Asp Leu Phe Tyr Gly Val Leu Gly Gly Leu Gly Gln Phe Gly Ile Ile
                245                 250                 255

Thr Arg Ala Arg Ile Ala Leu Glu Pro Ala Pro Lys Lys Val Lys Trp
                    260                 265                 270

Ile Arg Val Leu Tyr Ser Asp Phe Ser Thr Phe Ser Tyr Asp Gln Glu
                275                 280                 285

His Leu Ile Ser Ser Glu Asn Ser Phe Asp Tyr Ile Glu Gly Phe Val
            290                 295                 300

Ile Ile Asn Arg Thr Gly Leu Leu Asn Asn Trp Arg Ser Thr Phe Asn
305                 310                 315                 320

Pro Lys Asp Pro Leu Leu Ala Lys Glu Phe Ser Ser Glu Gly Lys Val
                325                 330                 335

Leu Tyr Cys Leu Glu Val Ala Lys Tyr Phe Asn Pro Glu Glu Thr Thr
                340                 345                 350

Lys Thr Asp Gln Asn Val Asp Val Leu Leu Ser Lys Leu Asn Tyr Ile
            355                 360                 365

Gln Ser Thr Leu Phe Gln Ser Glu Val Ser Tyr Val Asp Phe Leu Asp
            370                 375                 380

Arg Val His Val Ser Glu Met Lys Leu Gln Lys Gly Leu Trp Asp
385                 390                 395                 400

Ile Pro His Pro Trp Leu Asn Leu Leu Ile Pro Lys Ser Lys Ile His
                405                 410                 415

Asp Phe Ala Arg Glu Val Phe Gly Lys Ile Leu Thr Asp Thr Ser His
                420                 425                 430

Gly Pro Ile Leu Ile Tyr Pro Val Asn Lys Ser Lys Trp Arg Lys Gly
            435                 440                 445

Thr Ser Val Val Thr Pro Glu Glu Asp Val Met Tyr Leu Ile Ala Phe
450                 455                 460

Leu Ser Ser Ala Met Pro Ser Ser Thr Gly Lys Asp Gly Val Glu Tyr
465                 470                 475                 480

Ile Leu Asn Lys Asn Lys Lys Ile Leu Asn Phe Cys Arg Lys Ala His
                485                 490                 495

Ile Gly Met Lys Gln Tyr Leu Pro His Tyr Thr Thr Gln Glu Asp Trp
            500                 505                 510

Lys Gly His Phe Gly Pro Gln Trp Glu Thr Phe Lys Arg Arg Lys Ser
            515                 520                 525

Thr Tyr Asp Pro Leu Ala Ile Leu Ala Pro Gly Gln Arg Ile Phe Arg
            530                 535                 540

Arg Ala Ser Gly Val Gln Gln Gln
545                 550

<210> SEQ ID NO 59
<211> LENGTH: 1632
<212> TYPE: DNA
<213> ORGANISM: Nicotiana tabacum

<400> SEQUENCE: 59
atgaaattac catcccattt tttatttaag caaaatgact tgctcctgaa attgcttata      60

-continued

```
ttcatactct gcagttgttc aagcaacaaa aataaactct gctgtaatta tcatcagttt     120
gccacccctg cagtttctac cccctcaagt ttctcactga attatttatc attgaaacaa     180
ttacaacttg aaggttacct taaatttgac aacttagaac atgcagccaa agactttggt     240
aatagatgcc acttccttcc attagcagtt ttgtacccaa atcagtttc tgatatctct     300
tccactataa acatgtctt tgaaataggt tccaaaactg atttaactgt tgctgctaga     360
ggccatggcc attctctaga aggtcaagct caagcttatc aaggagtagt gattagtatg     420
gaatcactac aaacaccagc aatgaaattc aagactggag aattgcctta tgttgatgtt     480
tctgctggag agctttggat taatatcctg aaagaaagtc ttaaacttgg gcttgcacct     540
aaatcttgga ctgattatct tcacctcaca gttggcggca ctttgtctaa tgctggaatc     600
agtggacaag ctttccgcca cggaccgcag atcaataacg tccaacaact tgaagttgtc     660
actggtaaag gagaggtgat tacttgttca gaggagcaga atgcagactt gtttcatggt     720
gtactaggag gactggggca atttggtatt attaccagag caaggattgc tcttgaaaca     780
gcacctaaac aggtcaagtg gattagagtg ctgtattcag atttttccat attttccaat     840
gatcaagagc acttgatatc aactcaggat acatttgact atattgaagg ttttgtcact     900
atcaaccaaa ctggattatt aaataactgg aggtctgctt tcaatcctaa agatccagtt     960
ctagccagca atttcagttc tgagggtaga gttttgttct gcttagaaat tgccaaatac    1020
ttcaatccag aagtcacaga tagtattgat cagaacattg atgtgatctt atcaaagttg    1080
aattatatcc gatccacgct gttcctatca gaagtctcct acacagaatt cctcgacagg    1140
gtgcatgtct ctgagatgaa actccaagaa atgtttctc atccatggct aaatcttcta    1200
ataccaaaaa gcaggattct tgaatttgca caacaagttt ttggcaagat tcttactgac    1260
actagcaatg tcctttact catctaccct gtcaacaaat caaagtggag aaaaggaaca    1320
tccatggtta cccctgacga agatgttttt tatctgatcg cgttcctatc ttctgctatg    1380
tcatcttcaa caggaaacga tggactaaga catattcttg ctcagagcaa aaggatactg    1440
aacttttgtg aagaaacaaa tatcggaatg aaacaatatt taccaaatta caagactaag    1500
gaagagtgga aggatcactt tggtcatcaa tgggaagcat tgctagaag gaaatctaca    1560
tatgaccctt tggcaatact tgctcctggc cagagaattt tcagaagggc agaagcctgt    1620
gaacaacaat aa                                                       1632
```

<210> SEQ ID NO 60
<211> LENGTH: 543
<212> TYPE: PRT
<213> ORGANISM: Nicotiana tabacum

<400> SEQUENCE: 60

```
Met Lys Leu Pro Ser His Phe Leu Phe Lys Gln Asn Asp Leu Leu Leu
1               5                   10                  15

Lys Leu Leu Ile Phe Ile Leu Cys Ser Cys Ser Ser Asn Lys Asn Lys
            20                  25                  30

Leu Cys Cys Asn Tyr His Gln Phe Ala Thr Pro Ala Val Ser Thr Pro
        35                  40                  45

Ser Ser Phe Ser Leu Asn Tyr Leu Ser Leu Lys Gln Leu Gln Leu Glu
    50                  55                  60

Gly Tyr Leu Lys Phe Asp Asn Leu Glu His Ala Ala Lys Asp Phe Gly
65                  70                  75                  80

Asn Arg Cys His Phe Leu Pro Leu Ala Val Leu Tyr Pro Lys Ser Val
                85                  90                  95
```

-continued

```
Ser Asp Ile Ser Ser Thr Ile Lys His Val Phe Glu Ile Gly Ser Lys
            100                 105                 110

Thr Asp Leu Thr Val Ala Ala Arg Gly His Gly His Ser Leu Glu Gly
            115                 120                 125

Gln Ala Gln Ala Tyr Gln Gly Val Val Ile Ser Met Glu Ser Leu Gln
        130                 135                 140

Thr Pro Ala Met Lys Phe Lys Thr Gly Glu Leu Pro Tyr Val Asp Val
145                 150                 155                 160

Ser Ala Gly Glu Leu Trp Ile Asn Ile Leu Lys Glu Ser Leu Lys Leu
                165                 170                 175

Gly Leu Ala Pro Lys Ser Trp Thr Asp Tyr Leu His Leu Thr Val Gly
            180                 185                 190

Gly Thr Leu Ser Asn Ala Gly Ile Ser Gly Gln Ala Phe Arg His Gly
        195                 200                 205

Pro Gln Ile Asn Asn Val Gln Gln Leu Glu Val Val Thr Gly Lys Gly
        210                 215                 220

Glu Val Ile Thr Cys Ser Glu Gln Asn Ala Asp Leu Phe His Gly
225                 230                 235                 240

Val Leu Gly Gly Leu Gly Gln Phe Gly Ile Ile Thr Arg Ala Arg Ile
                245                 250                 255

Ala Leu Glu Thr Ala Pro Lys Gln Val Lys Trp Ile Arg Val Leu Tyr
            260                 265                 270

Ser Asp Phe Ser Ile Phe Ser Asn Asp Gln Glu His Leu Ile Ser Thr
        275                 280                 285

Gln Asp Thr Phe Asp Tyr Ile Glu Gly Phe Val Thr Ile Asn Gln Thr
        290                 295                 300

Gly Leu Leu Asn Asn Trp Arg Ser Ala Phe Asn Pro Lys Asp Pro Val
305                 310                 315                 320

Leu Ala Ser Asn Phe Ser Ser Glu Gly Arg Val Leu Phe Cys Leu Glu
                325                 330                 335

Ile Ala Lys Tyr Phe Asn Pro Glu Val Thr Asp Ser Ile Asp Gln Asn
            340                 345                 350

Ile Asp Val Ile Leu Ser Lys Leu Asn Tyr Ile Arg Ser Thr Leu Phe
        355                 360                 365

Leu Ser Glu Val Ser Tyr Thr Glu Phe Leu Asp Arg Val His Val Ser
        370                 375                 380

Glu Met Lys Leu Gln Glu Asn Val Ser His Pro Trp Leu Asn Leu Leu
385                 390                 395                 400

Ile Pro Lys Ser Arg Ile Leu Glu Phe Ala Gln Gln Val Phe Gly Lys
                405                 410                 415

Ile Leu Thr Asp Thr Ser Asn Gly Pro Leu Leu Ile Tyr Pro Val Asn
            420                 425                 430

Lys Ser Lys Trp Arg Lys Gly Thr Ser Met Val Thr Pro Asp Glu Asp
        435                 440                 445

Val Phe Tyr Leu Ile Ala Phe Leu Ser Ser Ala Met Ser Ser Ser Thr
        450                 455                 460

Gly Asn Asp Gly Leu Arg His Ile Leu Ala Gln Ser Lys Arg Ile Leu
465                 470                 475                 480

Asn Phe Cys Glu Glu Thr Asn Ile Gly Met Lys Gln Tyr Leu Pro Asn
                485                 490                 495

Tyr Lys Thr Lys Glu Glu Trp Lys Asp His Phe Gly Gln Trp Glu
            500                 505                 510
```

```
Ala Phe Ala Arg Arg Lys Ser Thr Tyr Asp Pro Leu Ala Ile Leu Ala
        515                 520                 525

Pro Gly Gln Arg Ile Phe Arg Arg Ala Glu Ala Cys Glu Gln Gln
    530                 535                 540

<210> SEQ ID NO 61
<211> LENGTH: 960
<212> TYPE: DNA
<213> ORGANISM: Nicotiana tabacum

<400> SEQUENCE: 61
atgagaaact cttcactaat gtgcaaacaa gtatggccaa ctttgcgaaa tttgcctcaa      60
aaggacaagg ttgtgtttgt gatgggagtc accggcgccg gaaaatcaag actgtcaata    120
gacttagcca ctcaattcag aggagaaata gtgaactccg acaaaataca agtgtacaaa    180
ggtcttgata ttgccactaa caaaatcaca caagaagaac gttgtggtgt accacaccat    240
ctcctaggcg taattgatcc ttacaaagaa ttcaccacca aaaacttctg caacatggct    300
tcacttgcag ttaactctat aaccgaccgc ggtaaacttc cgatcatcgt tggaggttcc    360
aattcgttta tcgaggcgct tgtccacgac aactctcata attttcgtac gaggtatgat    420
tgttgtttcc tatgggtcga tgtgtccatg aacgtactaa attcattttt gtacgaacga    480
gtggacaaaa tgatggagca aggtatgact gacgaagtaa aagcatgtt caatccaaaa     540 aacacagatt ataccaaagg catacgtaaa gcaattggcg taccagaatt cgatagttat    600
tttcgagctg aattatcaaa ttctgttgac gtggagacgc gcgagaggct actaaaagaa    660
gctattaatg aagtgaagat caataactgt atactagcaa gtaagcaact agagaaaata    720
aagagactca taaatgttaa gggatggaaa attcaaagat tagatgcaac agaagttttt    780
aggaggaaac agagaaatgc agaggaagaa gccgaggaaa tttggaagaa tatggtgatg    840
ggacagagca taagattgt gggtaaattt ttatgcgaaa ataatcggag caaaatggtt     900
tacagaaatg atgtgacagc cattaagaga gcagcagcgt cggccatagc tcaatattag    960

<210> SEQ ID NO 62
<211> LENGTH: 319
<212> TYPE: PRT
<213> ORGANISM: Nicotiana tabacum

<400> SEQUENCE: 62

Met Arg Asn Ser Ser Leu Met Cys Lys Gln Val Trp Pro Thr Leu Arg
1               5                   10                  15

Asn Leu Pro Gln Lys Asp Lys Val Val Phe Val Met Gly Val Thr Gly
            20                  25                  30

Ala Gly Lys Ser Arg Leu Ser Ile Asp Leu Ala Thr Gln Phe Arg Gly
        35                  40                  45

Glu Ile Val Asn Ser Asp Lys Ile Gln Val Tyr Lys Gly Leu Asp Ile
    50                  55                  60

Ala Thr Asn Lys Ile Thr Gln Glu Glu Arg Cys Gly Val Pro His His
65                  70                  75                  80

Leu Leu Gly Val Ile Asp Pro Tyr Lys Glu Phe Thr Thr Lys Asn Phe
                85                  90                  95

Cys Asn Met Ala Ser Leu Ala Val Asn Ser Ile Thr Asp Arg Gly Lys
            100                 105                 110

Leu Pro Ile Ile Val Gly Gly Ser Asn Ser Phe Ile Glu Ala Leu Val
        115                 120                 125

His Asp Asn Ser His Asn Phe Arg Thr Arg Tyr Asp Cys Cys Phe Leu
```

```
               130                 135                 140
Trp Val Asp Val Ser Met Asn Val Leu Asn Ser Phe Leu Tyr Glu Arg
145                 150                 155                 160

Val Asp Lys Met Met Glu Gln Gly Met Thr Asp Glu Val Arg Ser Met
                165                 170                 175

Phe Asn Pro Lys Asn Thr Asp Tyr Thr Lys Gly Ile Arg Lys Ala Ile
            180                 185                 190

Gly Val Pro Glu Phe Asp Ser Tyr Phe Arg Ala Glu Leu Ser Asn Ser
        195                 200                 205

Val Asp Val Glu Thr Arg Glu Arg Leu Leu Lys Glu Ala Ile Asn Glu
    210                 215                 220

Val Lys Ile Asn Asn Cys Ile Leu Ala Ser Lys Gln Leu Glu Lys Ile
225                 230                 235                 240

Lys Arg Leu Ile Asn Val Lys Gly Trp Lys Ile Gln Arg Leu Asp Ala
                245                 250                 255

Thr Glu Val Phe Arg Arg Lys Gln Arg Asn Ala Glu Glu Ala Glu
            260                 265                 270

Glu Ile Trp Lys Asn Met Val Met Gly Gln Ser Ile Lys Ile Val Gly
        275                 280                 285

Lys Phe Leu Cys Glu Asn Asn Arg Ser Lys Met Val Tyr Arg Asn Asp
    290                 295                 300

Val Thr Ala Ile Lys Arg Ala Ala Ala Ser Ala Ile Ala Gln Tyr
305                 310                 315

<210> SEQ ID NO 63
<211> LENGTH: 930
<212> TYPE: DNA
<213> ORGANISM: Nicotiana tabacum

<400> SEQUENCE: 63
atggaagctg ctcaacaaca aaaccagcag cactatcttc accaacaaca tttatcaatt      60
ggacaggtgg caaacaacat tgaagatggt gttggtggta atagcagcaa aaacaacagc     120
agcagtttca tgtgcaggca agtagtacg aggtggacac ccacaactga ccagataaga     180
attttgaagg acctttacta caacaatgga gttaggtctc caactgctga acagattcag     240
aggatctctg ctaagttaag acagtacggt aagattgaag caagaatgt gttttattgg     300 tttcagaacc ataaagctcg tgaaaggcaa agaagaggc ttattgctgc tgctgccact     360
gataacaaca taatatccc catgcaaatg agaggtgttt ggagatctgc tgatgatccc     420
attcaccaca gtataacaa cactacaggt attcactgtc catcagcttc ttctcatggt     480
gtactagcag ttggacagaa tggaaactat ggttatggaa ctgtagctat ggagaagagc     540
tttagggact gttcaatatc accaggtggt aactccaacg atcaatgggt catcaaaac     600 attacatggg ttggagttga tccctacact tctcatcaag catcccttt tcttgaaag     660 actaaacatt tgattgaaac cctagacgat tatgaggaac tgcaacaaga agaagaaat     720 taccaaagag cctctgcttt agaaactctc ccactttttc ccatgcacga agagaacatt     780
tccagtttct gcaacatcaa acatgaatct tcaggcggat tctacacaga atggtatcgt     840
tcagatgatc ataacttggc tgctgcggcc agagcttctc ttgaactcag tctcaactct     900
ttcattggca gatctcctaa ttccccttaa                                     930

<210> SEQ ID NO 64
<211> LENGTH: 309
<212> TYPE: PRT
```

<213> ORGANISM: Nicotiana tabacum

<400> SEQUENCE: 64

```
Met Glu Ala Ala Gln Gln Asn Gln Gln His Tyr Leu His Gln Gln
1               5                   10                  15

His Leu Ser Ile Gly Gln Val Ala Asn Asn Ile Glu Asp Gly Val Gly
            20                  25                  30

Gly Asn Ser Ser Lys Asn Asn Ser Ser Phe Met Cys Arg Gln Ser
        35                  40                  45

Ser Thr Arg Trp Thr Pro Thr Thr Asp Gln Ile Arg Ile Leu Lys Asp
    50                  55                  60

Leu Tyr Tyr Asn Asn Gly Val Arg Ser Pro Thr Ala Glu Gln Ile Gln
65              70                  75                  80

Arg Ile Ser Ala Lys Leu Arg Gln Tyr Gly Lys Ile Glu Gly Lys Asn
                85                  90                  95

Val Phe Tyr Trp Phe Gln Asn His Lys Ala Arg Glu Arg Gln Lys Lys
            100                 105                 110

Arg Leu Ile Ala Ala Ala Thr Asp Asn Asn Asn Ile Pro Met
        115                 120                 125

Gln Met Arg Gly Val Trp Arg Ser Ala Asp Asp Pro Ile His His Lys
    130                 135                 140

Tyr Asn Asn Thr Thr Gly Ile His Cys Pro Ser Ala Ser Ser His Gly
145             150                 155                 160

Val Leu Ala Val Gly Gln Asn Gly Asn Tyr Gly Tyr Gly Thr Val Ala
                165                 170                 175

Met Glu Lys Ser Phe Arg Asp Cys Ser Ile Ser Pro Gly Gly Asn Ser
            180                 185                 190

Asn Gly Ser Met Gly His Gln Asn Ile Thr Trp Val Gly Val Asp Pro
        195                 200                 205

Tyr Thr Ser His Gln Ala Tyr Pro Phe Leu Glu Lys Thr Lys His Phe
    210                 215                 220

Asp Glu Thr Leu Asp Asp Tyr Glu Glu Leu Gln Gln Glu Glu Asn
225             230                 235                 240

Tyr Gln Arg Ala Ser Ala Leu Glu Thr Leu Pro Leu Phe Pro Met His
                245                 250                 255

Glu Glu Asn Ile Ser Ser Phe Cys Asn Ile Lys His Glu Ser Ser Gly
            260                 265                 270

Gly Phe Tyr Thr Glu Trp Tyr Arg Ser Asp Asp His Asn Leu Ala Ala
        275                 280                 285

Ala Ala Arg Ala Ser Leu Glu Leu Ser Leu Asn Ser Phe Ile Gly Arg
    290                 295                 300

Ser Pro Asn Ser Pro
305
```

<210> SEQ ID NO 65
<211> LENGTH: 822
<212> TYPE: DNA
<213> ORGANISM: Nicotiana tabacum

<400> SEQUENCE: 65

```
atggaagctg cccaacaaca aaaccagcag cactatcttc accaacaaca tttatcaatt    60
ggacaggtga caacaacat tattgaagat ggtgttggtg gtaatagcag caaaacaac    120 agcagcagtt tcatgtgcag gcaaagtagt acgaggtgga cacccacaac tgaccagata    180
agaatcttga aggatcttta ctacaacaat ggagttaggt ctccaactgc tgaacagatt    240
```

```
cagaggatct ctgctaagtt aagacagtac ggtaagattg aaggcaagaa tgtgttttat    300
tggtttcaga accataaagc tcgtgaaagg caaaagaaga ggcttattgc tgctgctgct    360
actgatagca acaataatat tcccatgcac atgagaggtg tttggagatc tgctgatgat    420
cctatccacc acaagtataa caacactaca ggtattcact gtccatcagc ttcttctcat    480
ggtgtactgg ccgttggaca gaatggaaac tatggttatg gaactttagc tatggaaaag    540
agctttagga ctaaacattt tgatgaaacc ctagtagacg attatgagga actgcaacaa    600
gaagaagaaa attaccaaag agcctctgct ttagaaactc tcccactttt tcccatgcat    660
gaagagaaca tctccagttt ctgcaacatc aaacatgaat cttcaggcgg attctacaca    720
gaatggtacc gttcagatga tcataacttg gctgctgcgg ccagagcttc tcttgaactt    780
agtctcaact ctttcattgg cagatctcct aattcccctt aa                      822

<210> SEQ ID NO 66
<211> LENGTH: 273
<212> TYPE: PRT
<213> ORGANISM: Nicotiana tabacum

<400> SEQUENCE: 66

Met Glu Ala Ala Gln Gln Asn Gln Gln His Tyr Leu His Gln Gln
1               5                  10                  15

His Leu Ser Ile Gly Gln Val Thr Asn Asn Ile Ile Glu Asp Gly Val
            20                  25                  30

Gly Gly Asn Ser Ser Lys Asn Asn Ser Ser Phe Met Cys Arg Gln
        35                  40                  45

Ser Ser Thr Arg Trp Thr Pro Thr Thr Asp Gln Ile Arg Ile Leu Lys
    50                  55                  60

Asp Leu Tyr Tyr Asn Asn Gly Val Arg Ser Pro Thr Ala Glu Gln Ile
65                  70                  75                  80

Gln Arg Ile Ser Ala Lys Leu Arg Gln Tyr Gly Lys Ile Glu Gly Lys
                85                  90                  95

Asn Val Phe Tyr Trp Phe Gln Asn His Lys Ala Arg Glu Arg Gln Lys
            100                 105                 110

Lys Arg Leu Ile Ala Ala Ala Thr Asp Ser Asn Asn Asn Ile Pro
        115                 120                 125

Met His Met Arg Gly Val Trp Arg Ser Ala Asp Asp Pro Ile His His
    130                 135                 140

Lys Tyr Asn Asn Thr Thr Gly Ile His Cys Pro Ser Ala Ser Ser His
145                 150                 155                 160

Gly Val Leu Ala Val Gly Gln Asn Gly Asn Tyr Gly Tyr Gly Thr Leu
                165                 170                 175

Ala Met Glu Lys Ser Phe Arg Thr Lys His Phe Asp Glu Thr Leu Val
            180                 185                 190

Asp Asp Tyr Glu Glu Leu Gln Gln Glu Glu Asn Tyr Gln Arg Ala
        195                 200                 205

Ser Ala Leu Glu Thr Leu Pro Leu Phe Pro Met His Glu Glu Asn Ile
    210                 215                 220

Ser Ser Phe Cys Asn Ile Lys His Glu Ser Ser Gly Gly Phe Tyr Thr
225                 230                 235                 240

Glu Trp Tyr Arg Ser Asp Asp His Asn Leu Ala Ala Ala Arg Ala
                245                 250                 255

Ser Leu Glu Leu Ser Leu Asn Ser Phe Ile Gly Arg Ser Pro Asn Ser
            260                 265                 270
```

Pro

<210> SEQ ID NO 67
<211> LENGTH: 291
<212> TYPE: DNA
<213> ORGANISM: Arabidopsis thaliana

<400> SEQUENCE: 67

| | | | | | |
|---|---|---|---|---|---|
| atggattcga | agagttttct | gctactacta | ctactcttct | gcttcttgtt | ccttcatgat | 60 |
| gcttctgatc | tcactcaagc | tcatgctcac | gttcaaggac | tttccaaccg | caagatgatg | 120 |
| atgatgaaaa | tggaaagtga | atgggttgga | gcaaatggag | aagcagagaa | ggcaaagacg | 180 |
| aagggtttag | gactacatga | agagttaagg | actgttcctt | cgggacctga | cccgttgcac | 240 |
| catcatgtga | acccaccaag | acagccaaga | aacaactttc | agctcccttg | a | 291 |

<210> SEQ ID NO 68
<211> LENGTH: 96
<212> TYPE: PRT
<213> ORGANISM: Arabidopsis thaliana

<400> SEQUENCE: 68

Met Asp Ser Lys Ser Phe Leu Leu Leu Leu Leu Phe Cys Phe Leu
1               5                   10                  15

Phe Leu His Asp Ala Ser Asp Leu Thr Gln Ala His Ala His Val Gln
            20                  25                  30

Gly Leu Ser Asn Arg Lys Met Met Met Lys Met Glu Ser Glu Trp
        35                  40                  45

Val Gly Ala Asn Gly Glu Ala Glu Lys Ala Lys Thr Lys Gly Leu Gly
    50                  55                  60

Leu His Glu Glu Leu Arg Thr Val Pro Ser Gly Pro Asp Pro Leu His
65                  70                  75                  80

His His Val Asn Pro Pro Arg Gln Pro Arg Asn Asn Phe Gln Leu Pro
                85                  90                  95

<210> SEQ ID NO 69
<211> LENGTH: 396
<212> TYPE: DNA
<213> ORGANISM: Nicotiana tabacum

<400> SEQUENCE: 69

| | | | | | |
|---|---|---|---|---|---|
| atgtgtattc | catatcttga | tccgtttgtt | tcttactcac | ttatagatca | acaacttgca | 60 |
| tctactgcat | ttctgttcgc | ttctgaaatg | actaatttca | ctgccaaacg | tttcaccctc | 120 |
| ttcctcttgc | tgtgtgtttt | ggttgtgcaa | gaatctcatg | ggtgcactag | tagctcaaaa | 180 |
| tgcatttcac | aaaaggaagt | tgcttctgtg | agaatactaa | acagaaaggt | tttaggaagc | 240 |
| cagcgggctg | cttttggaaa | gggcttaaat | ggaaactaca | atcattcagg | gaagattaat | 300 |
| gacaagtttg | ctgattggga | gcttagggga | attccagctg | tcctgatcc | attgcaccac | 360 |
| aatggtgcta | atccgaagaa | accccggact | ccataa | | | 396 |

<210> SEQ ID NO 70
<211> LENGTH: 131
<212> TYPE: PRT
<213> ORGANISM: Nicotiana tabacum

<400> SEQUENCE: 70

Met Cys Ile Pro Tyr Leu Asp Pro Phe Val Ser Tyr Ser Leu Ile Asp
1               5                   10                  15

-continued

```
Gln Gln Leu Ala Ser Thr Ala Phe Leu Phe Ala Ser Glu Met Thr Asn
         20                  25                  30

Phe Thr Ala Lys Arg Phe Thr Leu Phe Leu Leu Leu Cys Val Leu Val
         35                  40                  45

Val Gln Glu Ser His Gly Cys Thr Ser Ser Lys Cys Ile Ser Gln
 50                  55                  60

Lys Glu Val Ala Ser Val Arg Ile Leu Asn Arg Lys Val Leu Gly Ser
 65                  70                  75                  80

Gln Arg Ala Ala Phe Gly Lys Gly Leu Asn Gly Asn Tyr Asn His Ser
                 85                  90                  95

Gly Lys Ile Asn Asp Lys Phe Ala Asp Trp Glu Leu Arg Gly Ile Pro
             100                 105                 110

Ala Gly Pro Asp Pro Leu His His Asn Gly Ala Asn Pro Lys Lys Pro
         115                 120                 125

Arg Thr Pro
     130
```

<210> SEQ ID NO 71
<211> LENGTH: 1158
<212> TYPE: DNA
<213> ORGANISM: Nicotiana tabacum

<400> SEQUENCE: 71

```
atgttaggat cctttggttc atcatctcaa tctcatgatg aagaagctga tgatcaacgg      60
cggagatgca gttccacttc ccctgcaatc caaatccggc aactactcat tagctgcgcg     120
gagttaatct cacggtccga tttctcggcg gcaaacagac tcctcaccat tttatcaact     180
aactcttccc cttttgccac taatttcttg cacctaatg catcatctaa tgttgttgaa      240
agttcaaatg attcagctct acttcagtca tcctatcttt ccctaaacca agtgacccct     300
tttattagat ttagtcagct aactgctaat caagcgattt tagaagctat taacgataac     360
caacaagcga tccacatcgt tgattttgat attaatcacg tgttcaatg gccaccgtta      420
atgcaagcac tagctgatcg ttaccctcct ccaactcttc ggattaccgg tactggaaat     480
gacctcgata cccttcgtag aaccggagat cgtttagcta aatttgctca ctctttaggc     540
cttagatttc agtttcaccc tcttttgatc accaataata tgacaatga tcatgaccct      600
tcaatcattt cttctattgt tcttctccct gatgagacat tagcaatcaa ctgtgtattt     660
tatcttcaca ggctcttaaa agaccgcgaa atgttaagga ttttttttgca taggattaaa    720
tccatgaacc ctaaagttgt aacactggcc gagagagaag caaatcataa tcacccactt     780
tttttgcaaa gatttgtgga ggctttggat tattatgcag ctgtctttga ttcattggaa     840
gcaactttgc cgccgagcag tagagagagg atgcagtgg agcaagtttg gttcggaaga      900
gaaattatag atatagtagc agcagaagga gataagagaa gagaaagaca cgagagattc     960
agatcatggg aagtaatgtt gaggagctgt ggatttagca atgttgcttt aagtcctttt    1020
gcactttcac aagctaaact tctcttgaga cttcattacc cttctgaagg ataccagctt    1080
agtgtttcga gtacgagtaa ttctttcttc ttgggttggc aaaatcaacc cctttttttcc   1140
atatcttctt ggcgttaa                                                  1158
```

<210> SEQ ID NO 72
<211> LENGTH: 385
<212> TYPE: PRT
<213> ORGANISM: Nicotiana tabacum

<400> SEQUENCE: 72

```
Met Leu Gly Ser Phe Gly Ser Ser Gln Ser His Asp Glu Glu Ala
1               5                   10                  15

Asp Asp Gln Arg Arg Cys Ser Ser Thr Ser Pro Ala Ile Gln Ile
            20                  25                  30

Arg Gln Leu Leu Ile Ser Cys Ala Glu Leu Ile Ser Arg Ser Asp Phe
        35                  40                  45

Ser Ala Ala Asn Arg Leu Leu Thr Ile Leu Ser Thr Asn Ser Ser Pro
    50                  55                  60

Phe Ala Thr Asn Phe Leu Thr Pro Asn Ala Ser Ser Asn Val Val Glu
65                  70                  75                  80

Ser Ser Asn Asp Ser Ala Leu Leu Gln Ser Ser Tyr Leu Ser Leu Asn
                85                  90                  95

Gln Val Thr Pro Phe Ile Arg Phe Ser Gln Leu Thr Ala Asn Gln Ala
            100                 105                 110

Ile Leu Glu Ala Ile Asn Asp Asn Gln Gln Ala Ile His Ile Val Asp
        115                 120                 125

Phe Asp Ile Asn His Gly Val Gln Trp Pro Leu Met Gln Ala Leu
130                 135                 140

Ala Asp Arg Tyr Pro Pro Thr Leu Arg Ile Thr Gly Thr Gly Asn
145                 150                 155                 160

Asp Leu Asp Thr Leu Arg Arg Thr Gly Asp Arg Leu Ala Lys Phe Ala
                165                 170                 175

His Ser Leu Gly Leu Arg Phe Gln Phe His Pro Leu Leu Ile Thr Asn
            180                 185                 190

Asn Asn Asp Asn Asp His Asp Pro Ser Ile Ile Ser Ser Ile Val Leu
        195                 200                 205

Leu Pro Asp Glu Thr Leu Ala Ile Asn Cys Val Phe Tyr Leu His Arg
    210                 215                 220

Leu Leu Lys Asp Arg Glu Met Leu Arg Ile Phe Leu His Arg Ile Lys
225                 230                 235                 240

Ser Met Asn Pro Lys Val Val Thr Leu Ala Glu Arg Glu Ala Asn His
                245                 250                 255

Asn His Pro Leu Phe Leu Gln Arg Phe Val Glu Ala Leu Asp Tyr Tyr
            260                 265                 270

Ala Ala Val Phe Asp Ser Leu Glu Ala Thr Leu Pro Pro Ser Ser Arg
        275                 280                 285

Glu Arg Met Thr Val Glu Gln Val Trp Phe Gly Arg Glu Ile Ile Asp
    290                 295                 300

Ile Val Ala Ala Glu Gly Asp Lys Arg Arg Glu Arg His Glu Arg Phe
305                 310                 315                 320

Arg Ser Trp Glu Val Met Leu Arg Ser Cys Gly Phe Ser Asn Val Ala
                325                 330                 335

Leu Ser Pro Phe Ala Leu Ser Gln Ala Lys Leu Leu Leu Arg Leu His
            340                 345                 350

Tyr Pro Ser Glu Gly Tyr Gln Leu Ser Val Ser Ser Thr Ser Asn Ser
        355                 360                 365

Phe Phe Leu Gly Trp Gln Asn Gln Pro Leu Phe Ser Ile Ser Ser Trp
    370                 375                 380

Arg
385
```

<210> SEQ ID NO 73

<211> LENGTH: 1224
<212> TYPE: DNA
<213> ORGANISM: Nicotiana tabacum

<400> SEQUENCE: 73

```
atgttaggat cctttggttc atcatctcaa tctcatgatg aagaaactga tgatcaacgg    60
cggagattca gttccacttc ccctgcaatc caaatccggc aactactcat tagctgcgcg   120
gagttaatct cgcggtccga tttctcggcc gcaaacagac tcctcaccat tttatcaact   180
aactcttccc cttttggtga ttcaactgaa agattagtcc atcagttcac tcgcgcactt   240
tctcttcgcc tcaaccgtta tatctcttca gccactaatt tcttgacacc atctaatgtt   300
gttgaaagtt caaatgattc agctctactt cagtcatcct atctttccct aaaccaagtg   360
actcctttca ttagatttag tcagctaact gctaatcaag cgattttgga agctattaac   420
gataaccaac aagcgatcca catcgttgat tttgatatta atcacggtgt tcaatggcca   480
ccgttaatgc aagcactagc tgatcgttac cctcctccaa ctcttcggat taccggtact   540
ggaaatgacc ttgataccct tcgtagaacc ggagatcgtt tagctaaatt tgctcactct   600
ttaggcctta gatttcagtt tcaccctctt ttgattacca ataataatga caatgatcat   660
gacccttcaa taatttcttc tattgttctt ctccctgatg agacattagc tatcaactgt   720
gtatttatc ttcacaggct cttgaaagac cgcgaaaagt taaggatttt tttgcatagg   780
attaaatcca tgaaccctaa agttgtaacg ctggccgaga gagaagcaaa tcataatcac   840
ccactttttt tgcaaagatt tgtggaggct ttggattatt atgcagctgt gtttgattca   900
ttggaagcaa ctttgccacc gagcagtaga gagaggatga cagtggaaca agtttggttc   960
gggagagaaa taattgatat agtagcagca aaggagata agagaagaga aagacacgag  1020
agattcagat catgggaagt aatgttgagg agctgtggat ttagcaatgt tgctttaagc  1080
cctttgcac tctcacaagc taaacttctc ttgagacttc attacccatc tgaaggatac  1140
cagcttagtg tttcgagtac gagtaattct tcttcttgg gttggcaaaa tcaacccctt  1200
ttttccatat cttcttggcg ttaa                                          1224
```

<210> SEQ ID NO 74
<211> LENGTH: 407
<212> TYPE: PRT
<213> ORGANISM: Nicotiana tabacum

<400> SEQUENCE: 74

```
Met Leu Gly Ser Phe Gly Ser Ser Gln Ser His Asp Glu Glu Thr
1               5                   10                  15

Asp Asp Gln Arg Arg Arg Phe Ser Ser Thr Ser Pro Ala Ile Gln Ile
            20                  25                  30

Arg Gln Leu Leu Ile Ser Cys Ala Glu Leu Ile Ser Arg Ser Asp Phe
        35                  40                  45

Ser Ala Ala Asn Arg Leu Leu Thr Ile Leu Ser Thr Asn Ser Ser Pro
    50                  55                  60

Phe Gly Asp Ser Thr Glu Arg Leu Val His Gln Phe Thr Arg Ala Leu
65                  70                  75                  80

Ser Leu Arg Leu Asn Arg Tyr Ile Ser Ser Ala Thr Asn Phe Leu Thr
                85                  90                  95

Pro Ser Asn Val Val Glu Ser Ser Asn Asp Ser Ala Leu Leu Gln Ser
            100                 105                 110

Ser Tyr Leu Ser Leu Asn Gln Val Thr Pro Phe Ile Arg Phe Ser Gln
        115                 120                 125
```

Leu Thr Ala Asn Gln Ala Ile Leu Glu Ala Ile Asn Asp Asn Gln Gln
    130                 135                 140

Ala Ile His Ile Val Asp Phe Asp Ile Asn His Gly Val Gln Trp Pro
145                 150                 155                 160

Pro Leu Met Gln Ala Leu Ala Asp Arg Tyr Pro Pro Thr Leu Arg
            165                 170                 175

Ile Thr Gly Thr Gly Asn Asp Leu Asp Thr Leu Arg Arg Thr Gly Asp
            180                 185                 190

Arg Leu Ala Lys Phe Ala His Ser Leu Gly Leu Arg Phe Gln Phe His
            195                 200                 205

Pro Leu Leu Ile Thr Asn Asn Asn Asp Asn Asp His Asp Pro Ser Ile
    210                 215                 220

Ile Ser Ser Ile Val Leu Leu Pro Asp Glu Thr Leu Ala Ile Asn Cys
225                 230                 235                 240

Val Phe Tyr Leu His Arg Leu Leu Lys Asp Arg Glu Lys Leu Arg Ile
                245                 250                 255

Phe Leu His Arg Ile Lys Ser Met Asn Pro Lys Val Val Thr Leu Ala
            260                 265                 270

Glu Arg Glu Ala Asn His Asn His Pro Leu Phe Leu Gln Arg Phe Val
            275                 280                 285

Glu Ala Leu Asp Tyr Tyr Ala Ala Val Phe Asp Ser Leu Glu Ala Thr
    290                 295                 300

Leu Pro Pro Ser Ser Arg Glu Arg Met Thr Val Glu Gln Val Trp Phe
305                 310                 315                 320

Gly Arg Glu Ile Ile Asp Ile Val Ala Ala Glu Gly Asp Lys Arg Arg
                325                 330                 335

Glu Arg His Glu Arg Phe Arg Ser Trp Glu Val Met Leu Arg Ser Cys
            340                 345                 350

Gly Phe Ser Asn Val Ala Leu Ser Pro Phe Ala Leu Ser Gln Ala Lys
        355                 360                 365

Leu Leu Leu Arg Leu His Tyr Pro Ser Glu Gly Tyr Gln Leu Ser Val
    370                 375                 380

Ser Ser Thr Ser Asn Ser Phe Phe Leu Gly Trp Gln Asn Gln Pro Leu
385                 390                 395                 400

Phe Ser Ile Ser Ser Trp Arg
                405

<210> SEQ ID NO 75
<211> LENGTH: 1014
<212> TYPE: DNA
<213> ORGANISM: Nicotiana tabacum

<400> SEQUENCE: 75
atggggagag ctccatgttg tgataaagca atgtgaaga gagggccatg gtctcctgaa     60
gaagatgcta aactcaaaga tttcattcac aaatatggaa ctggtggaaa ttggattgct    120
cttcctcaaa aagctggtct aaagagatgt gggaagagtt gtagattgag atggctaaat    180
tatttaaggc ctaacattaa acatggtgat ttttctgagg aagaagatag agttatttgc    240
accttgtatt ccaccattgg aagcaggtgg tcaataatag cagctcaatt accgggaaga    300
actgacaatg atatcaagaa ttactggaat actaagctca agaaaaaacc tatgggatta    360
atgcaatcaa ctaaccaaag aaaatcacca tattttccag ctactaattc tcttcaaacc    420
caaccccaga taaattcaag tcttttttaga gacttatatt acaccccaaa taataggcct    480

```
aatattacag gcctaaatca tcagtccatt tcttctgccc accagacaaa ttttctctac      540
actaataata acatgaactt tcctaatttg ggtgctacaa ataatcaata tccttataat      600
atccaaagtc ataatttact tatgtttgga gaagcaagtt gttcttcatc agatggaagt      660
tgcagccaaa tgagttttgg taaagaaatc aagagagaag aaattatgag taatagttta      720
caacaaggtc aaatttcaag tgttaatgct tttgaagaaa accaccagaa ttttactctt      780
gattatggca atagtagtag taattgggtg atcaaaaac caaatgtgta ttttggtact       840
actactactc aagtacttca gtatgataat gttgaagaag ttaagcagca gctaacaagt      900
tgtaccaatg gcaacaatgg tagtactatt ggatgtaaca acaacaacag tatgttcgtg      960
ttcaatgatg agaattataa caagtcaaat gagatagaga tgttctatta ctga           1014
```

<210> SEQ ID NO 76
<211> LENGTH: 337
<212> TYPE: PRT
<213> ORGANISM: Nicotiana tabacum

<400> SEQUENCE: 76

```
Met Gly Arg Ala Pro Cys Cys Asp Lys Ala Asn Val Lys Arg Gly Pro
1               5                   10                  15

Trp Ser Pro Glu Glu Asp Ala Lys Leu Lys Asp Phe Ile His Lys Tyr
            20                  25                  30

Gly Thr Gly Gly Asn Trp Ile Ala Leu Pro Gln Lys Ala Gly Leu Lys
        35                  40                  45

Arg Cys Gly Lys Ser Cys Arg Leu Arg Trp Leu Asn Tyr Leu Arg Pro
    50                  55                  60

Asn Ile Lys His Gly Asp Phe Ser Glu Glu Glu Asp Arg Val Ile Cys
65                  70                  75                  80

Thr Leu Tyr Ser Thr Ile Gly Ser Arg Trp Ser Ile Ile Ala Ala Gln
                85                  90                  95

Leu Pro Gly Arg Thr Asp Asn Asp Ile Lys Asn Tyr Trp Asn Thr Lys
            100                 105                 110

Leu Lys Lys Lys Pro Met Gly Leu Met Gln Ser Thr Asn Gln Arg Lys
        115                 120                 125

Ser Pro Tyr Phe Pro Ala Thr Asn Ser Leu Gln Thr Gln Pro Gln Ile
    130                 135                 140

Asn Ser Ser Leu Phe Arg Asp Leu Tyr Tyr Thr Pro Asn Asn Arg Pro
145                 150                 155                 160

Asn Ile Thr Gly Leu Asn His Gln Ser Ile Ser Ser Ala His Gln Thr
                165                 170                 175

Asn Phe Leu Tyr Thr Asn Asn Asn Met Asn Phe Pro Asn Leu Gly Ala
            180                 185                 190

Thr Asn Asn Gln Tyr Pro Tyr Asn Ile Gln Ser His Asn Leu Leu Met
        195                 200                 205

Phe Gly Glu Ala Ser Cys Ser Ser Ser Asp Gly Ser Cys Ser Gln Met
    210                 215                 220

Ser Phe Gly Lys Glu Ile Lys Arg Glu Glu Ile Met Ser Asn Ser Leu
225                 230                 235                 240

Gln Gln Gly Gln Ile Ser Ser Val Asn Ala Phe Glu Glu Asn His Gln
                245                 250                 255

Asn Phe Thr Leu Asp Tyr Gly Asn Ser Ser Ser Asn Trp Val Asp Gln
            260                 265                 270

Lys Pro Asn Val Tyr Phe Gly Thr Thr Thr Gln Val Leu Gln Tyr
        275                 280                 285
```

Asp Asn Val Glu Glu Val Lys Gln Gln Leu Thr Ser Cys Thr Asn Gly
            290                 295                 300

Asn Asn Gly Ser Thr Ile Gly Cys Asn Asn Asn Ser Met Phe Val
305                 310                 315                 320

Phe Asn Asp Glu Asn Tyr Asn Lys Ser Asn Glu Ile Glu Met Phe Tyr
                325                 330                 335

Tyr

<210> SEQ ID NO 77
<211> LENGTH: 1011
<212> TYPE: DNA
<213> ORGANISM: Nicotiana tabacum

<400> SEQUENCE: 77
atggggagag ctccatgttg tgataaagca aatgtgaaga gagggccatg gtctcctgaa      60
gaagatgcta aactcaaaga tttcattcac aaatatggaa ctggtggaaa ttggattgct     120
cttccccaaa aagcaggtct aaagagatgt gggaagagtt gtagattgag atggctaaat     180
tatctaaggc ctaatatcaa acatggtgat ttttcggagg aagaagatag agttatttgc     240
agcttgtatt ccaccattgg aagcaggtgg tcaataatag cagctcaatt accaggaagg     300
actgacaatg atatcaagaa ttactggaat actaaactca agaaaaagct tatgggatta     360
atgcaatcaa caaaccaaag aaaatcacca tattttccag ctactaattc tcttcaaacc     420
caaccccaga taaattcaag tcttttttaga gacttatatt acaacccaaa taataggcct     480
attattacag gcctaaatca gtccatttct tctgcccacc agccaaattt tctctacact     540
aatagtaaca tgaattttcc taatttgggt gctacaaata gtcaatatcc ttataatatt     600
caaagtcata atttacttat gtttggagaa gcaagttgtt cttcatcaga tggaagttgt     660
agccaaatga gttttggcaa agaaatcaag agagaggaaa ttatgagtaa ttgtttacaa     720
caaggtcaaa tttcaagtgt taatgctttt gaagaaaatc agaatttcac tcttgattat     780
ggtaacagta gtagtaattg ggtggatcaa aaaccaaatg tgtattttgg aaatactact     840
actactactc aagtacttca gtatgatgtt gaagaagtta agcagcagct aacaagttgt     900
accaatggca acaatggcag tactattgga tgtaacaaca caacagtat gttcgtgttc     960 aatgatgaga attataacaa gtcaaatgag atagggatgt tctattactg a             1011

<210> SEQ ID NO 78
<211> LENGTH: 336
<212> TYPE: PRT
<213> ORGANISM: Nicotiana tabacum

<400> SEQUENCE: 78

Met Gly Arg Ala Pro Cys Cys Asp Lys Ala Asn Val Lys Arg Gly Pro
1               5                   10                  15

Trp Ser Pro Glu Glu Asp Ala Lys Leu Lys Asp Phe Ile His Lys Tyr
            20                  25                  30

Gly Thr Gly Gly Asn Trp Ile Ala Leu Pro Gln Lys Ala Gly Leu Lys
        35                  40                  45

Arg Cys Gly Lys Ser Cys Arg Leu Arg Trp Leu Asn Tyr Leu Arg Pro
    50                  55                  60

Asn Ile Lys His Gly Asp Phe Ser Glu Glu Glu Asp Arg Val Ile Cys
65                  70                  75                  80

Ser Leu Tyr Ser Thr Ile Gly Ser Arg Trp Ser Ile Ile Ala Ala Gln
                85                  90                  95

Leu Pro Gly Arg Thr Asp Asn Asp Ile Lys Asn Tyr Trp Asn Thr Lys
            100                 105                 110

Leu Lys Lys Lys Leu Met Gly Leu Met Gln Ser Thr Asn Gln Arg Lys
            115                 120                 125

Ser Pro Tyr Phe Pro Ala Thr Asn Ser Leu Gln Thr Gln Pro Gln Ile
            130                 135                 140

Asn Ser Ser Leu Phe Arg Asp Leu Tyr Tyr Asn Pro Asn Asn Arg Pro
145                 150                 155                 160

Ile Ile Thr Gly Leu Asn Gln Ser Ile Ser Ser Ala His Gln Pro Asn
                165                 170                 175

Phe Leu Tyr Thr Asn Ser Asn Met Asn Phe Pro Asn Leu Gly Ala Thr
            180                 185                 190

Asn Ser Gln Tyr Pro Tyr Asn Ile Gln Ser His Asn Leu Leu Met Phe
            195                 200                 205

Gly Glu Ala Ser Cys Ser Ser Ser Asp Gly Ser Cys Ser Gln Met Ser
            210                 215                 220

Phe Gly Lys Glu Ile Lys Arg Glu Glu Ile Met Ser Asn Cys Leu Gln
225                 230                 235                 240

Gln Gly Gln Ile Ser Ser Val Asn Ala Phe Glu Glu Asn Gln Asn Phe
                245                 250                 255

Thr Leu Asp Tyr Gly Asn Ser Ser Ser Asn Trp Val Asp Gln Lys Pro
            260                 265                 270

Asn Val Tyr Phe Gly Asn Thr Thr Thr Thr Gln Val Leu Gln Tyr
            275                 280                 285

Asp Val Glu Glu Val Lys Gln Gln Leu Thr Ser Cys Thr Asn Gly Asn
            290                 295                 300

Asn Gly Ser Thr Ile Gly Cys Asn Asn Asn Ser Met Phe Val Phe
305                 310                 315                 320

Asn Asp Glu Asn Tyr Asn Lys Ser Asn Glu Ile Gly Met Phe Tyr Tyr
                325                 330                 335

<210> SEQ ID NO 79
<211> LENGTH: 495
<212> TYPE: DNA
<213> ORGANISM: Bacillus amyloliquefaciens

<400> SEQUENCE: 79
atgaaaagga atcagcttca catgatgaaa atgggaggta ttgctttgaa aaaacgatta      60
tcgtggattt ccgtttgttt actggtgctt gtctccgcgg cggggatgct gttttcaaca     120
gctgccaaaa cggaaacatc ttctcacaag gcacacacag aagcacaggt tatcaacacg     180
tttgacgggg ttgcggatta tcttcagaca tatcataagc tacctgataa ttacattaca     240
aaatcagaag cacaagccct cggctgggtg gcatcaaaag ggaaccttgc agacgtcgct     300
ccggggaaaa gcatcggcgg agacatcttc tcaaacaggg aaggcaaact cccgggcaaa     360
agcggacgaa catggcgtga agcggatatt aactatacat caggcttcag aaattcagac     420
cggattcttt actcaagcga ctggctgatt tacaaaacaa cggaccatta tcagaccttt     480
acaaaaatca gataa                                                     495

<210> SEQ ID NO 80
<211> LENGTH: 164
<212> TYPE: PRT
<213> ORGANISM: Bacillus amyloliquefaciens

<400> SEQUENCE: 80

```
Met Lys Arg Asn Gln Leu His Met Met Lys Met Gly Gly Ile Ala Leu
1               5                   10                  15

Lys Lys Arg Leu Ser Trp Ile Ser Val Cys Leu Leu Val Leu Val Ser
                20                  25                  30

Ala Ala Gly Met Leu Phe Ser Thr Ala Ala Lys Thr Glu Thr Ser Ser
            35                  40                  45

His Lys Ala His Thr Glu Ala Gln Val Ile Asn Thr Phe Asp Gly Val
        50                  55                  60

Ala Asp Tyr Leu Gln Thr Tyr His Lys Leu Pro Asp Asn Tyr Ile Thr
65                  70                  75                  80

Lys Ser Glu Ala Gln Ala Leu Gly Trp Val Ala Ser Lys Gly Asn Leu
                85                  90                  95

Ala Asp Val Ala Pro Gly Lys Ser Ile Gly Gly Asp Ile Phe Ser Asn
            100                 105                 110

Arg Glu Gly Lys Leu Pro Gly Lys Ser Gly Arg Thr Trp Arg Glu Ala
        115                 120                 125

Asp Ile Asn Tyr Thr Ser Gly Phe Arg Asn Ser Asp Arg Ile Leu Tyr
    130                 135                 140

Ser Ser Asp Trp Leu Ile Tyr Lys Thr Thr Asp His Tyr Gln Thr Phe
145                 150                 155                 160

Thr Lys Ile Arg

<210> SEQ ID NO 81
<211> LENGTH: 1290
<212> TYPE: DNA
<213> ORGANISM: Arabidopsis thaliana

<400> SEQUENCE: 81
atgaacaaca acattttcag tactactacc accatcaatg acgactacat gttattccct       60
tataatgacc attattcctc acaaccattg ctccctttta gcccttcttc ttccattaac      120
gacatcttga ttcactccac ctctaacaca tcaaacaatc atcttgacca tcatcatcaa      180
ttccaacaac cttctccttt ttctcacttc gaatttgccc cggactgcgc cctcctcacc      240
tctttccacc cagaaaacaa tggccatgat gataaccaaa ccatcccaaa cgacaatcat      300
catccatcac ttcactttcc cttgaacaac accattgtag aacaaccac tgagccctcg       360 gaaactataa accttataga agattcccag agaatctcaa cttctcaaga cccaaaaatg      420
aaaaaagcca gaaacccag cagaacggac aggcacagca agatcaaaac ggccaaaggg       480
acacgagatc gtaggatgag actctcgcta gatgtcgcca agagttgtt tggcttacaa       540 gacatgcttg gatttgacaa agccagcaaa accgttgaat ggttgcttac acaagcaaaa      600
cctgagatca taaagatcgc gacaacccct tctcaccatg ctgcttcag cagcggcgat       660 gagtctcata tccgatccat ggacacatct tctgatctat gtgaacttgc atccatgtgg      720
acggtcgacg atagaggcag caatactaac acgaccgaaa caagaggaaa caaggtcgat      780
gggagatcga tgagggaa gagaaagagg ccagaaccgc gaacgcccat tttaaagaag        840
ttgtccaagg aggagagagc gaaagctaga gaaagagcaa agggtagaac aatggagaaa      900
atgatgatga agatgaaagg aagatcacaa ttagtgaaag ttgtggaaga agacgctcat      960
gatcatggtg agataataaa gaataataat agaagccaag tgaatcggag ttctttgag      1020 atgcacacact gcgaagacaa gatcgaagaa ctttgcaaga acgatcgttt tgcagtttgc    1080 aacgaatttta tcatgaataa gaaagatcac atttcaaatg aatcttatga cttagtcaac    1140
```

```
tacaaaccga actcatcatt cccagtgatt aaccaccatc gcagccaagg agcagctaat    1200
tccattgagc agcatcagtt tacggatctt cattactcct tcggcgcgaa accaagagac    1260
ctcatgcaca actatcaaaa catgtattga                                     1290
```

<210> SEQ ID NO 82
<211> LENGTH: 429
<212> TYPE: PRT
<213> ORGANISM: Arabidopsis thaliana

<400> SEQUENCE: 82

```
Met Asn Asn Asn Ile Phe Ser Thr Thr Thr Ile Asn Asp Asp Tyr
1               5                   10                  15

Met Leu Phe Pro Tyr Asn Asp His Tyr Ser Ser Gln Pro Leu Leu Pro
            20                  25                  30

Phe Ser Pro Ser Ser Ile Asn Asp Ile Leu Ile His Ser Thr Ser
        35                  40                  45

Asn Thr Ser Asn Asn His Leu Asp His His Gln Phe Gln Gln Pro
    50                  55                  60

Ser Pro Phe Ser His Phe Glu Phe Ala Pro Asp Cys Ala Leu Leu Thr
65              70                  75                  80

Ser Phe His Pro Glu Asn Asn Gly His Asp Asp Asn Gln Thr Ile Pro
                85                  90                  95

Asn Asp Asn His His Pro Ser Leu His Phe Pro Leu Asn Asn Thr Ile
            100                 105                 110

Val Glu Gln Pro Thr Glu Pro Ser Glu Thr Ile Asn Leu Ile Glu Asp
        115                 120                 125

Ser Gln Arg Ile Ser Thr Ser Gln Asp Pro Lys Met Lys Lys Ala Lys
130                 135                 140

Lys Pro Ser Arg Thr Asp Arg His Ser Lys Ile Lys Thr Ala Lys Gly
145                 150                 155                 160

Thr Arg Asp Arg Arg Met Arg Leu Ser Leu Asp Val Ala Lys Glu Leu
                165                 170                 175

Phe Gly Leu Gln Asp Met Leu Gly Phe Asp Lys Ala Ser Lys Thr Val
            180                 185                 190

Glu Trp Leu Leu Thr Gln Ala Lys Pro Glu Ile Ile Lys Ile Ala Thr
        195                 200                 205

Thr Leu Ser His His Gly Cys Phe Ser Ser Gly Asp Glu Ser His Ile
    210                 215                 220

Arg Ser Met Asp Thr Ser Ser Asp Leu Cys Glu Leu Ala Ser Met Trp
225                 230                 235                 240

Thr Val Asp Asp Arg Gly Ser Asn Thr Asn Thr Glu Thr Arg Gly
                245                 250                 255

Asn Lys Val Asp Gly Arg Ser Met Arg Gly Lys Arg Lys Arg Pro Glu
            260                 265                 270

Pro Arg Thr Pro Ile Leu Lys Lys Leu Ser Lys Glu Glu Arg Ala Lys
        275                 280                 285

Ala Arg Glu Arg Ala Lys Gly Arg Thr Met Glu Lys Met Met Met Lys
    290                 295                 300

Met Lys Gly Arg Ser Gln Leu Val Lys Val Glu Glu Asp Ala His
305                 310                 315                 320

Asp His Gly Glu Ile Ile Lys Asn Asn Arg Ser Gln Val Asn Arg
                325                 330                 335

Ser Ser Phe Glu Met Thr His Cys Glu Asp Lys Ile Glu Glu Leu Cys
            340                 345                 350
```

```
Lys Asn Asp Arg Phe Ala Val Cys Asn Glu Phe Ile Met Asn Lys Lys
            355                 360                 365

Asp His Ile Ser Asn Glu Ser Tyr Asp Leu Val Asn Tyr Lys Pro Asn
    370                 375                 380

Ser Ser Phe Pro Val Ile Asn His His Arg Ser Gln Gly Ala Ala Asn
385                 390                 395                 400

Ser Ile Glu Gln His Gln Phe Thr Asp Leu His Tyr Ser Phe Gly Ala
                405                 410                 415

Lys Pro Arg Asp Leu Met His Asn Tyr Gln Asn Met Tyr
                420                 425

<210> SEQ ID NO 83
<211> LENGTH: 299
<212> TYPE: DNA
<213> ORGANISM: Artificial Sequence
<220> FEATURE:
<223> OTHER INFORMATION: Description of Artificial Sequence:
      Synthetic polynucleotide

<400> SEQUENCE: 83
atgtatccgc caagcaacag ctgcaactac agccccattt tcaacatccc ttctccttgt      60
atgcaatatg gagacgaact attcttccaa tattatcctg accatttcct tcaacagcaa     120
caagtgcctt tgatagaaga tcagagtgtt gacatcttag ctgattgcac tgagaatgtt     180
actaacgaag aaactgtcat caatactgat actgtaaaag ttctttatga cacaggagct     240
gttacaaaca gtcagtgttg gggaggaaat gaagaagtag aagaaggccg cgaaaacaa      299

<210> SEQ ID NO 84
<211> LENGTH: 318
<212> TYPE: DNA
<213> ORGANISM: Artificial Sequence
<220> FEATURE:
<223> OTHER INFORMATION: Description of Artificial Sequence:
      Synthetic polynucleotide

<400> SEQUENCE: 84
atggctcgct ccttgtgttt catggcattt gcagtcttgg caatgatgct ctttgttgcc      60
tatgaggtgc aagctagaga atgcaaaaca gaaagcaata cattccctgg attatgcatt     120
accaaaccac catgcagaaa agcttgtatc agtgagggat ttactgatgg tcattgtagc     180
aaaatcctca gaaggtgcct atgcactaag ccatgtgtgt ttgatgagaa gatgatcaaa     240
acaggagctg aaacttttgc tgaggaagca aaaactttgg ctgcagcttt gcttgaagaa     300
gagataatgg ataactaa                                                   318

<210> SEQ ID NO 85
<211> LENGTH: 300
<212> TYPE: DNA
<213> ORGANISM: Artificial Sequence
<220> FEATURE:
<223> OTHER INFORMATION: Description of Artificial Sequence:
      Synthetic polynucleotide

<400> SEQUENCE: 85
atggcaggga aggttgagaa agtgcttgca gtagtgatgc ttgcaatgct tctgttttcg      60
gagcatttaa tggctgctaa tcatgaaatt aaaacaactg aagataactc tactattagc     120
cctttctgct agtaaaaatg tttatttgga tgtagggggt tgccacctgt acaagcatcc     180
atttgtgctg ctcaatgtta tttaaagtgc cgtgaccaag atgcggccaa tattgctgaa     240
```
actaagggca taattggtga gactgcatac aaccagtatg atgttggatg tgcccttggc    300

<210> SEQ ID NO 86
<211> LENGTH: 300
<212> TYPE: DNA
<213> ORGANISM: Artificial Sequence
<220> FEATURE:
<223> OTHER INFORMATION: Description of Artificial Sequence:
      Synthetic polynucleotide

<400> SEQUENCE: 86
atgtatccgt caagcaacag ctgtaattac agcctcaata tttcctcctc aaataactta     60
tttcacattc catctccgaa ttctatgcaa tatgaacacg aacttttcca atattttcat    120
gaccatcatc tccttcaacc ccaacaacaa caacaacaac aacaactctt gactacacct    180
gatcattata tggcagcaga ttccaacaaa gacaccgtaa tcagtagtac taatcaagat    240
cctgaagaag ttgaattaca aggccgctgc aagaacaaaa aaggtgacaa taagagacgt    300

<210> SEQ ID NO 87
<211> LENGTH: 362
<212> TYPE: DNA
<213> ORGANISM: Artificial Sequence
<220> FEATURE:
<223> OTHER INFORMATION: Description of Artificial Sequence:
      Synthetic polynucleotide

<400> SEQUENCE: 87
atggaaaagg ttcatgagaa accgctatct ctttataatg gatcattatc tgttttaga      60 ttaggagatt tggctgtgaa aataacaaag gtgaaaaagg gatcattaaa taatgataat    120
ctttcacccc caacttcatt gttagttgtt tcaccaatca taccaggaac ttatccagtt    180
ttactctttt ttcatggctt cgttctcaag cctatatggt acaagtctct ccttcaacat    240
atttcttccc acggctatat agttgttgct ccacaggttt ctcaaagcga agaagtgaaa    300
aaagcagcca agttacaga atggttaagt aaagccctcg aatccgtact gccggagaaa    360
gt                                                                  362

<210> SEQ ID NO 88
<211> LENGTH: 300
<212> TYPE: DNA
<213> ORGANISM: Artificial Sequence
<220> FEATURE:
<223> OTHER INFORMATION: Description of Artificial Sequence:
      Synthetic polynucleotide

<400> SEQUENCE: 88
atgtgtttgt taataaaggt ggcgaatcca ggagaatccg gcgagcatga cagaattcca     60
tcaacgggag gtgattcaga aagtacaact actaccacag aaggaggaat tccgcagcta    120
tatgaacaat tacaatcaca atcacaatca tttgaagaaa tgttgcggca acaaatacaa    180
caagaaacag agtatttgat gtcttcatct gcaactccta tgttttcacg gtatagtcag    240
acaagggaga tgtcggcaat ggtaacggcg ttaacgcatg tggtatcagg acggagagag    300

<210> SEQ ID NO 89
<211> LENGTH: 300
<212> TYPE: DNA
<213> ORGANISM: Artificial Sequence
<220> FEATURE:
<223> OTHER INFORMATION: Description of Artificial Sequence:
      Synthetic polynucleotide

<400> SEQUENCE: 89

```
atggcacatt tcttctctat aaattcaacg ttagcaggaa cgaataaagc atccaaaaca    60
aatttcacat attcaactca agaaacagaa aaaccaaaaa taaagatcat cttactcttg   120
ttttctcttg cattagttcc cttgtcagcg atggcaactt gcaccactga tactccaaac   180
caagcactat tgagggatgt acacgatata atggtaaccc ccttcaagt aaaagccagg    240 tacttcatat ttccagttat tggcggtggt ggtgtacggc ttgctaatct tggagatcaa   300
```

<210> SEQ ID NO 90
<211> LENGTH: 348
<212> TYPE: DNA
<213> ORGANISM: Artificial Sequence
<220> FEATURE:
<223> OTHER INFORMATION: Description of Artificial Sequence:
      Synthetic polynucleotide

<400> SEQUENCE: 90

```
atggctgagc aacaccagcg ccaccagcaa cagcagcagc agcagcagat gcaagtgggc    60
cacccgacgg aggcaatcaa gagccttctt cctcaaaggg gtccctctaa atcccaagtc   120
cttgctgtcg tcactctctt ccctgttggt ggggccctcc tctgccttgc tggactgacg   180
ctcgccggaa ctctgatcgg gcttgcagtc gctacgccgg ttttcttact gttcagcccg   240
gttttggtcc ccgctgccct gacaatcgcg ttggccgtca ctggattctt gacttccggc   300
gcctttggaa taacggcgct gtcgtcgctc tcgtggatca ttaactat                348
```

<210> SEQ ID NO 91
<211> LENGTH: 300
<212> TYPE: DNA
<213> ORGANISM: Artificial Sequence
<220> FEATURE:
<223> OTHER INFORMATION: Description of Artificial Sequence:
      Synthetic polynucleotide

<400> SEQUENCE: 91

```
atgaacggtg gttcatgtgg tggtgctgat cgtgagtata ataacaataa caacaataat    60
gttgtaggtg gaggaggtgg cgggccttgt ggtgcatgca gtttcttag aagaaaatgt    120 gtgaggggat gcatatttgc acctattttt gattctgatc aaggcactgc tcatttcgct   180
gctgtacata aggtgtttgg tgctagcaat gcctctaaat tgctgctcag aattccagcg   240
cataaacgtc tggatgctgt cgttacactt tgctatgagg ctcttgctag agttagagac   300
```

<210> SEQ ID NO 92
<211> LENGTH: 300
<212> TYPE: DNA
<213> ORGANISM: Artificial Sequence
<220> FEATURE:
<223> OTHER INFORMATION: Description of Artificial Sequence:
      Synthetic polynucleotide

<400> SEQUENCE: 92

```
atgtcggata aaaaatctgt ctcgacgcca tttgaatgtt gcagaatctt gtttaagttt    60
ctgctgttta tggttattat cagtaatgtg gcgatccatg taacagcttt gagtgggcga   120
gaaggaataa ccccaagtac ggaatggggt ttggggcctc tggtgaagag aggagaaaga   180
aaactagtag tttcaactga aaatggggag gtctcttcag tcagagtagc tgatggaatc   240
accggttcct atcatcttca gttcatcaca ttggagccca ttccctctt ccttcctgtt    300
```

<210> SEQ ID NO 93
<211> LENGTH: 293

```
<212> TYPE: DNA
<213> ORGANISM: Artificial Sequence
<220> FEATURE:
<223> OTHER INFORMATION: Description of Artificial Sequence:
      Synthetic polynucleotide

<400> SEQUENCE: 93
atgggcgtac cagaatcgga ggtggtgtca caaggtgagg ttgaatcacc attgcaacca      60
gatcaaaacc agcacaagaa ccatcagttc ccgtccctcg gtagacaagc atcgatctac     120
tccctcactc tcgacgaatt ccaacacacc ctatgtgaaa gtggcaagaa tttcgggtcg     180
atgaatatgg atgaattcct aacagcattt ggactgctga agaaaaccaa gcccacgcac     240
acgcccatgc ccatgccgcg cacgggcatg cgcacgcgca ttctcatgct cat            293

<210> SEQ ID NO 94
<211> LENGTH: 300
<212> TYPE: DNA
<213> ORGANISM: Artificial Sequence
<220> FEATURE:
<223> OTHER INFORMATION: Description of Artificial Sequence:
      Synthetic polynucleotide

<400> SEQUENCE: 94
atggaggaaa aagatgaact tgaggaagaa gaagaatatg ttgatgatga aatcaagaac      60
aatttaccag tccaaaactc atcttcaata agttggttca caaaaatgat atctttacaa     120
gtagagatct tcaccactat cttagttttcc cccattttct atatcctctc ttttgtatct    180
gacttcaact tcctccgccc tgaagaaacc gaaaagaacg tagctgtagc tgtaaatgct     240
gctgctacag taccttcaaa agtagtacat ggaagtactt tactgctcaa gaaatttggt     300

<210> SEQ ID NO 95
<211> LENGTH: 300
<212> TYPE: DNA
<213> ORGANISM: Artificial Sequence
<220> FEATURE:
<223> OTHER INFORMATION: Description of Artificial Sequence:
      Synthetic polynucleotide

<400> SEQUENCE: 95
atgtataact caagcaacta cagctgtaat tacaacccca ttttctcatc taatttattc      60
aacatccctt ctccttgtat gcaatatgaa cacgaacttt tcttccaata ttaccatgat     120
caacttcaac agaatcttga cgatacctta gctgagatca gtactgagac tgccattatt     180
aacacggcag attccagcaa agacgaggct ataatcagta gaaatgaact tgaacaagat     240
caggaagcgc gtaagaataa aaagggtaaa gtaagcagca caagagagt gtctaagaaa      300

<210> SEQ ID NO 96
<211> LENGTH: 300
<212> TYPE: DNA
<213> ORGANISM: Artificial Sequence
<220> FEATURE:
<223> OTHER INFORMATION: Description of Artificial Sequence:
      Synthetic polynucleotide

<400> SEQUENCE: 96
atgggaactg gtacttatgg agaagtggga cgtacaatac atcaaagatc aggaacacat      60
atacctcaaa ttctcgatcc gcctttgcta ggggatagtg attgcaagcg agaaggcaaa     120
catgtagaat ttatgcctcc aatcatgggt gaaaacttaa aagcagctaa tcaatttgaa     180
ctgatggccc cgtcaattgc attcaaatca tatccctatt cggaggtacc acaatattct     240
```
ggtggcaatg tggctgctgc atgtggtgaa tctttggtac atcaaaatat agaaagatca   300

<210> SEQ ID NO 97
<211> LENGTH: 320
<212> TYPE: DNA
<213> ORGANISM: Artificial Sequence
<220> FEATURE:
<223> OTHER INFORMATION: Description of Artificial Sequence:
      Synthetic polynucleotide

<400> SEQUENCE: 97
aggacaaggt tgtgtttgtg atgggagtca ccggcgccgg aaaatcaaga ctgtcaatag    60
acttagccac tcaattcaga ggagaaatag tgaactccga caaaatacaa gtgtacaaag   120
gtcttgatat tgccactaac aaaatcacac aagaagaacg ttgtggtgta ccacaccatc   180
tcctaggcgt aattgatcct tacaaagaat tcaccaccaa aaacttctgc aacatggctt   240
cacttgcagt taactctata accgaccgcg gtaaacttcc gatcatcgtt ggaggttcca   300
attcgtttat cgaggcgctt                                                320

<210> SEQ ID NO 98
<211> LENGTH: 297
<212> TYPE: DNA
<213> ORGANISM: Artificial Sequence
<220> FEATURE:
<223> OTHER INFORMATION: Description of Artificial Sequence:
      Synthetic polynucleotide

<400> SEQUENCE: 98
gaagatggtg ttggtggtaa tagcagcaaa acaacagca gcagtttcat gtgcaggcaa      60
agtagtacga ggtggacacc cacaactgac cagataagaa tcttgaagga tctttactac   120
aacaatggag ttaggtctcc aactgctgaa cagattcaga ggatctctgc taagttaaga   180
cagtacggta agattgaagg caagaatgtg ttttattggt ttcagaacca taaagctcgt   240
gaaaggcaaa agaagaggct tattgctgct gctgctactg atagcaacaa taatatt      297

<210> SEQ ID NO 99
<211> LENGTH: 339
<212> TYPE: DNA
<213> ORGANISM: Artificial Sequence
<220> FEATURE:
<223> OTHER INFORMATION: Description of Artificial Sequence:
      Synthetic polynucleotide

<400> SEQUENCE: 99
tctaatgttg ttgaaagttc aaatgattca gctctacttc agtcatccta tctttcccta    60
aaccaagtga ctcctttcat tagatttagt cagctaactg ctaatcaagc gattttggaa   120
gctattaacg ataaccaaca agcgatccac atcgttgatt ttgatattaa tcacggtgtt   180
caatggccac cgttaatgca agcactagct gatcgttacc ctcctccaac tcttcggatt   240
accggtactg gaaatgacct tgatacccct cgtagaaccg gagatcgttt agctaaattt   300
gctcactctt taggccttag atttcagttt cacctctct                          339

<210> SEQ ID NO 100
<211> LENGTH: 480
<212> TYPE: DNA
<213> ORGANISM: Artificial Sequence
<220> FEATURE:
<223> OTHER INFORMATION: Description of Artificial Sequence:
      Synthetic polynucleotide

<400> SEQUENCE: 100

```
actgacaatg atatcaagaa ttactggaat actaagctca agaaaaaacc tatgggatta    60
atgcaatcaa ctaaccaaag aaaatcacca tattttccag ctactaattc tcttcaaacc   120
caacccagaa taaattcaag tcttttaga gacttatatt acaccccaaa taataggcct    180
aatattacag gcctaaatca tcagtccatt tcttctgccc accagacaaa ttttctctac   240
actaatagta acatgaattt tcctaatttg ggtgctacaa atagtcaata tccttataat   300
attcaaagtc ataatttact tatgtttgga gaagcaagtt gttcttcatc agatggaagt   360
tgtagccaaa tgagttttgg caaagaaatc aagagagagg aaattatgag taattgttta   420
caacaaggtc aaatttcaag tgttaatgct tttgaagaaa atcagaattt cactcttgat   480
```

```
<210> SEQ ID NO 101
<211> LENGTH: 900
<212> TYPE: DNA
<213> ORGANISM: Artificial Sequence
<220> FEATURE:
<223> OTHER INFORMATION: Description of Artificial Sequence:
      Synthetic polynucleotide

<400> SEQUENCE: 101
atgaattcaa agaaaaacaa ctcaccaaga aaaaggttga gaaaatatca tacaagaaaa    60
gctcctatta ttagctctta tatggacatg gctgaagcta aagagaaat tgttcatgct   120 ttacaacttc atcgatcttc atcttcatct ccaactccgt ctattaatag cccaaagaag   180
tacacattat tgggtcaagg agttgtaagc tctcaacaat attactatta ctcaatagtg   240
gaatctatgc ctattcctga accaacatgg tctacaacgg ctccggcaat acttaatgca   300
atgggaactg gtacttatgg agaagtggga cgtacaatac atcaaagatc aggaacacat   360
atacctcaaa ttctcgatcc gccttttgcta ggggatagtg attgcaagcg agaaggcaaa   420
catgtagaat ttatgcctcc aatcatgggt gaaaacttaa aagcagctaa tcaatttgaa   480
ctgatggccc cgtcaattgc attcaaatca tatccctatt cggaggtacc acaatattct   540
ggtggcaatg tggctgctgc atgtggtgaa tctttggtac atcaaaatat agaaagatca   600
atgtctgatc cccttgtgat tggtagagtg attggggaag ttgttgatta tttcactcca   660
agtgttaaga tgtctgttac ttataacagc agcaagcatg tttataatgg gcatgaactc   720
tttccttcct cagtcacctc taaacctagg gttgaagttc atggaggtga tttgagatct   780
ttctttacaa tgatcatgat agacccagat gttcctggtc ctagtgatcc atatctcagg   840
gaacacctac actggattgt cacagacatt ccaggcacta cagattgctc gtttgggaaa   900
```

```
<210> SEQ ID NO 102
<211> LENGTH: 150
<212> TYPE: DNA
<213> ORGANISM: Artificial Sequence
<220> FEATURE:
<223> OTHER INFORMATION: Description of Artificial Sequence:
      Synthetic polynucleotide

<400> SEQUENCE: 102
caccacatag attgaacgga gggaataata gtgtagcccc attgggaaac accatattta    60
tataggtaga agaaatactc cagatttaac tagaatttct actgacaaaa gatcttttac   120
actatcaatc acttaaaaga taactacagg                                   150
```

```
<210> SEQ ID NO 103
<211> LENGTH: 141
<212> TYPE: DNA
```

```
<213> ORGANISM: Artificial Sequence
<220> FEATURE:
<223> OTHER INFORMATION: Description of Artificial Sequence:
      Synthetic polynucleotide

<400> SEQUENCE: 103
cactaagctt tcttttcctc ataacctcac ttgcttctcc tttgttcttc tttcgtctcc      60
tcctttgttt cgcctcccct tgttctggta actcttgagt gtagatacca ggatagtact     120
gagaaatgag tatcatttga t                                              141

<210> SEQ ID NO 104
<211> LENGTH: 150
<212> TYPE: DNA
<213> ORGANISM: Artificial Sequence
<220> FEATURE:
<223> OTHER INFORMATION: Description of Artificial Sequence:
      Synthetic polynucleotide

<400> SEQUENCE: 104
catgaaccaa cacaatagga ggcaaatcag tgttagtctt ttttgaatca tctgttttaa      60
ggctagtttc caaatttggc ttgaaaagcc aatcgctcag agtctgggaa acatcaccgg     120
ccactgaaac agctctgtca attggaatgt                                     150

<210> SEQ ID NO 105
<211> LENGTH: 165
<212> TYPE: DNA
<213> ORGANISM: Artificial Sequence
<220> FEATURE:
<223> OTHER INFORMATION: Description of Artificial Sequence:
      Synthetic polynucleotide

<400> SEQUENCE: 105
gttatcacaa ttcacaaggg aaagttcata acatgaccac tgtcgaatca aaagggaaa       60 gttcatatat aatacgctta ggctttgggt ttttcaaatg aagggtagag ttcttcataa     120
acgaaattcc acattgttac ttcatatttc acatattccc gaata                    165

<210> SEQ ID NO 106
<211> LENGTH: 153
<212> TYPE: DNA
<213> ORGANISM: Artificial Sequence
<220> FEATURE:
<223> OTHER INFORMATION: Description of Artificial Sequence:
      Synthetic polynucleotide

<400> SEQUENCE: 106
ttctccttat acctcctgag taccataatt tacactcatc tatgtccaat gccttacatc      60
ccacccatct aatttcctga acacaagcta cactaatctt ctaatgagcg caaaatacaa     120
cacaaaatta ttgctcgcta gtcaaagata ata                                 153

<210> SEQ ID NO 107
<211> LENGTH: 180
<212> TYPE: DNA
<213> ORGANISM: Artificial Sequence
<220> FEATURE:
<223> OTHER INFORMATION: Description of Artificial Sequence:
      Synthetic polynucleotide

<400> SEQUENCE: 107
tgggacattt gatagttaga cgttgtaact ttaggttgaa atctgcagtc gagttcattg      60
ttctctttat aataatcact tgaaactggt tgctggctac acgctgctgt tgcttcaaca    120
```
tgcagatatg gcgctaccgg ccgtagtgca gatgtgggag tttccatttc aggcttggca    180

<210> SEQ ID NO 108
<211> LENGTH: 560
<212> TYPE: DNA
<213> ORGANISM: Nicotiana tabacum

<400> SEQUENCE: 108
attactctta actttaaata gatttcttat atatgggttc aaaaatgtct gatcccttg     60 tgattggtag agtgattggg aagttgttg attatttcac tccaagtgtt aagatgtctg   120
ttacttataa cagcagcaag catgtttata atgggcatga actctttcct tcctcagtca   180
cctctaaacc tagggttgaa gttcatggag gtgatttgag atctttcttt acaatgatca   240
tgatagaccc agatgttcct ggtcctagtg atccatatct cagggaacac ctacactgga   300
ttgtcacaga cattccaggc actacagatt gctcgtttgg gaaagaaata gttggctatg   360
aaatgccaag gccaaatatt ggaattcaca ggtttgtatt tctgctgttc aagcagaaga   420
agaggcaaac agtattgact gcacctctct ccagggatcg atttaatacg cgtaaattcg   480
cagaagaaaa tgagcttggg tctcctgttg cagcagtttt cttcaattgc cagagggaaa   540
ctgctgccag aaggcgttga                                                560

<210> SEQ ID NO 109
<211> LENGTH: 522
<212> TYPE: DNA
<213> ORGANISM: Nicotiana tabacum

<400> SEQUENCE: 109
atggctcaaa tgacagatcc ccttgtgatt agtagggtgg ttggagatgt tgttgattat    60
ttctctccaa gtgttaagat gtgtgttatt tataacccca gtaagcatgt ctataatggg   120
catgaactct ttccatccct tgttacctct aaacctaagg ttgaagttca tggaggtgac   180
atgagatcct tctttacact gatcatgact gaccctgatg ttcctggtcc tagcgatcca   240
tatcttaggg agcacttaca ttgggtaatt acagacattc caggcactac agattcctcg   300
tttggaaaag aagtggtggg ctatgaaatg ccaatgccta acattggaat ccataggttt   360
gtgtttctgc tcttcaagca gaagaagagg caaacagtga gcgcaccatt atccagggac   420
cgattcaata cgcggaaata cgcagaagaa aatgagcttg gctctccagt tgctgctgtt   480
ttcttcaact gccaaaggga aaccgcggcc agaaagcgtt ga                       522

<210> SEQ ID NO 110
<211> LENGTH: 453
<212> TYPE: DNA
<213> ORGANISM: Nicotiana tabacum

<400> SEQUENCE: 110
atggctcaaa tgagtacaga tccccttgtg attggcaggg tggttggaga tgttgttgat    60
tatttctccc caagtgttaa aatgtctgtt atttgtaacc ccagcaaaca tgtctataat   120
gggcatgaac tctttccatc ctctgttacc tctaaaccta aggttgaagt taacggaggt   180
gacatgacat ccttctttac attgatcatg actgaccctg atgttcctgg tcctagtgat   240
ccatatatta gggagcactt gcactggaaa agaattaagt ggtgggctat gaaatgccaa   300
tgccaaataa aggaatccat aggtttgtgt ttgtgctgtt caagcagaag aaaaggcaaa   360
cagtatgcat tatccaggga ccgattcaat accaatacag ctgctgctgt tttcttcaat   420
tgccaagggg aaaccgcggc cagaaggcgt tga                                 453

<210> SEQ ID NO 111
<211> LENGTH: 3155
<212> TYPE: DNA
<213> ORGANISM: Artificial Sequence
<220> FEATURE:
<223> OTHER INFORMATION: Description of Artificial Sequence: Synthetic construct for transforming plants

<400> SEQUENCE: 111

```
aagcttccag aaggtaatta tccaagatgt agcatcaaga atccaatgtt tacgggaaaa      60
actatggaag tattatgtga gctcagcaag aagcagatca atatgcggca catatgcaac     120
ctatgttcaa aaatgaagaa tgtacagata caagatccta tactgccaga atacgaagaa     180
gaatacgtag aaattgaaaa agaagaacca ggcgaagaaa agaatcttga agacgtaagc     240
actgacgaca caatgaaaa gaagaagata aggtcggtga ttgtgaaaga gacatagagg      300
acacatgtaa ggtggaaaat gtaagggcgg aaagtaacct tatcacaaag gaatcttatc     360
ccccactact tatccttta tatttttccg tgtcattttt gcccttgagt tttcctatat      420
aaggaaccaa gttcggcatt tgtgaaaaca agaaaaaatt tggtgtaagc tatttctt       480
gaagtactga ggatacaact tcagagaaat ttgtaagttt gtggatcctg caggctagcg     540
tgcactctag actcgacgaa ctgacgagct cgaatttccc cgatcgttca acatttggc      600
aataaagttt cttaagattg aatcctgttg ccggtcttgc gatgattatc atataatttc     660
tgttgaatta cgttaagcat gtaataatta acatgtaatg catgacgtta tttatgagat     720
gggtttttat gattagagtc ccgcaattat acatttaata cgcgatagaa acaaaatat      780
agcgcgcaaa ctatgataaa ttatcgcgcg cggtgtcatc tatgttacta gatcgggaat     840
tcctcgagca actattttta tgtatgcaag agtcagcata tgtataattg attcagaatc     900
gttttgacga gttcggatgt agtagtagcc attatttaat gtacatacta atcgtgaata     960
gtgaatatga tgaaacattg tatcttattg tataaatatc cataaacaca tcatgaaaga    1020
cactttcttt cacggtctga attaattatg atacaattct aatagaaaac gaattaaatt    1080
acgttgaatt gtatgaaatc taattgaaca agccaaccac gacgacgact aacgttgcct    1140
ggattgactc ggtttaagtt aaccactaaa aaacggagc tgtcatgtaa cacgcggatc     1200
gagcaggtca cagtcatgaa gccatcaaag caaagaact aatccaaggg ctgagatgat     1260
taattagttt aaaaattagt taacacgagg gaaaaggctg tctgacagcc aggtcacgtt    1320
atctttacct gtggtcgaaa tgattcgtgt ctgtcgattt taattatttt ttgaaaggc     1380
cgaaaataaa gttgtaagag ataaacccgc ctatataaat tcatatattt tcctctccgc    1440
tttgaattgt ctcgttgtcc tcctcacttt catcagccgt tttgaatctc cggcgacttg    1500
acagagaaga acaaggaaga agactaagag agaaagtaag agataatcca ggagattcat    1560
tctccgtttt gaatcttcct caatctcatc ttcttccgct ctttctttcc aaggtaatag    1620
gaactttctg gatctacttt atttgctgga tctcgatctt gttttctcaa tttccttgag    1680
atctggaatt cgtttaattt ggatctgtga acctccacta aatcttttgg ttttactaga    1740
atcgatctaa gttgaccgat cagttagctc gattatagct accagaattt ggcttgacct    1800
tgatggagag atccatgttc atgttacctg ggaaatgatt tgtatatgtg aattgaaatc    1860
tgaactgttg aagttagatt gaatctgaac actgtcaatg ttagattgaa tctgaacact    1920
gtttaaggtt agatgaagtt tgtgtataga ttcttcgaaa ctttaggatt tgtagtgtcg    1980
tacgttgaac agaaagctat ttctgattca atcagggttt atttgactgt attgaactct    2040
```

```
ttttgtgtgt ttgcagctca taaaaggtac caaacaatga ttgaacaaga tggattgcac    2100
gcaggttctc cggccgcttg ggtggagagg ctattcggct atgactgggc acaacagaca    2160
atcggctgct ctgatgccgc cgtgttccgg ctgtcagcgc aggggcgccc ggttctttt     2220 gtcaagaccg acctgtccgg tgccctgaat gaactgcagg acgaggcagc gcggctatcg    2280
tggctggcca cgacgggcgt tccttgcgca gctgtgctcg acgttgtcac tgaagcggga    2340
agggactggc tgctattggg cgaagtgccg gggcaggatc tcctgtcatc tcaccttgct    2400
cctgccgaga agtatccat catggctgat gcaatgcggc ggctgcatac gcttgatccg    2460
gctacctgcc cattcgacca ccaagcgaaa catcgcatcg agcgagcacg tactcggatg    2520
gaagccggtc ttgtcgatca ggatgatctg gacgaagagc atcagggct cgcgccagcc    2580 gaactgttcg ccaggctcaa ggcgcgcatg cccgacggcg aggatctcgt cgtgacccat    2640
ggcgatgcct gcttgccgaa tatcatggtg aaaatggcc gcttttctgg attcatcgac    2700
tgtggccggc tgggtgtggc ggaccgctat caggacatag cgttggctac ccgtgatatt    2760
gctgaagagc ttggcggcga atgggctgac cgcttcctcg tgctttacgg tatcgccgct    2820
cccgattcgc agcgcatcgc cttctatcgc cttcttgacg agttcttttg agcgggactc    2880
tggcgatcgc cccgatcgtt caaacatttg gcaataaagt ttcttaagat tgaatcctgt    2940
tgccggtctt gcgatgatta tcatataatt tctgttgaat tacgttaagc atgtaataat    3000
taacatgtaa tgcatgacgt tatttatgag atgggttttt atgattagag tcccgcaatt    3060
atacatttaa tacgcgatag aaaacaaaat atagcgcgca aactaggata aattatcgcg    3120
cgcggtgtca tctatgttac tagatcggga ctagt                               3155
```

<210> SEQ ID NO 112
<211> LENGTH: 11801
<212> TYPE: DNA
<213> ORGANISM: Artificial Sequence
<220> FEATURE:
<223> OTHER INFORMATION: Description of Artificial Sequence: Synthetic construct for transforming plants

<400> SEQUENCE: 112

```
tgagcgtcgc aaaggcgctc ggtcttgcct tgctcgtcgg tgatgtactt caccagctcc     60
gcgaagtcgc tcttcttgat ggagcgcatg gggacgtgct tggcaatcac gcgcacccc    120 cggccgtttt agcggctaaa aaagtcatgg ctctgccctc gggcggacca cgcccatcat    180
gaccttgcca agctcgtcct gcttctcttc gatcttcgcc agcagggcga ggatcgtggc    240
atcaccgaac cgcgccgtgc gcgggtcgtc ggtgagccag agtttcagca ggccgcccag    300
gcggcccagg tcgccattga tgcgggccag ctcgcggacg tgctcatagt ccacgacgcc    360
cgtgattttg tagccctggc cgacggccag caggtaggcc gacaggctca tgccggccgc    420
cgccgccttt tcctcaatcg ctcttcgttc gtctggaagg cagtacacct tgataggtgg    480
gctgcccttc ctggttggct tggtttcatc agccatccgc ttgccctcat ctgttacgcc    540
ggcggtagcc ggccagcctc gcagagcagg attcccgttg agcaccgcca ggtgcgaata    600
agggacagtg aagaaggaac accgctcgcg ggtgggcct acttcaccta tcctgcccgg    660
ctgacgccgt tggatacacc aaggaaagtc tacacgaacc ctttggcaaa atcctgtata    720
tcgtgcgaaa aaggatggat ataccgaaaa aatcgctata atgaccccga agcagggtta    780
tgcagcggaa aagcgccacg cttcccgaag ggagaaaggc ggacaggtat ccggtaagcg    840
gcagggtcgg aacaggagag cgcacgaggg agcttccagg gggaaacgcc tggtatcttt    900
```

```
atagtcctgt cgggtttcgc cacctctgac ttgagcgtcg attttttgtga tgctcgtcag      960
gggggcggag cctatggaaa aacgccagca acgcggcctt tttacggttc ctggccttttt    1020
gctggccttt tgctcacatg ttctttcctg cgttatcccc tgattctgtg gataaccgta     1080
ttaccgcctt tgagtgagct gataccgctc gccgcagccg aacgaccgag cgcagcgagt     1140
cagtgagcga ggaagcggaa gagcgccaga aggccgccag agaggccgag cgcggccgtg     1200
aggcttggac gctagggcag ggcatgaaaa agcccgtagc gggctgctac gggcgtctga     1260
cgcggtggaa aggggagggg gatgttgtct acatggctct gctgtagtga gtgggttgcg     1320
ctccggcagc ggtcctgatc aatcgtcacc ctttctcggt ccttcaacgt tcctgacaac     1380
gagcctcctt ttcgccaatc catcgacaat caccgcgagt ccctgctcga acgctgcgtc    1440
cggaccggct tcgtcgaagg cgtctatcgc ggcccgcaac agcggcgaga gcggagcctg    1500
ttcaacggtg ccgccgcgct cgccggcatc gctgtcgccg gcctgctcct caagcacggc    1560
cccaacagtg aagtagctga ttgtcatcag cgcattgacg cgtcccggg ccgaaaaacc    1620
cgcctcgcag aggaagcgaa gctgcgcgtc ggccgtttcc atctgcggtg cgcccggtcg    1680
cgtgccggca tggatgcgcg cgccatcgcg gtaggcgagc agcgcctgcc tgaagctgcg    1740
ggcattcccg atcagaaatg agcgccagtc gtcgtcggct ctcggcaccg aatgcgtatg    1800
attctccgcc agcatggctt cggccagtgc gtcgagcagc gcccgcttgt tcctgaagtg    1860
ccagtaaagc gccggctgct gaaccccaa ccgttccgcc agtttgcgtg tcgtcagacc     1920
gtctacgccg acctcgttca acaggtccag ggcggcacgg atcactgtat tcggctgcaa    1980
ctttgtcatg cttgacactt tatcactgat aaacataata tgtccaccaa cttatcagtg    2040
ataaagaatc cgcgcgttca atcggaccag cggaggctgg tccggaggcc agacgtgaaa    2100
cccaacatac ccctgatcgt aattctgagc actgtcgcgc tcgacgctgt cggcatcggc    2160
ctgattatgc cggtgctgcc gggcctcctg cgcgatctgg ttcactcgaa cgacgtcacc    2220
gcccactatg gcattctgct ggcgctgtat gcgttggtgc aatttgcctg cgcacctgtg    2280
ctgggcgcgc tgtcggatcg tttcgggcgg cggccaatct tgctcgtctc gctggccggc    2340
gccagatctg gggaaccctg tggttggcat gcacatacaa atggacgaac ggataaacct    2400
tttcacgccc tttttaaatat ccgattattc taataaacgc tcttttctct taggtttacc    2460
cgccaatata tcctgtcaaa cactgatagt ttaaactgaa ggcgggaaac gaagcttcca    2520
gaaggtaatt atccaagatg tagcatcaag aatccaatgt ttacgggaaa aactatggaa    2580
gtattatgtg agctcagcaa gaagcagatc aatatgcggc acatatgcaa cctatgttca    2640
aaaatgaaga atgtacagat acaagatcct atactgccag aatacgaaga agaatacgta    2700
gaaattgaaa aagaagaacc aggcgaagaa aagaatcttg aagacgtaag cactgacgac    2760
aacaatgaaa agaagaagat aaggtcggtg attgtgaaag agacatagag gacacatgta    2820
aggtggaaaa tgtaagggcg gaaagtaacc ttatcacaaa ggaatcttat cccccactac    2880
ttatcctttt atattttttcc gtgtcatttt tgcccttgag ttttcctata taggaaccca    2940
agttcggcat ttgtgaaaac aagaaaaaat ttggtgtaag ctattttctt tgaagtactg    3000
aggatacaac ttcagagaaa tttgtaagtt tgtggatcct gcaggctagc gtgcactcta    3060
gactcgacga actgacgagc tcgaattttcc ccgatcgttc aaacatttgg caataaagtt    3120
tcttaagatt gaatcctgtt gccggtcttg cgatgattat catataattt ctgttgaatt    3180
acgttaagca tgtaataatt aacatgtaat gcatgacgtt atttatgaga tgggttttta    3240
```

```
tgattagagt cccgcaatta tacatttaat acgcgataga aaacaaaata tagcgcgcaa    3300
actatgataa attatcgcgc gcggtgtcat ctatgttact agatcgggaa ttcctcgagc    3360
aactattttt atgtatgcaa gagtcagcat atgtataatt gattcagaat cgttttgacg    3420 agttcgatg  tagtagtagc cattatttaa tgtacatact aatcgtgaat agtgaatatg    3480
atgaaacatt gtatcttatt gtataaatat ccataaacac atcatgaaag acactttctt    3540
tcacggtctg aattaattat gatacaattc aatagaaaa  cgaattaaat tacgttgaat    3600
tgtatgaaat ctaattgaac aagccaacca cgacgacgac taacgttgcc tggattgact    3660
cggtttaagt taaccactaa aaaacggag  ctgtcatgta acacgcggat cgagcaggtc    3720
acagtcatga agccatcaaa gcaaagaac  taatccaagg gctgagatga ttaattagtt    3780
taaaaattag ttaacacgag ggaaaaggct gtctgacagc caggtcacgt tatctttacc    3840
tgtggtcgaa atgattcgtg tctgtcgatt ttaattattt ttttgaaagg ccgaaaataa    3900
agttgtaaga gataaacccg cctatataaa ttcatatatt ttcctctccg ctttgaattg    3960
tctcgttgtc ctcctcactt tcatcagccg ttttgaatct ccggcgactt gacagagaag    4020
aacaaggaag aagactaaga gagaaagtaa gagataatcc aggagattca ttctccgttt    4080
tgaatcttcc tcaatctcat cttcttccgc tctttctttc caaggtaata ggaacttctc    4140
ggatctactt tatttgctgg atctcgatct tgttttctca atttccttga gatctggaat    4200
tcgtttaatt tggatctgtg aacctccact aaatctttg  gttttactag aatcgatcta    4260
agttgaccga tcagttagct cgattatagc taccagaatt tggcttgacc ttgatggaga    4320
gatccatgtt catgttacct gggaaatgat tgtatatgt  gaattgaaat ctgaactgtt    4380
gaagttagat tgaatctgaa cactgtcaat gttagattga atctgaacac tgtttaaggt    4440
tagatgaagt ttgtgtatag attcttcgaa acttaggat  ttgtagtgtc gtacgttgaa    4500
cagaaagcta tttctgattc aatcagggtt tatttgactg tattgaactc ttttttgtgtg   4560 tttgcagctc ataaaaggta ccaaacaatg attgaacaag atggattgca cgcaggttct    4620
ccggccgctt gggtggagag gctattcggc tatgactggg cacaacagac aatcggctgc    4680
tctgatgccg ccgtgttccg gctgtcagcg caggggcgcc cggttctttt tgtcaagacc    4740
gacctgtccg gtgccctgaa tgaactgcag gacgaggcag cgcggctatc gtggctggcc    4800
acgacgggcg ttccttgcgc agctgtgctc gacgttgtca ctgaagcggg aagggactgg    4860
ctgctattgg gcgaagtgcc ggggcaggat ctcctgtcat ctcaccttgc tcctgccgag    4920
aaagtatcca tcatggctga tgcaatgcgg cggctgcata cgcttgatcc ggctacctgc    4980
ccattcgacc accaagcgaa acatcgcatc gagcgagcac gtactcggat ggaagccggt    5040
cttgtcgatc aggatgatct ggacgaagag catcaggggc tcgcgccagc cgaactgttc    5100
gccaggctca aggcgcgcat gcccgacggc gaggatctcg tcgtgaccca tggcgatgcc    5160
tgcttgccga atatcatggt ggaaaatggc cgcttttctg gattcatcga ctgtggccgg    5220
ctgggtgtgg cggaccgcta tcaggacata gcgttggcta cccgtgatat tgctgaagag    5280
cttggcggcg aatgggctga ccgcttcctc gtgctttacg gtatcgccgc tcccgattcg    5340
cagcgcatcg ccttctatcg ccttcttgac gagttctttt gagcgggact ctggcgatcg    5400
ccccgatcgt tcaaacattt ggcaataaag tttcttaaga ttgaatcctg ttgccggtct    5460
tgcgatgatt atcatataat ttctgttgaa ttacgttaag catgtaataa ttaacatgta    5520
atgcatgacg ttatttatga gatgggtttt tatgattaga gtcccgcaat tatacattta    5580
atacgcgata gaaaacaaaa tatagcgcgc aaactaggat aaattatcgc gcgcggtgtc    5640
```

```
atctatgtta ctagatcggg actagtttac accacaatat atcctgccac cagccagcca   5700
acagctcccc gaccggcagc tcggcacaaa atcaccactc gatacaggca gcccatcagt   5760
ccgggacggc gtcagcggga gagccgttgt aaggcggcag actttgctca tgttaccgat   5820
gctattcgga agaacggcaa ctaagctgcc gggtttgaaa cacggatgat ctcgcggagg   5880
gtagcatgtt gattgtaacg atgacagagc gttgctgcct gtgatcaaat atcatctccc   5940
tcgcagagat ccgaattatc agccttctta ttcatttctc gcttaaccgt gacaggctgt   6000
cgatcttgag aactatgccg acataatagg aaatcgctgg ataaagccgc tgaggaagct   6060
gagtggcgct atttctttag aagtgaacgt tgacgatatc aactccccta tccattgctc   6120
accgaatggt acaggtcggg acccgaagt tccgactgtc ggcctgatgc atccccggct   6180
gatcgacccc agatctgggg ctgagaaagc ccagtaagga acaactgta ggttcgagtc   6240
gcgagatccc ccggaaccaa aggaagtagg ttaaacccgc tccgatcagg ccgagccacg   6300
ccaggccgag aacattggtt cctgtaggca tcgggattgg cggatcaaac actaaagcta   6360
ctggaacgag cagaagtcct ccggccgcca gttgccaggc ggtaaaggtg agcagaggca   6420
cgggaggttg ccacttgcgg gtcagcacgg ttccgaacgc catggaaacc gcccccgcca   6480
ggcccgctgc gacgccgaca ggatctagcg ctgcgtttgg tgtcaacacc aacagcgcca   6540
cgcccgcagt tccgcaaata gcccccagga ccgccatcaa tcgtatcggg ctacctagca   6600
gagcggcaga gatgaacacg accatcagcg gctgcacagc gcctaccgtc gccgcgaccc   6660
cgcccggcag gcggtagacc gaaataaaca acaagctcca gaatagcgaa atattaagtg   6720
cgccgaggat gaagatgcgc atccaccaga ttcccgttgg aatctgtcgg acgatcatca   6780
cgagcaataa acccgccggc aacgcccgca gcagcatacc ggcgacccct cggcctcgct   6840
gttcgggctc cacgaaaacg ccggacagat gcgccttgtg agcgtccttg gggccgtcct   6900
cctgtttgaa gaccgacagc ccaatgatct cgccgtcgat gtaggcgccg aatgccacgg   6960
catctcgcaa ccgttcagcg aacgcctcca tgggcttttt ctcctcgtgc tcgtaaacgg   7020
acccgaacat ctctggagct ttcttcaggg ccgacaatcg gatctcgcgg aaatcctgca   7080
cgtcggccgc tccaagccgt cgaatctgag ccttaatcac aattgtcaat tttaatcctc   7140
tgtttatcgg cagttcgtag agcgcgccgt gcgtcccgag cgatactgag cgaagcaagt   7200
gcgtcgagca gtgcccgctt gttcctgaaa tgccagtaaa gcgctggctg ctgaaccccc   7260
agccggaact gaccccacaa ggccctagcg tttgcaatgc accaggtcat cattgaccca   7320
ggcgtgttcc accaggccgc tgcctcgcaa ctcttcgcag gcttcgccga cctgctcgcg   7380
ccacttcttc acgcgggtgg aatccgatcc gcacatgagg cggaaggttt ccagcttgag   7440
cgggtacggc tccggtgcg agctgaaata gtcgaacatc cgtcgggccg tcggcgacag   7500
cttgcggtac ttctcccata tgaatttcgt gtagtggtcg ccagcaaaca gcacgacgat   7560
ttcctcgtcg atcaggacct ggcaacggga cgttttcttg ccacggtcca ggacgcggaa   7620
gcggtgcagc agcgacaccg attccaggtg cccaacgcgg tcggacgtga agcccatcgc   7680
cgtcgcctgt aggcgcgaca ggcattcctc ggccttcgtg taataccggc cattgatcga   7740
ccagcccagg tcctggcaaa gctcgtagaa cgtgaaggtc atcggctcgc cgataggggt   7800
gcgcttcgcg tactccaaca cctgctgcca caccagttcg tcatcgtcgg cccgcagctc   7860
gacgccggtg taggtgatct tcacgtcctt gttgacgtgg aaaatgacct tgttttgcag   7920
cgcctcgcgc gggattttct tgttgcgcgt ggtgaacagg gcagagcggg ccgtgtcgtt   7980
```

```
tggcatcgct cgcatcgtgt ccggccacgg cgcaatatcg aacaaggaaa gctgcatttc   8040
cttgatctgc tgcttcgtgt gtttcagcaa cgcggcctgc ttggcctcgc tgacctgttt   8100
tgccaggtcc tcgccggcgg ttttcgctt cttggtcgtc atagttcctc gcgtgtcgat    8160
ggtcatcgac ttcgccaaac ctgccgcctc ctgttcgaga cgacgcgaac gctccacggc   8220
ggccgatggc gcgggcaggg caggggagc cagttgcacg ctgtcgcgct cgatcttggc    8280
cgtagcttgc tggaccatcg agccgacgga ctggaaggtt tcgcggggcg cacgcatgac   8340
ggtgcggctt gcgatggttt cggcatcctc ggcggaaaac cccgcgtcga tcagttcttg   8400
cctgtatgcc ttccggtcaa acgtccgatt cattcaccct ccttgcggga ttgccccgac   8460
tcacgccggg gcaatgtgcc cttattcctg atttgacccg cctggtgcct tggtgtccag   8520
ataatccacc ttatcggcaa tgaagtcggt cccgtagacc gtctggccgt ccttctcgta   8580
cttggtattc cgaatcttgc cctgcacgaa taccagcgac cccttgccca aatacttgcc   8640
gtgggcctcg gcctgagagc caaaacactt gatgcggaag aagtcggtgc gctcctgctt   8700
gtcgccggca tcgttgcgcc acatctaggt actaaaacaa ttcatccagt aaaatataat   8760
attttatttt ctcccaatca ggcttgatcc ccagtaagtc aaaaaatagc tcgacatact   8820
gttcttcccc gatatcctcc ctgatcgacc ggacgcagaa ggcaatgtca taccacttgt   8880
ccgccctgcc gcttctccca agatcaataa agccacttac tttgccatct ttcacaaaga   8940
tgttgctgtc tcccaggtcg ccgtgggaaa agacaagttc tcttcgggc ttttccgtct    9000 ttaaaaaatc atacagctcg cgcggatctt taaatggagt gtcttcttcc cagttttcgc   9060
aatccacatc ggccagatcg ttattcagta agtaatccaa ttcggctaag cggctgtcta   9120
agctattcgt atagggacaa tccgatatgt cgatggagtg aaagagcctg atgcactccg   9180 cataacagctc gataatcttt tcagggcttt gttcatcttc atactcttcc gagcaaagga   9240
cgccatcggc ctcactcatg agcagattgc tccagccatc atgccgttca aagtgcagga   9300
cctttggaac aggcagcttt ccttccagcc atagcatcat gtccttttcc cgttccacat   9360
cataggtggt ccctttatac cggctgtccg tcattttaa atataggttt tcatttctc     9420 ccaccagctt atatacctta gcaggagaca ttccttccgt atcttttacg cagcggtatt   9480
tttcgatcag tttttcaat tccggtgata ttctcatttt agccatttat tatttccttc    9540
ctcttttcta cagtatttaa agatacccca agaagctaat tataacaaga cgaactccaa   9600
ttcactgttc cttgcattct aaaaccttaa ataccagaaa acagcttttt caaagttgtt   9660
ttcaaagttg gcgtataaca tagtatcgac ggagccgatt ttgaaaccac aattatgggt   9720
gatgctgcca acttactgat ttagtgtatg atggtgtttt tgaggtgctc cagtggcttc   9780
tgtgtctatc agctgtccct cctgttcagc tactgacggg gtggtgcgta acggcaaaag   9840
caccgccgga catcagcgct atctctgctc tcactgccgt aaaacatggc aactgcagtt   9900
cacttacacc gcttctcaac ccggtacgca ccagaaaatc attgatatgg ccatgaatgg   9960
cgttggatgc cgggcaacag cccgcattat gggcgttggc ctcaacacga ttttacgtca   10020
cttaaaaaac tcaggccgca gtcggtaacc tcgcgcatac agccgggcag tgacgtcatc   10080 gtctgcgcg aaatggacga acagtggggc tatgtcgggg ctaaatcgcg ccagcgctgg    10140
ctgttttacg cgtatgacag tctccggaag acggttgttg cgcacgtatt cggtgaacgc   10200
actatggcga cgctggggcg tcttatgagc ctgctgtcac cctttgacgt ggtgatatgg   10260
atgacggatg gctggccgct gtatgaatcc cgcctgaagg gaaagctgca cgtaatcagc   10320
aagcgatata cgcagcgaat tgagcggcat aacctgaatc tgaggcagca cctggcacgg   10380
```

```
ctgggacgga agtcgctgtc gttctcaaaa tcggtggagc tgcatgacaa agtcatcggg    10440
cattatctga acataaaaca ctatcaataa gttggagtca tacccaatt atgatagaat     10500 ttacaagcta taaggttatt gtcctgggtt tcaagcatta gtccatgcaa gtttttatgc    10560
tttgcccatt ctatagatat attgataagc gcgctgccta tgccttgccc cctgaaatcc    10620
ttacatacgg cgatatcttc tatataaaag atatattatc ttatcagtat tgtcaatata    10680
ttcaaggcaa tctgcctcct catcctcttc atcctcttcg tcttggtagc ttttaaata    10740 tggcgcttca tagagtaatt ctgtaaaggt ccaattctcg ttttcatacc tcggtataat    10800
cttacctatc acctcaaatg gttcgctggg tttatcgcac ccccgaacac gagcacggca    10860
cccgcgacca ctatgccaag aatgcccaag gtaaaaattg ccggcccccgc catgaagtcc   10920 gtgaatgccc cgacggccga agtgaagggc aggccgccac ccaggccgcc gccctcactg    10980
cccggcacct ggtcgctgaa tgtcgatgcc agcacctgcg gcacgtcaat gcttccgggc    11040
gtcgcgctcg ggctgatcgc ccatcccgtt actgccccga tcccggcaat ggcaaggact    11100
gccagcgctg ccatttttgg ggtgaggccg ttcgcggccg aggggcgcag cccctggggg    11160
gatgggaggc ccgcgttagc gggccgggag ggttcgagaa ggggggcac cccccttcgg     11220 cgtgcgcggt cacgcgcaca gggcgcagcc ctggttaaaa acaaggttta taaatattgg    11280
tttaaaagca ggttaaaaga caggttagcg gtggccgaaa acgggcgga aacccttgca     11340 aatgctggat tttctgcctg tggacagccc ctcaaatgtc aataggtgcg ccctcatct    11400 gtcagcactc tgcccctcaa gtgtcaagga tcgcgcccct catctgtcag tagtcgcgcc    11460
cctcaagtgt caataccgca gggcacttat ccccaggctt gtccacatca tctgtgggaa   11520
actcgcgtaa aatcaggcgt tttcgccgat ttgcgaggct ggccagctcc acgtcgccgg   11580
ccgaaatcga gcctgcccct catctgtcaa cgccgcgccg ggtgagtcgg cccctcaagt   11640
gtcaacgtcc gcccctcatc tgtcagtgag ggccaagttt tccgcgaggt atccacaacg   11700
ccggcggccg cggtgtctcg cacacggctt cgacggcgtt tctggcgcgt ttgcagggcc   11760
atagacggcc gccagcccag cggcgagggc aaccagcccg g                       11801
```

<210> SEQ ID NO 113
<211> LENGTH: 2499
<212> TYPE: DNA
<213> ORGANISM: Nicotiana tabacum

<400> SEQUENCE: 113

```
tctaggagca aaaaaaaaaa aaaaaaaaa aacaagtagt agtagtagta gtaaatggaa      60
aaatagagag gcaattttt ttagtatctt actttatcca ttagcactta aaaacatag      120 gtttacatgc tctcattgtc acgccaggcc gctaattaaa tggtacattt catcatcccc    180
attttttggc ctcatagtta attatcacaa tttctgaaag caacatcaga acaaccccac    240
atttcttgtg gtcctataat tactgctaga gtagtccaaac ccatctgcct atttagggct   300
tgtgaatgag gattgaaaat ggtagagaat atttgcaaag gcatcatgca tatatggaaa    360
agactaaaga gagagttagt gccttgcaaa gcggattctc acagttgtag aaaaggactc    420
accattttca agaatactcc cggcatgaag atggacaatt aatataaaa aacaaagaaa     480 atagtaatta agtgcgttga gatgaatgaa atttatccgc tcttaattga atatgggaa     540 ttgaaagaaa tttctgataa taaattaatg agtcttacat gacgtggatc cgacttaatc    600
tagtctattt aaactaagaa tagataagaa tagagaatat agacaaaaga gaggctcatt    660
```

```
ggctagggtt tcaagggagt tccttgaaca taagtggcaa gtacaagcac aaagccaatt      720
tccatggact aaagatgaat aagatgtgtc gtgtggtatg gtgggaaggt gaggaggtat      780
ggggtaattg gagatgctaa acctctctaa aagctctttt gctccaaata tctaaatcca      840
tctctatcac ttttggcgac tgccccaaaa tttgcaactt atgaattaaa gttttaatat      900
ttttaagtta ataaattctg aattaataat ttaacatatt caataaactt tttaaaacaa      960
attacgtata taccatcaaa ctggctgcac catgatcact ttctaaactc acaatgacat     1020
atggatttaa tcaggcacaa agtcatgttg atagaaagag atagtacgga gaatgaagaa     1080
aaaaggtagg ggagagagat ggggtgagtg gggaaaagat agggttctct ttttagtgaa     1140
agcgacaggg tctgagaacc ctaggtcaaa agttgcataa acctctatac aggcttcttc     1200
actcccttac tactaatata ctctcattaa ggcttgaggt ttaattcatt aaaattgtgg     1260
tttaattatt gtatcccctc aaacgaaata attgtccttg tcgaggttag acaatgttgc     1320
gtactatttt caaacgcagt cagccattat tctcctatcc tttacagtcg agattcaaag     1380
acagaaagta gcatgcaagc tgttattaat ttactttgat taggactttg ccaagaaaat     1440
gaagaacctt ttcttttttc ttttaattta gttatcttac aacatgtaat ttttcctagc     1500
aagcaaatac ggtaacttt tttttttattc tcatttaatt tgttggagct attgctactt     1560
tgatgacttc aaccaaatcc tggttggtag gcggagggtg ctgacgatgg aaactacccc     1620
tcttgtccaa atacgataac ctaaaaaata gaataatagc ttattgtact gtgctgcaaa     1680
aattgcattg tcagtataca taattaaaat ctattttgaa tgtgtggagg gcaaagaggg     1740
gtgactggtc tagggttgta gaaatcaggt gggagagaga atggtatttg tctctgtgtc     1800
agctgatatc acgtgaagag gcacaataag aagtccttcg tatccattca cttcccaaaa     1860
ataccggcat tactacaaat atagtactag cacttgcttt ctctatcccc atctttgcta     1920
tttcctttcc ctttccaact ttttggcttt agaattgcaa agatggaggg aattgtggtt     1980
ctttgtatct gtaaaatttt tcctccaagc tccagttgta gctagcttaa tgcgtggacg     2040
cgcgcgcaca cactagaaat ctgcaatcta tatatatatt cacaaggcac tcacatatca     2100 aaaccacat agacattgta tagagagagc tgtcgttctc aagcagaaaa atgatatga      2160 tttcatcagc atgtggtcaa ccaaatagtt caattctagt ctttgcttcc tctttctaat     2220
tactgtataa atagagccac aaggacatag aattgagaaa ataaagaca ataaaaacaa       2280 atctagctac ttaagcgaat gatgatgact ctctctcagt agtcttaact cttaataccc     2340
ttgttttcct tcttgtgctg cagtttgatt ggttaattaa cctaatcaaa agatgtttta     2400
actgtgtttt atccgtcttt ctcaagatct atcttagtcc caccacatag ctccctcaag     2460
ctacagctgc aaaatatata ctatatatat atataacaa                            2499
```

<210> SEQ ID NO 114
<211> LENGTH: 2500
<212> TYPE: DNA
<213> ORGANISM: Nicotiana tabacum
<400> SEQUENCE: 114

```
tgacattgct ttggtggttt aagttctcag ccagtatatg cattgtccta ataggtctca       60
catggaagca gcactgagag ttgtaagata cataaaagaa gctcctggct taggtctctt      120
cttgcctgta aaatcttcag atcaactaag tgctttttgt gactcagatt ggggagcatg      180
tatacaaatt agaaggttag ttacagggta cttggtaaag tttgaaagtg ctcttatatc      240
ctggaagtct aagaagcaga gtactgtgtc taggagctct aatgaagctg agtttataag      300
```

```
tatggcttca tgtgcagcag aagttacctg gccggtagga ctgttcagtg aacttggtgt    360
caaggttaaa cttcctataa acttggtatg tgatagtaaa gctgcaatcc aaattgcagc    420
aaatccaatc ttccatgaaa gaacaaaaca tattgatata gactgtcact ttgtaaagga    480
aaagctaagt ctaaggatgc taaaaactga gtatgtcaac atgaggatca actggcagat    540
atacttacaa aaggattgtg aagagctcaa catgtacatt tgctgaacaa gctagggttg    600
aagaatctgt atcaaccatc agcttgagag ggagtgttaa tcaacatggt taccactagt    660
ttatttataa agtgtaaatg ctaaaccata gctagtgagt tagttaatag ttagttgagt    720
ttgttataaa tattagtcag ctgtacagtt taacatagct tctctttcag aaatgaaaat    780
tgctcttctc tcatttcctc tcttctagat tcttcttctc cctccttctc ttagctcaga    840
tctctcttat gacagctaac aataaatacg aatatttctt gtaacggttg ctcattgaat    900
gttgtctttc tcaaccgata tctttctttc aagttttccc cccgattcga gtatttttga    960
aactcactca gcaccggtca catattcgta atcggtgcca gctatttgct tactcatatc   1020
ttatttgact tcattgtcac gtgtcagaca gaagtatgtg cgcatatacc atcaagtctc   1080
aatttgaaat aaaatcaact taagcagtta aaagtcaaat ctcttttagt tcggtcttta   1140
aaataataat ttaataatg aacctataaa acacgcaact cacactgaat ataggggcag   1200
acataaaagc cgaaagactg aattccgaac cggaccgaat tatttcggta tttcgatatc   1260
ggtttattca gtatttcggt actatttcgg tataggattt ttagttattc ggtatttcgg   1320
tacgatcctc ggtattgaaa tttcgatatt tcggtatacc gaaataccga ataatttaag   1380
tacaccttcc ttcactgccc agcccgttat caattttcag cccaagtttc taacttgtta   1440
tttctttccc ttagccagta gcctactaag attaagccca acgccccaac ctaacattag   1500
aaattattat aattagaaaa gtataaagaa agtactcaca ttctactgct atgctcatgt   1560
agtgatttct attagaaatt attagaagtg aaggtactgc ccacattttc ttgttgctat   1620
actcattatc acgcaattag aaattttcta atgaattaga attcagtagt tcagcacaga   1680
ggcggatgta gcgtattacc tacgggttca actgaaccta taactttcga cacagagtaa   1740
aaatttatat gtaaaaattc tttaaaattg taaaaatcgt agatatgaac ccataacttt   1800
aaaaatataa tgggtaacat taaaattgaa cccatagaat ttaaatcctg gattcgcctc   1860
tggttcagca ttgtttagtt cacaaaaata tggtacgatg ccgaaccgta tcgaaaccat   1920
accgaaccaa acaagaagat atcgaacaat accgaactac tttggtacag tatttggtat   1980
gcacacttga tatatcgaat accgaaatac cgaaccgtaa ttttcgaata ccgtaccgaa   2040
ataccgaaca ctcacccata actaaacatt aaaaagctag aactcaggtg tttaatgact   2100
aaacggaagt aagatctaga taatccgtca ctctgttgat ttgtaaggct atcgacatgc   2160
aaaagtggaa gcaaatggaa gccgaaattt taacaaaaat gctgaaccaa taccatgaaa   2220
ttgatgaatg gtgggaccct atttcactct tttagaattt gcgtaagacc agaaaataac   2280
ttcaatcgaa atcaaaataa ataccaaccc ttttaggccc caaatcacta cgtgtgattt   2340
gcaaacgtca ttagccttat gtaaacagtg acctcatgcc aacatattat cgcagcctat   2400
aaatcttagt ttacatttca ttttctttca aacacacaca cctcacaata gaactaagtt   2460
gtaagagttt cattttcttt gttctttctc acaaaccaaa                         2500
```

<210> SEQ ID NO 115
<211> LENGTH: 2500
<212> TYPE: DNA

<213> ORGANISM: Nicotiana tabacum

<400> SEQUENCE: 115

```
tgccagacag tctaaaattc aaaaatagga cagcccacat cccctccacc ccactagatc      60
tcactacttc ttaattagga cttgtggggg ggagtagagg gatttgcaaa ggcggccgcg     120
gcatgcatat acggaaaaga gaagttagtg gtttgcaaag atgattgtgg aaaagggctt     180
acctaacaat gaagaagagg aagagggtag atggataata ataactcaaa aatagaaaga     240
agagggacaa gtgggggctc aatggctaag gttttaaggg aggtcttgga aacatcatta     300
gcaagtacat gcagtattac caccctacat cagactgtgg ggtctgatgg aatattcttc     360
tactatactc ttttaaatag agggaattaa tgagccttta taatgttgaa atttataaga     420
aaatagtata acttttaaa tctcttaatt atgtatcaaa tcaaatctca tatttaccct     480
ttagtggatc tattcactga agtctgaata aatcgtacca gtaattcata ccgaatgtgt     540
aaataatttg aaagaaagat agacaaggcc tcaatgkcta gggatttgtt agcatcaata     600
gcaagtataa gcagaaatat ataccaccaa ggagtgaggt ggaagaatta agatttactc     660
taatgaaata tatatatcaa gattgagtca tgtgaatgaa gaatttctta gtaccttaaa     720
ttaagcgaat atcacataac agaggtgtaa aaaaacgaaa gatggacaag ctaagtggct     780
ctcaatggct ggggttttaa gggatcggag gtcttgttaa catcagacgg aagtacaatt     840
agagtatata tgctactcta ataatacttg gctacaaaca taaaaaaata tctctatcac     900
tatctctcaa ctcgccatat agacttaatt ggcacaaagt catgctgatg aaagagata      960
taaggagaat gggaagacaa aaaaaaaagt ggggatagaa agagtgtcca agtagctaga    1020
aggggtggg ggtggggggt ggggagttg ttgttttagt tgtggaagag ataggtttct    1080
cttttagtg aaagtgacat atatagctag actgagaacc ctggtcaaaa gttgctttgc    1140
cttaacgttt ctaaatgcct gacctctgag aggctatctt ctcctctcat tctctcgacc    1200
cttactgttc atatacccc aaatttgagg tctaatttat ccacactatg gtttcttact    1260
gttgtcttct tctctgaaac aatattgctt gtcgatcttg gacttggcca cgtcaacgtg    1320
taacttcagc aactagggtg actccaagtc atagacagat ctaggtcgac ttctgtgaat    1380
ttaactaaac aaattattta atttcgactc aaaatagata tgtactatat atatatatag    1440
taaacttatt gtgaacttac taacttaaaa ttttcaagtt tgcagtattt tttgaataa     1500
gaaagggaa aaagaggcag aaaacccat atttcttcct ctttggagtt gacgctaaag    1560
ggataaagct aacatgcaag ctcttaacaa ataacatact cagtataatc tcacaaatgg    1620
ggtatagaga ggataaaacg tacacaaatc ttaacaatat acacagtgta attccataag    1680
tgagttctgt ggacggtagt agcttacccc ttgcctttaa catgcaagct cttaagcttt    1740
gtattttat tttgttcttt cttttttggag aggaagaagt ggtggttgaa gactagagat    1800
aaggaagaaa agagaaggat ttttgtcagt tgctatcacg tgaactgaag gggcacaatt    1860
agagagaagt ctatatgctt cacttcccat aaaatcagtt gtaactacaa caagtactaa    1920
gagtgtcccc tccattttct ttcttccct caattccctt tcatacttt aaagcttaat     1980
tccacagcta gaaaagaag ccttctttt tctctagagg tatttagcaa agatggaagg    2040
acaatattac agctctcttt gtctctacag gtaacaaacc attgcctgtc tttctcaatc    2100
tccagtattt ccagctatct tataatgctt tgagtactcc cacaaaacac atgcattata    2160
gccactagct acatatatat atatatttgt aaaaccacac attaatttag ctgtcattct    2220
caaccaaaaa gctatgttat catcaacata ttgacaaatt acctataatt ccttcccctc    2280
```

```
tagctatatg atctatctca ctttattatg cacttaaaaa gttatgttgt ccctctcaaa    2340
agtcttaatt aattaaccct tgttttgcatc ttgctgcagc tagctagctt attaaattga    2400
caaactcaga agatgttgtg gttctttcaa cttcaataaa aagctaagag tagtacttgt    2460
gcttgtatat ccgtccttct caagctcaag tcccacttca                          2500
```

<210> SEQ ID NO 116
<211> LENGTH: 3433
<212> TYPE: DNA
<213> ORGANISM: Nicotiana tabacum
<220> FEATURE:
<221> NAME/KEY: modified_base
<222> LOCATION: (3171)..(3178)
<223> OTHER INFORMATION: a, c, t or g

<400> SEQUENCE: 116

```
gttggagcta aaataagag aaatggacaa gtgtcaaatt ctagcgtcca tggtagcgcg      60
acgcactatt gtggcgctag aaatagaaga ccaaaatttc caatgttggc gtcgaccttg     120
cgttgcggta tttttttctat ttcgctaggg acaagattat ttcaacaaaa ggggttctaa   180
acctaatttg gaggatatct aacatacttt gaaggcgaat tcacgtaagg gaatacaaac    240
cacgcttgga agggcttttc aactagtttt tcttctcttc ttttctcttc ctttcatctc     300
attatgtatt agttctaggg ttgttggtac ttacattaac gttatagttt gaagcttgga    360
ttatcttatt attttatcat attggtttat ttattcaatc ttgcgcttga taatttaatt   420
ttaattgatt gatcaccaat taaatactat ctacgaattt aggattgaaa tcgggagaga    480
aaattttaga ttgcatatag gattgagtag agtaagatct tgaacctgaa ttacgaggga    540
acgaatttgc gattaggata taaggatata cctaatcgtc ttgcttggtt actatacggg    600
aattattaat acgttcttat taatcctaat ccactggaat ataggcgttg agttagcttg    660
aacaggcgag tagtacttcg ggagaatact acgagtaata ttaaattgtc aatcaataaa   720
ctagataaat ttataagata gtttaagtaa aaaactcaat gagattgtta gttgacccat    780
aactctgaaa tattttctcc cattagattg tctttaagct tgccggcata gtttttctag    840
ttttctagtt tacaactcta gattagttat agttaacaat cacactttag aaaatcgctt    900
gagtagatta attgttaatt tagttgatag ttaatcataa gtcatcgagg gaacgatact    960
ctacttatca ctttattact tatcgaccac gtatacttga gtgcgtttgg gagcaacaaa   1020
tttttgacgc cgttgccggg acgttagttg atgttttcaa ctagtgaaca aaatgcaaat   1080
atgttatgca attcggtgcc atttacacgt ctatgaggag ttatattaaa gaactttatg   1140
taggatgttg gttggatcct acaagctaaa attatggcta agaaaattgt gaattactaa   1200
taaacttgta ataagataaa aaataatttc ctagaacgta atagaattga agtgagatta    1260
gaccgacacc tcttcgtcgg aaaactatgt tatatatgta ggttatttta tatatatata   1320
tatatatata tataattttc ttggcgttta attttttata ttttgattct tcctactaat    1380
aattctaact ctatcactga attaaacgta caggattcat ttcttataca aaagaggttg    1440
atcattatta ggtctgggca ctgtcagagg ctgaccgata tgagtagttc ttcacatgct   1500
tggcagcaat ttgaactgtg attgcttgag gggcgaaaaa gagagtagaa tctaagttcg   1560
gtaattttta tctgaattct gtatttgtct taaaaattta ttgagtatgc ataaaattat   1620
tattttaaac tcagtaattt aaaaaattta gaattcgaac tcataaattt caaattggga   1680
ctccacctct gattgtttgt aagtggagtt taggggcaga actagctcaa aaagttcggg   1740
```

```
ttcgattgaa ctcagtaaat tgattcaaa gtctatatat ttattgaaaa atcaactaaa      1800
tatgtatata tacaataaat ttcaaattca taaaaattta atcctgaat taacctaata      1860 gtaaaaccgc agactctaac tagtggtcta gtttagagag tcaaattatg gttttttaaca    1920 accttaaaca agcacaaata cttttccact attggttcaa ttttggttgt taacaacctt    1980
gattggtaat tacgtacttg catgggcatt tgaaaattaa gttacgtacg tgtaaaacgt    2040
tttagagtag tccgtactaa ttaagaacac aaacactgct tgagattttg tggcggaagt    2100
ttgttttgac ttagcatggg taggcccacg aattccccat tttgaataaa agacaacctg    2160
tgctagtcga ttagctatta tttaattact agaatattac ttactccctc ctttttaatt    2220
tagacgattt agtttgactt ggcacaaagt ttaaagaaaa aaaaaagact tttgaaatat    2280
gtggtgttaa atcttaatg ggcaaaagct aagtggagtc atgatatttg tgtgactata    2340
aaaacttctc attaagaata aagtgagtaa aataaaaaat taaagtcaaa ttatttctaa    2400
atatagaaat atatcattct tttttgaacg gactaatacg gaaagtgtgt catttaaatt    2460
aaaataaata aagtaatatt tatcatatga ttttaacatg taaatatcat acaagtaatc    2520
taatcgtcaa gcgcggatct aataaataag ggacgggtat tttgtttagg ctgtgtatat    2580 ataattttt aaaatctact aaaaaagaac aaataataga tttgtaaatt agagggtatat   2640 ggtagaatct aactataaac ccttaaagtt caaatcttgt atctgcttgt ggtaatagtg    2700
tatatatatt ttttacacgt ttttgttgta tagaactcaa actaaaaagg gcattccagt    2760
gcacaaagca tctcctattc acacacaatt cggtgaaggg ccgcactgta tgcaaggggt    2820
gtgatatcgg cagtctatcc tgatgcaagc atcaatggtt gattccacgg ctcgaatccg    2880
ttacctatag gtcatacgga gataaacttta ccgttactcc aagtcccct tctacataaa    2940 acttgcatca atagctgatt tcacgactcg aacccataac ctagttgata cgaagataac   3000
tttaccgttg cttcaaggtc cgtctacaca aaactgatca aattattttc ataaataaag    3060
aagctatcat ttctctataa atagaactag agtccttgca tattccaaca taagtatcag    3120
ttccaggaaa atcaagacat aatctgttag cttttctctt tgccattctc nnnnnnnnat    3180
ggattcctta ccagtctcct ccattgaatc tctagtcatt gagatcaaga aagagatgtt    3240
ctcaaaccaa gaatttaaca cttttgtcac cccaatatct gcctatgaca ctgcttggtt    3300
ggccatgatt tcttataata atcaagaaga agccattaat ggtcattctt tttctggccc    3360
tatgtttaag agttgtttaa attggattct caacaaccaa aatgagcaag gatttttggggg 3420 agaatccaat ggt                                                        3433

<210> SEQ ID NO 117
<211> LENGTH: 2512
<212> TYPE: DNA
<213> ORGANISM: Nicotiana tabacum

<400> SEQUENCE: 117
aagctggtac ccttatgttt agtccaagaa aaataaccat acccaaatat aagggtttgt     60
tgaagacgga aatatataaa caaataaaca aatatcatca tatctccgat agtttaaaat   120
tttagattgg atatttcaca caatttatca aaatttttcaa aaaaaaattc tacttttttct 180 tgcttggaac ttggaagggg aaggggtggt ggtggagata gggcggggca tcttctatct   240
agtctatgtg attaatataa caaaacaaaa agggcgaggc aaaaacatgg atgaatggtg   300
gtccttttct atatttatat ggattgttac gatacgtcga tttcactttg caaaatacca   360
attagattca tttagttatc ttttttgatca ctctgctttt actatcatat atatatagga   420
```

```
gtccttccac gtttcgcatg tgtcattgtt tatattttcc atggtcttcc ttccaaatgg    480
ctaaaaaaat ttgacacagt ggtcccaaaa gtttatagaa atagaattca acagtgaggc    540
atatacctat gaattctatt ttacatcttc atcgtataaa atagaatgtg ttataaactt    600
tacctcgtga tgcttacaag gggtgaaaat ataaaagcac tttatagatt tacaagagtc    660
acaccttgat ttatcctaag attttatttt tttacatgcc aaacaatgaa gtatgggaga    720
tccaattgga ataacatcaa atttaataaa attcgaaata gtcagagagc tgtctactga    780
ggtatattga aacttatttt tttttaatag aaaatatcaa atacttagca atatattaaa    840
atgtttcata aattacattg tttaaaccaa gcgttgaaac atatgctgat acgaggtagg    900
cttattgatg aatttataag ggcctcattg gaaaagacga tccaaagcaa tgggctaaaa    960
aattggccca ttttctgcca cccagtgtat ggttattact agtttcaccc acacagattt   1020
gcacttcatt agaggacaat gttgctgaat ttgaaacata agtccattta tctccactgt   1080
acagtccttc ctggagtcca atcctgacca tatcttcatg attttatgta atgtggtgaa   1140
taagcaaagt ttcatgttat gctttgtctc attttatagc aaattcattt cctcataaaa   1200
tttacttcaa aaaagtttcg tttgattttc agaaatcaaa atatgctttt cggtaaccaa   1260
atggttttca attttgttta cgaagaactt aaaactttcc aacaccctac atctatgatt   1320
gcaagtaaaa attgcagaaa tatgacactt tttggagtgg tctttatcgt ttaacttcac   1380
ttgcacttta agggcaaaag ttaaaagtgt ttccatgaag caagcgaggg ataacactta   1440
ttaaacttga aattctactc atagaccaaa acaaggacaa aaattcaaga ctatctatgt   1500
gggtaaacgt acgaaaattg ggcttctcca gattagagcc ggaccttgtg gaaagacaga   1560
gaaattcgag gcccacttcc agtttctaag gagattaagc ctatcaaacg atggtccaga   1620
acgaaatatg tctttcttta ttctctacta tatagctgac tcagaatcgt tagaatttgc   1680
aatttcctca taataaaatg tgaggcagta tagattcgaa aacctttgtt gaagattatt   1740
gactcagcta cgcgaaacaa actgtagtat ccaatgtacc gattaacaag cgactggtta   1800
actatgaatt tgttagctcg acaaaatcac cggttaataa tgagtttgtg agttcgataa   1860
aatctaattt tctgatagaa attttatata ttatgcagaa atttaataaa agtagactta   1920
acttatatat tttagcattg actcttttga agtaaaatcc attccatcta aattatgact   1980
tccctacatc gagtaagtaa gttgcgtctg tatcctcatt ttacccactt ttcgctatgc   2040
aattattcaa ggatctttac acaaatagca agccaatatt aattatttat tttttttagt   2100
catatatata aattatacat atattatata cccattaatt atttttaatt taagtgatag   2160
attggacgac tatttggatt aattcttcgt tattcaagat aatagatgtc gtctctaata   2220
catgagctag aagataataa ggattactag gccgaaaggc tgatggaaat gaacaagaag   2280
ataagctcct aaatggaaac agtacggaaa aagtcaaaga gcagtgcatg ggaggaatca   2340
tcagtcagaa aaggaagcca cgtgtcaagt agaaacaagc acgtgtccat gcaaaagcca   2400
cgtaactccc ttccatcaca tcttccttct tcaaaacctc gtgttttact ctctcttttc   2460
tcactgccag tgatcgtcag gactgtgcat gtttgtttaa aaactaaagg ca           2512
```

<210> SEQ ID NO 118  
<211> LENGTH: 941  
<212> TYPE: DNA  
<213> ORGANISM: Nicotiana tabacum
<400> SEQUENCE: 118

| | |
|---|---|
| tttaaaacgc caaaaaataa gggacggcca tggcgtagca atgactattg ttccgtaggt | 60 |
| catttgtgaa ggaccgacaa aatttttaggc gatccgggtc cgattttttcg gttctgctca | 120 |
| agaaaactcg atctgcacga atagcttata atcaaaccct tttttttttt tcaagaatgt | 180 |
| ctaattgatc ctaaaaagac aaccttatat gttccaccat ggcaggatcg gccttattac | 240 |
| taagggtttg ccaatagaca cgttttttaac attcaagtaa aaaaaacatt tattcttaat | 300 |
| aacccaccta ctatagtacg ttatttggca gtagactacg ttgtacattt gggaccattt | 360 |
| ggaacactcg tcttttcacga gtcactaatt tttgtgttga atgcataaaa tttgttttttt | 420 |
| tcttttttcga aattgaacaa ttttatcttc gatcacacct atagtatatt attaccttat | 480 |
| tgttagaaaa tatttttattt tattattgac tcctaataaa aagtgggggta aatttgggtc | 540 |
| tttttttttaa agaatgtgaa ctactcattt cactttggtt agaacaaata tgagaagatt | 600 |
| tgctaatgac agcaaaatga atagaccaaa agcgtaacga atattaaaaa taaacaattc | 660 |
| cgaataactg gttactgaaa attgtggaac tctacatagc cgttgtgagt atggtattgt | 720 |
| ttgttcttgt gggcagaata actagttacg gaaaatttat gaatttgctt cacattattt | 780 |
| ttttcatttt cttttttttgct tcaaaagata agtacaagtt tttatactct tatttcattg | 840 |
| cctataaata cctctattga gttactgctc attcacaact ctaaatagca atctttctta | 900 |
| ttattaaaat tcctatcctt ttttactcat tcagagaaac g | 941 |

<210> SEQ ID NO 119
<211> LENGTH: 3013
<212> TYPE: DNA
<213> ORGANISM: Artificial Sequence
<220> FEATURE:
<223> OTHER INFORMATION: Description of Artificial Sequence:
      Synthetic polynucleotide

<400> SEQUENCE: 119

| | |
|---|---|
| tttaaaacgc caaaaaataa gggacggcca tggcgtagca atgactattg ttccgtaggt | 60 |
| catttgtgaa ggaccgacaa aatttttaggc gatccgggtc cgattttttcg gttctgctca | 120 |
| agaaaactcg atctgcacga atagcttata atcaaaccct tttttttttt tcaagaatgt | 180 |
| ctaattgatc ctaaaaagac aaccttatat gttccaccat ggcaggatcg gccttattac | 240 |
| taagggtttg ccaatagaca cgttttttaac attcaagtaa aaaaaacatt tattcttaat | 300 |
| aacccaccta ctatagtacg ttatttggca gtagactacg ttgtacattt gggaccattt | 360 |
| ggaacactcg tcttttcacga gtcactaatt tttgtgttga atgcataaaa tttgttttttt | 420 |
| tcttttttcga aattgaacaa ttttatcttc gatcacacct atagtatatt attaccttat | 480 |
| tgttagaaaa tatttttattt tattattgac tcctaataaa aagtgggggta aatttgggtc | 540 |
| tttttttttaa agaatgtgaa ctactcattt cactttggtt agaacaaata tgagaagatt | 600 |
| tgctaatgac agcaaaatga atagaccaaa agcgtaacga atattaaaaa taaacaattc | 660 |
| cgaataactg gttactgaaa attgtggaac tctacatagc cgttgtgagt atggtattgt | 720 |
| ttgttcttgt gggcagaata actagttacg gaaaatttat gaatttgctt cacattattt | 780 |
| ttttcatttt cttttttttgct tcaaaagata agtacaagtt tttatactct tatttcattg | 840 |
| cctataaata cctctattga gttactgctc attcacaact ctaaatagca atctttctta | 900 |
| ttattaaaat tcctatccta atttactcaa acagagaaac gatgtatccg ccaagcaaca | 960 |
| gctgcaacta cagccccatt ttcaacatcc cttctccttg tatgcaatat ggagacgaac | 1020 |
| tattcttcca atattatcct gaccatttcc ttcaacagca acaagtgcct ttgatagaag | 1080 |

```
atcagagtgt tgacatctta gctgattgca ctgagaatgt tactaacgaa gaaactgtca    1140
tcaatactga tactgtaaaa gttctttatg acacaggagc tgttacaaac agtcagtgtt    1200
ggggaggaaa tgaagaagta gaagaaggcc gcgaaaacaa agaaatgac atgagaagca     1260 ccattagtat tattcatgta cggaaaaaca agaaatgttc caataaagat cgacatagca    1320
agattaacac tgctcgtggc ctcagagacc gaaggatgag actttcccct gatgcagctc    1380
gcaagttttt cagtttacaa gacatgttgg ggttcgataa ggcaagtaaa actgtagaat    1440
ggttgcttat caaatcggag tctgaaatcg aagagctagc caaaggcaat aaaggaggag    1500
gcattcctaa acaaagctgc agtactacta atggaattgg tgcaattagt actgcaatat    1560
cctctatttc tgagtgtgag gttatatcag gaactgatga atctttctct attacttata    1620
aaaagaagct gaaaactgct aaggagcct cgaaaaagac ggctaaaact gctcgtagag     1680
ctgcatttga tcgtcttatt acaagggaaa cgaggaatca agcaagggct agggctagag    1740
agagaacaaa aataaagaaa agcctcggta aatccaaaga gaacagtgct gattactgta    1800
atttggtgga taattatgga gattggagtc aatttagtat cttcaactat cagaaaaatg    1860
cagttggaat ttcccatgat caggtgggtt caataattaa acaacatgat ttttttaggat   1920 ttcaataggc tcgctccttg tgtaacatgg cataagcagt cttggcaatg atgctctttg    1980
ttgcctatgg tttgtctcca tttattcctc taatacccca taaaataat aaaatataaa     2040 ttacatctac atgactggtt ttgaattatg ataatgaaca tgaagttaca cttcttatga    2100 tttttttcaag tacattgtgt tttgattacc gcataaatat ttaagcatgg tcatcttttt   2160
tttgattcat ttgttgttag agtgactaat taatctgtag tatatgtctg gaggcttgag    2220
gaatctgaaa aaatgtgcgt gtttgcatag ttcttttcaaa atagtatagg acaatatatt   2280
cttttaaaaa aaggagtccg gtgcacaaag catgtcgcat tgttccgagt aaaagctgca    2340
cccaaagagt gtgatgcaga caacctactc taatacaagc attaatgaac gcgttgctcc    2400
aaggctccgg cccccttcaat atatttcttt atgaaccgtg aatttattca tgtttaaaag   2460 cttttctttca attccatctt ttcttttgtt ctaacatttg ttagtaaacg tgaatgaatg    2520
tagaggttca agctagagaa tgcaaaacag aaagcaatac attccctgga ttatgcatta    2580
ccaaaccacc atgcagaaaa gcttgtatca gtgagggatt tactgatggt cattgtagca    2640
aaatcctcag aaggtgccta tgcactaagc catgtgtgtt tgatgagaag atgatcaaaa    2700
caggagctga aacttttgct gaggaagcaa aaactttggc tgcagctttg cttgaagaag    2760
agataatgga taactaatta gagattagag gaaaggatta ttcagtgtc acacataata     2820 aagttgctgc cttctttaaa aggatagcta atgtattggc ttttagtagc ctttgttacc    2880
ctaaaataag tgtgacatgt caatccttt gatctagtac caagtttatg tatgttttaa     2940
tgaaaaatga tcttctatgg tcattgcaat cccattatat tccaagaaca aaacttcatt    3000
attttcttgg tcc                                                        3013
```

<210> SEQ ID NO 120
<211> LENGTH: 120
<212> TYPE: DNA
<213> ORGANISM: Artificial Sequence
<220> FEATURE:
<223> OTHER INFORMATION: Description of Artificial Sequence:
      Synthetic polynucleotide

<400> SEQUENCE: 120
tagcaatctt tcttattatt aaaattccta tccttttta ctcattcaga gaaacgatgg    60
ctcgctcctt gtgtttcatg gcatttgcag tcttggcaat gatgctcttt gttgcctatg      120

<210> SEQ ID NO 121
<211> LENGTH: 5668
<212> TYPE: DNA
<213> ORGANISM: Artificial Sequence
<220> FEATURE:
<223> OTHER INFORMATION: Description of Artificial Sequence:
      Synthetic polynucleotide

<400> SEQUENCE: 121
tttaaaacgc caaaaaataa gggacggcca tggcgtagca atgactattg ttccgtaggt       60
catttgtgaa ggaccgacaa aattttaggc gatccgggtc cgattttcg gttctgctca      120
agaaaactcg atctgcacga atagcttata atcaaacccct ttttttttt tcaagaatgt      180
ctaattgatc ctaaaaagac aaccttatat gttccaccat ggcaggatcg gccttattac      240
taagggtttg ccaatagaca cgttttaac attcaagtaa aaaaaacatt tattcttaat      300
aacccaccta ctatagtacg ttatttggca gtagactacg ttgtacattt gggaccattt      360
ggaacactcg tctttcacga gtcactaatt tttgtgttga atgcataaaa tttgttttt      420
tcttttcga aattgaacaa ttttatcttc gatcacacct atagtatatt attaccttat      480
tgttagaaaa tattttattt tattattgac tcctaataaa aagtggggta aatttgggtc      540
tttttttaa agaatgtgaa ctactcattt cactttggtt agaacaaata tgagaagatt      600
tgctaatgac agcaaaatga atagaccaaa agcgtaacga atattaaaaa taaacaattc      660
cgaataactg gttactgaaa attgtggaac tctacatagc cgttgtgagt atggtattgt      720
tgttcttgt gggcagaata actagttacg gaaaatttat gaatttgctt cacattattt      780
ttttcatttt cttttttgct tcaaaagata agtacaagtt tttatactct tatttcattg      840
cctataaata cctctattga gttactgctc attcacaact ctaaatagca atctttctta      900
ttattaaaat tcctatccta atttactcaa acagagaaac gtctaggagc aaaaaaaaa      960
aaaaaaaaaa aaacaagtag tagtagtagt agtaaatgga aaaatagaga ggcaatttt     1020
tttagtatct tactttatcc attagcactt aaaaaacata ggtttacatg ctctcattgt     1080
cacgccaggc cgctaattaa atggtacatt tcatcatccc cattttttgg cctcatagtt     1140
aattatcaca atttctgaaa gcaacatcag acaaccccca catttcttgt ggtcctataa     1200
ttactgctag atagtccaaa cccatctgcc tatttagggc ttgtgaatga ggattgaaaa     1260
tggtagagaa tatttgcaaa ggcatcatgc atatatggaa aagactaaag agagagttag     1320
tgccttgcaa agcggattct cacagttgta gaaaaggact caccattttc aagaatactc     1380
ccggcatgaa gatggacaat ttaatataaa aaacaaagaa aatagtaatt aagtgcgttg     1440
agatgaatga aatttatccg ctcttaattg aatatgggga attgaaagaa atttctgata     1500
ataaattaat gagtcttaca tgacgtggat ccgacttaat ctagtctatt taaactaaga     1560
atagataaga atagagaata tagacaaaag agaggctcat ggctagggt ttcaagggag     1620
ttccttgaac ataagtggca agtacaagca caaagccaat ttccatggac taaagatgaa     1680
taagatgtgt cgtgtggtat ggtgggaagg tgaggaggta tggggtaatt ggagatgcta     1740
aacctctcta aaagctcttt tgctccaaat atctaaatcc atctctatca cttttggcga     1800
ctgccccaaa atttgcaact tatgaattaa agttttaata ttttaagtt aataaattct     1860
gaattaataa tttaacatat tcaataaact ttttaaaaca aattacgtat ataccatcaa     1920
actggctgca ccatgatcac tttctaaact cacaatgaca tatggattta atcaggcaca     1980

```
aagtcatgtt gatagaaaga gatagtacgg agaatgaaga aaaaaggtag gggagagaga    2040
tggggtgagt ggggaaaaga tagggttctc tttttagtga aagcgacagg gtctgagaac    2100
cctaggtcaa aagttgcata aacctctata caggcttctt cactcccctta ctactaatat   2160 actctcatta aggcttgagg tttaattcat taaaattgtg gtttaattat tgtatcccct    2220
caaacgaaat aattgtcctt gtcgaggtta dacaatgttg cgtactattt tcaaacgcag    2280
tcagccatta ttctcctatc ctttacagtc gagattcaaa dacagaaagt agcatgcaag    2340
ctgttattaa tttactttga ttaggacttt gccaagaaaa tgaagaacct tttctttttt    2400
cttttaattt agttatctta caacatgtaa ttttttcctag caagcaaata cggtaacttt   2460
tttttttatt ctcatttaat ttgttggagc tattgctact ttgatgactt caaccaaatc    2520
ctggttggta ggcggagggt gctgacgatg gaaactaccc ctcttgtcca aatacgataa    2580
cctaaaaaat agaataatag cttattgtac tgtgctgcaa aaattgcatt gtcagtatac    2640
ataattaaaa tctattttga atgtgtggag ggcaaagagg ggtgactggt ctagggttgt    2700
agaaatcagg tgggagagag aatggtattt gtctctgtgt cagctgatat cacgtgaaga    2760
ggcacaataa gaagtccttc gtatccattc acttcccaaa aataccggca ttactacaaa    2820
tatagtacta gcacttgctt tctctatccc catctttgct atttccttttc cctttccaac    2880 tttttggctt tagaattgca aagatggagg gaattgtggt tctttgtatc tgtaaaattt    2940
ttcctccaag ctccagttgt agctagctta atgcgtggac gcgcgcgcac acactagaaa    3000
tctgcaatct atatatatat tcacaaggca ctcacatatc aaaaaccaca tagacattgt    3060
atagagagag ctgtcgttct caagcagaaa aaatgatatg atttcatcag catgtggtca    3120
accaaatagt tcaattctag tctttgcttc ctctttctaa ttactgtata aatagagcca    3180
caaggacata gaattgagaa aataaaagac aataaaaaca aatctagcta cttaagcgaa    3240
tgatgatgac tctctctcag tagtcttaac tcttaatacc cttgttttcc ttcttgtgct    3300
gcagtttgat tggttaatta acctaatcaa aagatgtttt aactgtgttt tatccgtctt    3360
tctcaagatc tatcttagtc ccaccacata gctccctcaa gctacagctg caaaatatat    3420
actatatata tatataacaa atgtatccgt caagcaacag ctgtaattac agcctcaata    3480
tttcctcctc aaataactta tttcacattc catctccgaa ttctatgcaa tatgaacacg    3540
aacttttcca atattttcat gaccatcatc tccttcaacc ccaacaacaa caacaacaac    3600
aacaactctt gactacacct gatcattata tggcagcaga ttccaacaaa gacaccgtaa    3660
tcagtagtac taatcaagat cctgaagaag ttgaattaca aggccgctgc aagaacaaaa    3720
aaggtgacaa taagagacgt gttgcttaca agaaagatag acacagcaag attaacactg    3780
ctcacgsccc tagagaccga agaatgagac tttctctcga tgtagctcgc aaattttttca    3840 atttgcaaga cttgcttgga ttcgataagg ctagcaaaac tgtggagtgg ttgctaacaa    3900
agtccaaatg tgctgtcaat gagctcgtcc aaggcataaa taagaaaaat tgcgctactg    3960
ctaatattgg tgcaattagt acatgctcta ctacatctga gtgtgaagtt gtatcaggaa    4020
ttgatgaatc tacaaccact aatgatattc agaagcagtc aaatagaggt aaagtagggg    4080
agaagaagaa ggctaataaa ctagttcgta gagctgcatt taatcctgtg gcaaaggaat    4140
caagaaagca agctagagcg agggcaaggg agagaacaaa aataaagaaa gcttttttaa    4200
atattggtga tcagtctatg gcggctgatg atttaaaacg attaggatgt tggagtcttt    4260
ttgaaacagt gaagaatca ggtattcaag gtactaatca tcaaattgaa gaacacacca    4320
cgcaccacga ggagcctctt ttggggacta atgagaatgt tgatgattgt aatttggttg    4380
```

```
ttaccggcaa ctggaaccca tataccatct tcaattatca ccacagtact gaaatttctc    4440
acgaggtagg ttttacactt catttaaatc caagagtaat tcttttagag ttcaagattc    4500
tgatattttt tttggtggcg agacccttc ttatatcaaa gcaaccttca aggtacatac    4560
aagattggat aaaccaattc tgagctcgct ccttgtgtaa catggcataa gcagtcttgg    4620
caatgatgct ctttgttgcc tatggtttgt ctccatttat tcctctaata ccccataaaa    4680
ataataaaat ataaattaca tctacatgac tggttttgaa ttatgataat gaacatgaag    4740
ttacacttct tatgattttt tcaagtacat tgtgttttga ttaccgcata aatatttaag    4800
catggtcatc ttttttttga ttcatttgtt gttagagtga ctaattaatc tgtagtatat    4860
gtctggaggc ttgaggaatc tgaaaaaatg tgcgtgtttg catagttctt tcaaaatagt    4920
ataggacaat atattctttt aaaaaaagga gtccggtgca caaagcatgt cgcattgttc    4980
cgagtaaaag ctgcacccaa agagtgtgat gcagacaacc tactctaata caagcattaa    5040
tgaacgcgtt gctccaaggc tccggccccct tcaatatatt tctttatgaa ccgtgaattt    5100
attcatgttt aaaagctttc tttcaattcc atcttttctt ttgttctaac atttgttagt    5160
aaacgtgaat gaatgtagag gttcaagcta gagaatgcaa aacagaaagc aatacattcc    5220
ctggattatg cattaccaaa ccaccatgca gaaaagcttg tatcagtgag ggatttactg    5280
atggtcattg tagcaaaatc ctcagaaggt gcctatgcac taagccatgt gtgtttgatg    5340
agaagatgat caaaacagga gctgaaactt ttgctgagga agcaaaaact ttggctgcag    5400
ctttgcttga agaagagata atggataact aattagagat tagaggaaag gattaattca    5460
gtgtcacaca taataaagtt gctgcctttc ttaaaaggat agctaatgta ttggctttta    5520
gtagcctttg ttaccctaaa ataagtgtga catgtcaatc cttttgatct agtaccaagt    5580
ttatgtatgt tttaatgaaa aatgatcttc tatggtcatt gcaatcccat tatattccaa    5640
gaacaaaact tcattatttt cttggtcc                                       5668
```

<210> SEQ ID NO 122
<211> LENGTH: 130
<212> TYPE: DNA
<213> ORGANISM: Artificial Sequence
<220> FEATURE:
<223> OTHER INFORMATION: Description of Artificial Sequence:
      Synthetic polynucleotide

<400> SEQUENCE: 122

```
gacctaggat cccaccacat agattgaacg gagggaataa tagtgtagcc ccattgggaa      60
acaccatatt tatataggta gaagaaatac tccagattta actagaattt ctactgacaa     120
aagatctttt                                                             130
```

<210> SEQ ID NO 123
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 123

```
ttttcgaggc tcctttagca                                                   20
```

<210> SEQ ID NO 124
<211> LENGTH: 20
<212> TYPE: DNA

```
<213> ORGANISM: Artificial Sequence
<220> FEATURE:
<223> OTHER INFORMATION: Description of Artificial Sequence:
      Synthetic oligonucleotide

<400> SEQUENCE: 124
catgttgggg ttcgataagg                                                     20

<210> SEQ ID NO 125
<211> LENGTH: 26
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 125
ccttttttac tcattcagag aaacga                                              26

<210> SEQ ID NO 126
<211> LENGTH: 25
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 126
gtgtgacact gaattaatcc tttcc                                               25

<210> SEQ ID NO 127
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 127
aggcttgctg aagcaaaaga                                                     20

<210> SEQ ID NO 128
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 128
tcggcgaaat tacagtctca                                                     20

<210> SEQ ID NO 129
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 129
ttgtgtcatg gtgcaatcaa                                                     20

<210> SEQ ID NO 130
<211> LENGTH: 20
<212> TYPE: DNA
<213> ORGANISM: Artificial Sequence
```

```
<220> FEATURE:
<223> OTHER INFORMATION: Description of Artificial Sequence:
      Synthetic oligonucleotide

<400> SEQUENCE: 130
tccaacttag gcctcacacc                                                    20

<210> SEQ ID NO 131
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 131
ttgcaatgct tctgttttcg                                                    20

<210> SEQ ID NO 132
<211> LENGTH: 19
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 132
atattggccg catcttggt                                                     19

<210> SEQ ID NO 133
<211> LENGTH: 21
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 133
ttctcttccc gagaaacagt g                                                  21

<210> SEQ ID NO 134
<211> LENGTH: 21
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 134
cggagttgga gatgaagatg a                                                  21

<210> SEQ ID NO 135
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 135
cctgtggcaa aggaatcaag                                                    20

<210> SEQ ID NO 136
<211> LENGTH: 20
<212> TYPE: DNA
<213> ORGANISM: Artificial Sequence
<220> FEATURE:
```

```
<223> OTHER INFORMATION: Description of Artificial Sequence:
      Synthetic oligonucleotide

<400> SEQUENCE: 136
tgcgtggtgt gttcttcaat                                                 20

<210> SEQ ID NO 137
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 137
gggtgctttg aagtcccttt                                                 20

<210> SEQ ID NO 138
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 138
gaatcctgct ccaaacaagc                                                 20

<210> SEQ ID NO 139
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 139
tgggcagcag aaataagaga                                                 20

<210> SEQ ID NO 140
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 140
gctgatcttg ttgtggcttg                                                 20

<210> SEQ ID NO 141
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 141
caccataagc acaggtgcaa                                                 20

<210> SEQ ID NO 142
<211> LENGTH: 20
<212> TYPE: DNA
<213> ORGANISM: Artificial Sequence
<220> FEATURE:
<223> OTHER INFORMATION: Description of Artificial Sequence:
```

Synthetic oligonucleotide

<400> SEQUENCE: 142
tccgccttgc tttatgaaaa                                            20

<210> SEQ ID NO 143
<211> LENGTH: 21
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 143
tcctctttgc catttctctc a                                          21

<210> SEQ ID NO 144
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 144
ggccagaaaa agaatgacca                                            20

<210> SEQ ID NO 145
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 145
gggtccctct aaatcccaag                                            20

<210> SEQ ID NO 146
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 146
ccggaagtca agaatccagt                                            20

<210> SEQ ID NO 147
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 147
tggacatgag gcatttgcta                                            20

<210> SEQ ID NO 148
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 148
gcatcgcgag atcaagagtt                                          20

<210> SEQ ID NO 149
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 149
aagcccgcct ttctacctta                                          20

<210> SEQ ID NO 150
<211> LENGTH: 22
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 150
tcttgatcat cgaacgaatc ac                                       22

<210> SEQ ID NO 151
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 151
ccaattccct cttccttcct                                          20

<210> SEQ ID NO 152
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 152
atccatccaa gtcagccttc                                          20

<210> SEQ ID NO 153
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 153
tggttgaggc cccaatatac                                          20

<210> SEQ ID NO 154
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

```
<400> SEQUENCE: 154
ccccgctatc gacttgatta                                              20

<210> SEQ ID NO 155
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 155
cggaagagcc tgtggtatga                                              20

<210> SEQ ID NO 156
<211> LENGTH: 21
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 156
tgaaatcaga ttcaggcatc a                                            21

<210> SEQ ID NO 157
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 157
agatcaggaa gcgcgtaaga                                              20

<210> SEQ ID NO 158
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 158
cagagttttg ctggccttct                                              20

<210> SEQ ID NO 159
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 159
gtggcaaagg aatcaaggaa                                              20

<210> SEQ ID NO 160
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 160
```

```
atgggttcca gttgccagta                                          20
```

<210> SEQ ID NO 161
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 161

```
cggtccttta gcagtttcca                                          20
```

<210> SEQ ID NO 162
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 162

```
catgttgggg ttcgataagg                                          20
```

<210> SEQ ID NO 163
<211> LENGTH: 22
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 163

```
atctggagta tttcttctac ct                                       22
```

<210> SEQ ID NO 164
<211> LENGTH: 22
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 164

```
cttaaactct ctgccgaata aa                                       22
```

<210> SEQ ID NO 165
<211> LENGTH: 24
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 165

```
tccttctttc tgtctgtttc tctt                                     24
```

<210> SEQ ID NO 166
<211> LENGTH: 21
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 166

```
gtcctcactg ctgtctttct c                                              21
```

<210> SEQ ID NO 167
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 167

```
gcacttctgg tggtgaaaga                                                20
```

<210> SEQ ID NO 168
<211> LENGTH: 26
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 168

```
gtcattctca gttatgttac ggaaag                                         26
```

<210> SEQ ID NO 169
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 169

```
agctgctcca taaccgaaat                                                20
```

<210> SEQ ID NO 170
<211> LENGTH: 22
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 170

```
cgaccctgaa tttcctctag tt                                             22
```

<210> SEQ ID NO 171
<211> LENGTH: 23
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 171

```
ggatgtaagg cattggacat aga                                            23
```

<210> SEQ ID NO 172
<211> LENGTH: 22
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 172

```
gagttcccta tcaaccgaaa ca                                             22
```

<210> SEQ ID NO 173
<211> LENGTH: 23
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 173
ggcgagtcat taacctccta ttt                                          23

<210> SEQ ID NO 174
<211> LENGTH: 22
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 174
gtcttagcgt ccaagtgcta at                                           22

<210> SEQ ID NO 175
<211> LENGTH: 22
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 175
gctgaagaac ctttgccttt ac                                           22

<210> SEQ ID NO 176
<211> LENGTH: 22
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 176
gccgatttct caacacaaag aa                                           22

<210> SEQ ID NO 177
<211> LENGTH: 2399
<212> TYPE: DNA
<213> ORGANISM: Nicotiana tabacum

<400> SEQUENCE: 177
ttagcactta aaaacatag gtttacatgc tctcattgtc acgccaggcc gctaattaaa    60
tggtacattt catcatcccc attttttggc ctcatagtta attatcacaa tttctgaaag   120
caacatcaga acaaccccac atttcttgtg gtcctataat tactgctaga tagtccaaac   180
ccatctgcct atttagggct tgtgaatgag gattgaaaat ggtagagaat atttgcaaag   240
gcatcatgca tatatggaaa agactaaaga gagagttagt gccttgcaaa gcggattctc   300
acagttgtag aaaaggactc accattttca agaatactcc cggcatgaag atggacaatt   360
taatataaaa aacaaagaaa atagtaatta agtgcgttga gatgaatgaa atttatccgc   420
tcttaattga atatggggaa ttgaaagaaa tttctgataa taaattaatg agtcttacat   480
gacgtggatc cgacttaatc tagtctattt aaactaagaa tagataagaa tagagaatat   540

| | |
|---|---|
| agacaaaaga gaggctcatt ggctagggtt tcaagggagt tccttgaaca taagtggcaa | 600 |
| gtacaagcac aaagccaatt tccatggact aaagatgaat aagatgtgtc gtgtggtatg | 660 |
| gtgggaaggt gaggaggtat ggggtaattg gagatgctaa acctctctaa aagctctttt | 720 |
| gctccaaata tctaaatcca tctctatcac ttttggcgac tgccccaaaa tttgcaactt | 780 |
| atgaattaaa gttttaatat ttttaagtta ataaattctg aattaataat ttaacatatt | 840 |
| caataaactt tttaaaacaa attacgtata taccatcaaa ctggctgcac catgatcact | 900 |
| ttctaaactc acaatgacat atggatttaa tcaggcacaa agtcatgttg atagaaagag | 960 |
| atagtacgga gaatgaagaa aaaggtaggg gagagagat ggggtgagtg gggaaaagat | 1020 |
| agggttctct ttttagtgaa agcgacaggg tctgagaacc ctaggtcaaa agttgcataa | 1080 |
| acctctatac aggcttcttc actcccttac tactaatata ctctcattaa ggcttgaggt | 1140 |
| ttaattcatt aaaattgtgg tttaattatt gtatccctc aaacgaaata attgtccttg | 1200 |
| tcgaggttag acaatgttgc gtactatttt caaacgcagt cagccattat tctcctatcc | 1260 |
| tttacagtcg agattcaaag acagaaagta gcatgcaagc tgttattaat ttactttgat | 1320 |
| taggactttg ccaagaaaat gaagaacctt ttcttttttc ttttaattta gttatcttac | 1380 |
| aacatgtaat ttttcctagc aagcaaatac ggtaactttt ttttttattc tcatttaatt | 1440 |
| tgttggagct attgctactt tgatgacttc aaccaaatcc tggttggtag gcggagggtg | 1500 |
| ctgacgatgg aaactacccc tcttgtccaa atacgataac ctaaaaaata gaataatagc | 1560 |
| ttattgtact gtgctgcaaa aattgcattg tcagtataca taattaaaat ctattttgaa | 1620 |
| tgtgtggagg gcaaagaggg gtgactggtc tagggttgta gaaatcaggt gggagagaga | 1680 |
| atggtatttg tctctgtgtc agctgatatc acgtgaagag gcacaataag aagtccttcg | 1740 |
| tatccattca cttcccaaaa ataccggcat tactacaaat atagtactag cacttgcttt | 1800 |
| ctctatcccc atctttgcta tttccttttcc cttccaact ttttggcttt agaattgcaa | 1860 |
| agatggaggg aattgtggtt ctttgtatct gtaaaatttt tcctccaagc tccagttgta | 1920 |
| gctagcttaa tgcgtggacg cgcgcgcaca cactagaaat ctgcaatcta tatatatatt | 1980 |
| cacaaggcac tcacatatca aaaccacat agacattgta tagagagagc tgtcgttctc | 2040 |
| aagcagaaaa aatgatatga tttcatcagc atgtggtcaa ccaaatagtt caattctagt | 2100 |
| ctttgcttcc tctttctaat tactgtataa atagagccac aaggacatag aattgagaaa | 2160 |
| ataaaagaca ataaaaacaa atctagctac ttaagcgaat gatgatgact ctctctcagt | 2220 |
| agtcttaact cttaataccc ttgttttcct tcttgtgctg cagtttgatt ggttaattaa | 2280 |
| cctaatcaaa agatgtttta actgtgtttt atccgtcttt ctcaagatct atcttagtcc | 2340 |
| caccacatag ctccctcaag ctacagctgc aaaatatata ctatatatat atataacaa | 2399 |

<210> SEQ ID NO 178
<211> LENGTH: 300
<212> TYPE: DNA
<213> ORGANISM: Nicotiana tabacum

<400> SEQUENCE: 178

| | |
|---|---|
| tctttgcttc ctctttctaa ttactgtata aatagagcca caaggacata gaattgagaa | 60 |
| aataaaagac aataaaaaca atctagctac ttaagcgaa tgatgatgac tctctctcag | 120 |
| tagtcttaac tcttaataccc cttgttttcc ttcttgtgct gcagtttgat tggttaatta | 180 |
| acctaatcaa aagatgtttt aactgtgttt tatccgtctt tctcaagatc tatcttagtc | 240 |
| ccaccacata gctccctcaa gctacagctg caaaatatat actatatata tatataacaa | 300 |

<210> SEQ ID NO 179
<211> LENGTH: 1901
<212> TYPE: DNA
<213> ORGANISM: Nicotiana tabacum

<400> SEQUENCE: 179

```
aatctagtct atttaaacta agaatagata agaatagaga atatagacaa aagagaggct      60
cattggctag ggtttcaagg gagttccttg aacataagtg gcaagtacaa gcacaaagcc     120
aatttccatg gactaaagat gaataagatg tgtcgtgtgg tatggtggga aggtgaggag     180
gtatggggta attggagatg ctaaacctct ctaaaagctc ttttgctcca aatatctaaa     240
tccatctcta tcacttttgg cgactgcccc aaaatttgca acttatgaat taaagttttta    300
atattttttaa gttaataaat tctgaattaa taatttaaca tattcaataa actttttaaa    360
acaaattacg tatataccat caaactggct gcaccatgat cactttctaa actcacaatg    420
acatatggat ttaatcaggc acaaagtcat gttgatagaa agatagtagta cggagaatga    480
agaaaaaagg taggggagag agatggggtg agtggggaaa agatagggtt ctcttttttag    540
tgaaagcgac agggtctgag aaccctaggt caaaagttgc ataaacctct atacaggctt    600
cttcactccc ttactactaa tatactctca ttaaggcttg aggtttaatt cattaaaatt    660
gtggtttaat tattgtatcc cctcaaacga ataattgtc cttgtcgagg ttagacaatg     720
ttgcgtacta ttttcaaacg cagtcagcca ttattctcct atcctttaca gtcgagattc    780
aaagacagaa agtagcatgc aagctgttat taatttactt tgattaggac tttgccaaga    840
aaatgaagaa ccttttcttt tttcttttaa tttagttatc ttacaacatg taattttttcc   900
tagcaagcaa atacggtaac ttttttttttt attctcattt aatttgttgg agctattgct    960
actttgatga cttcaaccaa atcctggttg gtaggcggag ggtgctgacg atggaaacta   1020
cccctcttgt ccaaatacga taacctaaaa aatagaataa tagcttattg tactgtgctg   1080
caaaaattgc attgtcagta tacataatta aaatctattt tgaatgtgtg gagggcaaag   1140
aggggtgact ggtctagggt tgtagaaatc aggtgggaga gagaatggta tttgtctctg   1200
tgtcagctga tatcacgtga agaggcacaa taagaagtcc ttcgtatcca ttcacttccc   1260
aaaaataccg gcattactac aaatatagta ctagcacttg ctttctctat ccccatcttt   1320
gctatttcct ttccctttcc aacttttttgg ctttagaatt gcaaagatgg agggaattgt   1380
ggttctttgt atctgtaaaa tttttcctcc aagctccagt tgtagctagc ttaatgcgtg   1440
gacgcgcgcg cacacactag aaatctgcaa tctatatata tattcacaag gcactcacat   1500
atcaaaaacc acatagacat tgtatagaga gagctgtcgt tctcaagcag aaaaaatgat   1560
atgatttcat cagcatgtgg tcaaccaaat agttcaattc tagtctttgc ttcctctttc   1620
taattactgt ataaatagag ccacaaggac atagaattga gaaaatataaaa gacaataaaa   1680
acaaatctag ctacttaagc gaatgatgat gactctctct cagtagtctt aactcttaat   1740
accccttgttt tccttcttgt gctgcagttt gattggttaa ttaacctaat caaaagatgt   1800
tttaactgtg ttttccgtct ttctcaagat ctatcttagt cccaccacat agctccctca   1860
agctacagct gcaaaatata tactatatat atatataaca a                        1901
```

<210> SEQ ID NO 180
<211> LENGTH: 2500
<212> TYPE: DNA
<213> ORGANISM: Nicotiana tabacum

<400> SEQUENCE: 180

```
atgtttagtc caagaaaaat aaccataccc aaatataagg gtttgttgaa gacggaaata      60
tataaacaaa taaacaaata tcatcatatc tccgatagtt taaaatttta gattggatat     120
ttcacacaat ttatcaaaat tttcaaaaaa aaattctact ttttcttgct tggaacttgg     180
aaggggaagg ggtggtggtg gagatagggc ggggcatctt ctatctagtc tatgtgatta     240
atataacaaa acaaaaaggg cgaggcaaaa acatggatga atggtggtcc ttttctatat     300
ttatatggat tgttacgata cgtcgatttc actttgcaaa ataccaatta gattcattta     360
gttatctttt tgatcactct gcttttacta tcatatatat ataggagtcc ttccacgttt     420
cgcatgtgtc attgtttata ttttccatgg tcttccttcc aaatggctaa aaaaatttga     480
cacagtggtc ccaaaagttt atagaaatag aattcaacag tgaggcatat acctatgaat     540
tctattttac atcttcatcg tataaaatag aatgtgttat aaactttacc tcgtgatgct     600
tacaaggggt gaaatataaa aagcacttta tagatttaca agagtcacac cttgatttcc     660
taagatttta ttttttttaca tgccaaacaa tgaagtatgg gagatccaat tggaataaca     720
tcaaatttaa taaaattcga aatagtcaga gagctgtcta ctgaggtata ttgaaactta     780
tttttttta atagaaaata tcaaatactt agcaatatat taaaatgttt cataaattac     840
attgtttaaa ccaagcgttg aaacatatgc tgatacgagg taggcttatt gatgaattta     900
taagggcctc attggaaaag acgatccaaa gcaatgggct aaaaaattgg cccattttct     960
gccacccagt gtatggttat tactagtttc acccacacag atttgcactt cattagagga    1020
caatgttgct gaatttgaaa cataagtcca tttatctcca ctgtacagtc cttcctggag    1080
tccaatcctg accatatctt catgatttta tgtaatgtgg tgaataagca agtttcatg     1140
ttatgctttg tctcatttta tagcaaattc atttcctcat aaaatttact tcaaaaaagt    1200
ttcgtttgat tttcagaaat caaaatatgc ttttcggtaa ccaaatggtt ttcaattttg    1260
tttacgaaga acttaaaact ttccaacacc ctacatctat gattgcaagt taaaattgca    1320
gaaatatgac acttttgga gtggtcttta tcgtttaact tcacttgcac tttaagggca    1380
aaagttaaaa gtgttttccat gaagcaagcg agggaaaccc tacacttatt aaacttgaaa    1440
ttctactcat agaccaaaac aaggacaaaa attcaagact atctatgtgg gtaaacgtac    1500
gaaaattggg cttctccaga ttagagccgg accttgtgga aagacagaga aattcgaggc    1560
ccacttccag tttctaagga gattaagcct atcaaacgat ggtccagaac gaaatatgtc    1620
tttctttatt ctctactata tagctgactc agaatcgtta gaatttgcaa tttcctcata    1680
ataaaatgtg aggcagtata gattcgaaaa cctttgttga agattattga ctcagctacg    1740
cgaaacaaac tgtagtatcc aatgtaccga ttaacaagcg actggttaac tatgaatttg    1800
ttagctcgac aaaatcaccg gttaataatg agtttgtgag ttcgataaaa tctaattttc    1860
tgatagaaat tttatatatt atgcagaaat ttaataaaag tagacttaac ttatatattt    1920
tagcattgac tcttttgaag taaaatccat tccatctaaa ttatgacttc cctacatcga    1980
gtaagtaagt tgcgtctgta tcctcatttt acccacttttt cgctatgcaa ttattcaagg    2040
atctttacac aaaatagcaag ccaatattaa ttatttattt tttttagtca tatatataaa    2100
ttatacatat attatatacc cattaattat ttttaattta agtgatagat tggacgacta    2160
tttggattaa ttcttcgtta ttcaagataa tagatgtcgt ctctaataca tgagctagaa    2220
gataataagg attactaggc cgaaaggctg atggaaatga acaagaagat aagctcctaa    2280
atggaaacag tacggaaaaa gtcaaagagc agtgcatggg aggaatcatc agtcagaaaa    2340
```

```
ggaagccacg tgtcaagtag aaacaagcac gtgtccatgc aaaagccacg taactcccct    2400
ccatcacatc ttccttcttc aaaacctcgt gttttactct ctcttttctc actgccagtg    2460
atcgtcagga ctgtgcatgt ttgtttaaaa actaaaggca                           2500
```

<210> SEQ ID NO 181
<211> LENGTH: 528
<212> TYPE: DNA
<213> ORGANISM: Nicotiana tabacum

<400> SEQUENCE: 181

```
atgggttcaa aaatgtctga tccccttgtg attgggagag tgattgggga agttgttgat      60
tatttcactc caagtgttaa gatgtctgtt acttataaca gcagcaagca tgtttataat     120
gggcatgaac tctttccttc ctcagtcacc tctaaaccta gggttgaagt tcatggaggt     180
gatttgagat ctttctttac aatgatcatg atagacccag atgttcctgg tcctagtgat     240
ccatatctca gggaacacct acactggatt gtcacagaca ttccaggcac tacagattgc     300
tcgtttggga agaaatagt tggctatgaa atgccaaggc caaatattgg aattcacagg      360
tttgtatttc tgctgttcaa gcagaagaag aggcaaacag tattgactgc acctctctcc    420
agggatcgat ttaatacgcg taaattcgca gaagaaaatg agcttgggtc tcctgttgca    480
gcagttttct tcaattgcca gagggaaact gctgccagaa ggcgttga                  528
```

<210> SEQ ID NO 182
<211> LENGTH: 1728
<212> TYPE: DNA
<213> ORGANISM: Arabidopsis thaliana

<400> SEQUENCE: 182

```
atgggattga cctcatcctt acggttccat agacaaaaca acaagacttt cctcggaatc      60
ttcatgatct tggttctaag ctgtatacca ggtagaacca atctttgttc caatcattct     120
gttagtaccc caaaagaatt accttcttca aatccttcag atattcgttc ctcattagtt     180
tcactagatt tggagggtta tataagcttc gacgatgtcc acaatgtggc caaggacttt     240
ggcaacagat accagttacc acctttggca attctacatc aaggtcagt ttttgatatt      300 tcatcgatga tgaagcatat agtacatctg ggctccacct caaatcttac agtagcagct    360
agaggccatg gtcactcgct tcaaggacaa gctctagctc atcaaggtgt tgtcatcaaa     420
atggagtcac ttcgaagtcc tgatatcagg atttataagg ggaagcaacc atatgttgat     480
gtctcaggtg gtgaaatatg gataaacatt ctacgcgaga ctctaaaata cggtctttca     540
ccaaagtcct ggacagacta ccttcatttg accgttggag gtacactatc taatgctgga     600
atcagcggtc aagcattcaa gcatggaccc caaatcaaca cgtctacca gctagagatt      660 gttacaggga aggagaagt cgtaacctgt tctgagaagc ggaattctga acttttcttc     720
agtgttcttg gcgggcttgg acagtttggc ataatcaccc gggcacggat ctctcttgaa    780
ccagcaccgc atatggttaa atggatcagg gtactctact ctgactttc tgcattttca      840 agggaccaag aatatctgat ttcgaaggag aaaacttttg attacgttga aggatttgtg    900
ataatcaata gaacagacct tctcaataat tggcgatcgt cattcagtcc caacgattcc    960
acacaggcaa gcagattcaa gtcagatggg aaaactcttt attgcctaga agtggtcaaa   1020
tatttcaacc cagaagaagc tagctctatg gatcaggaaa ctggcaagtt acttcagag    1080 ttaaattata ttccatccac tttgttttca tctgaagtgc catatatcga gtttctggat   1140
```

```
cgcgtgcata tcgcagagag aaaactaaga gcaaagggtt tatgggaggt tccacatccc    1200
tggctgaatc tcctgattcc taagagcagc ataccaat  ttgctacaga agttttcaac    1260
aacattctca caagcaacaa caacggtcct atccttattt atccagtcaa tcaatccaag    1320
tggaagaaac atacatcttt gataactcca aatgaagata tattctatct cgtagccttt    1380
ctcccctctg cagtgccaaa ttcctcaggg aaaaacgatc tagagtacct tttgaaacaa    1440
aaccaaagag ttatgaactt ctgcgcagca gcaaacctca acgtgaagca gtatttgccc    1500
cattatgaaa ctcaaaaaga gtggaaatca cactttggca aaagatggga aacatttgca    1560
cagaggaaac aagcctacga ccctctagcg attctagcac ctggccaaag aatattccaa    1620
aagacaacag gaaaattatc tcccatccaa ctcgcaaagt caaaggcaac aggaagtcct    1680
caaaggtacc attacgcatc aatactgccg aaacctagaa ctgtataa                1728

<210> SEQ ID NO 183
<211> LENGTH: 1644
<212> TYPE: DNA
<213> ORGANISM: Nicotiana tabacum

<400> SEQUENCE: 183
atgaaattac caccccattt tttatttaag caaaatgact tgctcctgaa attgcttata      60
ttcatactat gcagttgttc aagcaacaaa aataaactct gctgtaacaa tcatcagttt     120 gccaccctg  cagtttctac ctcctcaagt ttctcactga actatttatc attgaaacaa     180
ttacaacttg aagggtacct taattttgac aacttagaac atgcagccaa agactttggt     240
aatagatgcc acttcctccc attagcagtt ctgtacccaa atcagtttc  tgacatctct     300 tccactataa aacttatctt tgaaatgggt tccaaaactg gcataactgt tgctgctaga     360
ggccatggcc attctttaga aggccagtct caagcttatc aaggactagt gattagtatg     420
gaatcactac aaacaccagc aatgaaattc aagactggag aagtacctta tgttgatgta     480
tctgctggag agctttggat aaacatcctg catgaaagtc ttaaacttgg gattgcgcct     540
aaatcttgga ctgattatat tcacctcaca gttggtggca cttttgtctaa tgctggaatc     600 agtggacaag cttccggca  tggacccag  atcaataacg tccaacaact tgaagttgtc     660
actggtaaag gagaggtgat tacttgttcg gaggagaaga atgcagactt gtttcatggt     720
gtactaggtg gactggggca atttggtatt attaccagag caaggattgc tcttgaaaca     780
gcacctaaac aggtcaagtg gattagagtg ctgtattcag atttt gccat atttt ccaat     840 gatcaagagc atttgatatc aactcaggat acatttgatt atattgaagg gtttgtcatt     900
atcaaccaaa ctggattatt gaatagctgg aggtctagtt tcaatcgtaa agattcagtt     960
ctagccagca atttcagttc tgagggtaga gttttgttct gcctagaagt tgccaaatac    1020
ttcaatccag aagacacaga tagtattgat cagaacattg atatcctctt atcaaagttg    1080
aactttatgc gatccacgct gttcctatca gaagtctcct acgtggaatt cctcgacaga    1140
gtgcatgtct ctgagatgga actccaagaa aaagggttgt gggatgttcc tcatccatgg    1200
ctaaatcttc taataccaaa aagcaggatt cttgaatttg cacaagaagt ttttggcaag    1260
attcttactg acactagcaa tggtcccttta ctcatctacc ctgtcaacaa atcaaagtgg    1320
agaaaaggaa catccatggt tacccctgac gaagatgttt tctacctgat cgcattccta    1380
tcttccgcca tgccatcttc aacaggcagc gatggactaa gacatattct tgctcagaac    1440
aaaaggatac taaattttg  tgaaaaaata aatattggaa tgaaacaata tttgccaaat    1500
tacaagactc aggaagagtg gaaagatcac tttggcccac aatggatacc atttgctaga    1560
```

```
aggaaatcca catatgaccc tttggcaatg cttgctcctg ccagagaat tttcagaagg    1620 gcagaagcct gtgaacaaca ataa                                          1644

<210> SEQ ID NO 184
<211> LENGTH: 1659
<212> TYPE: DNA
<213> ORGANISM: Nicotiana tabacum

<400> SEQUENCE: 184
atgaagtcac caccaactca tgtcttcttt aaacataaaa gtatgcttct taggttgctt     60
atattcatac taggcatttg ctcaataaac agaactaacc tttgttgtga ccaaccttt    120 gccaccccaa tatcttcttc ttcttctacc ccttcaagtt tttcagtgat tcaatcatca   180
ttgaaacagt taaatattga agggtatttt agtttcaaga atttcgatca cgcggccaaa   240
gactttggca acagatatca cttcttgcca tcggcagttc tgtatccaaa atcagtttct   300
gatatatcat ctaccataaa acatgttttt gacatgggtg ttactacaga cctaactgtt   360
gctgctagag gccatggcca ttctttagaa ggccaagctc aagcttacca aggagtagtg   420
atcaatatgg aatcgcttcg agcgccagca atgcgtttcc acacagggaa tcaagaactg   480
ccttttgttg atgtctctgc aggagaactt tggataaaca tcctgcatga aagtcttaaa   540
cttggattaa caccaaaatc ttggactgat tatcttcacc tcaccgttgg agggactttg   600
tcgaatgccg aatcagtgg tcaagcattc aaacatggac cacagatcaa taatgtttac   660
caacttgagg ttgtcactgg taaggagag gtgattactt gttcagagga gaagaatgct   720
gacctgttct atggtgtatt aggaggacta ggccagtttg gtatcatcac aagggctaga   780
attgctcttg aaccagcacc taaaaaggta aagtggatca gagtgctgta ttcagatttc   840
tccacatttt cctatgatca agaacacttg atatcatccg agaactcttt tgactatata   900
gaaggatttg tcattatcaa tagaacagga ttgttaaaca actggaggtc tactttcaat   960
cctaaagatc cacttctagc caaagagttc agttctgagg gaaaagttct gtactgccta  1020
gaagttgcca atacttcaa tccagaagag acaaccaaaa ctgatcagaa tgttgatgtt  1080
cttttatcaa agttgaatta tatccaatcg acgctgttcc aatcagaagt atcctacgtg  1140
gatttcctcg acagagttca cgtatccgag atgaaacttc aagagaaggg gttatgggat  1200
attcctcatc catggctaaa ccttctaatt ccaaagagca agattcatga ctttgcacga  1260 gaagttttg ggaagatact taccgacact agccacggtc ctatactcat ctacccagtc  1320
aacaaatcaa agtggagaaa aggaacatca gtagttacac ctgaagaaga tgttatgtat  1380
ctaatagcat ttctatcttc tgccatgcca tcttcaacag gaaggacgg cgtagaatat  1440 attctaaata agaataagaa gatactaaac ttttgcagaa aagcacatat tggaatgaaa  1500
cagtatttgc cacactacac aacgcaggaa gactggaaag gtcactttgg tccccagtgg  1560
gaaacattta aaaggaggaa atctacatat gaccctttgg ctatcctagc tcctggccag  1620
agaattttta gaagagcatc aggcgttcaa caacaatga                         1659

<210> SEQ ID NO 185
<211> LENGTH: 1593
<212> TYPE: DNA
<213> ORGANISM: Nicotiana tabacum

<400> SEQUENCE: 185
atgaaatcac caccaactca tgtcttcttt aaacataaaa gtatgtttct taggtttctt    60
```

```
atattcatat taggcatttg ctcaataaac aaaactaacc tctgttgtga ccaaactttt      120
gccaccccaa tatcttcttc ttcttctatc ccttcaaatt tttcagtgat tcaatcatca      180
ctgaaacagt taaatattga agggtatttt agtttcaaga atttcgatca cgcggccaag      240
gactttggca acagatatca tttcttaccg tcggcagttc tgtatccaaa atcagtttct      300
gatatatcat ctaccataaa acatgtgttt gacatgggta gcaatacaga cctaactgtt      360
gctgctagag gtcatggtca ttctctagaa ggccaagctc aagcttacca aggagtagtg      420
atcaatatgg aatctcgagc gctgactttt gttgatgttt ctgctggtga actttggata      480
aacatcctgc atgaaagtct aaacttgga ttaacaccaa atcttggac tgattatctt       540 cacctaaccg ttggagggac tttgtcgaat gccggaatca gtggtcaagc attcaaacat      600
ggaccacaga tcaataatgt ttaccaactt gaggttgtca ctggtaaagg agaggtgatt      660
acttgttcag aggagcagaa tgctgacctg ttctatggtg tattaggagg actaggccag      720
tttggtatca tcacaagggc taggattgct cttgaaccag cacctaaaaa ggtacaggta      780
aagtggatca gagtgctgta ttcagatttc tccacatttt cctatgatca agaacacttg      840
atatcattgg agaattcttt cgactatata gaaggatttg tcattatcaa tagaacagga      900
ttgttaaaca actggaggtc tactttcaat cctaaagatc cacttctagc caaagttct      960 ctactgccta gaagttgcca atacttcaa tccagaagac agaatgttga tgctcttta       1020 tcaaagttga attatatcca atcgacgttg ttccaatcag aagtctcgta tgttgatttt     1080
ctcgacagag tccatgtatc cgagatgaaa ctccaagaga aggggttatg ggatgttcct     1140
catccatggc taaaccttct aattccaaag accaggattc atgacttcgc acaagaagtt     1200
tttgggaaga tacttaccga cactagccac ggtcctatac tcatctaccc agtcaacaaa     1260
tcaaagtgga gaaaaggaac atcactagtt acacccgaag aagatgttat gtacttaata     1320
gcatttctat cttctgccat gccatcttca acaggaaagg acggcgtaga atatattcta     1380
aataagaata agaagatact aaactttttgc agaaaagcac atattggaat gaacagtat    1440 ttgccacact acacaacaca ggaagactgg aaaagtcact tggtttccaa atgggaaaca     1500
tttaatagga ggaaatccac atatgaccct tggctatcc tagctcctgg ccatagaatt      1560
tttagaagag catcaggcgt tcaacaacaa tga                                  1593
```

<210> SEQ ID NO 186
<211> LENGTH: 1632
<212> TYPE: DNA
<213> ORGANISM: Nicotiana tabacum

<400> SEQUENCE: 186

```
atgaaattac catcccattt tttatttaag caaaatgact tgctcctgaa attgcttata       60
ttcatactct gcagttgttc aagcaacaaa aataaactct gctgtaatta tcatcagttt      120 gccaccctg cagtttctac cccctcaagt ttctcactga attatttatc attgaaacaa       180
ttacaacttg aaggttacct taaatttgac aacttagaac atgcagccaa agactttggt      240
aatagatgcc acttccttcc attagcagtt ttgtacccaa atcagtttc tgatatctct       300 tccactataa acatgtcttt tgaaataggt tccaaaactg atttaactgt tgctgctaga      360
ggccatggcc attctctaga aggtcaagct caagcttatc aaggagtagt gattagtatg      420
gaatcactac aaaacaccagc aatgaaattc aagactggag aattgcctta tgttgatgtt    480
tctgctggag agctttggat taaatcctg aaagaaagtc ttaaacttgg gcttgcacct      540
aaatcttgga ctgattatct tcacctcaca gttggcggca cttttgtctaa tgctggaatc    600
```

```
agtggacaag ctttccgcca cggaccgcag atcaataacg tccaacaact tgaagttgtc    660
actggtaaag gagaggtgat tacttgttca gaggagcaga atgcagactt gtttcatggt    720
gtactaggag gactggggca atttggtatt attaccagag caaggattgc tcttgaaaca    780
gcacctaaac aggtcaagtg gattagagtg ctgtattcag atttttccat attttccaat    840
gatcaagagc acttgatatc aactcaggat acatttgact atattgaagg ttttgtcact    900
atcaaccaaa ctggattatt aaataactgg aggtctgctt tcaatcctaa agatccagtt    960
ctagccagca atttcagttc tgagggtaga gttttgttct gcttagaaat tgccaaatac    1020
ttcaatccag aagtcacaga tagtattgat cagaacattg atgtgatctt atcaaagttg    1080
aattatatcc gatccacgct gttcctatca gaagtctcct acacagaatt cctcgacagg    1140
gtgcatgtct ctgagatgaa actccaagaa aatgtttctc atccatggct aaatcttcta    1200
ataccaaaaa gcaggattct tgaatttgca caacaagttt ttggcaagat tcttactgac    1260
actagcaatg gtcctttact catctaccct gtcaacaaat caaagtggag aaaaggaaca    1320
tccatggtta cccctgacga agatgttttt tatctgatcg cgttcctatc ttctgctatg    1380
tcatcttcaa caggaaacga tggactaaga catattcttg ctcagagcaa aaggatactg    1440
aacttttgtg aagaaacaaa tatcggaatg aaacaatatt taccaaatta caagactaag    1500
gaagagtgga aggatcactt tggtcatcaa tgggaagcat tgctagaag gaaatcctaca    1560 tatgacccctt tggcaatact tgctcctggc cagagaattt tcagaagggc agaagcctgt    1620
gaacaacaat aa                                                       1632
```

<210> SEQ ID NO 187
<211> LENGTH: 1572
<212> TYPE: DNA
<213> ORGANISM: Nicotiana tabacum

<400> SEQUENCE: 187

```
atggctaaac tttattccct aggttactta gttatattct tcaccattag ccgtttagtg    60
tccatcatag gtaaaccttc aattacaaat gaagttcttt cccaccttga tattgcaaca    120
agacttagtg taaatatttc agatgccact atagcaactt ccactgattt tggaaaactt    180
gttcaagaaa tcccagctgc agttctttac ccttcctcca ttcatgacat tgttaagctc    240
ataaactact ccaacaatgg cgccatttct gccccttttg gcgtcgcggc gagaggacat    300
ggccattcag tgagggggaca agccatgtca ccaaatgggg ttgtggtggt catgagttct    360
ttgaataata ataataataa taataatgga aaaattgggg tttttggga gagtagttta    420 gggttttatt atgcagatgt gggaggtgag cagcttcgga ttgatgtttt gcatgccact    480
ttagagcatg gacttgcacc tgtctcttgg actgattatt tatatctctc cgttggagga    540
actctctcta atgctggaat tagtggccaa acttccaaat atggtcctca gattagtaat    600
gttcttgaaa tggatgttat cacaggtaaa ggggaacttg tcacttgttc caagcggaca    660
aattcggagc tgttttttgc agttttagga agtctaggcc agtttgggat cataatcaga    720
gcaagaattg tcttagagaa agcaccaaca agagtactcg gggttagagt attgtatagg    780 gattttttcaa aattcacaag agaccaagaa aaactgatct ccattaatga tggcatggac    840
tatgtggaag gctctctaat gatgaatcaa agtcctccaa ataattggag atcttctttt    900
ttctcaactt ccaaccaatc taaaatactt tccttgatat ccaaatatgg aattatctac    960
tgtttggaaa tggtcaagta ctatgatgat cagactgcta atacagttga taggaattg    1020
```

| | |
|---|---|
| cagaagatga tgagaggttt gaactttgtg tttggacaca tattcaagaa agatacagcc | 1080 |
| tttgtacatt ttctgaatag agtgagaagt ggtgagctaa tgttgcaatc aaagggaatg | 1140 |
| tgggatgttc ctcacccttg gctcaatctc tttgtaccaa agtccagtat tatggacttt | 1200 |
| aatgttggtg tcttttttgga catcattctc agacaaaaca agtccacagg acctattctt | 1260 |
| gtgtacccaa caaccagaaa aagatgggat gatcggatgt ctgttgtgat accagaagag | 1320 |
| gacacattct actgcgtagg gctattgcat tctagtagat tcaatgactg ggaagttttg | 1380 |
| gatggacaaa atgaagaaat cataaactgc tgtgaaaaag ctggtctcaa cgtcaagcag | 1440 |
| tatcttccgc attacaaaac caaggaagct tggatgaatc attttggcaa aaaatggaaa | 1500 |
| atatttcaac aaaggaaaag tcagtttgat ccaaagatga ttctgtcacc aggacaaaag | 1560 |
| attttcattt ag | 1572 |

<210> SEQ ID NO 188
<211> LENGTH: 1563
<212> TYPE: DNA
<213> ORGANISM: Nicotiana tabacum

<400> SEQUENCE: 188

| | |
|---|---|
| atggctaaac tttattccct aggttactta attattttct tcaccattag ccctttagtg | 60 |
| tccatcatag gtaaaccttc aattccatat gaagttcttt tccaccttga tattgcaaca | 120 |
| agacttagtg taaatatttc agatgccact atagcaactt ccactgattt tggaaaactt | 180 |
| gttcaaaaaa tcccagctgc agttctttac ccttcctcca tacatgacat tattaagctc | 240 |
| attaactact ccaacaatgg cgccatttct gtcccttttg gtgtcgcggc gagaggacat | 300 |
| ggccattcag tgagggggaca agccatgtcg ccaaatgggg ttgtggtggt catgagttct | 360 |
| ttgaagaata ataacaatgg aaaaattagg gttttatggg agagttgttt agggtttat | 420 |
| tatgcagatg tgggaggtga gcagctttgg attgatgttt tgcatgccac tttagagcat | 480 |
| ggacttgcac ctgtctcttg gactgattat ttgtatctct ctgttggagg aactctctct | 540 |
| aatgctggaa ttagtggcca aactttcaaa tacggtcctc agattagcaa tgttcttgaa | 600 |
| atggatgtta tcacaggtaa agggcaactt gtcacttgtt ccaagcagac aaaattcggag | 660 |
| ctgtttttg cagttttagg gggtctaggc cagtttggaa tcataaccag agcaaggatt | 720 |
| gtcttagaga aagcaccaac aagagtgaaa tgggttagag tgttctatag tgattttca | 780 |
| aaattcacaa aagaccaaga aaactgatc tccattaata tggcatgga ctatgtggaa | 840 |
| ggctctctaa tgatgaatca agtcctcca ataattgga gatcttcctt tttctcaact | 900 |
| tccaaccaat ctaaaataat ttccttgata tccaaatatg gaattatcta ctgtttggaa | 960 |
| atggtcaagt actatgatga tcagtgtgct aatactgttg ataaggaatt gcagaagatg | 1020 |
| atgagaggtt tgaactttct gtctggacac atattcaaga aagatacaac atttgtacat | 1080 |
| tttctgaata gagtaagaag tggtgagcta aggctgcaat caaatggaat gtgggatgtt | 1140 |
| cctcacccctt ggctcaatct ctttgtacca aaatccagta ttatggactt taatgttggt | 1200 |
| gtcttcttgg acattattct cagacaaaac aagaccacag gacctattct tgtgtaccca | 1260 |
| acaaccagaa aaagatggga tgatcggatg tctgttgtga taccagaaga ggacacattc | 1320 |
| tactgcgtag ggctattgca ttctagtgga ttcaatgact gggaagtttt ggatggacaa | 1380 |
| aatgaagaaa tcataaacta ctgtgaaaaa gctggtctca acatcaagca gtatcttcca | 1440 |
| cattacaaat ccaaggaagc ttggatgaac cattttggca aaaaatggaa atatttcaa | 1500 |
| caaaggaaaa gtcagtttga tccaaagatg attctgtcac caggacaaaa gattttcatt | 1560 |

```
tag                                                                    1563

<210> SEQ ID NO 189
<211> LENGTH: 1593
<212> TYPE: DNA
<213> ORGANISM: Nicotiana tabacum

<400> SEQUENCE: 189
atgacgtgcc aaagctttgt tttcaccaga aaaagaacg ttctgttcct aagaagcttc     60
acaattttag tgctaagctg ggtaattatc aaaccaaatt tttgtttttc cagtgtcctg    120
tcctcattga aagcccttca tttagaaggc catattactt tcgaaaacaa tgagtttgca    180
gcccgagatt tcggcaatca aattcatgtc cacccttag cagtagtcca tccgaaatcc     240
gttgctgata tttcagaaat aataaaacat gtttggcaaa tgggtccgag ttctgaattg    300
accgtggcag cacgaggcca cggtcattcg cttcagggcc aggcacaagc gcgacgagga    360
gttataatca atatggagtc attccagggt caaggaatgc aggtccacag gggccaattc    420
ccttatgtag atgtctcagc tggtgaattg tggattaata tattgcatga aaccttgaaa    480
tatggattag caccaaaatc ttggactgat tacctccatc ttactgttgg aggtacactg    540
tctaatgctg gcatcagtgg gcaagcattt cgacacggcc ctcagatcag taatgtccat    600
cagctggagg ttgttacagg aaaaggagaa gtcttaattt gttcgaagga acagaatgca    660
gacctattcc atgctgtttt gggaggactt ggacagtttg cataataac tagagcaaga     720 atctctctgg aacgagcccc aaaaatggtg aaatggataa gagtgttgta ctctgatttc    780
tccacatttg ctagagacca agagcatttg atatctgctg caaaaacatt tgattacata    840
gaagggctgg tgataaagaa caaaacaggt ctaatgaata actggagagc atcttttgac    900
cctcaagatc ctgttcaagc tagccatttt gtatcagatg gaagaacact ctattgcctt    960
gaacttacca aaaatttata ccccgaaaaa tcggatacag taaaccagga aattaaagac   1020
ttattatcgc aactaagtta tatcccatca acactattta tgtcagaagt tccatacata   1080
gaatttttgg acagagttca tgcatcagag ctaaaacttc gatcgaaagg actatgggat   1140
ctcccacacc catggctcaa tcttctagtt cccaaaagca aaatacaaca ctttgctaag   1200 gaagttttg gcaacatcct aagagatact aacaatggcc ctgttcttgt ctacccatt    1260 cataaatcaa agttggataa cagaacctca tttgtttctc caaacgatga tattatctac   1320
ctagtggcat ttttatccca tgcaaatcct tcatccaatg aactgacag tttagaatat    1380 gtcttaactc agaacaaaag aatattagac ttctgtgatg tggcacacct aggagtcaag   1440
caatatttgc ctcattacac aacacaagaa cagtggagga cccactttgg tccaaaatgg   1500
gaagtattta tacagaggaa atctgcttat gacccttag ctatgcttgc tcctggtcag    1560
agaattttcc aaaaggcagt atcagtttca taa                                1593

<210> SEQ ID NO 190
<211> LENGTH: 1593
<212> TYPE: DNA
<213> ORGANISM: Nicotiana tabacum

<400> SEQUENCE: 190
atgacgtgcc aaagctttgt tttcaccaga aaaagaacg ttctgttcct aagaagcttc     60
acaattttag tgctaagctg ggtaattatc aaaccagaat tttgtttttc cagtgtccta    120
tcctcattga aagcccttca tttacaaggc catattactt tcgaaaacaa tgagtttgca    180
```

```
gcccgagatt tcggcaacca aattcatgtc cacccttag cagtagtcca tcccaaatcc      240
gttgctgata tttcagaaat aattaaacat gtctggcaaa tgggtccggg ttctgaatta      300
accgtagccg cgcgaggcca cggtcattcg cttcagggcc aggcgcaagc gcgacgtgga      360
gttataatca acatggagtc actacagggt caggaaatgc aggtctacag ggtcaattc       420 ccttatgtag atgtctcagc tggtgaattg tggattaata tattgcatga aactttgaaa      480
tatggattag caccaaaatc ttggactgac tacctccatc ttactgttgg aggtacactg      540
tctaatgctg gcatcagtgg acaggcattt cgacacggcc ctcagatcag taatgtccac      600
cagctggagg ttgttacagg aaaaggagaa gtcttaattt gttcaaagga acagaatgct      660
gacctattcc atgctgtttt gggaggactt ggacagtttg cataataac tagagcaaga       720 atctctctgg aacgagcccc aaaaatggtg aaatggataa gagtgttgta ctctgatttc      780
tccacatttg ccagagacca agagcatttg atatctgcag ctaaaacatt tgattacata      840
gaagggctgg tgataaagaa caaaacaggt ctaatgaata actggagagc atcttttgac      900
cctcaagatc ctgttcaagc cagccacttt gtatcagatg aagaacact  ctattgcctt      960 gaactaacca aaaatttata ccccgaaaaa tccgatacag taaaccaggt aattgaagat      1020
ttattatccc aactaagtta tattccatca acgttattta tgtcagaagt tccatacata      1080
gaatttttgg acagagttca tgcttcagag ctaaaacttc gatcgaaagg actttgggat      1140
ctcccacacc catggctcaa tcttctagtt cctaaaagca aaatacaaca cttcgctaag      1200 gaagttttg gcaacatcct taaagatact aacaatggcc ctgttcttgt ctacccatt       1260 cataaatcaa agttggataa cagaacctca tttgtttctc caaatgaaga tattatctac      1320
ctggtggcct ttttatcca tgcaaatcct tcatccagtg aactgacag tttagaacat        1380 gtcttaactc agaacaaaag aatattagat ttctgtgatg tggcacacct aggagtcaag      1440
caatatttgc ctcattacac aacacaagaa cagtggagga cccacttggg tccaaaatgg      1500
gaagtatttg tacagagaaa atctgcttat gaccctttag ctatgctagc acctggtcag      1560
agaattttcc aaaaggcagt atcagtttca taa                                   1593
```

<210> SEQ ID NO 191
<211> LENGTH: 1533
<212> TYPE: DNA
<213> ORGANISM: Nicotiana tabacum

<400> SEQUENCE: 191

```
atgtctaagc ttctttctcc tagttataac ttcattattt tctttattat cagtcgttta       60
atgtctatta taggaaagtt aaagccatgg aataatcctt ctattcctta tgaaattctt      120
tcccttgata tagcttctaa acttagtaca aattcagatt ccattagtga aacctccaca      180
gattttggga aaattgttca agaaatccca gctgctgttc tttatccttc ttctattatt      240
gatatagttg agttaattaa atttcctat ggtctttcta tcccttttca tatagcagca       300
agaggtcatg gccattccat tagaggacaa gccatggcac aaaatggtgt tgttgtggaa      360
atgaattctc tgaataacaa caacaacaac aataatatta ataataataa aaatggaagt      420
tgtggaatta gggtttcttg ggattcttct ttagggtttt acgctgatgt aggaggcgag      480
cagttatgga ttgatgttct tgtgctacc ctcgagcatg ggctttcgcc tgtctcgtgg        540
actgattact tgtaccttac ggttggaggt actctctcta atgcaggaat tagtggccaa      600
actttccgac atgcccctca aattagtaat gtccatgaaa tggacgttat tacaggtaca      660
ggtaaagggg aatttgtgac ttgctccaaa cacaagaatt cagaactgtt ctttgcagtg      720
```

```
aaatgggtga gaatgctata tgtagatttc tcaaaattca caaaagacca agaacatttg    780
atttcaattg atggcctgga ttatgttgaa ggatctctaa tgatggaaca aagcagtcta    840
aataattgga gatcttcatt tttctcacca tctaatcaga ccaaaatagc ttcgttgtta    900
tcacaaaatg gcattattta ttgcctagaa atggtcaagt actatgatga tcagactgct    960
aatactgttg acgaggaatt gaagaagttg gtaaaaggtt tgaactttt gcctggattt   1020 atcttcaaga aagatgtcac atttgtggat tttttgaata gagtaagaag tggagagcta   1080
gagctacaat caaaaggaca atgggatgtt ccacatccat ggcttaatct ctttgtacca   1140
aaatccaata tcatggattt caatgctggt gttttgtgg acattattct cagacaaaac    1200
aagacaacag gacctatcct tgtctaccca acaagcagga aaagatggga tgagaggatg   1260
tctgcagtga taccagaaga ggagacattt tactgtgtgg ggctattgca ttcaagtgga   1320
tttaatgact ggaaaaattt ggatgatcaa aatgaagaaa tcttgaatta ctgtgataaa   1380
gctggcctca agataaagca atatcttcca cattataaaa caaggagga ttggataaaa    1440 cattttggca aaaagtggaa tatttttcaa caaaggaaaa gtcagtttga tccaaagatg   1500
attctatcac caggacaaag aattttaat tag                                1533

<210> SEQ ID NO 192
<211> LENGTH: 1524
<212> TYPE: DNA
<213> ORGANISM: Nicotiana tabacum

<400> SEQUENCE: 192
atgtctaagc ttctttctcc tagttataac ttcattattt tcttcattat tagtcgttta     60
gtgtctatca taggaaagtt aaagccatgg aataatcctt caattccttg tgaaattctt    120
tcccttgata tatcttctaa acttagtaca aattcagatt ccattatgga aacttccaca    180
gattttggga aaattgttca agaaatccca gctgctgttc tttatccttc ttctattaat    240
gatatagttg agttaactaa attttcctat ggtctttcta tcccttttca tatagcagca    300
agaggtcatg gccattccat taggggacaa gccatggcac aaaatggtgt tgttgtggaa    360
atgaattctc tgaataataa taataataat aataataata ataataataa taacaacaac    420
ggaaatagtg gaattagggt ttcttgggat tcttctttag ggttttacgc tgatgtagga    480
ggcgaacagt tatggattga tgttcttcga gctaccctcg agcatggcct ttcgcctgtc    540
acgtggactg attacttgta cctcactgtt ggtggtactc tctctaatgc aggaattagt    600
ggccaaactt tccgacatgg tcctcaaatt agtaacgtcc atgaaatgga cattattaca    660
ggtacttcag aactgttctt tgcagtttta ggaggtttgg gacagtttgg aataataacc    720
agggcaagaa ttgtcttaga taaagcacca acaagagtga aatgggtgag aatgctatat    780
gcagatttct caaaattcac aaaagaccaa gaacatttga tttcaattta tggcctggat    840
tatgttgaag gatcactgat gatggaacaa agctctctaa ataactggag atcttcattt    900
ttctcacctt ctaatcagac caaaatagct tccttattat cccaaaatgg cattatttat    960
tgcctagaaa tggtcaagta ctatgatgat cagactgcta atactgttga tgaggaattg   1020
aagaagttgg taaaaggttt gaactttttg cctggattta tattcaagaa agatgtcaca   1080
tttgtggatt ttctgaatag agttagaaga ggagagttag agctaaaatc aaaaggacaa   1140
tgggatgttc cacatccatg gctcaacaat gctggtgttt tgtggacat tattctcaga    1200 caaaacaaga caacaggacc tatccttgtc tacccaacaa gcaggaaaag atgggatgac   1260
```

| | |
|---|---|
| aggatgtctg cagtgatacc agaagaggag acattttact gtgtgggggct attacattca | 1320 |
| agtggattta atgactggaa aagtttggat gatcaaaatg aagaaatctt gaagtattgt | 1380 |
| gataaagctg gcttaaagat aaagcaatat cttccacatt ataaaacaaa gcattttggc | 1440 |
| aaaaagtgga atattttca acaaagaaaa agtcagtttg atccaaagat gattctatca | 1500 |
| ccaggacaaa gaattttaa ttag | 1524 |

<210> SEQ ID NO 193
<211> LENGTH: 1404
<212> TYPE: DNA
<213> ORGANISM: Nicotiana tabacum

<400> SEQUENCE: 193

| | |
|---|---|
| atggctacta aacttttgtt gacacttgct atatgtcggc ttattgtaac cgttgggttt | 60 |
| acgtttgacc cgaccgagct tttacggctc gggctcaacg gaaacctcag cgtagcggca | 120 |
| gccgatttag aaaccgcctc cgtggacttc ggccggttgc atagagccga ccgatggcg | 180 |
| gttcttcacc cagctacagc cgaggacgta gcgcggcttg tgaaagcggc gtatgactcg | 240 |
| gctcgtggct tcaccgtgtc ggctagagga cacggacatt ctataaatgg tcaggctatg | 300 |
| acaacaaaag gagttgtgat tccaatgctg gtattagtgg acaagctttc aatcatggcc | 360 |
| ctcaaattaa caatgttcat gagcttgatg ttgttacagg ttaagggtga gctattaaca | 420 |
| tgttcagaaa agaaaactc cgagctgttt catgctgctc ttggtggatt aggacaattt | 480 |
| gggatcataa caagggcaag aattgcactt gaacaagctc cccaaagggt aaggtggatc | 540 |
| cgagtttat attcgaattt ttcaacattt accgaagacc aagaatatct aatatctcta | 600 |
| caggcaaaac cagcttccca aaaatttgac tatgttgaag gatttgttat agttgatgaa | 660 |
| ggcctcatta caactggag atcttctttc ttctccccaa gtaaccctgt gaagatttct | 720 |
| tctcttaagg ctgacggagg agttttatat tgcttagaaa tcaccaaaaa ttatcacctt | 780 |
| tcaaatgctg atatcgttga tcaggagata gagactttgt taaaaaagct aaaatatata | 840 |
| ccagcatcag ttttcacaac agaccttcct tacgtggatt tcttggaccg ggttcacaag | 900 |
| gcagagttga aactccggtc taagggggttga tgggaagtgc cacacccatg ctaaaccta | 960 |
| tttgttccaa atcaagaat tgtggacttc gataaaggag ttttaaggg cattttgggg | 1020 |
| aataagacca gtggtcccat actcatctac cccatgaaca agaacaagtg ggacgagagg | 1080 |
| agttcagtag tgacaccaga ggaggaggtt ttttacttag tgggattct gaggtcggca | 1140 |
| ttgacaaaca gtgacgagac acagacatta gagtacctca gcaatcaaaa ctacgaaata | 1200 |
| ttgaagttt gtgaagatgc aaatatcaaa atcaaacaat acctgcctca ttacacaaca | 1260 |
| caaagagaat ggagggacca ttttggagat aagtattgga ccagatttca gcaaaggaaa | 1320 |
| ttagagtttg acccaagaca tattttagct accggccaac gtattttcat gccttctttt | 1380 |
| aatcctaata ctgcctcttg gtga | 1404 |

<210> SEQ ID NO 194
<211> LENGTH: 1404
<212> TYPE: DNA
<213> ORGANISM: Nicotiana tabacum

<400> SEQUENCE: 194

| | |
|---|---|
| atggctacta aacttttgtt gacacttgct atatgtcggc ttattgtaac cgtcgggttt | 60 |
| aggtttgacc cgactgagct tttacggctc gggctcaacg gaaacctcag cgtggcgta | 120 |
| gccgatttag aaactgcgtc cgtggacttc ggcgggttgc atagagctga gccgatggcg | 180 |

| | |
|---|---|
| gttcttaacc cggctacagc cgaggacgta gcgcggcttg tgaaagccgc gtacgactcg | 240 |
| gctcatgggt ttaccgtgtc ggctagagga cacggacatt ctataaatgg acaggctatg | 300 |
| ataacaaatg gtgttgtgat cccaatgctg gtattagtgg acaagctttc aatcatggcc | 360 |
| ctcaaattaa caatgttcat gagcttgatg ttgttacagg ttaagggtga gctattaaca | 420 |
| tgttcagaaa agaaaactc cgagctgttt catgctgctc ttggtggatt aggacaattt | 480 |
| gggattataa caagggcaag aattgcactt gaacaagctc cccaaagggt gaggtggatc | 540 |
| cgagttttat attcaaattt ttcaacattt accgaagacc aagaatatct aatatctcta | 600 |
| catgaaaaac cagcttccca aaaatttgac tatgttgaag gatttgttat agttgatgaa | 660 |
| ggcctcatta caactggag atcttctttt ttctccccaa gtaaccctgt caagatttct | 720 |
| tctcttaagt ctgaaggagg agtttttatat tgcttagaaa tcaccaaaaa ttatcacctt | 780 |
| tcaaatgctg atatcgttga ccaggagata gagacattgt taaagaagct aaaatatata | 840 |
| ccagcatcag ttttttacaac agaccttcct tacgtggatt tcttggaccg ggttcacaag | 900 |
| gcagagttga aactccggtc taaaggattg tgggaagtgc cacacccatg gctaaaccta | 960 |
| tttgtcccaa atcaagaat tgcagacttc gataaaggag tttttaaggg cattttgggg | 1020 |
| aataagacca gtggtcccat actcatctac cccatgaaca agaacaagtg ggacgagagg | 1080 |
| agttcagtag tgacgccaga agaggaagtg ttttacttag tgggatttct gaggtcagca | 1140 |
| ttgacaaatg gtgacgagac acaaacatta gagtacctca gcaatcaaaa ctaccaaata | 1200 |
| ttgaagtttt gtgaagatgc aaagatcaaa atcaaacaat acctgcctca ttacacaaca | 1260 |
| caaagagaat ggagggacca ttttggagat aaatattgga ccagatttca gcaaaggaaa | 1320 |
| ttagattttg acccaagaca tattttagcc accggccaac gcattttcat gccttctttt | 1380 |
| aatcctaata ctgcctcttg gtga | 1404 |

<210> SEQ ID NO 195
<211> LENGTH: 1671
<212> TYPE: DNA
<213> ORGANISM: Nicotiana tabacum

<400> SEQUENCE: 195

| | |
|---|---|
| atgggaaatc aagttttcct atttgcttgc acaatggctc ttctagcttc ttattcctca | 60 |
| ttggtttcag ctgaagttgt taaccattct tttcatgtac caaattcagc aaaaaagatg | 120 |
| ttagcgtgtt tagttgaaag atttgtggct gagaatgacg ctgattcaat acctgaacct | 180 |
| gaaaaaatcg acgacggcgt tttgaaagac ttggacattg aaggaagcat tgattatgga | 240 |
| ctcacggtta ccggtttagc cggtaaagat tttggcggca tgtatgcagt gaagccgtta | 300 |
| gccgttatac gtccggccgg tgccgatgac gtcgcgcggg tgattaggca agcgttacac | 360 |
| tcaccatcat taacggtagc ggcgaggggt aacggtcatt ccattaacgg ccaagctatg | 420 |
| gcccaccatg gactcgttat caatatgaaa tcaatgggcg ataataacag aatcgacgtc | 480 |
| agcgtctccg ccatgtacgc cgacgtaggt ggcggagcat tatgggctga tgtcttgaaa | 540 |
| cgctgcgttt tgggatatgg cttggctcct acctcgtgga cggattatct tgatttaacg | 600 |
| gtcggaggta ctttgtctaa cgccggcgtc agtggccaag ctttccgtta tggaccccaa | 660 |
| acgtcaaccg taacggaatt ggaagtggtt accggaaacg gagagagaac cgtctgctca | 720 |
| aactctcaaa attctgaact cttcttctct gttcttggcg gacttggtca gtttggtatc | 780 |
| atcactagag ctcggatttt gcttcaaccc gccccggata tggtaaggtg gataagagtg | 840 |

| | |
|---|---|
| gtatacagtg aattcgacga gtttactcgt gatgctgagt tactggtaat gagtccggaa | 900 |
| tcgttcgatt atgtggaagg atttgtgttt gtgaatagtg atgacccggt aaatgggtgg | 960 |
| ccgtcggtgc cattggattc aaatcattca tttgacccga cccatttacc aacaaacact | 1020 |
| ggcccggttc tctattgcct tgaagtggcc ctgcattatc acaaccatga ccatccctcc | 1080 |
| actgtaaata tgatggtgga gaaattgttt ggacgatcga gatttatcga acacttgagg | 1140 |
| tttgagattg acttgaatta tatggatttc ttgttacgag taaaacgcgt agaacaaatg | 1200 |
| gctagggata atggtatatg ggatgcacct catccatggc ttaacatgtt cgtttccaag | 1260 |
| agagacattg ccgcgttcaa tcgaattgtg ttccaaaaca tcttaaaaga tggtatcaat | 1320 |
| ggtcctatgt tgacatatcc tctcatccga agcaagtggg ataatcgatc atcagtggtg | 1380 |
| ttaccccaag gtgaaatatt ttacttagtg gctctgcttc ggtttagcca tgcacatcca | 1440 |
| aaagagtctg aaataaacga gatggtagca cagaaccaag agatcttgca aacttgcata | 1500 |
| aacaatgggt ttgatttcaa gttgtaccct ccgcattaca agtcaacaga ggaatggaag | 1560 |
| aagcactttg gggatcaatg gggaagattt gtagagagaa agagccagtt tgatccaaag | 1620 |
| gctatccttg cacctggcca aaaaatattt actagaaacc atctactcta a | 1671 |

<210> SEQ ID NO 196
<211> LENGTH: 1671
<212> TYPE: DNA
<213> ORGANISM: Nicotiana tabacum

<400> SEQUENCE: 196

| | |
|---|---|
| atggggcatc aacttttcct gtttgcttgt accatggctc ttcttgcttc ttattcctca | 60 |
| ttggtttcag ctgaagttgt tggccattct tttcatgtac caatttcagc aaaaaggatg | 120 |
| ttagcgtgtt tagttgagag atttgttgct gagaatgaag ctgattcaat acctgaacct | 180 |
| gaaaaaattg acgacggcgt tttgaaaaac ttggacattg aaggaagcat tgattatgga | 240 |
| ctcacggtaa ccggtttagc cggtaaagat tttggcggca tgtatgcagt gaagccgtta | 300 |
| gcggttgtac gtccggccgg tgccgatgac gttgcgcggg tgattaggca agcgttacac | 360 |
| tcaccaacat taacggtagc ggcgaggggt aacggtcatt ccattaacgg tcaagctatg | 420 |
| gcccatcatg gactcgttat cgacatgaaa tcattgggcg ataataacag aatcgacgtc | 480 |
| aacgtctcca ccatgtatgc cgacgtgggt ggcggagcat tatgggctga cgtcttgaaa | 540 |
| cgctgcgttt tgggttacgg cttggctcct atctcgtgga cggattatct tgatttaaca | 600 |
| gtcggaggta ctctgtctaa cgccggcgtc agtggccaag cttccgtta tggaccccaa | 660 |
| acgtcaactg taacggaatt ggaagtggtt accggcaacg gagagagaac cgtctgctca | 720 |
| aactctcaaa attctgaact cttcttctct gttcttgggg gacttggtca gtttggtatc | 780 |
| atcactagag ctcgggttat gcttcaaccc gccccggata tggtgaggtg ataagagtg | 840 |
| gtatacagtg aattcgacga gtttactcgt gatgcgagt tactggtaat gagtccggaa | 900 |
| tcgttcgatt atgtggaagg atttgtgttt gtaaacagtg atgacccggt aaatgggtgg | 960 |
| ccgtcggtgc cattggattc aaatcattca tttgacccga cccagttacc cacaaacact | 1020 |
| ggcccggttc tctattgcct tgaagtggcc ctgcattatc acaaccatga ccatcccacc | 1080 |
| actgtaaata tgatggtgga gaaattgtta gcgcgattga ggtttatcga gcacttgagg | 1140 |
| tttgaggccg acatgactta catggatttc ttgttacgag taaagcgcgt agaacaaatg | 1200 |
| gctagggata atggtatatg ggatgcgcct catccatggc ttaacatgtt cgtttccaag | 1260 |
| agagacattg gcacgttcaa tcgaattgtg ttccaaaaca tcttaaaaga tggtatcaat | 1320 |

-continued

```
ggccctatgt tgacatatcc tctcatccgt agcaagtgga ataatcgatc gtcagtggtg    1380
ttacccaaag gtgaaatatt ttacttagtg gctctgcttc ggtttagcca tgcacatcca    1440
aaagagtctg aaataaatga gatggtggca cagaaccaag agatcttgca aacttgcata    1500
aataatggat ttgatttcaa gttgtacctt ccgcattaca aatccacaga ggaatggaag    1560
aagcattttg gagatcaatg gggaagattt gtcgagagaa agagccagtt tgatccaaag    1620
gctgtccttg cgcctggcca aaaaatattt actagaaacc atcaacgcta a             1671
```

GENETIC CONTROL OF AXILLARY BUD GROWTH IN TOBACCO PLANTS

CROSS-REFERENCE TO RELATED APPLICATIONS AND INCORPORATION OF SEQUENCE LISTING

This application is a continuation of U.S. patent application Ser. No. 14/875,928, filed Oct. 6, 2015, which claims the benefit of U.S. Provisional Application No. 62/060,473, filed Oct. 6, 2014, both of which are incorporated by reference in their entireties herein. A sequence listing contained in the file named "P34468US01 SL.TXT" which is 322,059 bytes (measured in MS-Windows®) and created on Oct. 1, 2019, is filed electronically herewith and incorporated by reference in its entirety.

TECHNICAL FIELD

This disclosure generally relates to tobacco plants.

BACKGROUND

Tobacco is a plant species that exhibits exceptionally strong apical dominance. Molecular signals from shoot apical meristem mediate a hormonal environment that effectively inhibits axillary bud growth. Upon removal of the apical meristem (also known as "topping"), the signal is lost, enabling the formation of new shoots (or "suckers") from axillary buds. Sucker growth results in loss of yield and leaf quality. Suckers have been controlled by manual removal and through the application of chemicals. Maleic hydrazide (MH) and flumetralin are routinely used on topped plants to inhibit axillary bud growth (suckering). However, labor and chemical agents to control suckers are very expensive. Control of axillary bud growth in tobacco through conventional breeding, mutation breeding, and transgenic approaches have been a major objective for several decades but, to date, successful inhibition has not been achieved through genetic approaches. Therefore, development of tobacco traits with limited or no axillary bud growth would result in a reduction of the use of chemical agents and would reduce costs and labor associated with tobacco production.

SUMMARY

A number of nucleotide and polypeptide sequences involved in the formation of axillary bud growth are described herein. Methods of using such sequences also are described. The methods described herein allow for tobacco plants to be produced that exhibit reduced axillary bud growth after topping.

In one aspect, a tobacco hybrid, variety, line, or cultivar is provided that includes plants having a mutation in one or more of the nucleic acids shown in SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 57, 59, 61, 63, 65, 69, 71, 73, 75, or 77. In some embodiments, the plants exhibit, and can be selected for, reduced axillary bud growth relative to a plant lacking the mutation.

In one aspect, seed produced by any of the tobacco hybrids, varieties, lines, or cultivars is provided, the seed includes the mutation in the one or more nucleic acids.

In another aspect, a method of making a tobacco plant is provided. Such a method generally includes the steps of inducing mutagenesis in *Nicotiana tabacum* cells to produce mutagenized cells; obtaining one or more plants from the mutagenized cells; and identifying at least one of the plants that comprises a mutation in one or more of the nucleic acids having a sequence shown in SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 57, 59, 61, 63, 65, 69, 71, 73, 75, or 77. Such a method can further include identifying at least one of the plants that exhibits reduced axillary bud growth relative to a plant lacking the mutation.

In some embodiments, mutagenesis is induced using a chemical mutagen or ionizing radiation. Representative chemical mutagens include, without limitation, nitrous acid, sodium azide, acridine orange, ethidium bromide, and ethyl methane sulfonate (EMS). Representative ionizing radiation includes, without limitation, x-rays, gamma rays, fast neutron irradiation, and UV irradiation. In some embodiments, mutagenesis is induced using TALEN. In some embodiments, mutagenesis is induced using zinc-finger technology.

In another aspect, a method for producing a tobacco plant is provided. Such a method generally includes the steps of: crossing at least one plant of a first tobacco line with at least one plant of a second tobacco line, and selecting for progeny tobacco plants that have the mutation. Typically, the plant of the first tobacco line has a mutation in one or more nucleic acids having a sequence shown in SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 57, 59, 61, 63, 65, 69, 71, 73, 75, or 77. In some embodiments, such a method can further include selecting for progeny tobacco plants that exhibit reduced axillary bud growth relative to a plant lacking the mutation.

In still another aspect, a tobacco product is provided that includes cured leaf from a tobacco plant having a mutation in one or more nucleic acids having a sequence shown in SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 57, 59, 61, 63, 65, 69, 71, 73, 75, or 77. In some embodiments, the tobacco plant exhibits reduced axillary bud growth relative to leaf from a plant lacking the mutation. In some embodiments, the tobacco plant exhibits reduced MH residue relative to leaf from a plant lacking the mutation.

In yet another aspect, a method of producing a tobacco product is provided. Such a method typically includes providing cured leaf from a tobacco plant having a mutation in one or more nucleic acids having a sequence shown in SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 57, 59, 61, 63, 65, 69, 71, 73, 75, or 77; and manufacturing a tobacco product using the cured leaves. In some embodiments, the tobacco plant exhibits reduced axillary bud growth relative to cured leaf from a plant lacking the mutation.

As used herein, a mutation can be a point mutation, an insertion, a deletion, and a substitution.

In one aspect, a transgenic tobacco plant is provided that includes a plant expression vector having a nucleic acid molecule at least 25 nucleotides in length and at least 91% sequence identity to a sequence shown in SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, or 81. In some embodiments, the nucleic acid molecule has at least 91% sequence identity to a sequence shown in SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, or 81. In some embodiments, expression of the nucleic acid molecule results in a plant exhibiting reduced axillary bud growth relative to a tobacco plant not expressing the nucleic acid molecule.

In another aspect, seed produced by any of the transgenic tobacco plants described herein is provided, wherein the seed comprises the expression vector.

In another aspect, a transgenic tobacco plant is provided that includes a heterologous nucleic acid molecule of at least 25 nucleotides in length that hybridizes under stringent conditions to a nucleic acid sequence shown in SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, or 81. In some embodiments, the heterologous nucleic acid molecule hybridizes under stringent conditions to a nucleic acid sequence shown in SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, or 81. In some embodiments, expression of the heterologous nucleic acid molecule results in a plant exhibiting reduced axillary bud growth relative to a tobacco plant not expressing the nucleic acid molecule.

In some aspects, seed produced by any of the transgenic tobacco plants described herein is provided, where the seed comprises the heterologous nucleic acid molecule.

In still another aspect, a method of making a transgenic plant is provided. Such a method typically includes expressing a transgene encoding a double-stranded RNA molecule that inhibits expression from a nucleic acid sequence shown in SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 57, 59, 61, 63, 65, 69, 71, 73, 75, or 77, wherein the double-stranded RNA molecule comprises at least 25 consecutive nucleotides having 91% or greater sequence identity to a sequence shown in SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 57, 59, 61, 63, 65, 69, 71, 73, 75, or 77. In some embodiments, wherein expression of the transgene results in the plant exhibiting reduced axillary bud growth relative to a plant not expressing the transgene.

In another aspect, a tobacco product is provided that includes cured leaf from any of the transgenic tobacco plants described herein.

In still another aspect, a method of producing a tobacco product is provided, the method including providing cured leaf from any of the transgenic tobacco plants described herein; and manufacturing a tobacco product using the cured leaf.

In yet another aspect, a method of reducing axillary bud growth in a tobacco plant is provided. Such a method generally includes introducing a heterologous nucleic acid molecule operably linked to a promoter into tobacco cells to produce transgenic tobacco cells, and regenerating transgenic tobacco plants from the transgenic tobacco cells. Typically, the heterologous nucleic acid molecule includes at least 25 nucleotides in length and has at least 91% sequence identity to a nucleic acid sequence shown in SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, or 81. Such transgenic tobacco plants exhibit reduced axillary bud growth. In some embodiments, the heterologous nucleic acid molecule has at least 91% sequence identity to a nucleic acid sequence as shown in SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, or 81. In some embodiments, expression of the nucleic acid molecule results in a plant exhibiting reduced axillary bud growth relative to a tobacco plant not expressing the nucleic acid molecule. Such a method further can include selecting at least one of the transgenic tobacco plants that exhibits reduced axillary bud growth relative to a tobacco plant not expressing the heterologous nucleic acid molecule.

In one embodiment, the nucleic acid is in sense orientation. In some embodiments, the nucleic acid is in antisense orientation. In some embodiments, the nucleic acid molecule is introduced into the tobacco cells using particle bombardment, Agrobacterium-mediated transformation, microinjection, polyethylene glycol-mediated transformation, liposome-mediated DNA uptake, or electroporation. In some embodiments, the tobacco plant is a Burley type, a dark type, a flue-cured type, a Maryland type, or an Oriental type. In some embodiments, the tobacco plant is a variety selected from the group consisting of BU 64, CC 101, CC 200, CC 13, CC 27, CC 33, CC 35,CC 37, CC 65, CC 67, CC 301, CC 400, CC 500, CC 600, CC 700, CC 800, CC 900, CC 1063, Coker 176, Coker 319, Coker 371 Gold, Coker 48, CU 263, DF911, Galpao tobacco, GL 26H, GL 338, GL 350, GL 395, GL 600, GL 737, GL 939, GL 973, GF 157, GF 318, RJR 901, HB 04P, K 149, K 326, K 346, K 358, K394, K 399, K 730, NC 196, NC 37NF, NC 471, NC 55, NC 92, NC2326, NC 95, NC 925, PVH 1118, PVH 1452, PVH 2110, PVH 2254, PVH 2275, VA 116, VA 119, KDH 959, KT 200, KT204LC, KY 10, KY 14, KY 160, KY 17, KY 171, KY 907, KY907LC, KTY14 x L8 LC, Little Crittenden, McNair 373, McNair 944, msKY 14xL8, Narrow Leaf Madole, NC 100, NC 102, NC 2000, NC 291, NC 297, NC 299, NC 3, NC 4, NC 5, NC 6, NC7, NC 606, NC 71, NC 72, NC 810, NC BH 129, NC 2002, Neal Smith Madole, OXFORD 207, 'Perique' tobacco, PVH03, PVH09, PVH19, PVH50, PVH51, R 610, R 630, R 7-11, R 7-12, RG 17, RG 81, RG H51, RGH 4, RGH 51, RS 1410, Speight 168, Speight 172, Speight 179, Speight 210, Speight 220, Speight 225, Speight 227, Speight 234, Speight G-28, Speight G-70, Speight H-6, Speight H20, Speight NF3, TI 1406, TI 1269, TN 86, TN86LC, TN 90, TN90LC, TN 97, TN97LC, TN D94, TN D950, TR (Tom Rosson) Madole, VA 309, or VA359.

Unless otherwise defined, all technical and scientific terms used herein have the same meaning as commonly understood by one of ordinary skill in the art to which the methods and compositions of matter belong. Although methods and materials similar or equivalent to those described herein can be used in the practice or testing of the methods and compositions of matter, suitable methods and materials are described below. In addition, the materials, methods, and examples are illustrative only and not intended to be limiting. All publications, patent applications, patents, and other references mentioned herein are incorporated by reference in their entirety.

DESCRIPTION OF DRAWINGS

FIG. 3B shows various protein alignments (SEQ ID NOs: 2, 14, 34, 36, 38, and 56, top to bottom).

DETAILED DESCRIPTION

Figure 1A:
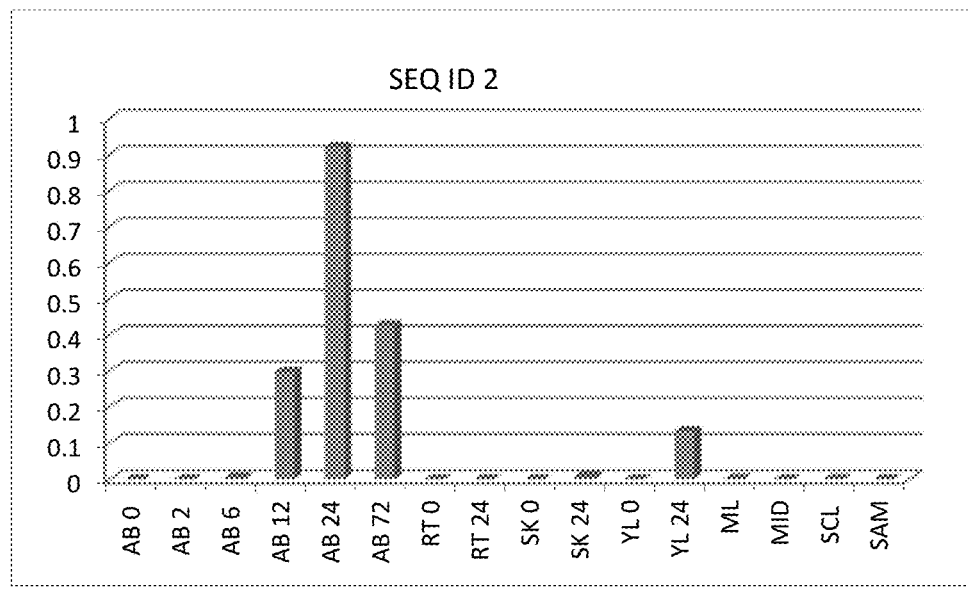
FIG. 1A is a graph showing gene expression verification of SEQ ID NO:2 using real time PCR analysis. AB0: axillary bud before topping; AB2: axillary bud 2 hr post-topping; AB6: axillary bud 6 hr post-topping; AB12: axillary bud 12 hr post-topping; AB48: axillary bud 48 hr post-topping; AB72: axillary bud 72 hr post-topping; RT0: roots before topping; RT24: roots 24 hr post-topping; YL0: young leaf before topping; YL24: young leaf 24 hr post-topping; ML: mature leaf; MID midrib; SK0: stalk before topping; SK24: stalk 24 hr post-topping; SAM: shoot apical meristem and SCL: senescent leaf.
Figure 1B:
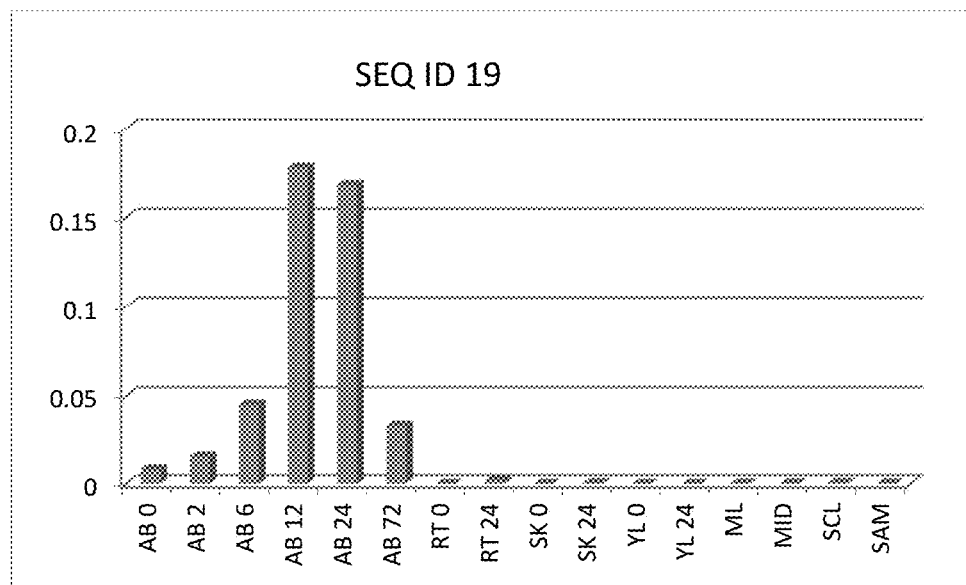
FIG. 1B is a graph showing gene expression verification of SEQ ID NO:19 using real time PCR analysis. AB0: axillary bud before topping; AB2: axillary bud 2 hr post-topping; AB6: axillary bud 6 hr post-topping; AB12: axillary bud 12 hr post-topping; AB48: axillary bud 48 hr post-topping; AB72: axillary bud 72 hr post-topping; RT0: roots before topping; RT24: roots 24 hr post-topping; YL0: young leaf before topping; YL24: young leaf 24 hr post-topping; ML: mature leaf; MID midrib; SK0: stalk before topping; SK24: stalk 24 hr post-topping; SAM: shoot apical meristem and SCL: senescent leaf.
Figure 1C:
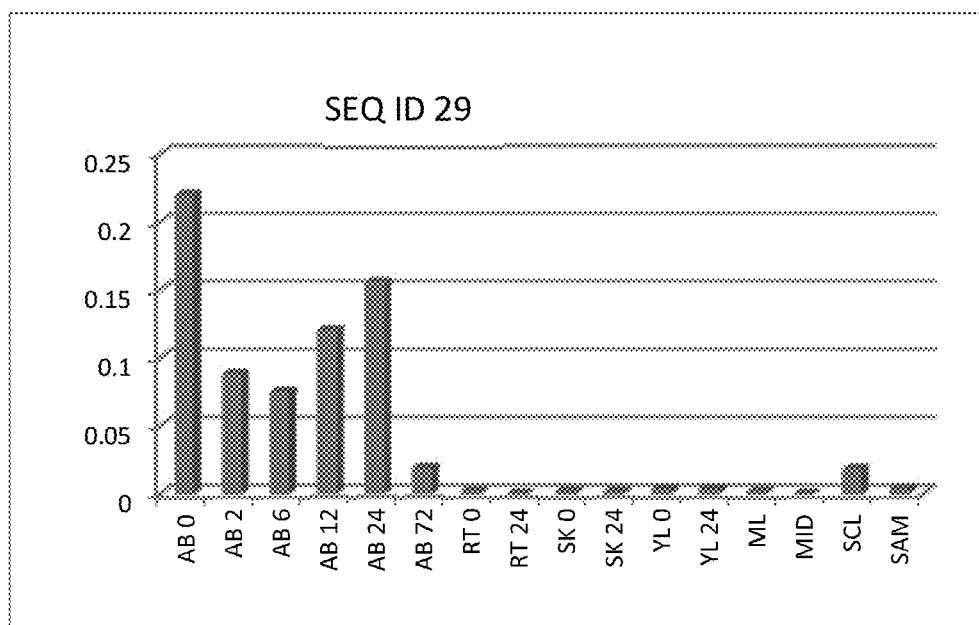
FIG. 1C is a graph showing gene expression verification of SEQ ID NO:29 using real time PCR analysis. AB0: axillary bud before topping; AB2: axillary bud 2 hr post-topping; AB6: axillary bud 6 hr post-topping; AB12: axillary bud 12 hr post-topping; AB48: axillary bud 48 hr post-topping; AB72: axillary bud 72 hr post-topping; RT0: roots before topping; RT24: roots 24 hr post-topping; YL0: young leaf before topping; YL24: young leaf 24 hr post-topping; ML: mature leaf; MID midrib; SK0: stalk before topping; SK24: stalk 24 hr post-topping; SAM: shoot apical meristem and SCL: senescent leaf.
Figure 1D:
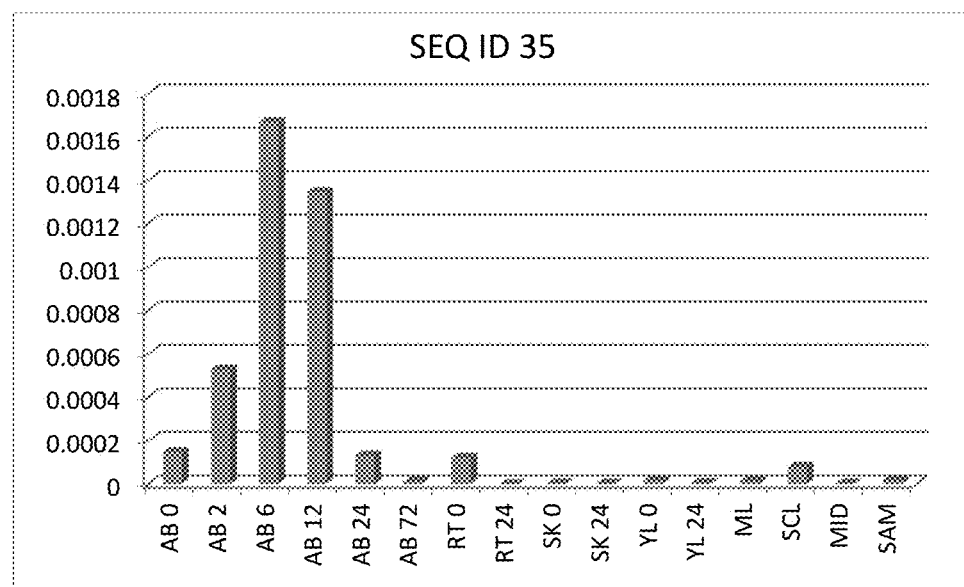
FIG. 1D is a graph showing gene expression verification of SEQ ID NO:35 using real time PCR analysis. AB0: axillary bud before topping; AB2: axillary bud 2 hr post-topping; AB6: axillary bud 6 hr post-topping; AB12: axillary bud 12 hr post-topping; AB48: axillary bud 48 hr post-topping; AB72: axillary bud 72 hr post-topping; RT0: roots before topping; RT24: roots 24 hr post-topping; YL0: young leaf before topping; YL24: young leaf 24 hr post-topping; ML: mature leaf; MID midrib; SK0: stalk before topping; SK24: stalk 24 hr post-topping; SAM: shoot apical meristem and SCL: senescent leaf.
Figure 1E:
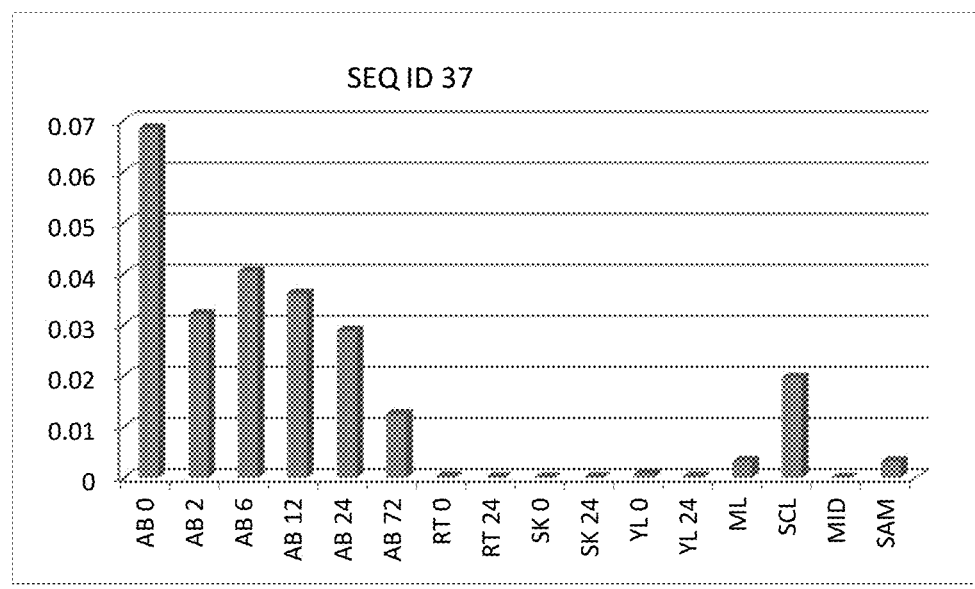
FIG. 1E is a graph showing gene expression verification of SEQ ID NO:37 using real time PCR analysis. AB0: axillary bud before topping; AB2: axillary bud 2 hr post-topping; AB6: axillary bud 6 hr post-topping; AB12: axillary bud 12 hr post-topping; AB48: axillary bud 48 hr post-topping; AB72: axillary bud 72 hr post-topping; RT0: roots before topping; RT24: roots 24 hr post-topping; YL0: young leaf before topping; YL24: young leaf 24 hr post-topping; ML: mature leaf; MID midrib; SK0: stalk before topping; SK24: stalk 24 hr post-topping; SAM: shoot apical meristem and SCL: senescent leaf.
Figure 1F:
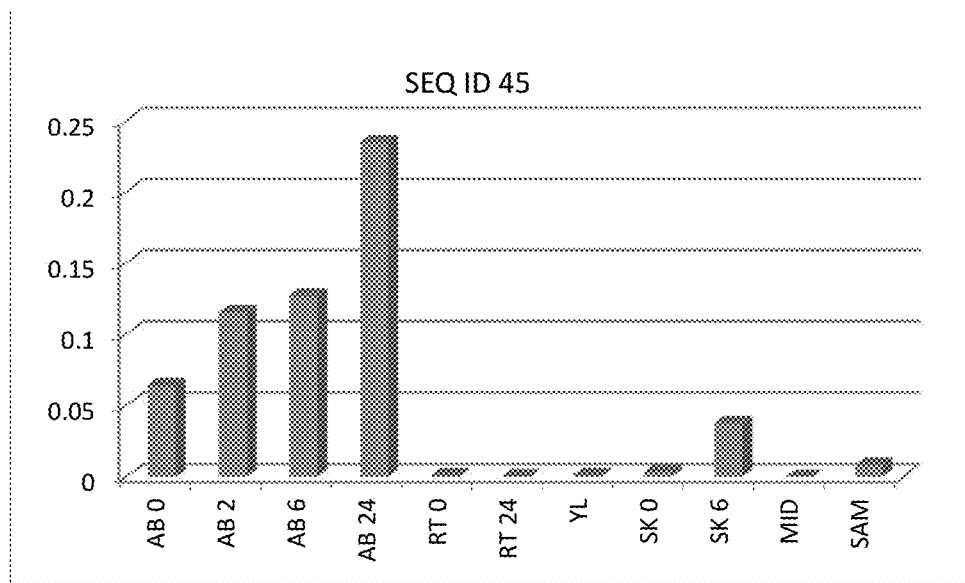
FIG. 1F is a graph showing gene expression verification of SEQ ID NO:45 using real time PCR analysis. AB0: axillary bud before topping; AB2: axillary bud 2 hr post-topping; AB6: axillary bud 6 hr post-topping; AB12: axillary bud 12 hr post-topping; AB48: axillary bud 48 hr post-topping; AB72: axillary bud 72 hr post-topping; RT0: roots before topping; RT24: roots 24 hr post-topping; YL0: young leaf before topping; YL24: young leaf 24 hr post-topping; ML: mature leaf; MID midrib; SK0: stalk before topping; SK24: stalk 24 hr post-topping; SAM: shoot apical meristem and SCL: senescent leaf.

This application describes approaches to produce tobacco with no or reduced sucker growth. For example, the description includes: axillary bud growth gene profiling to discover genes that are critical for axillary bud development; up regulation of axillary bud growth and/or sucker suppressor genes; down-regulation of axillary bud and/or sucker activator genes; and modulation of regulatory components of sucker growth; or initiation or induction of cell death mechanisms in axillary buds using axillary bud-specific promoters.

This disclosure is based on the discovery of nucleic acids encoding polypeptides from *N. tabacum, Arabidopsis thaliana* and *Bacillus amyloliquefaciens* that are involved in axillary bud growth and the regulation thereof. Such nucleic acids, SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, or 81, and the polypeptides encoded thereby, SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, or 82, are described and characterized herein. Based on this discovery, the level of expression of such nucleic acid sequences and/or the function of such polypeptides can be modulated in *Nicotiana* species, specifically, for example, *N. tabacum*. Modulating polypeptide function and/or gene expression can permit improved control of axillary bud growth.

Nucleic Acids and Polypeptides

Nucleic acids are provided herein (see, for example, SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, or 81). As used herein, nucleic acids can include DNA and RNA, and includes nucleic acids that contain one or more nucleotide analogs or backbone modifications. A nucleic acid can be single stranded or double stranded, which usually depends upon its intended use. The nucleic acids provided herein encode polypeptides (see, for example, SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, or 82).

Also provided are nucleic acids and polypeptides that differ from SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, or 81, and SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, or 82, respectively. Nucleic acids and polypeptides that differ in sequence from SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, or 81, and SEQ ID NOs: 2, 4, 6, 8, 10, 12, 14, 16, 18, 20, 22, 24, 26, 28, 30, 32, 34, 36, 38, 40, 42, 44, 46, 48, 50, 52, or 54, can have at least 50% sequence identity (e.g., at least 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, or 99% sequence identity) to SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, or 81, and SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, or 82, respectively.

In calculating percent sequence identity, two sequences are aligned and the number of identical matches of nucleotides or amino acid residues between the two sequences is determined. The number of identical matches is divided by the length of the aligned region (i.e., the number of aligned nucleotides or amino acid residues) and multiplied by 100 to arrive at a percent sequence identity value. It will be appreciated that the length of the aligned region can be a portion of one or both sequences up to the full-length size of the shortest sequence. It also will be appreciated that a single sequence can align with more than one other sequence and hence, can have different percent sequence identity values over each aligned region.

The alignment of two or more sequences to determine percent sequence identity can be performed using the computer program ClustalW and default parameters, which allows alignments of nucleic acid or polypeptide sequences to be carried out across their entire length (global alignment). Chenna et al., 2003, Nucleic Acids Res., 31(13): 3497-500. ClustalW calculates the best match between a query and one or more subject sequences, and aligns them so that identities, similarities and differences can be determined. Gaps of one or more residues can be inserted into a query sequence, a subject sequence, or both, to maximize sequence alignments. For fast pairwise alignment of nucleic acid sequences, the default parameters can be used (i.e., word size: 2; window size: 4; scoring method: percentage; number of top diagonals: 4; and gap penalty: 5); for an alignment of multiple nucleic acid sequences, the following parameters can be used: gap opening penalty: 10.0; gap extension penalty: 5.0; and weight transitions: yes. For fast pairwise alignment of polypeptide sequences, the following parameters can be used: word size: 1; window size: 5; scoring method: percentage; number of top diagonals: 5; and gap penalty: 3. For multiple alignment of polypeptide sequences, the following parameters can be used: weight matrix: blosum; gap opening penalty: 10.0; gap extension penalty: 0.05; hydrophilic gaps: on; hydrophilic residues: Gly, Pro, Ser, Asn, Asp, Gln, Glu, Arg, and Lys; and residue-specific gap penalties: on. ClustalW can be run, for example, at the Baylor College of Medicine Search Launcher website or at the European Bioinformatics Institute website on the World Wide Web.

Changes can be introduced into a nucleic acid molecule (e.g., SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, or 81), thereby leading to changes in the amino acid sequence of the encoded polypeptide (e.g., SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, or 82). For example, changes can be introduced into nucleic acid coding sequences using mutagenesis (e.g., site-directed mutagenesis, transcription activator-like effector nuclease (TALEN), PCR-mediated mutagenesis, clustered regularly interspaced short palindromic repeats (CRISPR) mutagenesis) or by chemically synthesizing a nucleic acid molecule having such changes. Such nucleic acid changes can lead to conservative and/or non-conservative amino acid substitutions at one or more amino acid residues. A "conservative amino acid substitution" is one in which one amino acid residue is replaced with a different amino acid residue having a similar side chain (see, for example, Dayhoff et al. (1978, in Atlas of Protein Sequence and Structure, 5(Suppl. 3):345-352), which provides frequency tables for amino acid substitutions), and a non-conservative substitution is one in which an amino acid residue is replaced with an amino acid residue that does not have a similar side chain.

As used herein, an "isolated" nucleic acid molecule is a nucleic acid molecule that is free of sequences that naturally flank one or both ends of the nucleic acid in the genome of the organism from which the isolated nucleic acid molecule is derived (e.g., a cDNA or genomic DNA fragment produced by PCR or restriction endonuclease digestion). Such an isolated nucleic acid molecule is generally introduced into a vector (e.g., a cloning vector, or an expression vector) for convenience of manipulation or to generate a fusion nucleic acid molecule, discussed in more detail below. In addition, an isolated nucleic acid molecule can include an engineered nucleic acid molecule such as a recombinant or a synthetic nucleic acid molecule.

As used herein, a "purified" polypeptide is a polypeptide that has been separated or purified from cellular components that naturally accompany it. Typically, the polypeptide is considered "purified" when it is at least 70% (e.g., at least 75%, 80%, 85%, 90%, 95%, or 99%) by dry weight, free from the polypeptides and naturally occurring molecules with which it is naturally associated. Since a polypeptide that is chemically synthesized is, by nature, separated from the components that naturally accompany it, a synthetic polypeptide is "purified."

Nucleic acids can be isolated using techniques routine in the art. For example, nucleic acids can be isolated using any method including, without limitation, recombinant nucleic acid technology, and/or the polymerase chain reaction (PCR). General PCR techniques are described, for example in PCR Primer: A Laboratory Manual, Dieffenbach & Dveksler, Eds., Cold Spring Harbor Laboratory Press, 1995. Recombinant nucleic acid techniques include, for example, restriction enzyme digestion and ligation, which can be used to isolate a nucleic acid. Isolated nucleic acids also can be chemically synthesized, either as a single nucleic acid molecule or as a series of oligonucleotides.

Polypeptides can be purified from natural sources (e.g., a biological sample) by known methods such as DEAE ion exchange, gel filtration, and hydroxyapatite chromatography. A polypeptide also can be purified, for example, by expressing a nucleic acid in an expression vector. In addition, a purified polypeptide can be obtained by chemical synthesis. The extent of purity of a polypeptide can be measured using any appropriate method, e.g., column chromatography, polyacrylamide gel electrophoresis, or HPLC analysis.

A vector containing a nucleic acid (e.g., a nucleic acid that encodes a polypeptide) also is provided. Vectors, including expression vectors, are commercially available or can be produced by recombinant DNA techniques routine in the art. A vector containing a nucleic acid can have expression elements operably linked to such a nucleic acid, and further can include sequences such as those encoding a selectable marker (e.g., an antibiotic resistance gene). A vector containing a nucleic acid can encode a chimeric or fusion polypeptide (i.e., a polypeptide operatively linked to a heterologous polypeptide, which can be at either the N-terminus or C-terminus of the polypeptide). Representative heterologous polypeptides are those that can be used in purification of the encoded polypeptide (e.g., 6xHis tag, glutathione S-transferase (GST)).

Expression elements include nucleic acid sequences that direct and regulate expression of nucleic acid coding sequences. One example of an expression element is a promoter sequence. Expression elements also can include introns, enhancer sequences, response elements, or inducible elements that modulate expression of a nucleic acid. Expression elements can be of bacterial, yeast, insect, mammalian, or viral origin, and vectors can contain a combination of elements from different origins. As used herein, operably linked means that a promoter or other expression element(s) are positioned in a vector relative to a nucleic acid in such a way as to direct or regulate expression of the nucleic acid (e.g., in-frame).

Additionally or alternatively, a vector can include sequences to direct homologous recombination of a nucleic acid (e.g., SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, or 81) into a genome. Representative sequences that can direct homologous recombination of a nucleic acid into a genome are known in the art and include TALEN sequences (e.g., Cermak et al., 2011, Nuc. Acids Res., 39:e82), CRISPR sequences (Jiang et al., 2013, Nuc. Acids Res., 41:e188), or zinc-finger nucleases (Guo et al., 2010, J. Mol. Biol., 400: 96).

Vectors as described herein can be introduced into a host cell. As used herein, "host cell" refers to the particular cell into which the nucleic acid is introduced and also includes the progeny of such a cell that carry the vector. A host cell can be any prokaryotic or eukaryotic cell. For example, nucleic acids can be expressed in bacterial cells such as *E. coli*, or in insect cells, yeast or mammalian cells (such as Chinese hamster ovary cells (CHO) or COS cells). Other suitable host cells are known to those skilled in the art and include plant cells. Many methods for introducing nucleic acids into host cells, both in vivo and in vitro, are well known to those skilled in the art and include, without limitation, electroporation, calcium phosphate precipitation, polyethylene glycol (PEG) transformation, heat shock, lipofection, microinjection, and viral-mediated nucleic acid transfer.

Nucleic acids can be detected using any number of amplification techniques (see, e.g., PCR Primer: A Laboratory Manual, 1995, Dieffenbach & Dveksler, Eds., Cold Spring Harbor Laboratory Press, Cold Spring Harbor, N.Y.; and U.S. Pat. Nos. 4,683,195; 4,683,202; 4,800,159; and 4,965,188) with an appropriate pair of oligonucleotides (e.g., primers). A number of modifications to the original PCR have been developed and can be used to detect a nucleic acid.

Nucleic acids also can be detected using hybridization. Hybridization between nucleic acids is discussed in detail in Sambrook et al. (1989, Molecular Cloning: A Laboratory Manual, 2nd Ed., Cold Spring Harbor Laboratory Press, Cold Spring Harbor, N.Y.; Sections 7.37-7.57, 9.47-9.57, 11.7-11.8, and 11.45-11.57). Sambrook et al. disclose suitable Southern blot conditions for oligonucleotide probes less than about 100 nucleotides (Sections 11.45-11.46). The Tm between a sequence that is less than 100 nucleotides in length and a second sequence can be calculated using the formula provided in Section 11.46. Sambrook et al. additionally disclose Southern blot conditions for oligonucleotide probes greater than about 100 nucleotides (see Sections 9.47-9.54). The Tm between a sequence greater than 100 nucleotides in length and a second sequence can be calculated using the formula provided in Sections 9.50-9.51 of Sambrook et al.

The conditions under which membranes containing nucleic acids are prehybridized and hybridized, as well as the conditions under which membranes containing nucleic acids are washed to remove excess and non-specifically bound probe, can play a significant role in the stringency of the hybridization. Such hybridizations and washes can be performed, where appropriate, under moderate or high stringency conditions. For example, washing conditions can be made more stringent by decreasing the salt concentration in the wash solutions and/or by increasing the temperature at which the washes are performed. Simply by way of example, high stringency conditions typically include a wash of the membranes in 0.2×SSC at 65° C.

In addition, interpreting the amount of hybridization can be affected, for example, by the specific activity of the labeled oligonucleotide probe, by the number of probe-binding sites on the template nucleic acid to which the probe has hybridized, and by the amount of exposure of an autoradiograph or other detection medium. It will be readily appreciated by those of ordinary skill in the art that although any number of hybridization and washing conditions can be used to examine hybridization of a probe nucleic acid molecule to immobilized target nucleic acids, it is more important to examine hybridization of a probe to target nucleic acids under identical hybridization, washing, and exposure conditions. Preferably, the target nucleic acids are on the same membrane.

A nucleic acid molecule is deemed to hybridize to a nucleic acid but not to another nucleic acid if hybridization to a nucleic acid is at least 5-fold (e.g., at least 6-fold, 7-fold, 8-fold, 9-fold, 10-fold, 20-fold, 50-fold, or 100-fold) greater than hybridization to another nucleic acid. The amount of hybridization can be quantified directly on a membrane or from an autoradiograph using, for example, a PhosphorImager or a Densitometer (Molecular Dynamics, Sunnyvale, Calif.).

Polypeptides can be detected using antibodies. Techniques for detecting polypeptides using antibodies include enzyme linked immunosorbent assays (ELISAs), Western blots, immunoprecipitations and immunofluorescence. An antibody can be polyclonal or monoclonal. An antibody having specific binding affinity for a polypeptide can be generated using methods well known in the art. The antibody can be attached to a solid support such as a microtiter plate using methods known in the art. In the presence of a polypeptide, an antibody-polypeptide complex is formed.

Detection (e.g., of an amplification product, a hybridization complex, or a polypeptide) is usually accomplished using detectable labels. The term "label" is intended to encompass the use of direct labels as well as indirect labels. Detectable labels include enzymes, prosthetic groups, fluorescent materials, luminescent materials, bioluminescent materials, and radioactive materials.

Plants Having Reduced Axillary Bud Growth and Methods of Making

Tobacco hybrids, varieties, lines, or cultivars are provided that have a mutation in one or more nucleic acids described herein (e.g., SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 57, 59, 61, 63, 65, 69, 71, 73, 75, or 77). As described herein, stalks of plants having a mutation in one or more of the nucleic acids (e.g., SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 57, 59, 61, 63, 65, 69, 71, 73, 75, or 77) can exhibit reduced axillary bud growth (e.g., compared to stalks of a plant that lacks the mutation). In some instances, the nucleic acid having the mutation can be an endogenous nucleic acid; in some instances, the nucleic acid having the mutation can be introduced recombinantly.

As used herein, axillary bud growth (or "suckering") describes the production of lateral buds (or "suckers") that grow between the leaf and the stalk after a tobacco plant is topped, as commonly understood in the art. Topping refers to the removal of the stalk apex, including the flowers and up to several adjacent leaves, when the plant is near maturity, and results in the loss of apical dominance. Provided axillary bud growth is sufficiently controlled, topping increases the yield and the value-per-acre as well as results in desirable modifications to physical and chemical properties of the leaf.

Methods of making a tobacco plant having a mutation are known in the art. Mutations can be random mutations or targeted mutations. For random mutagenesis, cells (e.g., Nicotiana tabacum cells) can be mutagenized using, for example, a chemical mutagen, ionizing radiation, or fast neutron bombardment (see, e.g., Li et al., 2001, Plant J., 27:235-42). Representative chemical mutagens include, without limitation, nitrous acid, sodium azide, acridine orange, ethidium bromide, and ethyl methane sulfonate (EMS), while representative ionizing radiation includes, without limitation, x-rays, gamma rays, fast neutron irradiation, and UV irradiation. The dosage of the mutagenic chemical or radiation is determined experimentally for each type of plant tissue such that a mutation frequency is obtained that is below a threshold level characterized by lethality or reproductive sterility. The number of $M_1$ generation seed or the size of $M_1$ plant populations resulting from the mutagenic treatments are estimated based on the expected frequency of mutations. For targeted mutagenesis, representative technologies include TALEN (see, for example, Li et al., 2011, Nucleic Acids Res., 39(14):6315-25) or the use of zinc-finger nucleases (see, for example, Wright et al., 2005, The Plant J., 44:693-705). Whether random or targeted, a mutation can be a point mutation, an insertion, a deletion, a substitution, or combinations thereof.

As discussed herein, one or more nucleotides can be mutated to alter the expression and/or function of the encoded polypeptide, relative to the expression and/or function of the corresponding wild type polypeptide. It will be appreciated, for example, that a mutation in one or more of the highly conserved regions would likely alter polypeptide function, while a mutation outside of those conserved regions would likely have little to no effect on polypeptide function. In addition, a mutation in a single nucleotide can create a stop codon, which would result in a truncated polypeptide and, depending on the extent of truncation, loss of function.

Preferably, a mutation in one of the novel nucleic acids disclosed herein results in reduced or even complete elimination of axillary bud growth after topping in a tobacco plant comprising the mutation. Suitable types of mutations in a coding sequence include, without limitation, insertions of nucleotides, deletions of nucleotides, or transitions or transversions in the wild-type coding sequence. Mutations in the coding sequence can result in insertions of one or more amino acids, deletions of one or more amino acids, and/or non-conservative amino acid substitutions in the encoded polypeptide. In some cases, the coding sequence comprises more than one mutation or more than one type of mutation.

Insertion or deletion of amino acids in a coding sequence, for example, can disrupt the conformation of the encoded polypeptide. Amino acid insertions or deletions also can disrupt sites important for recognition of a binding ligand or for activity of the polypeptide. It is known in the art that the insertion or deletion of a larger number of contiguous amino acids is more likely to render the gene product non-functional, compared to a smaller number of inserted or deleted amino acids. In addition, one or more mutations (e.g., a point mutation) can change the localization of the polypeptide, introduce a stop codon to produce a truncated polypeptide, or disrupt an active site or domain (e.g., a catalytic site or domain, a binding site or domain) within the polypeptide. In addition, a target or signal sequence can be mutated, thereby disrupting or altering the placement of the protein in the cell.

Non-conservative amino acid substitutions can replace an amino acid of one class with an amino acid of a different class. Non-conservative substitutions can make a substantial change in the charge or hydrophobicity of the gene product. Non-conservative amino acid substitutions can also make a substantial change in the bulk of the residue side chain, e.g., substituting an alanine residue for an isoleucine residue. Examples of non-conservative substitutions include a basic amino acid for a non-polar amino acid, or a polar amino acid for an acidic amino acid.

Following mutagenesis, $M_0$ plants are regenerated from the mutagenized cells and those plants, or a subsequent generation of that population (e.g., $M_1$, $M_2$, $M_3$, etc.), can be screened for a mutation in a sequence of interest (e.g., SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 57, 59, 61, 63, 65, 69, 71, 73, 75, or 77). Screening for plants carrying a mutation in a sequence of interest can be performed using methods routine in the art (e.g., hybridization, amplification, combinations thereof) or by evaluating the phenotype (e.g., detecting and/or determining axillary bud growth). Generally, the presence of a mutation in one or more of the nucleic acid sequences disclosed herein (e.g., SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 57, 59, 61, 63, 65, 69, 71, 73, 75, or 77) results in a reduction of axillary bud growth in the mutant plants compared to a corresponding plant (e.g., having the same varietal background) lacking the mutation.

As used herein, reduced axillary bud growth, also referred to as reduced sucker growth, refers to a reduction (e.g., a statistically significant reduction) in the number of axillary buds, a reduction (e.g., a statistically significant reduction) in the size of the axillary buds (e.g., biomass), and/or a reduction (e.g., a statistically significant reduction) of the impact the axillary buds have on agronomic performance (e.g., yield, quality and overall productivity of the plant) compared to a control plant. The effects can be demonstrated as impeding and/or eliminating axillary bud growth after topping, or reducing and/or eliminating the need for application of chemicals (e.g., MH and/or flumetralin) after topping. As used herein, statistically significant refers to a p-value of less than 0.05, e.g., a p-value of less than 0.025 or a p-value of less than 0.01, using an appropriate measure of statistical significance, e.g., a one-tailed two sample t-test.

An $M_1$ tobacco plant may be heterozygous for a mutant allele and exhibit a wild type phenotype. In such cases, at least a portion of the first generation of self-pollinated progeny of such a plant exhibits a wild type phenotype. Alternatively, an $M_1$ tobacco plant may have a mutant allele and exhibit a mutant phenotype. Such plants may be heterozygous and exhibit a mutant phenotype due to phenomena such as dominant negative suppression, despite the presence of the wild type allele, or such plants may be heterozygous due to different independently induced mutations in different alleles.

A tobacco plant carrying a mutant allele can be used in a plant breeding program to create novel and useful cultivars, lines, varieties and hybrids. Thus, in some embodiments, an $M_1$, $M_2$, $M_3$ or later generation tobacco plant containing at least one mutation is crossed with a second *Nicotiana tabacum* plant, and progeny of the cross are identified in which the mutation(s) is present. It will be appreciated that the second *Nicotiana tabacum* plant can be one of the species and varieties described herein. It will also be appreciated that the second *Nicotiana tabacum* plant can contain the same mutation as the plant to which it is crossed, a different mutation, or be wild type at the locus. Additionally or alternatively, a second tobacco line can exhibit a phenotypic trait such as, for example, disease resistance, high yield, high grade index, curability, curing quality, mechanical harvesting, holding ability, leaf quality, height, plant maturation (e.g., early maturing, early to medium maturing, medium maturing, medium to late maturing, or late maturing), stalk size (e.g., small, medium, or large), and/or leaf number per plant (e.g., a small (e.g., 5-10 leaves), medium (e.g., 11-15 leaves), or large (e.g., 16-21) number of leaves).

Breeding is carried out using known procedures. DNA fingerprinting, SNP or similar technologies may be used in a marker-assisted selection (MAS) breeding program to transfer or breed mutant alleles into other tobaccos, as described herein. Progeny of the cross can be screened for a mutation using methods described herein, and plants having a mutation in a nucleic acid sequence disclosed herein (e.g., SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 57, 59, 61, 63, 65, 69, 71, 73, 75, or 77) can be selected. For example, plants in the $F_2$ or backcross generations can be screened using a marker developed from a sequence described herein or a fragment thereof, using one of the techniques listed herein. Progeny plants also can be screened for axillary bud growth, and those plants having reduced axillary bud growth, compared to a corresponding plant that lacks the mutation, can be selected. Plants identified as possessing the mutant allele and/or the mutant phenotype can be backcrossed or self-pollinated to create a second population to be screened. Backcrossing or other breeding procedures can be repeated until the desired phenotype of the recurrent parent is recovered.

Successful crosses yield $F_1$ plants that are fertile and that can be backcrossed with a parent line if desired. In some embodiments, a plant population in the $F_2$ generation is screened for the mutation or variant gene expression using standard methods (e.g., PCR with primers based upon the nucleic acid sequences disclosed herein). Selected plants are then crossed with one of the parents and the first backcross ($BC_1$) generation plants are self-pollinated to produce a $BC_1F_2$ population that is again screened for variant gene expression. The process of backcrossing, self-pollination, and screening is repeated, for example, at least four times until the final screening produces a plant that is fertile and reasonably similar to the recurrent parent. This plant, if desired, is self-pollinated and the progeny are subsequently screened again to confirm that the plant contains the mutation and exhibits variant gene expression. Breeder's seed of the selected plant can be produced using standard methods including, for example, field testing, confirmation of the null condition, and/or planting to evaluate axillary bud growth.

The result of a plant breeding program using the mutant tobacco plants described herein are novel and useful cultivars, varieties, lines, and hybrids. As used herein, the term "variety" refers to a population of plants that share characteristics which separate them from other plants of the same species. A variety is often, although not always, sold commercially. While possessing one or more distinctive traits, a variety is further characterized by a very small overall variation between individuals within that variety. A "pure line" variety may be created by several generations of self-pollination and selection, or vegetative propagation from a single parent using tissue or cell culture techniques. A "line," as distinguished from a variety, most often denotes a group of plants used non-commercially, for example, in plant research. A line typically displays little overall variation between individuals for one or more traits of interest, although there may be some variation between individuals for other traits.

A variety can be essentially derived from another line or variety. As defined by the International Convention for the Protection of New Varieties of Plants (Dec. 2, 1961, as revised at Geneva on Nov. 10, 1972, On Oct. 23, 1978, and on Mar. 19, 1991), a variety is "essentially derived" from an initial variety if: a) it is predominantly derived from the initial variety, or from a variety that is predominantly derived from the initial variety, while retaining the expression of the essential characteristics that result from the genotype or combination of genotypes of the initial variety; b) it is clearly distinguishable from the initial variety; and c) except for the differences which result from the act of derivation, it confirms to the initial variety in the expression of the essential characteristics that result from the genotype or combination of genotypes of the initial variety. Essentially derived varieties can be obtained, for example, by the selection of a natural or induced mutant, a somaclonal variant, a variant individual plant from the initial variety, backcrossing, or transformation.

Tobacco hybrids can be produced by preventing self-pollination of female parent plants (i.e., seed parents) of a first variety, permitting pollen from male parent plants of a second variety to fertilize the female parent plants, and allowing $F_1$ hybrid seeds to form on the female plants. Self-pollination of female plants can be prevented by emasculating the flowers at an early stage of flower development. Alternatively, pollen formation can be prevented on the female parent plants using a form of male sterility. For example, male sterility can be produced by cytoplasmic male sterility (CMS), nuclear male sterility, genetic male sterility, molecular male sterility wherein a transgene inhibits microsporogenesis and/or pollen formation, or self-incompatibility. Female parent plants containing CMS are particularly useful. In embodiments in which the female parent plants are CMS, the male parent plants typically contain a fertility restorer gene to ensure that the $F_1$ hybrids are fertile. In other embodiments in which the female parents are CMS, male parents can be used that do not contain a fertility restorer. $F_1$ hybrids produced from such parents are male sterile. Male sterile hybrid seed can be interplanted with male fertile seed to provide pollen for seed-set on the resulting male sterile plants.

Varieties, lines and cultivars described herein can be used to form single-cross tobacco $F_1$ hybrids. In such embodiments, the plants of the parent varieties can be grown as substantially homogeneous adjoining populations to facilitate natural cross-pollination from the male parent plants to the female parent plants. The $F_2$ seed formed on the female parent plants is selectively harvested by conventional means. One also can grow the two parent plant varieties in bulk and harvest a blend of $F_1$ hybrid seed formed on the female parent and seed formed upon the male parent as the result of self-pollination. Alternatively, three-way crosses can be carried out wherein a single-cross $F_1$ hybrid is used as a female parent and is crossed with a different male parent. As another alternative, double-cross hybrids can be created wherein the $F_1$ progeny of two different single-crosses are themselves crossed. Self-incompatibility can be used to particular advantage to prevent self-pollination of female parents when forming a double-cross hybrid.

The tobacco plants used in the methods described herein can be a Burley type, a dark type, a flue-cured type, a Maryland type, or an Oriental type. The tobacco plants used in the methods described herein typically are from N. tabacum, and can be from any number of N. tabacum varieties. A variety can be BU 64, CC 101, CC 200, CC 13, CC 27, CC 33, CC 35, CC 37, CC 65, CC 67, CC 301, CC 400, CC 500, CC 600, CC 700, CC 800, CC 900, CC 1063, Coker 176, Coker 319, Coker 371 Gold, Coker 48, CU 263, DF911, Galpao tobacco, GL 26H, GL 338, GL 350, GL 395, GL 600, GL 737, GL 939, GL 973, GF 157, GF 318, RJR 901, HB 04P, K 149, K 326, K 346, K 358, K394, K 399, K 730, NC 196, NC 37NF, NC 471, NC 55, NC 92, NC2326, NC 95, NC 925, PVH 1118, PVH 1452, PVH 2110, PVH 2254, PVH 2275, VA 116, VA 119, KDH 959, KT 200, KT204LC, KY 10, KY 14, KY 160, KY 17, KY 171, KY 907, KY907LC, KTY14 x L8 LC, Little Crittenden, McNair 373, McNair 944, msKY 14xL8, Narrow Leaf Madole, NC 100, NC 102, NC 2000, NC 291, NC 297, NC 299, NC 3, NC 4, NC 5, NC 6, NC7, NC 606, NC 71, NC 72, NC 810, NC BH 129, NC 2002, Neal Smith Madole, OXFORD 207, 'Perique' tobacco, PVH03, PVH09, PVH19, PVH50, PVH51, R 610, R 630, R 7-11, R 7-12, RG 17, RG 81, RG H51, RGH 4, RGH 51, RS 1410, Speight 168, Speight 172, Speight 179, Speight 210, Speight 220, Speight 225, Speight 227, Speight 234, Speight G-28, Speight G-70, Speight H-6, Speight H20, Speight NF3, TI 1406, TI 1269, TN 86, TN86LC, TN 90, TN90LC, TN 97, TN97LC, TN D94, TN D950, TR (Tom Rosson) Madole, VA 309, or VA359.

In addition to mutation, another way in which axillary bud growth in tobacco can be reduced is to use inhibitory RNAs (e.g., RNAi). Therefore, transgenic tobacco plants are provided that contain a transgene encoding at least one RNAi molecule, which, when expressed, silences at least one of the endogenous nucleic acids described herein (e.g., SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 57, 59, 61, 63, 65, 69, 71, 73, 75, or 77). As described herein, such transgenic plants exhibit reduced axillary bud growth (e.g., compared to a plant lacking or not expressing the RNAi).

RNAi technology is known in the art and is a very effective form of post-transcriptional gene silencing. RNAi molecules typically contain a nucleotide sequence (e.g., from about 18 nucleotides in length (e.g., about 19 or 20 nucleotides in length) up to about 700 nucleotides in length) that is complementary to the target gene in both the sense and antisense orientations. The sense and antisense strands can be connected by a short "loop" sequence (e.g., about 5 nucleotides in length up to about 800 nucleotides in length) and expressed in a single transcript, or the sense and antisense strands can be delivered to and expressed in the target cells on separate vectors or constructs. A number of companies offer RNAi design and synthesis services (e.g., Life Technologies, Applied Biosystems).

The RNAi molecule can be expressed using a plant expression vector. The RNAi molecule typically is at least 25 nucleotides in length and has at least 91% sequence identity (e.g., at least 95%, 96%, 97%, 98% or 99% sequence identity) to one of the nucleic acid sequences disclosed herein (e.g., SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 57, 59, 61, 63, 65, 69, 71, 73, 75, or 77) or hybridizes under stringent conditions to one of the nucleic acid sequences disclosed herein (e.g., SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 57, 59, 61, 63, 65, 69, 71, 73, 75, or 77). Hybridization under stringent conditions is described above.

Further, certain of the sequences described herein can be overexpressed in plants to reduce axillary bud growth. Accordingly, transgenic tobacco plants are provided that are transformed with a nucleic acid molecule described herein (e.g., SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, or 81) or a functional fragment thereof under control of a promoter that is able to drive expression in plants. As discussed herein, a nucleic acid molecule used in a plant expression vector can have a different sequence than a sequence described herein, which can be expressed as a percent sequence identity (e.g., relative to SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, or 81) or based on the conditions under which the sequence hybridizes to SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, or 81.

As an alternative to using a full-length sequence, a portion of the sequence can be used that encodes a polypeptide fragment having the desired functionality (referred to herein as a "functional fragment"). When used with respect to nucleic acids, it would be appreciated that it is not the nucleic acid fragment that possesses functionality but the encoded polypeptide fragment. Based on the disclosure herein and the alignments shown in FIG. 3, one of skill in the art can predict the portion(s) of a polypeptide (e.g., one or more domains) that may impart the desired functionality.

Promoters that drive expression of a coding sequence in plants are known in the art. Representative promoters include, for example, the CaMV 35S promoter, the actin promoter, the ubiquitin promoter, the phaseolin promoter, a rubisco promoter, the zein promoter, an ACEI system promoter, the In2 promoter, or the H3 histone promoter. In addition, tissue- or developmentally-specific promoter sequences related to axillary bud growth are described herein and can be used to express or overexpress a nucleic acid coding sequence. Representative tissue- or developmentally-specific promoter sequences related to axillary bud growth are shown in SEQ ID NOs: 113, 114, 115, 116, 117, or 118. As described herein, the coding sequence can be any of the nucleic acid coding sequences described herein (e.g., SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, or 81); alternatively, a coding sequence can be derived from a gene that results in programmed cell death (e.g., nucleic acid molecules that encode a ribosome inactivating protein, nucleic acid molecules that encode proteins involved in the hypersensitive response plants initiate when confronted with a pathogen (e.g., a fungus or a bacteria)). Simply by way of example, a tissue- or developmentally-specific promoter sequence related to axillary bud growth as described herein can be used to express or overexpress a coding sequence whose expression is decreased after topping or a coding sequence involved in apoptosis.

Methods of introducing a nucleic acid (e.g., a heterologous nucleic acid) into plant cells are known in the art and include, for example, particle bombardment, Agrobacterium-mediated transformation, microinjection, polyethylene glycol-mediated transformation (e.g., of protoplasts, see, for example, Yoo et al. (2007, Nature Protocols, 2(7):1565-72)), liposome-mediated DNA uptake, or electroporation. Following transformation, the transgenic plant cells can be regenerated into transgenic tobacco plants. As described herein, expression of the transgene results in a plant that exhibits reduced axillary bud growth relative to a plant not expressing the transgene. The regenerated transgenic plants can be screened for axillary bud growth, and plants having reduced axillary bud growth, compared to a corresponding non-transgenic plant, can be selected for use in, for example, a breeding program as discussed herein.

In addition to overexpression or downregulation of axillary bud growth-related coding sequences, axillary bud growth can be controlled using any of the following approaches:

a. altering the expression of axillary bud growth-related regulatory genes that are critical for axillary bud development (as described in Examples 7 and 8);

b. altering meristem development-specific genes using axillary bud-specific promoters;

c. altering the hormonal signaling leading to axillary shoot growth inhibition. This can be accomplished through overexpression or downregulation of hormonal synthesis or transport genes driven by tissue specific or timing specific (e.g., after topping) promoters; and d. initiating cell death mechanisms in axillary buds using axillary bud specific promoters driving cell suicide or toxicity genes.

Nucleic acids that confer traits such as herbicide resistance (sometimes referred to as herbicide tolerance), insect resistance, or stress tolerance, can also be present in the novel tobacco plants described herein. Genes conferring resistance to a herbicide that inhibits the growing point or meristem, such as an imidazolinone or a sulfonylurea, can be suitable. Exemplary genes in this category encode mutant ALS and AHAS enzymes as described, for example, in U.S. Pat. Nos. 5,767,366 and 5,928,937. U.S. Pat. Nos. 4,761,373 and 5,013,659 are directed to plants resistant to various imidazolinone or sulfonamide herbicides. U.S. Pat. No. 4,975,374 relates to plant cells and plants containing a gene encoding a mutant glutamine synthetase (GS), which is resistant to inhibition by herbicides that are known to inhibit GS, e.g. phosphinothricin and methionine sulfoximine. U.S. Pat. No. 5,162,602 discloses plants resistant to inhibition by cyclohexanedione and aryloxyphenoxypropanoic acid herbicides.

Genes for resistance to glyphosate also are suitable. See, for example, U.S. Pat. Nos. 4,940,835 and 4,769,061. Such genes can confer resistance to glyphosate herbicidal compositions, including, without limitation, glyphosate salts such as the trimethylsulphonium salt, the isopropylamine salt, the sodium salt, the potassium salt and the ammonium salt. See, e.g., U.S. Pat. Nos. 6,451,735 and 6,451,732. Genes for resistance to phosphono compounds such as glufosinate ammonium or phosphinothricin, and pyridinoxy or phenoxy propionic acids and cyclohexones also are suitable. See, e.g., U.S. Pat. Nos. 5,879,903; 5,276,268; and 5,561,236; and European Application No. 0 242 246.

Other suitable herbicides include those that inhibit photosynthesis, such as a triazine and a benzonitrile (nitrilase). See U.S. Pat. No. 4,810,648. Other suitable herbicides include 2,2-dichloropropionic acid, sethoxydim, haloxyfop, imidazolinone herbicides, sulfonylurea herbicides, triazolopyrimidine herbicides, s-triazine herbicides and bromoxynil. Also suitable are herbicides that confer resistance to a protox enzyme. See, e.g., U.S. Pat. No. 6,084,155 and US 20010016956.

A number of genes are available that confer resistance to insects, for example, insects in the order *Lepidoptera*. Exemplary genes include those that encode truncated Cry1A (b) and Cry1A(c) toxins. See, e.g., genes described in U.S. Pat. Nos. 5,545,565; 6,166,302; and 5,164,180. See also, Vaeck et al., 1997, *Nature,* 328:33-37 and Fischhoff et al., 1987, *Nature Biotechnology,* 5:807-813. Particularly useful are genes encoding toxins that exhibit insecticidal activity against *Manduca sexta* (tobacco hornworm); *Heliothis virescens* Fabricius (tobacco budworm) and/or *S. litura* Fabricius (tobacco cutworm).

Tobacco Products and Methods of Making

Leaf from tobacco plants having reduced axillary bud growth can be cured, aged, conditioned, and/or fermented. Methods of curing tobacco are well known and include, for example, air curing, fire curing, flue curing and sun curing. Aging also is known and typically is carried out in a wooden drum (e.g., a hogshead) or cardboard cartons in compressed conditions for several years (e.g., 2 to 5 years), at a moisture content of from about 10% to about 25% (see, for example, U.S. Pat. Nos. 4,516,590 and 5,372,149). Conditioning includes, for example, a heating, sweating or pasteurization step as described in US 2004/0118422 or US 2005/0178398, while fermenting typically is characterized by high initial moisture content, heat generation, and a 10 to 20% loss of dry weight. See, e.g., U.S. Pat. Nos. 4,528,993, 4,660,577, 4,848,373 and 5,372,149. The tobacco also can be further processed (e.g., cut, expanded, blended, milled or comminuted), if desired, and used in a tobacco product.

Tobacco products are known in the art and include products made or derived from tobacco that are intended for human consumption, including any component, part, or accessory of a tobacco product. Representative tobacco products include, without limitation, smokeless tobacco products, tobacco-derived nicotine products, cigarillos, non-ventilated recess filter cigarettes, vented recess filter cigarettes, cigars, snuff, pipe tobacco, cigar tobacco, cigarette tobacco, chewing tobacco, leaf tobacco, shredded tobacco, and cut tobacco. Representative smokeless tobacco products include, for example, chewing tobacco, snuff, long-cut moist smokeless tobacco, snus, pouches, films, tablets, coated dowels, rods, and the like. Representative cigarettes and other smoking articles include, for example, smoking articles that include filter elements or rod elements, where the rod element of a smokeable material can include cured tobacco within a tobacco blend. In addition to the tobacco described herein, tobacco products also can include other ingredients such as, without limitation, binders, plasticizers, stabilizers, and/or flavorings. See, for example, US 2005/0244521; US 2006/0191548; US 2012/0024301; US 2012/0031414; and US 2012/0031416 for examples of tobacco products.

The invention will be further described in the following examples, which do not limit the scope of the methods and compositions of matter described in the claims.

EXAMPLES

Example 1—Sampling, RNA Preparation and Sequencing

Tobacco seeds from TN90, a Burley variety, were germinated. After 4 weeks, seedlings were transferred onto 4 inch pots. At layby stage (8-10 fully expanded leaves), a total of 10 different samples including axillary buds before topping (Aa), axillary buds after topping (Ab, Ac, Ad and Ae (2 h, 6 h, 24 h and 72 h, respectively), roots before topping (Ra), roots after topping (Rb, Rc (24 h and 72 h)), young leaf at the time of topping (YL), and shoot apical meristem (ST) were collected for next generation sequencing analysis. Each of the time points were represented by three independently collected samples. These three samples served as biological replicates.

RNA from the samples described above was isolated using RNeasy Plant Mini Kit (Qiagen, Mass.) and quality was tested using Agilent Plant RNA Nano Kit and a 2100 Bioanalyzer (Agilent Technologies, CA). Thirty cDNA libraries were constructed, with indexing using a TrueSeq RNA Library Prep Kit v.2 (Illumina). cDNA libraries made from the same biological replicates were pooled together, and each pooled replicate was analyzed on an Illumina HiSeq 2000, 100 bp single reads with a minimum of 30 million reads per sample. Two samples were tagged per lane for a total of 15 sequencing lanes. Axillary bud specific gene expression in TN90 tobacco was determined by RNA deep sequencing performed by ArrayXpress (Raleigh, N.C.).

Example 2—RNA Sequence Analysis

Gene expression data from five axillary buds, 3 roots, and one each of young leaf and shoot apical meristem samples were analyzed to identify axillary bud development-related genes compared to other tissues. Gene reads were mapped to our in-house tobaccopedia genome database (Table 1). EdgeR in CLC genomic workbench was used to perform differential gene expression. Gene expression data was filtered for axillary bud specific expression from other tissues. FDR adjustment was performed on all p-values and a cut-off of an FDR corrected p-value<0.05 was used. Results were then filtered for high axillary bud expression. The list of differentially expressed candidate genes for sucker control are listed in Table 2.

TABLE 1

Mapping of Next Generation Sequencing Reads Using In-House Tobaccopedia Database

| Samples | Reads Mapped | % mapped | Samples | Reads Mapped | % mapped |
|---------|--------------|----------|---------|--------------|----------|
| Aa1 | 23,920,938 | 92.03 | Ra1 | 39,732,686 | 92.02 |
| Aa2 | 49,392,444 | 91.21 | Ra2 | 40,262,611 | 91.16 |
| Aa3 | 28,288,803 | 86.23 | Ra3 | 33,248,092 | 92.13 |
| Ab1 | 24,848,558 | 92.2 | Rb1 | 35,937,062 | 93.06 |
| Ab2 | 35,727,478 | 92.23 | Rb2 | 40,036,265 | 92.43 |
| Ab3 | 34,000,094 | 92.25 | Rb3 | 46,268,788 | 92.34 |
| Ac1 | 45,951,075 | 92.04 | Rc1 | 35,595,122 | 92.84 |
| Ac2 | 48,242,863 | 92.15 | Rc2 | 37,925,157 | 92.25 |
| Ac3 | 41,733,418 | 91.67 | Rc3 | 34,832,062 | 92.18 |
| Ad1 | 33,474,960 | 92.08 | ST1 | 48,115,555 | 92.45 |
| Ad2 | 31,891,377 | 92.35 | ST2 | 41,373,361 | 92.41 |
| Ad3 | 40,791,919 | 92.23 | ST3 | 31,760,672 | 91.85 |
| Ae1 | 28,758,337 | 92.04 | YL1 | 41,811,850 | 92.63 |
| Ae2 | 38,369,793 | 92.26 | YL2 | 51,356,432 | 91.82 |
| Ae3 | 40,552,134 | 92.45 | YL3 | 40,252,190 | 91.95 |

TABLE 2

Differential gene expression of selected candidate genes

| Contig Number | Axillary Buds Before Topping (AB0) | Axillary Buds After Topping | | | | Roots Before Topping (RT0) | Roots After Topping | | Shoot Apical Meristem | Young Leaf |
|---|---|---|---|---|---|---|---|---|---|---|
| | | 2 hr (AB2) | 6 hr (AB6) | 24 hr (AB24) | 72 hr (AB72) | | 24 hr (RT24) | 72 hr (RT72) | | |
| C5787   | 1,072 | 998   | 1,346 | 663    | 652    | 7     | 9   | 11  | 180   | 47  |
| C16249  | 1,387 | 927   | 3,527 | 44,790 | 23,270 | 108   | 90  | 128 | 8,913 | 72  |
| C3898   | 763   | 1,132 | 1,852 | 5,559  | 2,644  | 110   | 156 | 80  | 513   | 7   |
| C2231   | 115   | 532   | 446   | 252    | 496    | 27    | 7   | 11  | 23    | 14  |
| C49345  | 2,342 | 2,357 | 2,992 | 3,143  | 2,190  | 38    | 28  | 27  | 26    | 103 |
| C64393  | 47    | 29    | 54    | 18     | 17     | 1     | 0   | 0   | 23    | 1   |
| C26207  | 128   | 131   | 187   | 69     | 54     | 0     | 1   | 1   | 13    | 0   |
| C83090  | 124   | 308   | 1,619 | 337    | 136    | 217   | 143 | 160 | 88    | 234 |
| C29909  | 3     | 162   | 186   | 9      | 9      | 22    | 22  | 29  | 6     | 2   |
| C82570  | 41    | 98    | 334   | 136    | 101    | 1     | 0   | 0   | 50    | 0   |
| C12866  | 1,479 | 1,486 | 4,216 | 16,176 | 12,228 | 46    | 36  | 33  | 2,144 | 839 |
| C34805  | 52    | 27    | 81    | 13     | 9      | 2     | 1   | 3   | 5     | 1   |
| C47069  | 152   | 114   | 135   | 46     | 45     | 2     | 2   | 2   | 1     | 0   |
| C73141  | 60    | 34    | 22    | 17     | 13     | 2     | 4   | 1   | 30    | 1   |
| C41568  | 176   | 131   | 385   | 48     | 43     | 14    | 12  | 15  | 19    | 10  |
| C50303  | 624   | 583   | 1,279 | 300    | 215    | 14    | 9   | 18  | 71    | 9   |
| C58496  | 176   | 121   | 253   | 95     | 70     | 7     | 1   | 1   | 69    | 27  |
| C68375  | 268   | 279   | 410   | 231    | 207    | 1     | 1   | 1   | 22    | 11  |
| C55919  | 193   | 241   | 366   | 117    | 123    | 2     | 2   | 2   | 13    | 1   |
| C40016  | 394   | 353   | 505   | 207    | 204    | 2     | 2   | 1   | 34    | 2   |
| C145337 | 2,110 | 2,953 | 8,542 | 1,362  | 2,095  | 337   | 181 | 337 | 305   | 131 |
| C348    | 1,022 | 1,253 | 2,580 | 715    | 762    | 79    | 53  | 59  | 164   | 13  |
| C131180 | 1,517 | 2,212 | 5,081 | 2,402  | 1,059  | 1,109 | 488 | 332 | 558   | 351 |
| C22266  | 222   | 265   | 479   | 290    | 187    | 2     | 3   | 1   | 20    | 3   |
| C53803  | 1,796 | 1,308 | 3,662 | 777    | 968    | 23    | 21  | 22  | 475   | 11  |
| C21860  | 104   | 75    | 68    | 107    | 46     | 0     | 1   | 0   | 3     | 0   |
| C11320  | 486   | 309   | 1,297 | 291    | 395    | 146   | 56  | 42  | 84    | 8   |
| C1838   | 364   | 175   | 126   | 152    | 97     | 1     | 0   | 0   | 36    | 14  |

Example 3—Confirmation of Selected Candidate Gene Expression

To confirm the expression pattern of selected candidate genes, the relative changes in transcripts from 10-16 different tissue samples (6 axillary bud samples (before topping and 2 hr, 6 hr, 12 hr, 24 hr and 72 hr after topping), young leaf 24 hr after topping, mature leaf, senescence leaf, midrib, stalk before topping, stalk 24 hr after topping, shoot apical meristem, root before topping and 24 hr after topping) were measured. In brief, total RNA was isolated using TRI Reagent (Sigma-Aldritch, St. Louis, Mo.). To remove DNA impurities, purified RNA was treated with RNase-free DNase (Turbo DNA-free, Ambion, Austin, Tex.). To synthesize the first cDNA strand, approximately 10 µg of total RNA was transcribed utilizing the High Capacity cDNA Kit (Applied Biosystems, Foster City, Calif.). To measure the level of selected gene transcripts in the samples, RT-PCR was performed using SYBR Green PCR Master Mix (Applied Biosystems, Foster City, Calif.) and the gene specific primers listed in Table 3. Real time gene expression verification of representative candidate genes are listed in FIGS. 1A-1G.

TABLE 3

Real time PCR Primers used for the confirmation of gene expression

| Primer Name | Forward primer | SEQ ID NO | Reverse primer | SEQ ID NO | Amplicon size |
|---|---|---|---|---|---|
| SCRT1 | TTTTCGAGGCTCCTTTAGCA       | 123 | CATGTTGGGGTTCGATAAGG      | 124 | 250 |
| SCRT2 | CCTTTTTTACTCATTCAGAGAAACGA | 125 | GTGTGACACTGAATTAATCCTTTCC | 126 | 380 |
| SCRT3 | AGGCTTGCTGAAGCAAAAGA       | 127 | TCGGCGAAATTACAGTCTCA      | 128 | 211 |
| SCRT4 | TTGTGTCATGGTGCAATCAA       | 129 | TCCAACTTAGGCCTCACACC      | 130 | 199 |
| SCRT5 | TTGCAATGCTTCTGTTTTCG       | 131 | ATATTGGCCGCATCTTGGT       | 132 | 193 |
| SCRT6 | TTCTCTTCCCGAGAAACAGTG      | 133 | CGGAGTTGGAGATGAAGATGA     | 134 | 217 |
| SCRT7 | CCTGTGGCAAAGGAATCAAG       | 135 | TGCGTGGTGTGTTCTTCAAT      | 136 | 200 |
| SCRT8 | GGGTGCTTTGAAGTCCCTTT       | 137 | GAATCCTGCTCCAAACAAGC      | 138 | 211 |
| SCRT9 | TGGGCAGCAGAAATAAGAGA       | 139 | GCTGATCTTGTTGTGGCTTG      | 140 | 200 |

TABLE 3-continued

Real time PCR Primers used for the confirmation of gene expression

| Primer Name | Forward primer | SEQ ID NO | Reverse primer | SEQ ID NO | Amplicon size |
|---|---|---|---|---|---|
| SCRT10 | CACCATAAGCACAGGTGCAA | 141 | TCCGCCTTGCTTTATGAAAA | 142 | 205 |
| SCRT11 | TCCTCTTTGCCATTTCTCTCA | 143 | GGCCAGAAAAAGAATGACCA | 144 | 201 |
| SCRT12 | GGGTCCCTCTAAATCCCAAG | 145 | cCGGAAGTCAAGAATCCAGT | 146 | 201 |
| SCRT13 | TGGACATGAGGCATTTGCTA | 147 | GCATCGCGAGATCAAGAGTT | 148 | 183 |
| SCRT14 | AAGCCCGCCTTTCTACCTTA | 149 | TCTTGATCATCGAACGAATCAC | 150 | 196 |
| SCRT15 | CCAATTCCCTCTTCCTTCCT | 151 | ATCCATCCAAGTCAGCCTTC | 152 | 203 |
| SCRT16 | TGGTTGAGGCCCCAATATAC | 153 | CCCCGCTATCGACTTGATTA | 154 | 198 |
| SCRT17 | CGGAAGAGCCTGTGGTATGA | 155 | TGAAATCAGATTCAGGCATCA | 156 | 203 |
| SCRT18 | AGATCAGGAAGCGCGTAAGA | 157 | CAGAGTTTTGCTGGCCTTCT | 158 | 193 |
| SCRT19 | GTGGCAAAGGAATCAAGGAA | 159 | ATGGGTTCCAGTTGCCAGTA | 160 | 283 |
| SCRT20 | CGGTCCTTTAGCAGTTTCCA | 161 | CATGTTGGGGTTCGATAAGG | 162 | 250 |
| SCRT21 | ATCTGGAGTATTTCTTCTACCT | 163 | CTTAAACTCTCTGCCGAATAAA | 164 | 111 |
| SCRT22 | TCCTTCTTTCTGTCTGTTTCTCTT | 165 | GTCCTCACTGCTGTCTTTCTC | 166 | 110 |
| SCRT23 | GCACTTCTGGTGGTGAAAGA | 167 | GTCATTCTCAGTTATGTTACGGAAAG | 168 | 102 |
| SCRT24 | AGCTGCTCCATAACCGAAAT | 169 | CGACCCTGAATTTCCTCAGTT | 170 | 108 |
| SCRT25 | GGATGTAAGGCATTGGACATAGA | 171 | GAGTTCCCTATCAACCGAAACA | 172 | 96 |
| SCRT26 | GGCGAGTCATTAACCTCCTATTT | 173 | GTCTTAGCGTCCAAGTGCTAAT | 174 | 117 |
| SCRT27 | GCTGAAGAACCTTTGCCTTTAC | 175 | GCCGATTTCTCAACACAAAGAA | 176 | 106 |

Example 4—Full Length Candidate Genes Cloning, Analysis and Selected Real Time PCR for Verification The candidate genes predicted to be involved in axillary bud initiation and growth were identified and annotated (Table 4), and RNAs from axillary bud tissues of TN90 plants, from before topping, and 12 hr, 24 hr and 48 hr after topping, were collected. cDNA libraries were created from the RNAs using the In-Fusion SMARTER Directional cDNA Library Construction Kit from Clontech (Cat #634933). Full length candidate genes were cloned using the gene specific primers designed from predicted full-length cDNA sequences. The full length coding sequences were confirmed by sequencing and are shown in SEQ ID NOs:1, 3, 5, 7, 9, 11, 13, 15, 17, 19, 21, 23, 25, 27, 29, 31, 33, 35, 37, 57, 59, or 69. The predicted protein sequences are shown in SEQ ID NOs:2, 4, 6, 8, 10, 12, 14, 16, 18, 20, 22, 24, 26, 28, 30, 32, 34, 36, 38, 58, 60, or 70.

TABLE 4

Selected Candidate Genes

| Contig Number | Coding Sequence | Nucleotide (bp) | Protein (aa) | SEQ ID NO (DNA/protein) |
|---|---|---|---|---|
| C5787 | Full length confirmed | 987 | 328 | 1/2 |
| C16249 | Full length confirmed | 318 | 105 | 3/4 |
| C3898 | Full length confirmed | 1797 | 598 | 5/6 |
| C7651 | Full length confirmed | 1392 | 463 | 7/8 |
| C49345 | Full length confirmed | 405 | 134 | 9/10 |
| C64393 | Full length confirmed | 630 | 209 | 11/12 |
| C26207 | Full length confirmed | 1143 | 380 | 13/14 |
| C83090 | Full length confirmed | 915 | 304 | 15/16 |
| C29909 | Full length confirmed | 1353 | 450 | 17/18 |
| C82570 | Full length confirmed | 732 | 243 | 19/20 |
| C12866 | Pseudo gene | — | — | — |
| C34805 | Full length confirmed | 471 | 156 | 21/22 |
| C47069 | Full length confirmed | 1437 | 478 | 23/24 |
| C73141 | Full length confirmed | 645 | 214 | 25/26 |
| C41568 | Full length confirmed | 2205 | 734 | 27/28 |
| C50303 | Full length confirmed | 1302 | 433 | 29/30 |
| C58496 | Full length confirmed | 1266 | 421 | 31/32 |
| C68375 | Full length confirmed | 597 | 198 | 33/34 |
| C55919 | Full length confirmed | 1038 | 345 | 35/36 |
| C40016 | Full length confirmed | 1014 | 337 | 37/38 |
| G47965 | Full length confirmed | 1659 | 553 | 57/58 |
| G88345 | Full length confirmed | 1632 | 544 | 59/60 |
| S10610 | Full length confirmed | 396 | 132 | 69/70 |

From RNA sequence analysis and RT-PCR confirmation, candidate putative full length gene sequences were selected for RNAi and full length *Agrobacterium transformation* analysis. The candidate sequences are listed in Table 5 and are shown in SEQ ID NOs:39, 41, 43, 45, 47, 49, 51, 53, 61, 63, 65, 71, 73, 75, or 77. The predicted protein sequences are shown in SEQ ID NOs:40, 42, 44, 46, 48, 50, 52, 54, 62, 64, 66, 72, 74, 76, or 78.

Figure 3A:
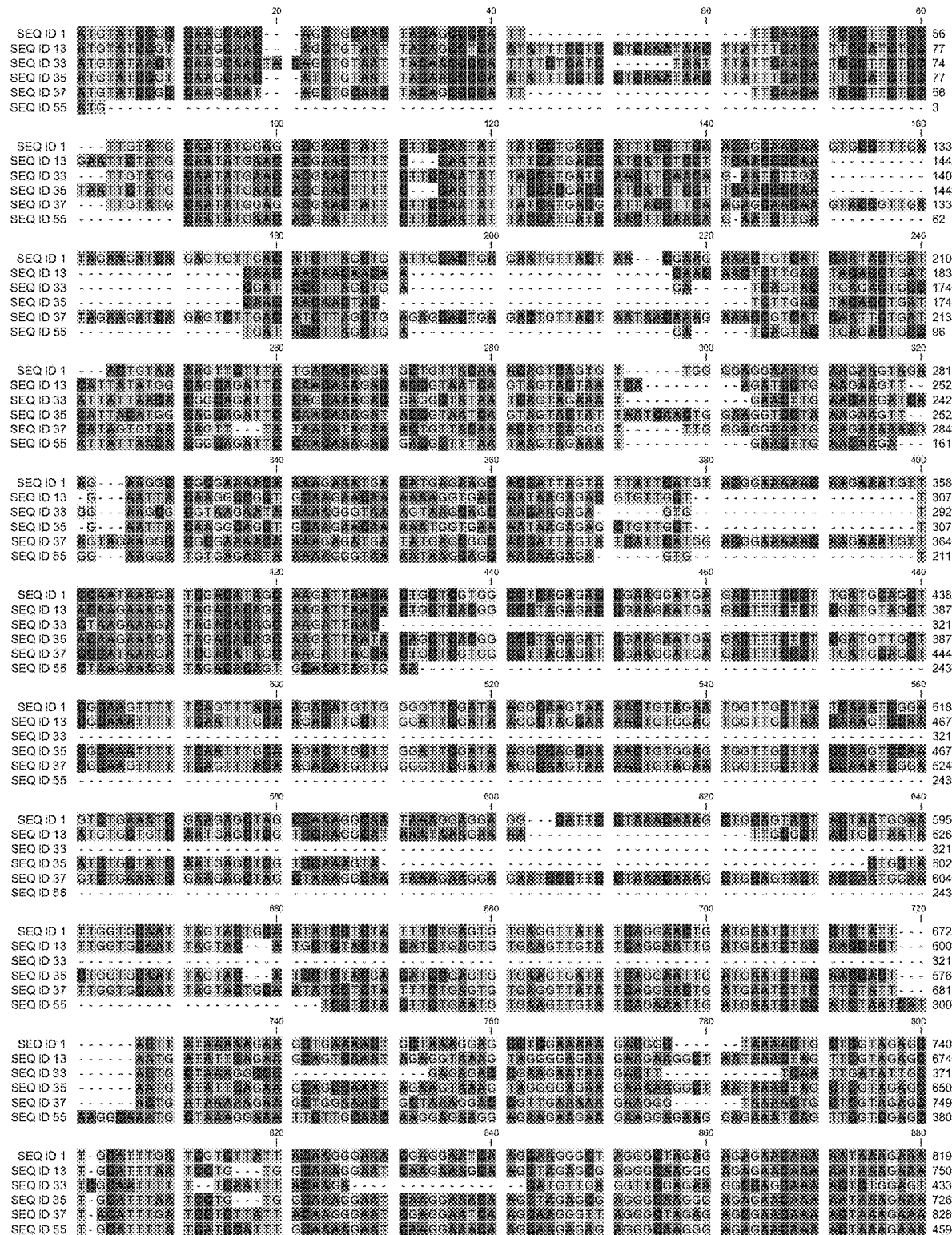
FIG. 3A shows various nucleic acid alignments (SEQ ID NOs: 1, 13, 33, 35, 37, and 55, top to bottom).
Figure 3A:
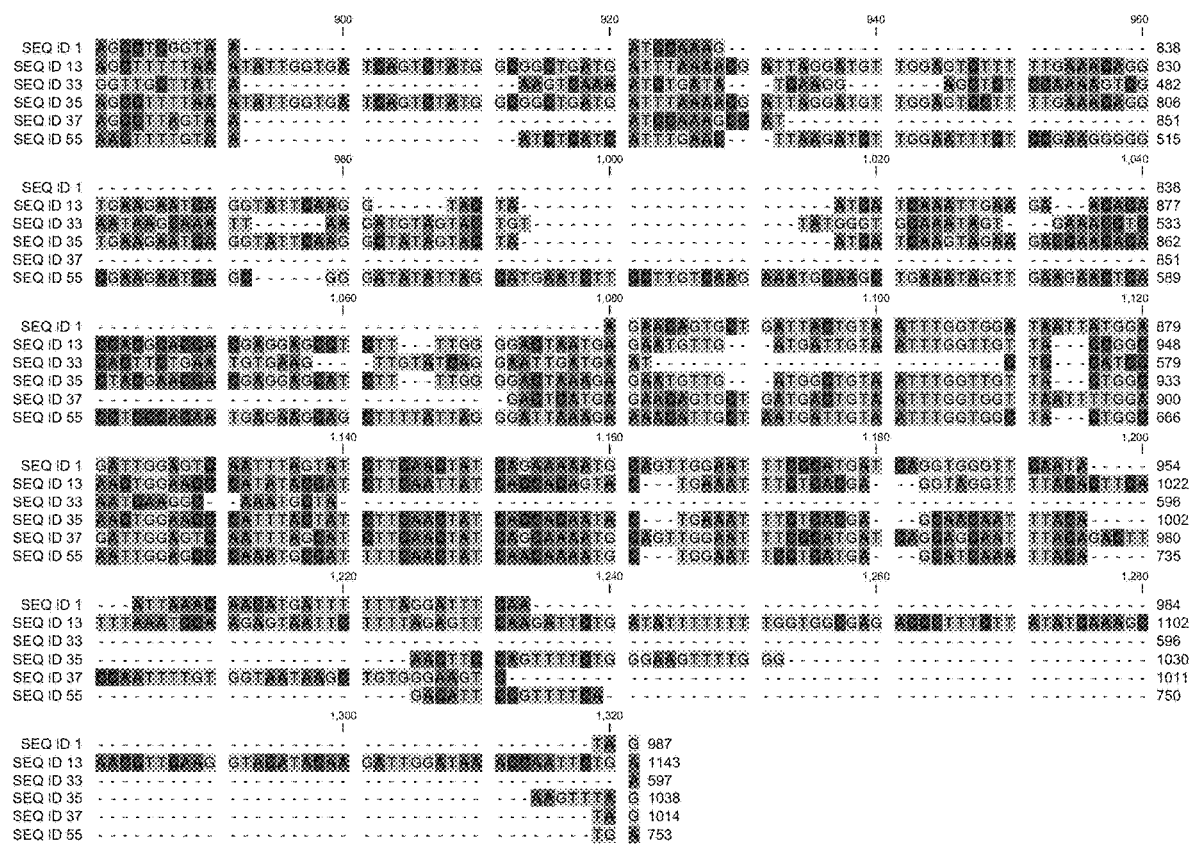
Figure 3B:
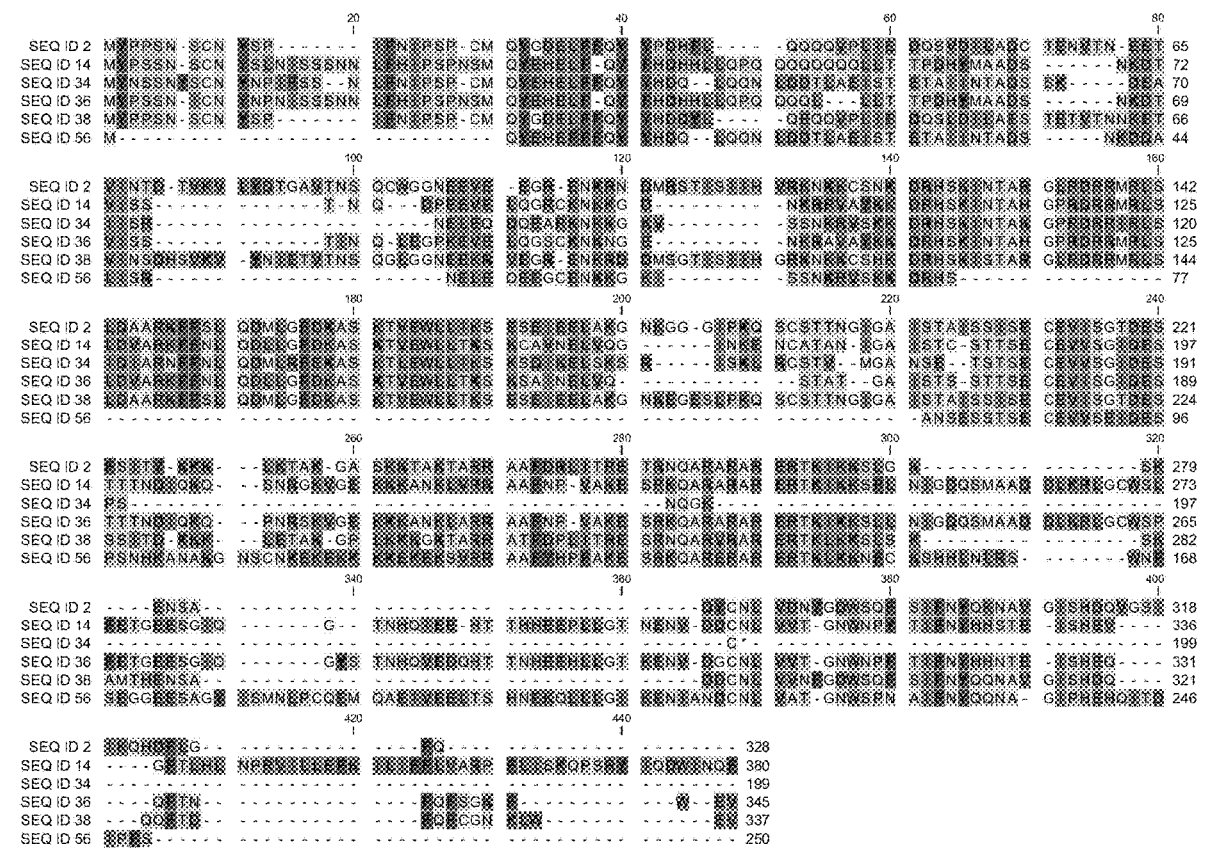

Six of the candidate genes are members of a transcription factor gene family based on the presence of a conserved domain (TCP domain). The nucleotide and protein sequence alignments are shown in FIG. 3. Members of this family are implicated in plant growth and development regulation. The conserved domain is thought to be responsible for DNA binding to cis-elements in promoters in order to regulate downstream genes.

TABLE 5

Selected candidate putative gene sequences

| Contig Number | Coding Sequence | Nucleotide (bp) | Protein (aa) | SEQ ID NO (DNA/protein) |
|---|---|---|---|---|
| C145337 | Predicted | 867 | 288 | 39/40 |
| C348 | Predicted | 2562 | 853 | 41/42 |
| C131180 | Predicted | 2790 | 929 | 43/44 |
| C22266 | Predicted | 2478 | 825 | 45/46 |
| C21860 | Confirmed | 1152 | 383 | 47/48 |
| C75660 | Predicted | 813 | 270 | 49/50 |
| C11320 | Predicted | 762 | 253 | 51/52 |
| C1838 | Predicted | 753 | 250 | 53/54 |
| G120126 | Predicted | 960 | 320 | 61/62 |
| G151887 | Predicted | 930 | 310 | 63/64 |
| G135280 | Predicted | 822 | 274 | 65/66 |
| G56830 | Predicted | 1158 | 386 | 71/72 |
| S4261 | Predicted | 1224 | 408 | 73/74 |
| S950 | Predicted | 1014 | 338 | 75/76 |
| S1904 | Predicted | 1011 | 337 | 77/78 |

Figure 2:
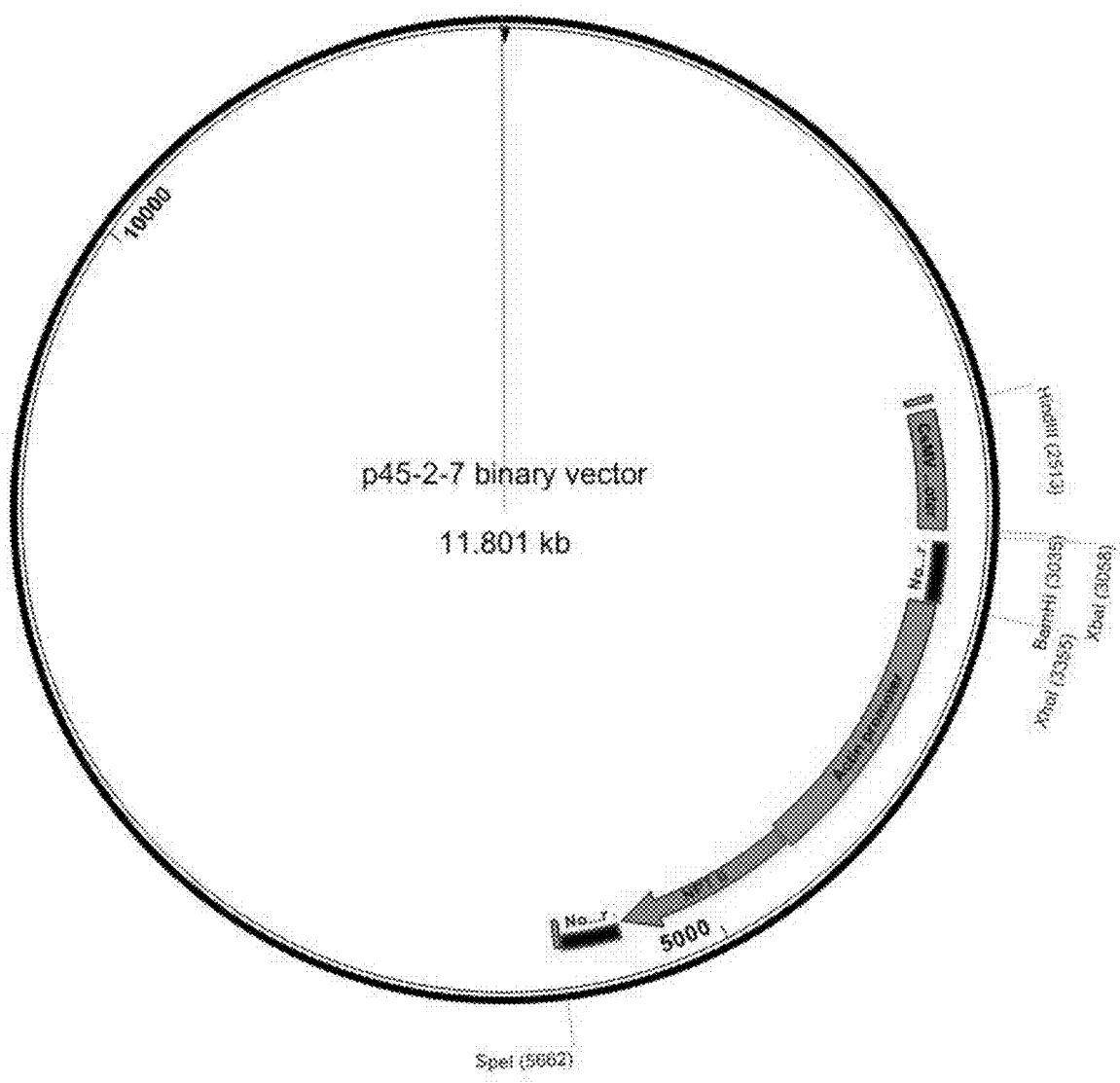
FIG. 2 is a schematic of the map of the Agrobacterium transformation vector, p45-2-7.

Example 5—Development of Transgenic Plants Containing RNAi or Over-Expression Constructs and Efficacy Testing To investigate the function of the candidate genes, three sets of transgenic plants were generated; a first using the full length coding sequence from tobacco (Table 4, SEQ ID NO:1, 3, 5, 7, 9, 11, 13, 15, 17, 19, 21, 23, 25, 27, 29, 31, 33, 35, 37, 39, 41, 43, 45, 47, 49, 51, 53, 57, 59, or 69), a second using non-tobacco origin full length genes (Table 4, SEQ ID NOs: 55, 67, 79, or 81); and a third using a RNAi sequence (SEQ ID NO: 83, 84, 85, 86, 87, 88, 89, 90, 91, 92, 93, 94, 95, 96, 97, 98, 99, 100, or 101). An expression vector, p45-2-7 (SEQ ID NO:112; FIG. 2), was used, which has a CsVMV promoter and a NOS terminator, as well as a cassette having a kanamycin selection marker (NPT II) under direction of the actin2 promoter and a NOS terminator. The nucleic acid constructs carrying the transgenes of interest were introduced into tobacco leaf discs using an *Agrobacterium* transformation approach. See, for example, Mayo et al., 2006, Nat Protoc., 1(3):1105-11 and Horsch et al., 1985, Science 227:1229-1231.

Briefly, tobacco plants (Narrow Leaf Madole (NLM)) were grown from magenta boxes, and leaf disks were cut into 15×150 mm plates. *Agrobacterium tumefaciens* containing the target plasmid were collected by centrifugation of 20 ml cell suspension in 50 ml centrifuge tube at 3500 rpm for 10 minutes. Supernatant was removed and *Agrobacterium* cell pellet was resuspended in 40 ml liquid resuspension medium. About 25 ml of the solution was transferred to each 15×100 mm Petri plates. In those 15×150 mm plates, tobacco leaves, avoiding the midrib, were cut into 0.6 cm disk. Leaf disks were placed upside down, a thin layer of MS/B5 liquid resuspension medium was added, and slices were made with a #15 razor blade. The leaf discs were poked uniformly with a fine point needle. Eight disks were placed, upside down, in each regeneration plate (15×100 mm). *Agrobacterium tumefaciens* suspension was added and the leaf discs were incubated for 10 minutes.

Leaf disks were transferred to co-cultivation plates (½ MS medium) and disks were placed upside down in contact with filter paper overlaid on the co-cultivation TOM medium (MS medium with 20 g sucrose/L; 1 mg/L IAA and 2.5 mg/L BAP). The plate was sealed with parafilm and labeled appropriately. Plates were incubated in dim light (60-80 mE/ms) and 18/6 photoperiods at 24° C. for three days. Leaf disks were transferred to regeneration/selection TOM K medium plates (TOM medium with 300 mg/l Kanamycin) and subculture bi-weekly to the same fresh medium in dim light at 24° C. until shoots become excisable. Shoots from leaves were removed with forceps and inserted in MS basal medium with 100 mg/L kanamycin at 24° C. and 18/6 photoperiods with light intensity of 6080 mE/ms for rooting.

When plantlets with both shoots and roots grew large enough (e.g., reach over half of a GA7 box), they were transferred to soil for acclimatization. During the transfer, the gel was washed from the root tissue with tap water. Established seedlings were transferred to the greenhouse for further analysis and to set seed.

Efficacy testing for sucker growth phenotypes were conducted by growing plants to laybe stage. These plants were topped and axillary bud growth was observed at specific time points after topping.

Figure 4A:
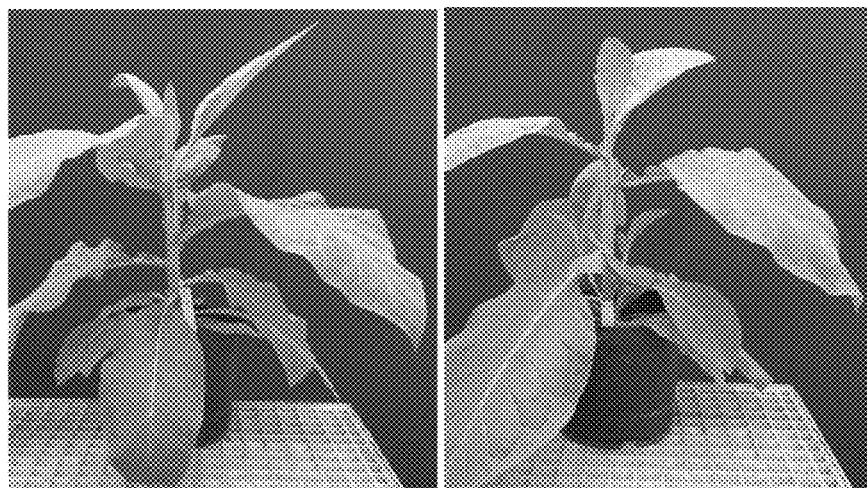
FIG. 4A are photographs of a wild type tobacco plant (left) and a tobacco plant transformed with RNA construct #1 (SEQ ID NO:29; right) before topping.
Figure 4B:
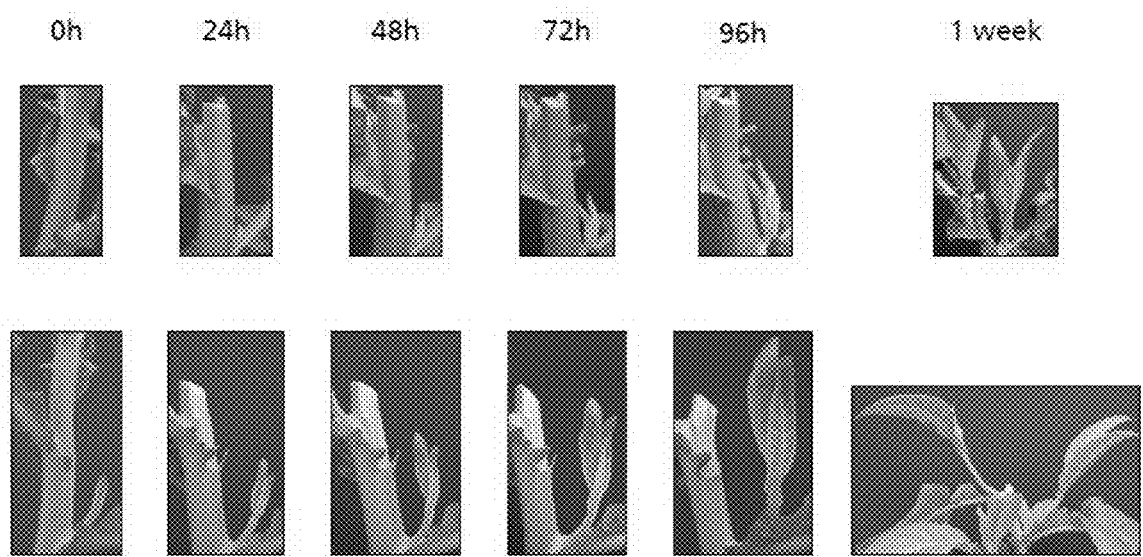
FIG. 4B are photographs of the wild type plant (top) and the plant transformed with RNA construct #1 (bottom) at the indicated time after topping.
Figure 4C:
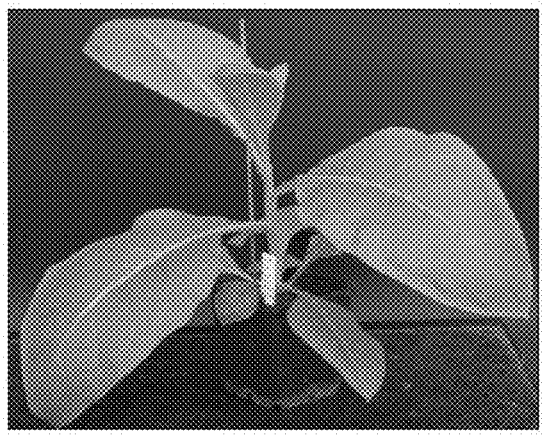
FIG. 4C are photographs showing the T1 generation produced from the wild-type plant (left) and the plant transformed with RNA construct #1 (right).
Figure 4C:
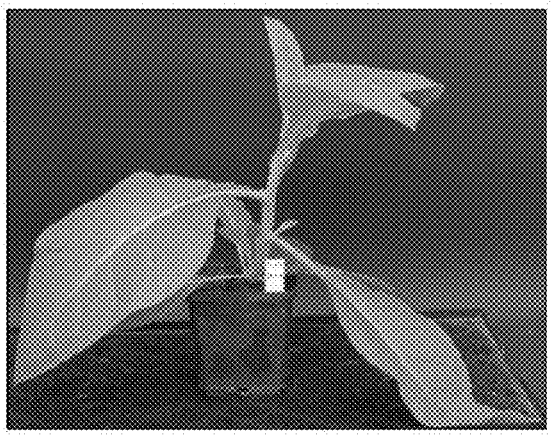

FIG. 4A show a wild type plant (left) and a plant transformed with RNA construct #1 (SEQ ID NO:55; right) before topping, and FIG. 4B show the wild type plant (top) and the plant transformed with RNA construct #1 (bottom) at the indicated times after topping. FIG. 4C shows the T1 generation of wild type plants (left) and plants transformed with RNA construct #1 (right). The growth of the axillary buds after topping was increased substantially in the transgenic plants relative to the wild type plants. Initiation of axillary bud growth in the transgenic plants was already beginning even before the plant was topped, and the rate of growth was increased for up to 1 week after topping. These results demonstrated that the expression of RNA construct #1 is likely responsible for bud dormancy, and down-regulation of the gene is a factor in sucker initiation and growth.

The sequence of the expression cassette is shown in SEQ ID NO:111, with the relevant portions indicated to the left.

Example 6—Promoter Cloning, Transformation and Analysis

The expression pattern of the 41 candidate genes were analyzed, promoters of the genes with high level expression in axillary bud, but low expression levels in other tissues, were selected (Table 6). Expression pattern of these clones were confirmed by real-time PCR analysis (FIG. 1). Six axillary meristem-specific promoters were cloned by PCR methods from TN90 genomic DNA using gene-specific primers. The sequences of the promoters are shown in SEQ ID NO:113-118.

Expressions of candidate promoters were analyzed by transformation of tobacco with a chimeric candidate promoter::beta-glucuronidase (GUS) reporter gene with the same cassette described in Example 5. The chimeric gene was introduced via *Agrobacterium*-mediated transformation into a NLM line. Gus staining was used to locate promoter expression following the method of Crone et al., 2001, *Plant*

Cell Environ., 24:869-874. Transgenic tobacco tissue was placed in cold 90% Acetone on ice. When all samples were harvested, samples were placed at room temperature for 20 minutes. Acetone was removed from the samples, and staining buffer (0.2% Triton X-100; 50 mM NaHPO4 Buffer, pH7.2; 2 mM Potassium Ferrocyanide) was added to samples, all the while keeping the samples on ice. X-Gluc was added to the staining buffer to a final concentration of 2 mM—from a 100 mM stock solution of X-Gluc in DMF, which must be kept in the dark at −20° C. Staining buffer was removed from samples and fresh staining buffer with X-Gluc was added. The samples were infiltrated under vacuum, on ice, for 15 to 20 minutes. The samples were incubated at 37° C. from 2 hours to overnight. The samples were removed from the incubator and the staining buffer was removed. Samples were washed through an ethanol series (i.e., from 10%, 30%, 50%, 70%; the sample can be heated to 60° C. to get rid of chloroplasts, if desired), to 95%, avoiding light, for 30 min each step. Finally, samples were kept in 100% ethanol.

Figure 5A:
FIG. 5A shows GUS staining of expression from an axillary meristem-specific promoter P1 (the promoter from the sequence shown in SEQ ID NO:31) and promoter P7 (SEQ ID NO:32).
Figure 5A:
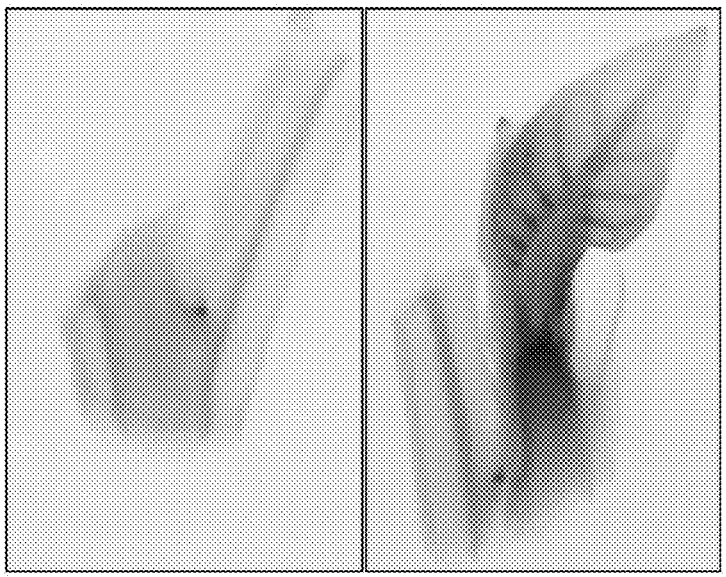
Figure 5B:
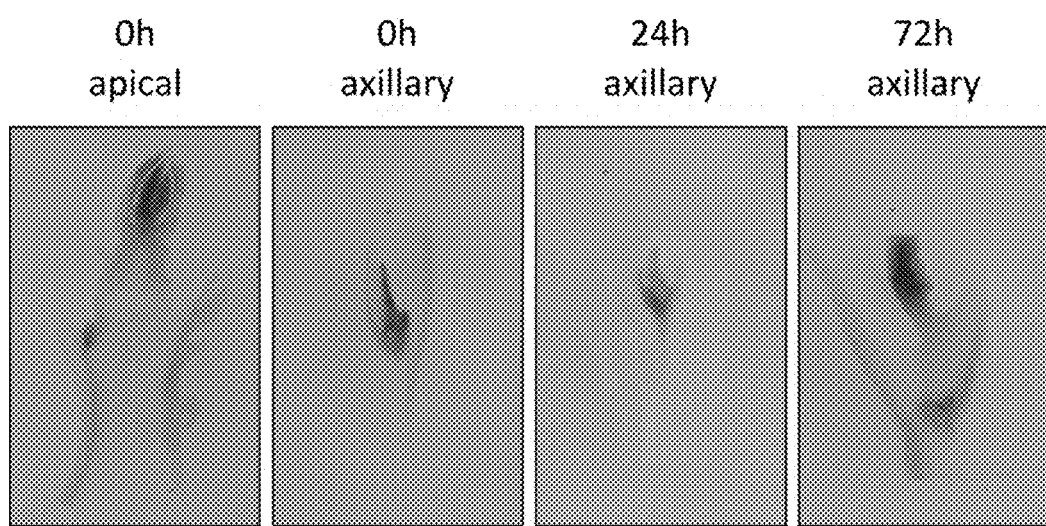
FIG. 5B shows GUS staining of expression from promoter P1 (P1:GUS expression vector) before topping (0 hour) and after topping (24 hr, 48 hr and 144 hr).
Figure 6A:
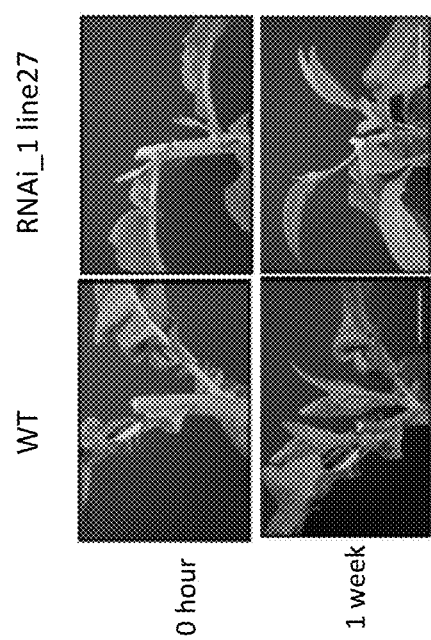
FIG. 6A are photographs that show the phenotype of the T0 generation for a transgenic line (RNAi_1 (SEQ ID NO:83 against the BRANCH tobacco homolog); right) in comparison to a wild type plant (left) at 0 h (top) and 1 week after topping (bottom).
Figure 6B:
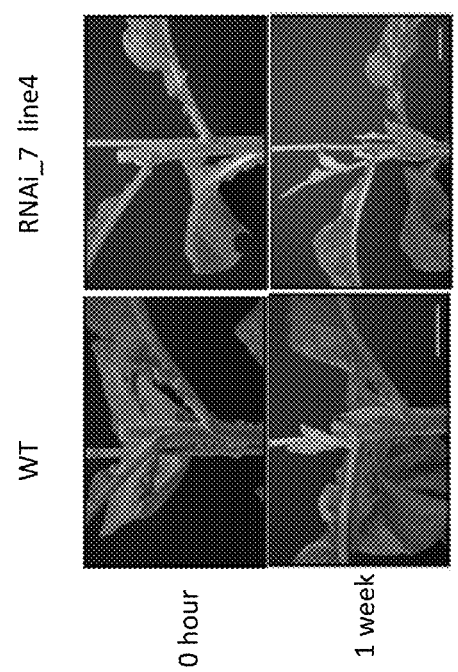
FIG. 6B are photographs that show the phenotype of the T0 generation for a transgenic line (RNAi_7 (SEQ ID NO:86 against the BRANCH tobacco homolog); right) in comparison to a wild type plant (left) at 0 h (top) and 1 week after topping (bottom).
Figure 6C:
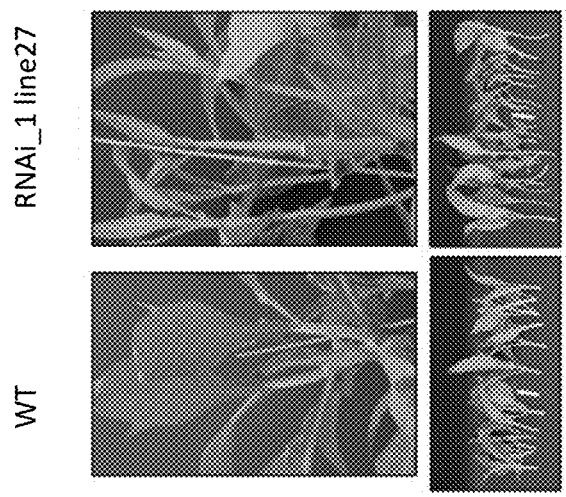
FIG. 6C are photographs that show the phenotype of T1 transgenic plants (RNAi_1; top right, bottom right) in comparison to wild type plants (top left and bottom left) two weeks after topping.
Figure 6D:
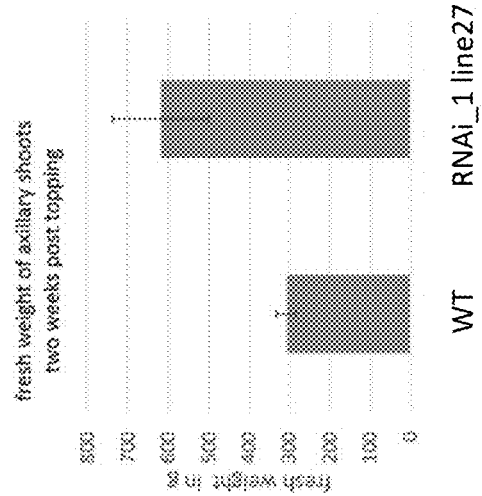
FIG. 6D is a graph showing that the fresh weight of axillary shoots of RNAi_1 plants was twice as much as that of wild type plant, indicating that silencing the BRANCH1 homolog in tobacco resulted in enhanced bud outgrowth.
Figure 7A:
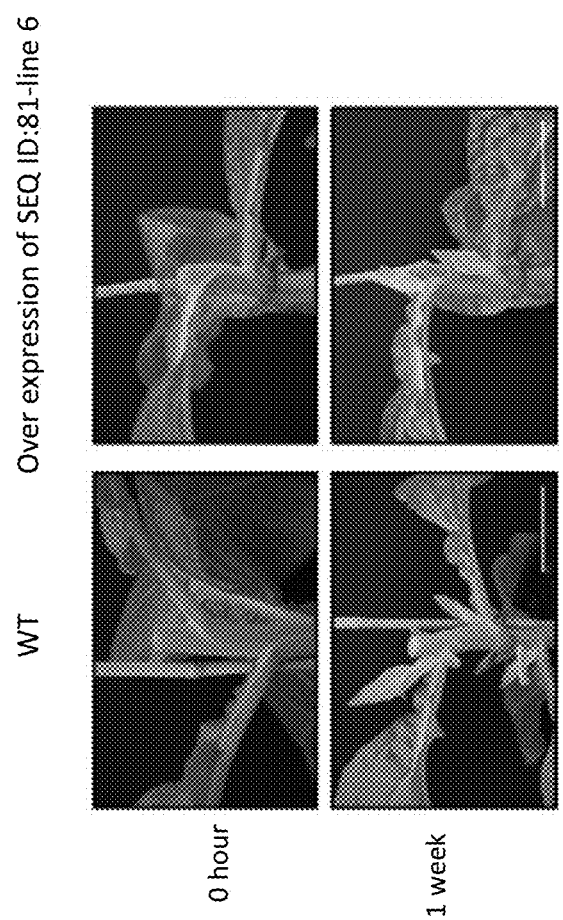
FIG. 7A are photographs that show that overexpression of the Arabidopsis BRANCH1 nucleic acid leads to reduced bud outgrowth (right) relative to wild type plants (left) within 1 week after topping (bottom).
Figure 7B:
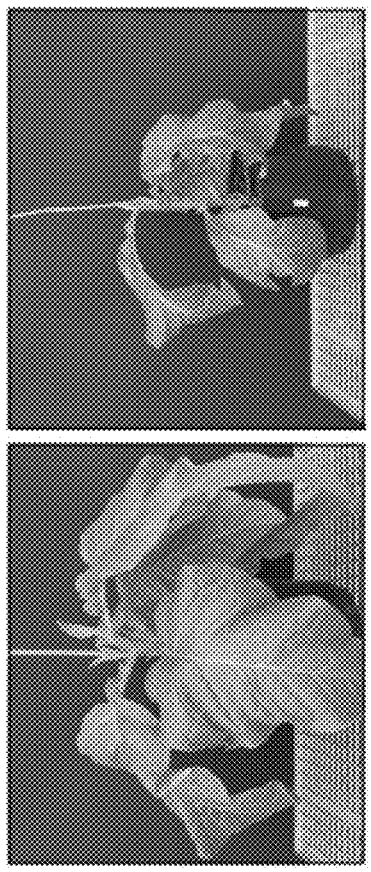
FIG. 7B are photographs that show that overexpression of the Arabidopsis BRANCH1 nucleic acid influences plant growth in general (right) relative to wild type plants (left).
Figure 8:
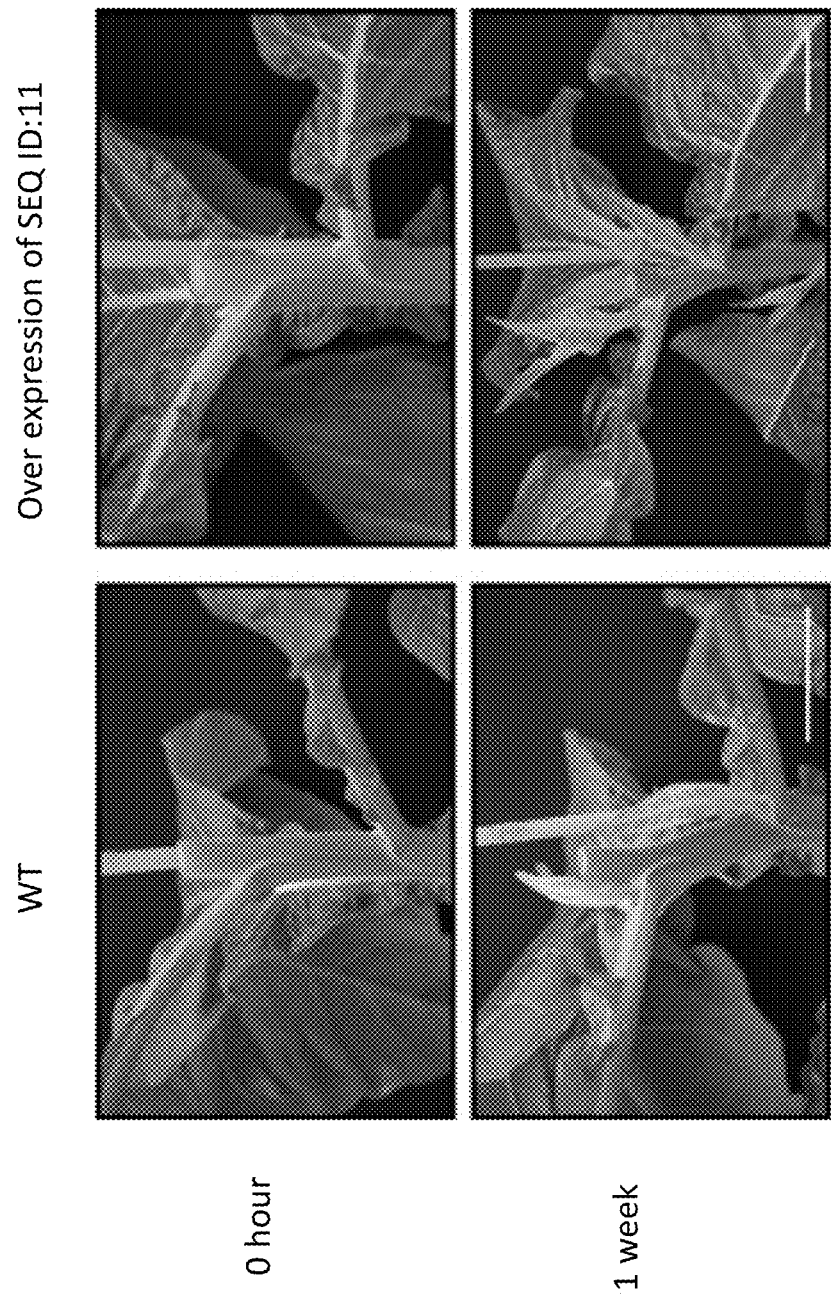
FIG. 8 are photographs that show that overexpression of the nucleic acid sequence shown in SEQ ID NO:11 leads to enhanced bud outgrowth after topping (right). The phenotype is exemplarily for one transgenic line in comparison to a wild type plant (left) 0 h (top) and 1 week after topping (bottom).
Figure 9:
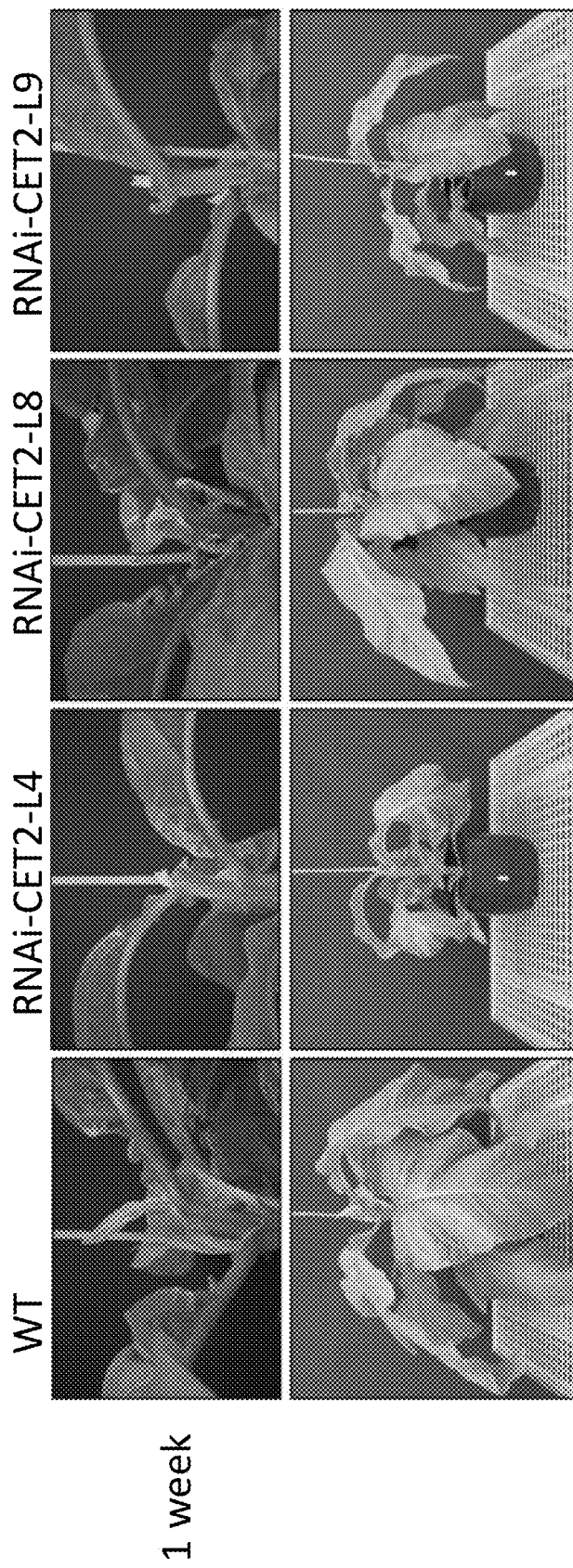
FIG. 9 are photographs (close-up, top; entire plant, bottom) that show that overexpression of RNAi_CET2 in three different transgenic lines down regulated sucker growth and resulted in reduced bud outgrowth. The phenotype of three lines transgenic for RNAi_CET2 in comparison to a wild type plant (left) 1 week after topping is shown.
Figure 10:
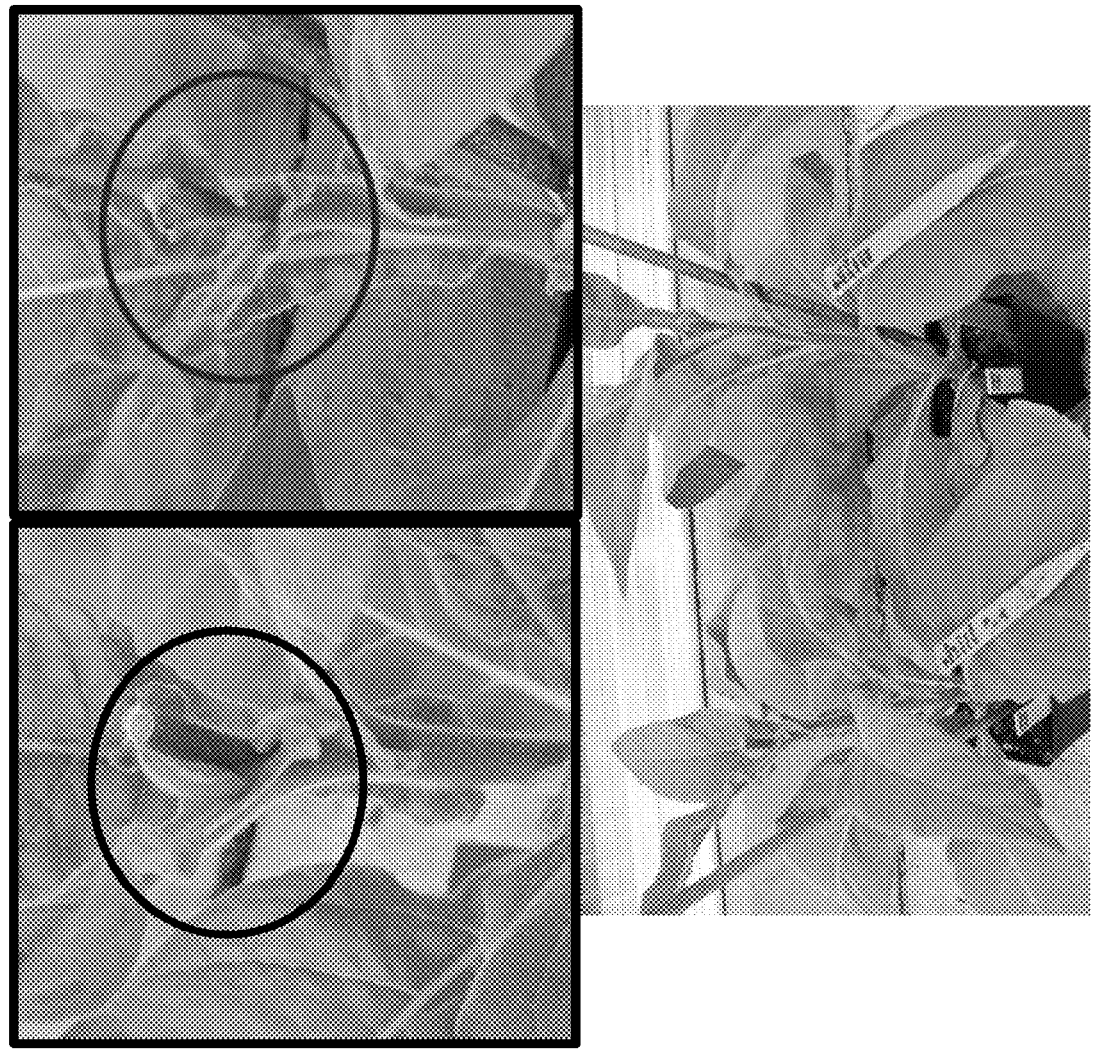
FIG. 10 are photographs taken 7 days after topping that show that expression of RNAi_26 reduced sucker growth (close-up, top right; entire plant, bottom) relative to a wild type plant (top left).
Figure 11:
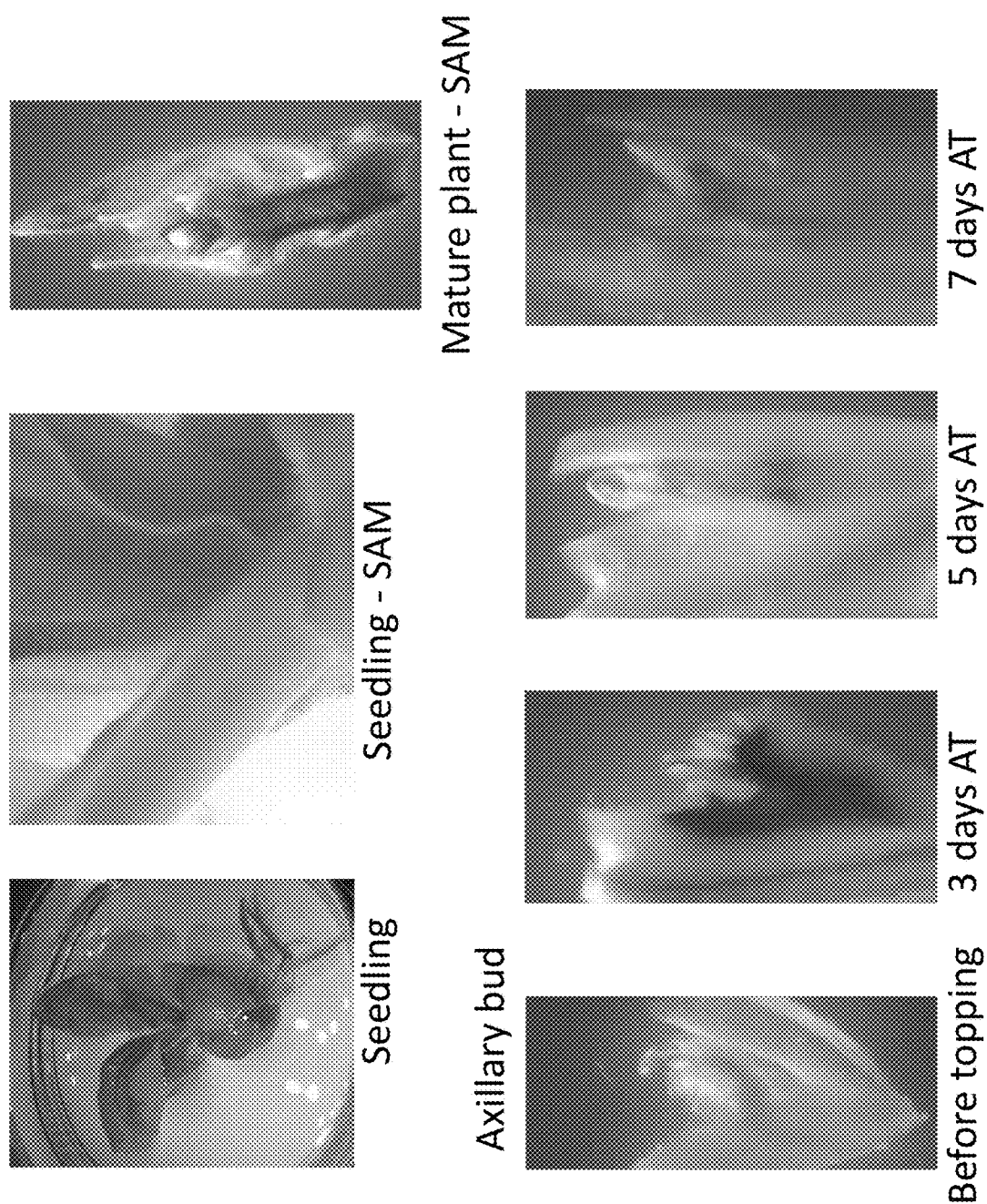
FIG. 11 are photographs showing the meristem-specific expression of GUS under control of the promoter having the sequence shown in SEQ ID NO:116. As labeled: no expression was observed in the seedling in the absence of SAM; in the seedling in the presence of SAM, blue color can be seen; weak expression on axillary buds was seen before topping; strong expression was observed 3 days after topping; GUS expression faded out within 5 days after topping; and GUS expression was absent by 7 days after topping.
Figure 12:
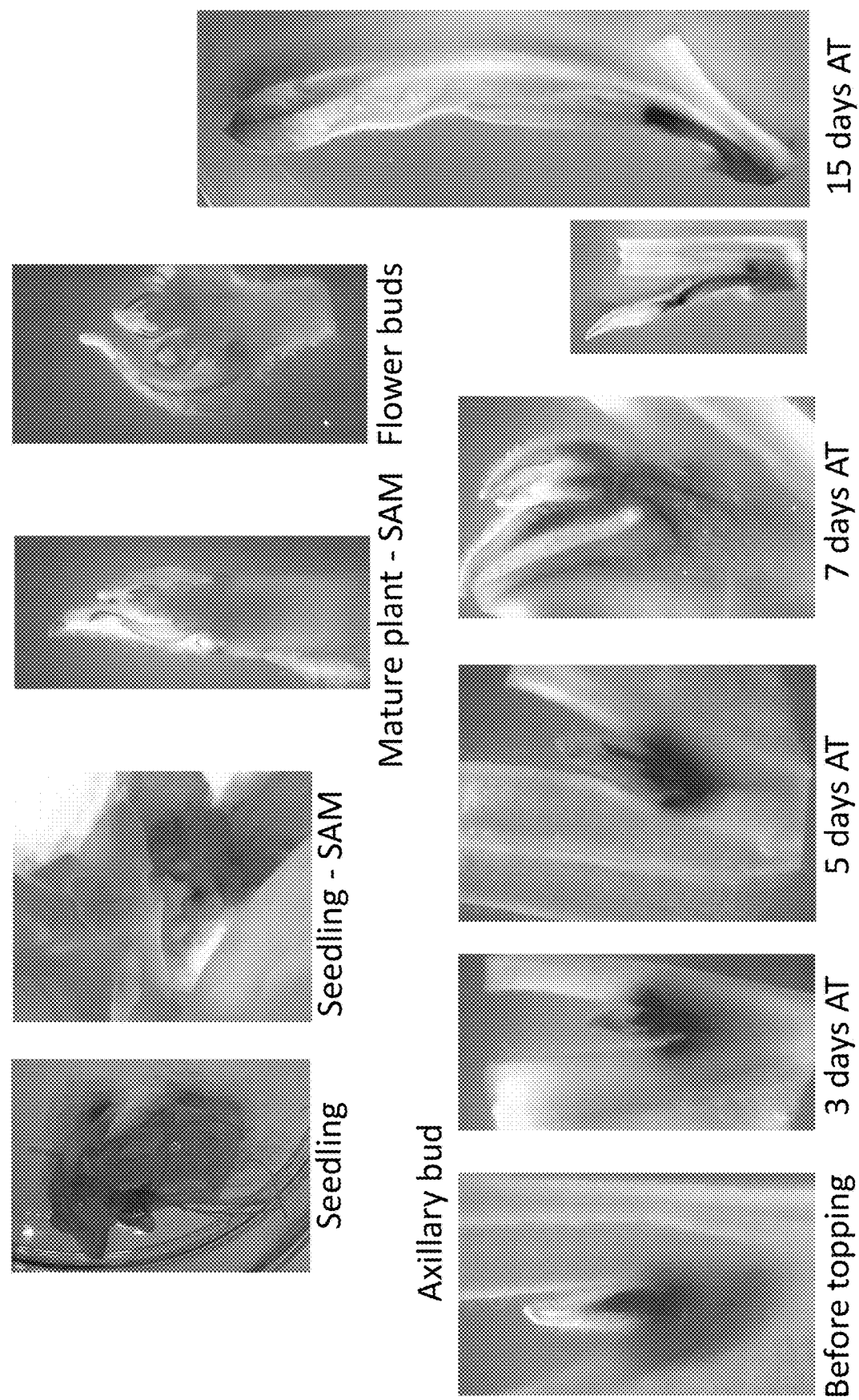
FIG. 12 are photographs showing the axillary bud-specific expression of GUS under control of the promoter having the sequence shown in SEQ ID NO:117. As labeled: no expression was observed in the seedling in the absence of SAM; GUS expression was observed in the axillary buds in the presence of SAM; in the mature plant, GUS expression was observed at the base and in the side buds; no GUS expression was observed in the flower buds; and strong GUS expression was observed in the axillary bud before topping and for up to 15 days after topping.
Figure 13:
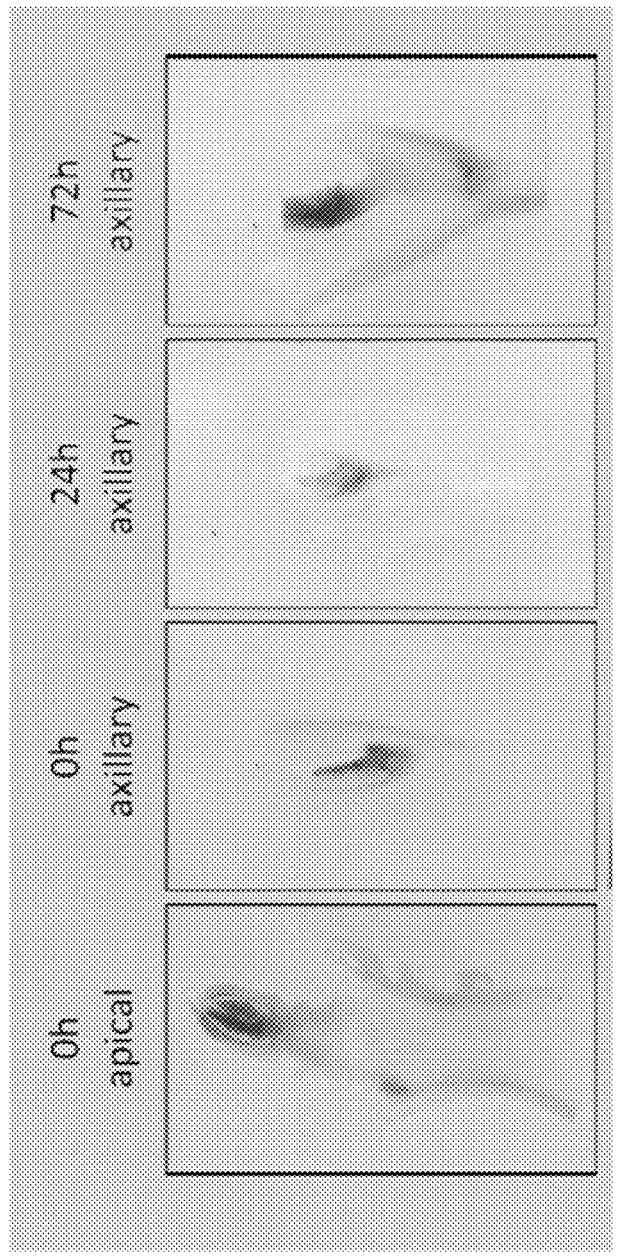
FIG. 13 are photographs showing meristem-specific GUS expression under control of the P1 promoter. GUS expression is observed, but is down-regulated after topping (at 0 hr).

The GUS-positive plant tissues were examined with a bright field microscope (Leica Q500MC, Cambridge, England) at a low magnification and photographed with a digital camera. See FIGS. 5A and 5B. Results of experiments using two different promoters described herein (SEQ ID NOs:113 and 115) are shown in FIG. 5. Young seedlings were stained. The GUS expression, indicated by the blue staining, is concentrated in the axillary bud, indicating that these two promoters are active in the axillary bud, but not in the stem or leaves (FIG. 5A). The expression of GUS under the direction of the SEQ ID NO:113 promoter also decreased after topping, which coincides with the gene expression pattern that was observed for the endogenous gene that is normally regulated by this promoter (FIG. 5B). These promoter sequences can be used to express genes only or predominantly in the axillary bud while limiting expression in the rest of the plant.

TABLE 6

Selected clones for the promoter analysis

| Contig Number | Length of Promoter | SEQ ID NO |
| --- | --- | --- |
| C5787 | 2248 | 113 |
| C7651 | 2800 | 114 |
| C26207 | 3356 | 115 |
| C12866 | 3150 | 116 |
| C41568 | 2964 | 117 |
| C16249 | 941 | 118 |

Example 7—Efficacy Test of Promoter and Gene Combinations

After testing of the tissue-specific expression patterns of candidate promoters using promoter::GUS fusion analysis in transgenic plants, we constructed serial vectors to express the candidate genes only in the axillary bud. Using *Agrobacterium*-mediated transformation, transgenic plants containing these constructs are generated. The expression of the candidate gene(s) in the transgenic plants can result in the plants suppressing axillary bud growth, resulting from either suppression or over-expression of candidate gene(s).

Some examples are shown as bellow:

Construct 1: Promoter (SEQ ID NO:113) and gene (SEQ ID NO: 17)
Construct 2: Promoter (SEQ ID NO:113) and gene (SEQ ID NO:104)
Construct 3: Promoter (SEQ ID NO:113) and gene (SEQ ID NO: 7)
Construct 4: Promoter (SEQ ID NO:113) and gene (SEQ ID NO: 41)
Construct 5: Promoter (SEQ ID NO:113) and gene (SEQ ID NO: 5)
Construct 6: Promoter (SEQ ID NO:118) and gene (SEQ ID NO: 17)
Construct 7: Promoter (SEQ ID NO:118) and gene (SEQ ID NO:104)
Construct 8: Promoter (SEQ ID NO:118) and gene (SEQ ID NO: 7)
Construct 9: Promoter (SEQ ID NO:118) and gene (SEQ ID NO: 41)
Construct 10: Promoter (SEQ ID NO:118) and gene (SEQ ID NO: 5)
Construct 11: Promoter (SEQ ID NO:115) and gene (SEQ ID NO: 17)
Construct 12: Promoter (SEQ ID NO:115) and gene (SEQ ID NO:104)
Construct 13: Promoter (SEQ ID NO:115) and gene (SEQ ID NO: 7)
Construct 14: Promoter (SEQ ID NO:115) and gene (SEQ ID NO: 41)
Construct 15: Promoter (SEQ ID NO:115) and gene (SEQ ID NO: 5)
Construct 16: Promoter (SEQ ID NO:117) and gene (SEQ ID NO: 17)
Construct 17: Promoter (SEQ ID NO:117) and gene (SEQ ID NO:104)
Construct 18: Promoter (SEQ ID NO:117) and gene (SEQ ID NO: 7)
Construct 19: Promoter (SEQ ID NO:117) and gene (SEQ ID NO: 41)
Construct 20: Promoter (SEQ ID NO:117) and gene (SEQ ID NO: 5)

Efficacy testing for the impact of constructs 1-20 will be carried out under greenhouse and field conditions. Transgenic plants and matched wild type controls will be grown to layby stage and topped. Sucker growth will be quantified with a metric including the total number of suckers, the rate of sucker growth, and the emergence of new suckers after sucker removal. These measurements will be conducted by hand or by digital imaging technology. Field efficacy testing will also determine the type and extent of sucker control chemical application needed under normal agronomical practices. With this metric the effect of gene expression constructs on axillary bud initiation and growth will be compared with wild type plants of the same variety. At the same time, the impact of this technology on costs related to sucker control and any changes in chemical residues found in the final cured leaf will be quantified.

Example 8—TALEN-Mediated Mutagenesis

Transcription activator-like effector nucleases (TALENs) technology was used to carry out genome modification in commercial tobacco varieties such as TN90, K326 and Narrow Leaf Madole. TALENs enable genetic modification through induction of a double strand break (DSB) in a DNA target sequence. The ensuing DNA break repair by either non-homologous end joining (NHEJ) or homology-directed repair (HDR)-mediated pathway can be exploited to introduce the desired modification (e.g. gene disruption, gene correction or gene insertion).

To introduce TALENs and a donor DNA into a plant cell, PEG-mediated protoplast transformation was used. Tobacco leaves of 4-8 weeks old tobacco plants from sterile culture were cut into small pieces and transferred in a petri dish containing filter-sterilized enzyme solution with 1.0% Cellulase onuzuka R10 and 0.5% Macerozym. The leaf strips in the petri dish were vacuum infiltrated for 30 min in the dark using a desiccator. After incubation, the digested leaves were resuspended by shaking at 45 rpm for 230 minutes and then filtered through a sterilized nylon filter (100 µm pore size) by collecting in a 50 ml centrifuge tube. The solution laid on Lymphoprep was separated with the centrifugation at 100 g for 10 min. The protoplast bands were collected using a Pasteur pipette, and purified protoplasts were washed with an equal volume of W5n solution containing with NaCl, $CaCl_2$, KCl, MES and Glucose, and centrifuged for 5 min at 2000 rpm. The protoplast pellets were resuspended at $2\times10^5$/ml in W5n solution, and left on ice for 30 mins. Afterwards, the supernatant was removed and the protoplast pellet was resuspended in filter-sterilized MMM solution containing mannitol, $MgCl_2$ and MES.

The PEG transfection of tobacco protoplasts was performed according to the method described by Zhang et al. (2012) with some modifications. A 500 µl aliquot of the protoplast suspension was transferred into 10 ml culture tube and 25 µl (10 µg) of plasmid DNA was added slowly to the protoplasts suspension. In the protoplast-DNA solution, 525 µl PEG solution was added, and mixed carefully by tapping the tube. The tube was incubated for 20 minutes, then 2.5 ml W5n solution was added to stop the reaction. The solution was centrifuged at 100 g for 5 min, and washed with protoplast culture media. The PEG-treated protoplasts were resuspended in 1 ml culture media containing with 0.1 mg/l NAA and 0.5 mg/l BAP, and mixed with 1 ml low-melting agar to make protoplast beads. The protoplast beads were cultured in liquid media, and calli growing from the protoplast beads were transferred onto solid shooting media. When shoots were well developed, the shoots were transferred in a magenta box for root formation. When root systems were fully developed and shoot growth had resumed, plants were transplanted into soil.

TALEN approaches that can be used to prevent or reduce sucker growth include: (1) for targeted genomic integration in tobacco varieties, gene-specific TALENs and a donor DNA with homology-derived recombination (HDR) are designed; (2) for sucker-specific promoter and target gene insertion in the tobacco genome; and (3) for target gene disruption, gene-specific TALENs with, e.g., non-homologous end joining (NHEJ) are used to direct the TALENs to the target gene disruption.

(1) Targeted Genomic Integration:

(A) Targeted genomic integration of a coding sequence into the promoter region of a gene with highly specific expression in axillary bud:

Instead of random gene insertion using conventional transformation methods, the targeted genomic integration of a coding sequence into the promoter region of a gene with highly specific expression in axillary bud can be used to control the expression of the coding sequence by the endogenous promoter activity. One example of the targeted genomic integration approach is the combination of a promoter (SEQ ID NO:118) and a coding sequence (SEQ ID NO:1). Using such a construct, a coding sequence (or more than one coding sequence) is homologously recombined into the genomic region of the promoter sequence and controlled by the promoter.

A TALEN donor sequence is shown in SEQ ID NO:119 (the promoter and target sequences are underlined, and the target gene sequence is in bold), and a TALEN target sequence is shown in SEQ ID NO:120 (the target sequences are underlined).

(B) Targeted genomic integration of a promoter and a coding sequence into the promoter region of a gene with highly specific expression in axillary bud:

To effectively provide a double dose of promoter control, a sucker-specific promoter and a coding sequence can be inserted into the promoter region of a gene highly expressed in axillary bud. In this approach, two promoters work together to control the coding sequence (or coding sequences). For example, in one end of a promoter (SEQ ID NO:118), a construct including a promoter (SEQ ID NO:113) and a coding sequence (SEQ ID NO:13) is inserted using TALEN technology, thereby directing expression of the coding sequence by both promoters (SEQ ID NO:118 and 113).

A TALEN donor sequence is shown in SEQ ID NO:121 (the endogenous promoter is underlined, the exogenous promoter is italicized, and the target gene is in bold).

(C) Sucker-specific promoter and coding sequence insertion

Another option of targeted gene integration is to insert a selected tobacco promoter and coding sequence into an effective location of the tobacco genome by TALEN.

(2) Target Gene Disruption

To disrupt the function of candidate genes without using RNAi constructs, gene-specific TALENs were designed and introduced into tobacco cells, resulting in deletions or insertions to knockout the endogenous gene (or genes). For example, potential TALEN target sites in a coding sequence (SEQ ID NO:104) were identified, and homologous recombination sites within the coding sequence of the gene were selected.

A TALEN target sequence is shown in SEQ ID NO:122 (the target sequences are underlined).

Example 9—Additional Transgenic Strategies

The following strategies to regulate sucker outgrowth are described herein.

The first strategy applied was to regulate axillary bud outgrowth gene expression. Mutant studies in Arabidopsis, rice, and barley suggest that the genetic pathways that regulate branching are complex. There are two general classes of genes that regulate branching. One class of genes restricts the out-growth of buds and is defined by mutants with increased branching. See, for example, the Arabidopsis BRANCHED1 gene (e.g., SEQ ID NO:81 and the possible tobacco homologs shown in SEQ ID NOs: 1, 13, 35, 37, 39) and the Arabidopsis More Axillary Branching (MAX) gene. The other class of genes promotes axillary meristem development and is defined by mutants with decreased branching. See, for example, the Arabidopsis Lateral Suppressor (LAS) gene and the possible homologues in tobacco (e.g., SEQ ID NOs: 71 or 73) as well as the Arabidopsis Regulator of Axillary Meristems (RAX) and the possible tobacco homologous (e.g., SEQ ID NOs: 75 and 77).

The second strategy applied was to regulate tobacco cytokinin synthesis and distribution. As a plant hormone, cytokinin plays many regulatory roles in shoot growth, retardation of leaf senescence, inhibition of root growth, seed germination, and stress responses. It is well-known that cytokinin promotes axillary bud outgrowth. When cytokinin is applied directly to axillary buds or supplied via the xylem stream, side branches are increased. Cytokinin oxidase/dehydrogenase (CKX) is an enzyme that degrades cytokinin. Overexpression of individual CKX genes established cytokinin deficient plants and revealed that cytokinin is a positive regulator of the shoot meristem activity. On the other hand, reduced expression of CKX in rice causes cytokinin accumulation in shoot meristems, which increases the number of buds such as floral buds, ultimately resulting in enhanced grain yield. Based on these results, CKX expression in axillary buds can inhibit or delay axillary bud outgrowth in tobacco after the shoot apical meristem has been topped.

Decapitation of the shoot apex releases axillary buds from their dormancy and they begin to grow out. Auxin derived from an intact shoot apex suppresses axillary bud outgrowth, whereas cytokinin induced by decapitation of the shoot apex stimulates axillary bud outgrowth. Depletion of cytokinin in the axillary bud region by overexpression of the relevant enzymes under control of an axillary bud specific promoter can be used to inhibit axillary meristem outgrowth. The candidate genes involved in this strategy are Arabidopsis cytokinin oxidase (CKX; SEQ ID NO:55 encoding SEQ ID NO:56); tobacco CKXs (SEQ ID NOs:57, 59, or 61); and tobacco adenosine phosphate-isopentenyltransferase (IPT) (SEQ ID NO: 61).

The third strategy applied was to control axillary bud outgrowth by destroying axillary apical meristem development. There are two types of the expression of transgenes in transgenic plants: constitutive expression and tissue specific expression. The constitutive gene expression can result in unexpected problems if a gene of critical importance in a certain tissue is miss-expressed in other tissues. Unlike constitutive expression of genes, tissue-specific expression is the result of gene regulation in a target tissue. For tissue-specific expression, promoters can control the expression of given genes in a tissue-dependent manner and according to the developmental stage of the plant. In our case, the promoters were obtained from genes specifically expressed in axillary buds, and the promoters were defined to regulate gene expression in buds. To control sucker growth after topping of a shoot apical meristem, the promoters (or modified promoters) can be used to direct expression of a heterologous gene in tobacco plants. As a result of axillary bud-specific expression, the heterologous gene (or the transgene) operably linked to the promoter is expressed in axillary buds where expression of the transgene is desired, leaving the rest of the plant unaffected by transgene expression.

Shoot meristems of plants are composed of stem cells that are continuously replenished through a classical feedback circuit involving the homeobox WUSCHEL (WUS) gene and the CLAVATA (CLV) gene signaling pathway. Targeting of the WUSHEL sequence or overexpression of the CLAVATA gene in axillary buds alters the pathway and causes a defect in shoot meristem development and inhibits shoot outgrowth. The candidate genes are WUS (SEQ ID NOs: 63 and 65) and CLV3 (SEQ ID NO: 67).

The CENTRORADIALIS (CEN) gene, which is required for indeterminate growth of the shoot meristem in Antirrhinum, was cloned and characterized. When the gene is expressed in tobacco, the tobacco plants showed an extended vegetative phase, delaying the switch to flowering. In tobacco, the CET genes (from "CEN-like genes from tobacco") are not expressed in the main shoot meristem; their expression is restricted to vegetative axillary meristems. It is clear that CET genes play a role in the development of vegetative axillary meristems to axillary bud growth, however, their actual function remains unknown. When their expression is silenced using an RNAi_CET construct, the transgenic plants show bud growth retardation after topping.

Example 10—Experimental Data

Plant tissues were stained for GUS by immersion in a staining solution (50 mM sodium phosphate buffer, pH 7.0, 1 mM EDTA, 0.5 mg/mL 5-bromo-4-chloro-3-indolyl-D GlcUA [X-Gluc; Biosynth AG], 0.4% Triton X-100, and 5 mM each of potassium ferri/ferrocyanide), and incubated at 37° C. for 6-24 h.

The promoter shown in SEQ ID NO:117 has been shown to be a good candidate for specific expression in the axillary bud before topping and for 15 days after topping. There was no expression in the shoot apical meristem region before topping. The promoter shown in SEQ ID NO:117 (about 2.5 kb) is the 5'end upstream of sequence of SEQ ID NO: 27, which encodes eukaryotic translation initiation factor 3, subunit A (eIF-3A), a component of the eukaryotic translation initiation factor 3 (eIF-3) complex, which is required for several steps in the initiation of protein synthesis.

Several genes were stacked by co-transformation to overexpress and/or knock down using, for example, RNAi, under the control of the promoter shown in SEQ ID NO:117. The following are the constructs and genes that were stacked together by co-transformation.

a) Promoter SEQ ID NO:117—RNAi_CET2-26-6, which targets CET2, SEQ ID NO: 11 and SEQ ID NO:49;

b) Promoter SEQ ID NO:117—RNAi_CET2-26-6, co-transformed with Promoter SEQ ID NO:117—AtBRC1 (SEQ ID NO:81);

c) Promoter SEQ ID NO:117—RNAi_CET2-26-6, co-transformed with Promoter SEQ ID NO:117—SEQ ID NO: 1; and d) Promoter SEQ ID NO:117—SEQ ID NO: 1, co-transformed with Promoter SEQ ID NO:117—AtBRC1 (SEQ ID NO:81).

It is to be understood that, while the methods and compositions of matter have been described herein in conjunction with a number of different aspects, the foregoing description of the various aspects is intended to illustrate and not limit the scope of the methods and compositions of matter. Other aspects, advantages, and modifications are within the scope of the following claims.

What is claimed is:

1. A cured leaf from a tobacco plant comprising a heterologous nucleic acid molecule operably linked to a promoter comprising a sequence selected from the group consisting of SEQ ID NOs: 113-118, wherein the cured leaf comprises the heterologous nucleic acid molecule.

2. The cured leaf of claim 1, wherein the heterologous nucleic acid comprises a nucleic acid sequence encoding a polypeptide having at least 90% sequence identity to an amino acid sequence encoded by a polynucleotide sequence of SEQ ID NO: 79.

3. The cured leaf of claim 2, wherein the tobacco plant exhibits reduced axillary bud growth after topping as compared to a control tobacco plant not expressing the heterologous nucleic acid molecule.

4. The cured leaf of claim 1, wherein the heterologous nucleic acid molecule has 100% identity to a polynucleotide sequence of SEQ ID NO: 79.

5. The cured leaf of claim 1, wherein the heterologous nucleic acid molecule encodes a polypeptide having at least 98% identity to a polypeptide sequence of SEQ ID NO: 80.

6. The cured leaf of claim 1, wherein the heterologous nucleic acid molecule encodes a polypeptide having 100% identity to a polypeptide sequence of SEQ ID NO: 80.

7. The cured leaf of claim 1, wherein the tobacco plant is selected from the group consisting of a Burley type, a dark type, a flue-cured type, a Maryland type, and an Oriental type.

8. The cured leaf of claim 1, wherein the tobacco plant is a variety selected from the group consisting of BU 64, CC 101, CC 200, CC 13, CC 27, CC 33, CC 35,CC 37, CC 65, CC 67, CC 301, CC 400, CC 500, CC 600, CC 700, CC 800, CC 900, CC 1063, Coker 176, Coker 319, Coker 371 Gold, Coker 48, CU 263, DF911, GL 26H, GL 338, GL 350, GL 395, GL 600, GL 737, GL 939, GL 973, GF 157, GF 318, RJR 901, HB 04P, K 149, K 326, K 346, K 358, K394, K 399, K 730, NC 196, NC 37NF, NC 471, NC 55, NC 92, NC2326, NC 95, NC 925, PVH 1118, PVH 1452, PVH 2110, PVH 2254, PVH 2275, VA 116, VA 119, KDH 959, KT 200, KT204LC, KY 10, KY 14, KY 160, KY 17, KY 171, KY 907, KY907LC, KTY14 x L8 LC, Little Crittenden, McNair 373, McNair 944, msKY 14xL8, Narrow Leaf Madole, NC 100, NC 102, NC 2000, NC 291, NC 297, NC 299, NC 3, NC 4, NC 5, NC 6, NC7, NC 606, NC 71, NC 72, NC 810, NC BH 129, NC 2002, Neal Smith Madole, OXFORD 207, PVH03, PVH09, PVH19, PVH50, PVH51, R 610, R 630, R 7-11, R 7-12, RG 17, RG 81, RG H51, RGH 4, RGH 51, RS 1410, Speight 168, Speight 172, Speight 179, Speight 210, Speight 220, Speight 225, Speight 227, Speight 234, Speight G-28, Speight G-70, Speight H-6, Speight H20, Speight NF3, TI 1406, TI 1269, TN 86, TN86LC, TN 90, TN9OLC, TN 97, TN97LC, TN D94, TN D950, TR (Tom Rosson) Madole, VA 309, or VA359.

9. The cured leaf of claim 1, wherein the cured leaf is selected from the group consisting of an air cured leaf, a fire cured leaf, a flue cured leaf, and a sun cured leaf.

10. A tobacco product comprising a cured leaf from a tobacco plant comprising a heterologous nucleic acid molecule operably linked to a promoter comprising a sequence selected from the group consisting of SEQ ID NOs: 113-118, wherein the cured leaf comprises the heterologous nucleic acid molecule.

11. The tobacco product of claim 10, wherein the heterologous nucleic acid comprises a nucleic acid sequence encoding a polypeptide having at least 90% sequence identity to an amino acid sequence encoded by a polynucleotide sequence of SEQ ID NO: 79.

12. The tobacco product of claim 11, wherein the tobacco plant exhibits reduced axillary bud growth after topping as compared to a control tobacco plant not expressing the heterologous nucleic acid molecule.

13. The tobacco product of claim 10, wherein the heterologous nucleic acid molecule has 100% identity to a polynucleotide sequence of SEQ ID NO: 79.

14. The tobacco product of claim 10, wherein the heterologous nucleic acid molecule encodes a polypeptide having at least 98% identity to a polypeptide sequence of SEQ ID NO: 80.

15. The tobacco product of claim 10, wherein the heterologous nucleic acid molecule encodes a polypeptide having 100% identity to a polypeptide sequence of SEQ ID NO: 80.

16. The tobacco product of claim 10, wherein the tobacco plant is selected from the group consisting of a Burley type, a dark type, a flue-cured type, a Maryland type, and an Oriental type.

17. The tobacco product of claim 10, wherein the tobacco plant is a variety selected from the group consisting of BU 64, CC 101, CC 200, CC 13, CC 27, CC 33, CC 35,CC 37, CC 65, CC 67, CC 301, CC 400, CC 500, CC 600, CC 700, CC 800, CC 900, CC 1063, Coker 176, Coker 319, Coker 371 Gold, Coker 48, CU 263, DF911, GL 26H, GL 338, GL 350, GL 395, GL 600, GL 737, GL 939, GL 973, GF 157, GF 318, RJR 901, HB 04P, K 149, K 326, K 346, K 358, K394, K 399, K 730, NC 196, NC 37NF, NC 471, NC 55, NC 92, NC2326, NC 95, NC 925, PVH 1118, PVH 1452, PVH 2110, PVH 2254, PVH 2275, VA 116, VA 119, KDH 959, KT 200, KT204LC, KY 10, KY 14, KY 160, KY 17, KY 171, KY 907, KY907LC, KTY14 x L8 LC, Little Crittenden, McNair 373, McNair 944, msKY 14xL8, Narrow Leaf Madole, NC 100, NC 102, NC 2000, NC 291, NC 297, NC 299, NC 3, NC 4, NC 5, NC 6, NC7, NC 606, NC 71, NC 72, NC 810, NC BH 129, NC 2002, Neal Smith Madole, OXFORD 207, PVH03, PVH09, PVH19, PVH50, PVH51, R 610, R 630, R 7-11, R 7-12, RG 17, RG 81, RG H51, RGH 4, RGH 51, RS 1410, Speight 168, Speight 172, Speight 179, Speight 210, Speight 220, Speight 225, Speight 227, Speight 234, Speight G-28, Speight G-70, Speight H-6, Speight H20, Speight NF3, TI 1406, TI 1269, TN 86, TN86LC, TN 90, TN9OLC, TN 97, TN97LC, TN D94, TN D950, TR (Tom Rosson) Madole, VA 309, or VA359.

18. The tobacco product of claim 10, wherein the tobacco product is selected from the group consisting of cigarillos, non-ventilated recess filter cigarettes, vented recess filter cigarettes, cigars, snuff, pipe tobacco, cigar tobacco, cigarette tobacco, chewing tobacco, leaf tobacco shredded tobacco, cut tobacco, snuff, long-cut moist smokeless tobacco, and snus.

19. The tobacco product of claim 10, wherein the tobacco product further comprises an ingredient selected from the group consisting of a binder, a plasticizer, a stabilizer, and a flavoring.

20. The tobacco product of claim 10, wherein the cured leaf is selected from the group consisting of an air cured leaf, a fire cured leaf, a flue cured leaf, and a sun cured leaf.

* * * * *